(12) United States Patent
Oo et al.

(10) Patent No.: US 10,995,325 B2
(45) Date of Patent: May 4, 2021

(54) ADDITIONAL PHYTASE VARIANTS AND METHODS

(71) Applicant: Fornia BioSolutions, Inc., Hayward, CA (US)

(72) Inventors: Khin Oo, Daly City, CA (US); Jie Yang, Foster City, CA (US); Xiyun Zhang, San Ramon, CA (US); Goutami Banerjee, Hayward, CA (US); Tatsuya Fukushima, Fremont, CA (US); Eric Lin Hu, Millbrae, CA (US); Imad N. Sawaya, Redwood City, CA (US); Stephen Joshua Macaso Millet, Tracy, CA (US); Jijiao Zeng, Albany, CA (US); Wenhua Lu, Dublin, CA (US)

(73) Assignee: Fornia BioSolutions, Inc., Hayward, CA (US)

( * ) Notice: Subject to any disclaimer, the term of this patent is extended or adjusted under 35 U.S.C. 154(b) by 0 days.

(21) Appl. No.: 16/566,494

(22) Filed: Sep. 10, 2019

(65) Prior Publication Data
US 2020/0299656 A1    Sep. 24, 2020

Related U.S. Application Data

(60) Provisional application No. 62/821,649, filed on Mar. 21, 2019.

(51) Int. Cl.
| | | |
|---|---|---|
| *C12N 9/16* | (2006.01) | |
| *A23K 20/189* | (2016.01) | |
| *C12N 15/81* | (2006.01) | |
| *E21B 33/129* | (2006.01) | |
| *E21B 43/26* | (2006.01) | |

(52) U.S. Cl.
CPC .............. *C12N 9/16* (2013.01); *A23K 20/189* (2016.05); *C12N 15/81* (2013.01); *C12Y 301/03008* (2013.01); *E21B 33/1293* (2013.01); *E21B 43/26* (2013.01)

(58) Field of Classification Search
CPC ........ C12N 9/16; C12N 15/81; A23K 20/189; C12Y 301/03008
See application file for complete search history.

(56) References Cited

U.S. PATENT DOCUMENTS

| | | | |
|---|---|---|---|
| 9,173,421 B2 * | 11/2015 | De Maria | ...... C12Y 301/03008 |
| 9,528,096 B1 | 12/2016 | Banerjee et al. | |
| 9,605,245 B1 | 3/2017 | Banerjee et al. | |
| 10,351,823 B2 | 7/2019 | Banerjee et al. | |
| 2017/0240872 A1 | 8/2017 | Guo et al. | |
| 2020/0275679 A1 * | 9/2020 | Raab | ...................... C07K 14/38 |

FOREIGN PATENT DOCUMENTS

| | | |
|---|---|---|
| EP | 3 263 699 A1 | 1/2018 |
| EP | 3 438 253 A1 | 2/2019 |

OTHER PUBLICATIONS

International Search Report and Written Opinion for International Application No. PCT/US2019/050429, dated Feb. 6, 2020, 18 pages.
Kim et al., "Cloning and expression of *Escherichia coli* K13 phytase gene (AppA13) isolated from seawater", Journal of Fisheries Science and Technology, vol. 6, No. 1, 2003, pp. 20-26.

* cited by examiner

*Primary Examiner* — Ganapathirama Raghu
(74) *Attorney, Agent, or Firm* — Morgan, Lewis & Bockius LLP

(57) ABSTRACT

The present invention relates to variant phytase enzymes and their use thereof.

40 Claims, 26 Drawing Sheets
Specification includes a Sequence Listing.

FIGURE 1A

| Colony Tracking Number | Total Activity Improvement | | Temp and/or BSA Tolerance Improvement | | | | pH Tolerance Improvement | | AA Mutations w.r.t. GSP (CX0808923) |
|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00047672 | 0.98 | 0.01 | 1.02 | 0.01 | | | | | D142R |
| CL00047694 | 1.02 | 0.01 | 1.12 | 0.02 | | | | | D142I |
| CL00047713 | 1.07 | 0.01 | 1.14 | 0.03 | | | | | A25N |
| CL00047716 | 1.02 | 0.02 | 1.15 | 0.04 | | | | | D142L |
| CL00047719 | 0.99 | 0.03 | 1.05 | 0.04 | | | | | D142T |
| CL00047720 | 1.10 | 0.03 | 1.80 | 0.04 | | | 1.10 | 0.04 | Insertion |
| CL00047731 | 1.13 | 0.02 | 1.04 | 0.03 | | | | | A25W |
| CL00047732 | 1.05 | 0.02 | 1.22 | 0.06 | | | | | D142Y |
| CL00047736 | 1.04 | 0.02 | 1.16 | 0.02 | | | | | D142A |
| CL00047749 | 1.23 | 0.02 | 1.21 | 0.04 | | | | | A25F |
| CL00047771 | 1.04 | 0.01 | 1.21 | 0.03 | | | | | D142M |
| CL00047777 | 1.03 | 0.01 | 1.15 | 0.02 | | | | | D142K |
| CL00047793 | 1.03 | 0.02 | 0.79 | 0.04 | | | | | D142P |
| CL00047794 | 1.01 | 0.01 | 1.24 | 0.02 | | | | | D142F |
| CL00047795 | 0.99 | 0.01 | 1.17 | 0.03 | | | | | D142H |
| CL00047796 | 1.01 | 0.01 | 1.17 | 0.03 | | | | | D142G |
| CL00047797 | 1.00 | 0.03 | 1.11 | 0.03 | | | | | D142V |
| CL00047807 | 1.01 | 0.02 | 1.14 | 0.02 | | | | | D142S |
| CL00047813 | 1.15 | 0.03 | 1.35 | 0.08 | | | | | A25D |
| CL00047828 | 1.03 | 0.01 | 1.18 | 0.03 | | | | | D142N |
| CL00047919 | 1.04 | 0.02 | 0.42 | 0.02 | | | | | G70E/A73P/K75C/A277T |
| CL00047923 | 0.71 | 0.02 | 1.35 | 0.02 | | | | | Q62W/A73P/G302S |
| CL00047924 | 0.74 | 0.08 | 1.52 | 0.08 | | | 0.74 | 0.09 | Q62W/A73P/A288R/E315G |
| CL00047952 | 0.99 | 0.01 | 1.07 | 0.04 | | | | | E402D |
| CL00047957 | 1.09 | 0.02 | 0.52 | 0.01 | | | | | K75C |
| CL00047970 | 1.15 | 0.03 | 0.59 | 0.04 | | | | | G70E/A73P/K75C |
| CL00047973 | 0.63 | 0.01 | 1.18 | 0.01 | | | | | W46E/Q62W/S146E/E402D |
| CL00047998 | 0.62 | 0.01 | 1.39 | 0.02 | | | | | W46E/Q62W/A73P/N180K/M276K/A277T/E402D |
| CL00048000 | 0.76 | 0.03 | 1.56 | 0.06 | | | | | Q62W/A277T/E315G |
| CL00048003 | 0.78 | 0.02 | 1.33 | 0.02 | | | | | Q62W/A288R |
| CL00048030 | 0.90 | 0.02 | 1.25 | 0.00 | | | | | G70E/P80S/E315G |
| CL00048031 | 0.65 | 0.01 | 1.33 | 0.05 | | | | | W46E/Q62W/A73P |
| CL00048099 | 1.07 | 0.02 | 1.15 | 0.06 | | | 1.56 | 0.03 | M276K/A288R |
| CL00048100 | 1.01 | 0.07 | 1.01 | 0.04 | | | 1.00 | 0.08 | G70E/A73P/E402D |
| CL00048101 | 0.73 | 0.04 | 1.49 | 0.04 | | | 0.73 | 0.05 | W46E/Q62W/E315G |
| CL00048119 | 0.47 | 0.01 | 0.44 | 0.00 | | | 1.27 | 0.01 | W46G/A277T/A288R |
| CL00048138 | 0.78 | 0.00 | 1.37 | 0.05 | | | 1.43 | 0.00 | W46E/Q62W |
| CL00048147 | 1.01 | 0.01 | 1.27 | 0.00 | | | 1.50 | 0.01 | W46E/G70E/E315G |
| CL00048153 | 1.02 | 0.01 | 1.36 | 0.02 | | | | | E315G |
| CL00048162 | 0.19 | 0.00 | 0.17 | 0.04 | | | 1.11 | 0.01 | K75L |
| CL00048196 | 0.94 | 0.01 | 1.43 | 0.04 | | | 1.47 | 0.03 | Q62W |
| CL00048199 | 0.88 | 0.04 | 1.14 | 0.07 | | | 1.40 | 0.03 | Q62W/G70E/F179L/A277T/A288R |
| CL00048201 | 0.75 | 0.04 | 1.40 | 0.04 | | | 1.44 | 0.01 | W46E/Q62W/P80S/H113Q/E315G/E402D |
| CL00048220 | 0.89 | 0.01 | 1.06 | 0.03 | | | 1.41 | 0.00 | M276K/E315G |
| CL00048249 | 1.07 | 0.03 | 1.23 | 0.03 | | | 1.57 | 0.02 | M276K/A277T |
| CL00048253 | 0.94 | 0.01 | 0.76 | 0.03 | | | 1.47 | 0.02 | K75W/M276K/A288R |
| CL00048269 | 0.86 | 0.06 | 1.75 | 0.05 | | | 0.86 | 0.06 | W46E/Q62W/A73P/K75C/A277T/A288R/E315G |
| CL00048270 | 0.60 | 0.01 | 1.26 | 0.04 | | | 1.38 | 0.01 | W46E/Q62W/N180K/E315G |
| CL00048280 | 0.97 | 0.04 | 1.35 | 0.03 | | | 0.97 | 0.04 | M276K/A288R/E315G |
| CL00048291 | 1.09 | 0.06 | 1.24 | 0.05 | | | 1.08 | 0.07 | M276K |
| CL00048294 | 0.82 | 0.03 | 1.54 | 0.03 | | | 1.48 | 0.01 | W46E/Q62W/F179L/M276K |
| CL00048310 | 0.81 | 0.01 | 1.48 | 0.03 | | | 1.50 | 0.03 | W46E/Q62W/M276K |
| CL00048351 | 0.96 | 0.01 | 0.98 | 0.01 | | | 1.44 | 0.06 | A288R |
| CL00048396 | 1.05 | 0.01 | 1.08 | 0.05 | | | 1.50 | 0.03 | A277T/A288R/E402D |
| CL00048423 | 0.87 | 0.00 | 1.25 | 0.03 | | | 1.49 | 0.02 | W46G/Q62W/A73P/S146E/A277T |
| CL00048427 | 0.84 | 0.02 | 1.21 | 0.04 | | | 1.45 | 0.02 | N180K/M276K/A277T/E315G/E402D |
| CL00048441 | 0.90 | 0.01 | 1.04 | 0.02 | | | 1.50 | 0.02 | G70E/A73P/M276K/E315G |
| CL00048457 | 0.99 | 0.01 | 1.27 | 0.02 | | | 1.54 | 0.01 | M276K/E315G/E402D |
| CL00048466 | 0.74 | 0.01 | 0.93 | 0.00 | | | 1.46 | 0.01 | W46E/Q62W/K75C/F179L/A277T |
| CL00048480 | 0.97 | 0.02 | 1.29 | 0.02 | | | 1.54 | 0.02 | P80S/M276K/E315G |
| CL00048509 | 0.80 | 0.01 | 0.62 | 0.01 | | | 1.43 | 0.00 | G70E/A288R |
| CL00048515 | 0.96 | 0.02 | 1.32 | 0.02 | | | 1.56 | 0.01 | M276K/A277T/E315G/E402D |
| CL00048537 | 1.01 | 0.02 | 1.39 | 0.05 | | | 1.58 | 0.03 | Q62W/P80S/M276K |
| CL00048541 (G4P) | 1.09 | 0.03 | 1.59 | 0.03 | | | 1.08 | 0.04 | M276K/A277T/E315G |
| CL00048556 | 1.08 | 0.01 | 1.26 | 0.02 | | | 1.58 | 0.01 | G70E/A73P/M276K |
| CL00048592 | 0.71 | 0.01 | 1.06 | 0.02 | | | 1.43 | 0.02 | W46E/Q62W/P80S |
| CL00048598 | 0.82 | 0.02 | 0.33 | 0.01 | | | 1.43 | 0.01 | W46E/G70E/K75C/A288R |

FIGURE 1B

| Colony Tracking Number | Total Activity Improvement | | Temp and/or BSA Tolerance Improvement | | | | pH Tolerance Improvement | | AA Mutations w.r.t. GSP (CL00085820) |
|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00048600 | 1.01 | 0.03 | 1.31 | 0.02 | | | 1.61 | 0.01 | Q62W/P80S/A277T |
| CL00048633 | 0.92 | 0.01 | 1.27 | 0.03 | | | 1.47 | 0.02 | N180K/M276K/E315G/E402D |
| CL00048664 | 1.00 | 0.02 | 1.03 | 0.05 | | | 1.52 | 0.04 | G70E |
| CL00048676 | 0.97 | 0.05 | 0.93 | 0.03 | | | 1.54 | 0.01 | F179L/A277T/A288R |
| CL00048687 | 0.71 | 0.02 | 1.10 | 0.04 | | | 1.37 | 0.04 | Q62W/A73P/P80S/A288R |
| CL00048701 | 1.03 | 0.02 | 1.15 | 0.02 | | | 1.57 | 0.03 | A73P/E402D |
| CL00048709 | 0.77 | 0.02 | 1.31 | 0.02 | | | 1.42 | 0.00 | Q62W/A73P/E402D |
| CL00048765 | 1.05 | 0.02 | 1.15 | 0.04 | | | 1.57 | 0.02 | P137M |
| CL00048766 | 0.91 | 0.02 | 0.78 | 0.01 | | | 1.33 | 0.02 | T114N |
| CL00048810 | 1.14 | 0.01 | 1.21 | 0.03 | | | | | P137S |
| CL00048843 | 1.10 | 0.02 | 1.01 | 0.05 | | | | | T114F |
| CL00048863 | 1.02 | 0.01 | 1.05 | 0.02 | | | | | T114S |
| CL00048869 | 1.05 | 0.01 | 1.17 | 0.04 | | | | | P137G |
| CL00048870 | 1.01 | 0.03 | 0.36 | 0.02 | | | | | P137C |
| CL00048872 | 1.12 | 0.01 | 1.28 | 0.06 | | | | | P137L |
| CL00048873 | 1.04 | 0.01 | 0.18 | 0.01 | | | | | T114C |
| CL00048877 | 1.04 | 0.05 | 1.27 | 0.04 | | | 1.04 | 0.06 | P137H/L316F |
| CL00048880 | 1.11 | 0.01 | 1.23 | 0.03 | | | | | P137F |
| CL00048896 | 1.07 | 0.02 | 1.12 | 0.04 | | | | | P137N |
| CL00048929 | 1.03 | 0.02 | 1.04 | 0.04 | | | | | P137Y |
| CL00048961 | 1.13 | 0.00 | 1.33 | 0.06 | | | | | T114P |
| CL00048965 | 1.00 | 0.02 | 1.03 | 0.02 | | | | | T114D |
| CL00048969 | 1.07 | 0.03 | 1.22 | 0.01 | | | | | P137W |
| CL00054568 | 1.25 | 0.00 | 0.68 | 0.02 | 0.98 | 0.04 | 1.28 | 0.03 | P4L/T280C |
| CL00054594 | 1.14 | 0.01 | 1.52 | 0.04 | 1.41 | 0.08 | 1.22 | 0.02 | T238A |
| CL00054681 | 1.15 | 0.01 | 1.44 | 0.02 | 1.36 | 0.08 | 1.16 | 0.02 | D35R |
| CL00054689 | 1.14 | 0.01 | 1.51 | 0.04 | 1.36 | 0.01 | 1.03 | 0.03 | V67A |
| CL00054693 | 1.10 | 0.00 | 1.66 | 0.02 | 1.45 | 0.05 | 1.19 | 0.01 | P173S |
| CL00054713 | 1.20 | 0.02 | 1.41 | 0.01 | 1.45 | 0.04 | 1.16 | 0.03 | S119R |
| CL00054720 | 1.39 | 0.01 | 2.04 | 0.03 | 1.92 | 0.01 | 1.61 | 0.04 | G381A |
| CL00054730 | 1.19 | 0.00 | 1.39 | 0.05 | 1.24 | 0.02 | 1.13 | 0.06 | A403K |
| CL00054753 | 1.20 | 0.02 | 1.38 | 0.02 | 1.35 | 0.01 | 1.19 | 0.04 | T280N |
| CL00054764 | 1.18 | 0.01 | 1.47 | 0.03 | 1.44 | 0.08 | 1.23 | 0.02 | A403G |
| CL00054765 | 1.11 | 0.03 | 1.31 | 0.03 | 1.35 | 0.01 | 0.80 | 0.02 | T238S/P372T |
| CL00054786 | 1.23 | 0.02 | 1.66 | 0.09 | 1.47 | 0.05 | 1.14 | 0.02 | T364I |
| CL00054801 | 1.25 | 0.02 | 1.42 | 0.02 | 1.41 | 0.03 | 1.19 | 0.02 | G381L |
| CL00054858 | 1.18 | 0.01 | 0.73 | 0.01 | 1.22 | 0.03 | 1.18 | 0.02 | R339M |
| CL00054884 | 1.20 | 0.01 | 0.58 | 0.02 | 1.20 | 0.03 | 1.22 | 0.02 | P4T/T280P |
| CL00054885 | 1.19 | 0.03 | 1.61 | 0.05 | 1.36 | 0.02 | 1.18 | 0.02 | P173Y |
| CL00054892 | 1.23 | 0.01 | 1.36 | 0.06 | 1.39 | 0.02 | 0.95 | 0.02 | P371Y |
| CL00054895 | 1.07 | 0.02 | 1.50 | 0.02 | 1.22 | 0.02 | 1.07 | 0.02 | P173N |
| CL00054918 | 1.18 | 0.02 | 1.48 | 0.02 | 1.37 | 0.04 | 1.09 | 0.01 | T238G |
| CL00054933 | 1.24 | 0.00 | 0.05 | 0.01 | 0.51 | 0.07 | 1.31 | 0.06 | P4W |
| CL00054938 | 1.16 | 0.05 | 1.91 | 0.07 | 1.46 | 0.04 | 1.12 | 0.04 | T238N |
| CL00054974 | 1.07 | 0.01 | 0.98 | 0.02 | 1.02 | 0.03 | 1.08 | 0.03 | P4K/T280N |
| CL00054992 | 1.04 | 0.01 | 0.97 | 0.02 | 1.09 | 0.05 | 1.03 | 0.02 | T280P |
| CL00055010 | 1.18 | 0.01 | 1.40 | 0.02 | 1.39 | 0.03 | 1.15 | 0.05 | T364V/P371M |
| CL00055011 | 1.26 | 0.00 | 0.89 | 0.03 | 1.31 | 0.05 | 1.32 | 0.05 | P4E |
| CL00055013 | 1.22 | 0.03 | 1.10 | 0.00 | 1.25 | 0.01 | 1.32 | 0.02 | P4Q |
| CL00055014 | 1.19 | 0.00 | 0.24 | 0.02 | 0.75 | 0.07 | 1.25 | 0.02 | P4M/T280G |
| CL00055025 | 0.96 | 0.02 | 1.29 | 0.04 | 1.03 | 0.03 | 0.94 | 0.04 | T238K |
| CL00055027 | 1.13 | 0.00 | 1.35 | 0.02 | 1.27 | 0.03 | 1.18 | 0.01 | T238Y |
| CL00055036 | 1.13 | 0.01 | 1.45 | 0.00 | 1.37 | 0.05 | 1.17 | 0.02 | Q192L |
| CL00055086 | 1.11 | 0.01 | 1.52 | 0.06 | 1.27 | 0.01 | 0.89 | 0.03 | T364W |
| CL00055087 | 1.20 | 0.05 | 1.43 | 0.13 | 1.38 | 0.09 | 1.13 | 0.00 | A403W |
| CL00055097 | 1.04 | 0.02 | 1.37 | 0.03 | 1.08 | 0.01 | 0.97 | 0.02 | E5K |
| CL00055100 | 1.14 | 0.03 | 1.37 | 0.03 | 1.29 | 0.04 | 1.08 | 0.10 | T238P |
| CL00055105 | 1.21 | 0.01 | 1.43 | 0.03 | 1.43 | 0.03 | 1.30 | 0.04 | A403L |
| CL00055111 | 1.11 | 0.02 | 1.15 | 0.02 | 1.22 | 0.02 | 1.06 | 0.02 | P371W |
| CL00055131 | 1.26 | 0.04 | 0.22 | 0.04 | 0.81 | 0.05 | 1.40 | 0.04 | P4L |
| CL00055144 | 1.04 | 0.03 | 1.49 | 0.02 | 1.23 | 0.02 | 1.05 | 0.04 | P173T |
| CL00055148 | 1.10 | 0.02 | 0.54 | 0.01 | 0.95 | 0.03 | 1.13 | 0.03 | G381C |
| CL00055182 | 1.08 | 0.02 | 1.40 | 0.07 | 1.21 | 0.06 | 1.06 | 0.03 | D35Y/T238G |
| CL00055201 | 1.30 | 0.00 | 1.53 | 0.04 | 1.47 | 0.01 | 1.46 | 0.03 | P4N |
| CL00055205 | 1.15 | 0.03 | 1.08 | 0.05 | 1.31 | 0.07 | 1.11 | 0.02 | L272S/A403Y |
| CL00055223 | 1.19 | 0.02 | 1.46 | 0.02 | 1.36 | 0.04 | 1.25 | 0.02 | Q192K |
| CL00055227 | 1.12 | 0.04 | 1.06 | 0.01 | 1.21 | 0.03 | 0.90 | 0.04 | P371V |
| CL00055228 | 1.13 | 0.02 | 1.28 | 0.07 | 1.26 | 0.04 | 1.04 | 0.01 | T238F |
| CL00055415 | 1.18 | 0.03 | 1.46 | 0.05 | 1.36 | 0.07 | | | S409R |
| CL00055480 | 1.21 | 0.01 | 1.31 | 0.01 | 1.31 | 0.01 | | | A193S |
| CL00055525 | 1.09 | 0.02 | 0.89 | 0.03 | 1.08 | 0.02 | | | S409W |
| CL00055562 | 1.31 | 0.02 | 2.09 | 0.04 | 1.56 | 0.02 | | | Q346P |
| CL00055565 | 1.09 | 0.01 | 1.16 | 0.02 | 1.17 | 0.03 | | | A193L |
| CL00055571 | 1.42 | 0.02 | 2.60 | 0.08 | 1.83 | 0.07 | | | Q346T |
| CL00055592 | 1.33 | 0.01 | 1.73 | 0.04 | 1.66 | 0.06 | | | S409H |

FIGURE 1C

| Colony Tracking Number | Total Activity Improvement | | Temp and/or BSA Tolerance Improvement | | | | pH Tolerance Improvement | | AA Mutations w.r.t. GSP (CL00085823) |
|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00055605 | 1.27 | 0.02 | 1.48 | 0.09 | 1.40 | 0.03 | | | S240A |
| CL00055625 | 1.19 | 0.01 | 1.36 | 0.01 | 1.36 | 0.05 | | | A193V |
| CL00055629 | 1.29 | 0.02 | 1.27 | 0.11 | 1.48 | 0.05 | | | S409L |
| CL00055635 | 1.28 | 0.01 | 1.63 | 0.01 | 1.49 | 0.02 | | | P281S |
| CL00055639 | 1.08 | 0.01 | 1.43 | 0.05 | 1.22 | 0.08 | | | S240K |
| CL00055746 | 0.99 | 0.03 | 0.89 | 0.02 | 1.10 | 0.05 | | | P281D |
| CL00055747 | 1.25 | 0.03 | 1.19 | 0.02 | 1.37 | 0.01 | | | A394I |
| CL00055805 | 1.23 | 0.03 | 1.34 | 0.07 | 1.38 | 0.05 | | | A193T/E384D |
| CL00055812 | 1.13 | 0.02 | 1.27 | 0.03 | 1.23 | 0.02 | | | P365W |
| CL00055813 | 1.00 | 0.01 | 1.32 | 0.02 | 1.10 | 0.03 | | | Q346K |
| CL00055846 | 1.44 | 0.01 | 2.57 | 0.02 | 1.89 | 0.03 | | | Q346S |
| CL00055852 | 1.39 | 0.01 | 1.73 | 0.02 | 1.62 | 0.04 | | | S409V |
| CL00055863 | 1.12 | 0.03 | 1.38 | 0.01 | 1.23 | 0.05 | | | S240G |
| CL00055864 | 1.04 | 0.05 | 1.16 | 0.05 | 1.11 | 0.02 | | | A394P |
| CL00055875 | 1.20 | 0.01 | 1.17 | 0.01 | 1.25 | 0.01 | | | A394L |
| CL00055893 | 1.04 | 0.01 | 1.29 | 0.05 | 1.21 | 0.03 | | | L58S/S409R |
| CL00055905 | 1.11 | 0.01 | 0.80 | 0.02 | 1.02 | 0.02 | | | Q398V |
| CL00055915 | 1.10 | 0.03 | 1.30 | 0.03 | 1.20 | 0.05 | | | S240R |
| CL00055932 | 1.18 | 0.03 | 1.14 | 0.03 | 1.21 | 0.06 | | | A394M |
| CL00055949 | 1.11 | 0.06 | 1.26 | 0.05 | 1.16 | 0.04 | | | A193I |
| CL00056011 | 1.30 | 0.02 | 1.64 | 0.05 | 1.48 | 0.03 | | | D362G |
| CL00056029 | 1.07 | 0.09 | 0.95 | 0.10 | 1.18 | 0.07 | | | A153Y/Q157P/E165D/P261L |
| CL00056067 | 1.23 | 0.02 | 1.46 | 0.03 | 1.36 | 0.02 | | | T292G |
| CL00056071 | 1.19 | 0.05 | 1.27 | 0.08 | 1.22 | 0.05 | | | E182F |
| CL00056072 | 1.24 | 0.04 | 1.54 | 0.06 | 1.38 | 0.03 | | | A202R |
| CL00056082 | 1.17 | 0.04 | 0.76 | 0.03 | 1.20 | 0.03 | | | N401A |
| CL00056085 | 1.49 | 0.02 | 2.05 | 0.04 | 1.83 | 0.05 | | | L410R |
| CL00056123 | 1.28 | 0.02 | 1.54 | 0.06 | 1.40 | 0.04 | | | E182A |
| CL00056126 | 1.19 | 0.03 | 1.01 | 0.04 | 1.26 | 0.04 | | | R65V |
| CL00056137 | 1.20 | 0.03 | 1.41 | 0.03 | 1.29 | 0.05 | | | D362S |
| CL00056138 | 1.08 | 0.06 | 1.36 | 0.06 | 1.11 | 0.06 | | | E165W |
| CL00056139 | 1.12 | 0.01 | 0.46 | 0.01 | 0.97 | 0.03 | | | N401L |
| CL00056159 | 1.04 | 0.05 | 1.03 | 0.03 | 1.08 | 0.07 | | | Q242L |
| CL00056180 | 1.25 | 0.02 | 1.32 | 0.03 | 1.35 | 0.02 | | | Q242E |
| CL00056203 | 1.20 | 0.03 | 1.49 | 0.07 | 1.36 | 0.04 | | | L410K |
| CL00056239 | 1.28 | 0.01 | 1.85 | 0.09 | 1.56 | 0.04 | | | L72S/L410F |
| CL00056247 | 1.17 | 0.02 | 1.28 | 0.02 | 1.31 | 0.01 | | | E165P |
| CL00056278 | 1.19 | 0.04 | 1.28 | 0.04 | 1.21 | 0.02 | | | D31I |
| CL00056284 | 1.19 | 0.01 | 1.19 | 0.03 | 1.29 | 0.05 | | | I110L |
| CL00056286 | 1.23 | 0.02 | 1.23 | 0.02 | 1.39 | 0.03 | | | T378A |
| CL00056314 | 1.00 | 0.04 | 1.15 | 0.06 | 1.15 | 0.05 | | | L366R |
| CL00056315 | 1.29 | 0.03 | 1.43 | 0.01 | 1.42 | 0.08 | | | A153N |
| CL00056317 | 1.29 | 0.03 | 1.42 | 0.04 | 1.45 | 0.05 | | | A153S |
| CL00056371 | 1.32 | 0.01 | 2.06 | 0.03 | 1.36 | 0.03 | | | E182S |
| CL00056385 | 1.27 | 0.01 | 1.49 | 0.03 | 1.38 | 0.05 | | | R65S |
| CL00056390 | 1.36 | 0.03 | 1.76 | 0.05 | 1.63 | 0.02 | | | R65G |
| CL00056416 | 1.29 | 0.01 | 0.34 | 0.02 | 0.29 | 0.01 | | | L410C |
| CL00056461 | 1.37 | 0.01 | 1.77 | 0.02 | 1.67 | 0.03 | | | L410A |
| CL00056481 | 1.14 | 0.01 | 1.38 | 0.06 | 1.20 | 0.02 | | | G395P |
| CL00056518 | 1.23 | 0.02 | 1.36 | 0.05 | 1.28 | 0.06 | | | L410I |
| CL00056559 | 1.39 | 0.04 | 1.70 | 0.04 | 1.72 | 0.05 | | | N401P |
| CL00056564 | 1.19 | 0.01 | 1.30 | 0.04 | 1.31 | 0.03 | | | L410E |
| CL00056605 | 1.15 | 0.00 | 1.84 | 0.03 | 1.30 | 0.01 | | | D31N |
| CL00056625 | 1.20 | 0.02 | 1.41 | 0.07 | 1.26 | 0.01 | | | D362N |
| CL00056633 | 1.05 | 0.02 | 1.58 | 0.05 | 1.11 | 0.02 | | | E182T |
| CL00056647 | 1.25 | 0.03 | 1.48 | 0.03 | 1.34 | 0.06 | | | L410G |
| CL00056658 | 1.27 | 0.03 | 1.03 | 0.01 | 1.33 | 0.04 | | | D362Y |

FIGURE 2A

| Colony Tracking Number | Total Activity Improvement | | Temp and/or BSA Tolerance Improvement | | | | pH Tolerance Improvement | | | | AA Mutations w.r.t. G5P (CL00060516) |
|---|---|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH3.0) | PF STD (pH3.0) | PF AVG (pH2.0) | PF STD (pH2.0) | |
| CL00060148 | 1.18 | 0.21 | 1.22 | 0.01 | 1.07 | 0.02 | 1.11 | 0.04 | 1.42 | 0.06 | A73P/A288R |
| CL00060150 | 1.34 | 0.26 | 1.14 | 0.01 | 1.09 | 0.02 | 1.13 | 0.02 | 1.52 | 0.12 | A288R |
| CL00060185 | 0.66 | 0.22 | 1.05 | 0.02 | 0.65 | 0.01 | 0.81 | 0.02 | 0.65 | 0.03 | Q62W/A288R |
| CL00060196 | 1.91 | 0.14 | 1.09 | 0.05 | 1.05 | 0.03 | 1.37 | 0.03 | 2.11 | 0.22 | Y61C/Q62W/A73P |
| CL00060210 | 1.37 | 0.08 | 1.22 | 0.01 | 1.12 | 0.01 | 1.14 | 0.03 | 1.22 | 0.18 | A73P |
| CL00060222 | 0.77 | 0.09 | 1.26 | 0.05 | 0.78 | 0.04 | 1.02 | 0.02 | 0.88 | 0.06 | Q62W |
| CL00060329 | 0.69 | 0.09 | 1.10 | 0.03 | 0.63 | 0.02 | 0.77 | 0.01 | 0.80 | 0.03 | Q62W/A73P/A288R |
| CL00060388 | 0.89 | 0.21 | 1.13 | 0.02 | 1.11 | 0.01 | 0.79 | 0.02 | 1.02 | 0.02 | K7N/D35R |
| CL00060419 | 0.95 | 0.27 | 1.41 | 0.02 | 1.16 | 0.04 | 0.75 | 0.03 | 0.88 | 0.03 | K7N/D35R/P173Y/T364I |
| CL00060424 | 0.73 | 0.14 | 1.24 | 0.05 | 0.96 | 0.14 | 0.74 | 0.02 | 0.79 | 0.03 | K7N/D35R/Q192K |
| CL00060428 | 0.90 | 0.18 | 1.29 | 0.03 | 1.10 | 0.03 | 0.43 | 0.03 | 0.79 | 0.07 | K7N/D35R/P173Y/T364W |
| CL00060430 | 0.94 | 0.22 | 1.62 | 0.03 | 1.35 | 0.02 | 0.96 | 0.06 | 1.15 | 0.15 | K7N/Q192L/T238A/T364W |
| CL00060439 | 1.06 | 0.18 | 1.51 | 0.01 | 1.26 | 0.03 | 1.01 | 0.03 | 1.05 | 0.04 | K7N/Q192K/T364W/T370K |
| CL00060451 | 1.61 | 0.12 | 1.88 | 0.03 | 1.49 | 0.03 | 1.37 | 0.04 | 1.51 | 0.18 | K7N/V67A/T238A/T364I |
| CL00060456 | 1.51 | 0.16 | 1.59 | 0.07 | 1.35 | 0.03 | 1.25 | 0.04 | 1.20 | 0.13 | K7N/Q192L/T364I |
| CL00060460 | 0.72 | 0.20 | 1.73 | 0.04 | 1.38 | 0.01 | 1.12 | 0.01 | 0.96 | 0.09 | K7N/V67A/Q192K/T364W |
| CL00060488 | 0.43 | 0.06 | 1.71 | 0.01 | 1.39 | 0.02 | 1.01 | 0.01 | 0.79 | 0.04 | K7N/T238G/T364W |
| CL00060493 | 1.46 | 0.12 | 1.63 | 0.02 | 1.42 | 0.02 | 1.28 | 0.04 | 1.21 | 0.22 | K7N/T238A |
| CL00060512 | 1.07 | 0.27 | 1.60 | 0.03 | 1.37 | 0.02 | 1.09 | 0.01 | 1.14 | 0.13 | K7N/P173Y/Q192K/A403G |
| CL00060516 (G5P) | 1.53 | 0.17 | 2.20 | 0.02 | 1.58 | 0.01 | 1.04 | 0.01 | 1.47 | 0.09 | K7N/D35R/V67A/T238G/T364I/G381A/A403G |
| CL00060520 | 1.73 | 0.09 | 1.93 | 0.01 | 1.53 | 0.03 | 1.39 | 0.04 | 1.39 | 0.06 | K7N/V67A/P173Y/T238A/T364I |
| CL00060537 | 1.34 | 0.05 | 1.52 | 0.04 | 1.29 | 0.01 | 1.21 | 0.05 | 1.12 | 0.06 | K7N/V67A/T364I |
| CL00060539 | 1.33 | 0.14 | 1.48 | 0.01 | 1.31 | 0.04 | 1.17 | 0.02 | 1.26 | 0.06 | K7N/P173Y |
| CL00060543 | 1.46 | 0.17 | 1.61 | 0.03 | 1.34 | 0.02 | 1.21 | 0.01 | 1.60 | 0.07 | K7N/P173Y/A403G |
| CL00060576 | 1.62 | 0.14 | 1.60 | 0.03 | 1.31 | 0.01 | 1.21 | 0.02 | 1.45 | 0.12 | K7N/V67A/Q192K |
| CL00060581 | 1.91 | 0.20 | 1.73 | 0.04 | 1.42 | 0.03 | 1.45 | 0.05 | 1.72 | 0.08 | K7N/V67A/G381L |
| CL00060587 | 1.35 | 0.29 | 1.35 | 0.03 | 1.24 | 0.01 | 1.19 | 0.02 | 1.28 | 0.06 | K7N |
| CL00060595 | 1.09 | 0.05 | 1.34 | 0.01 | 1.11 | 0.02 | 0.92 | 0.02 | 0.87 | 0.11 | K7N/P173Y/Q192K/T364I |
| CL00060597 | 1.19 | 0.21 | 1.38 | 0.05 | 1.18 | 0.03 | 1.10 | 0.04 | 1.28 | 0.05 | K7N/V67A/P173Y |
| CL00060598 | 1.89 | 0.27 | 1.77 | 0.02 | 1.42 | 0.01 | 1.46 | 0.04 | 1.61 | 0.10 | K7N/V67A |
| CL00060600 | 1.13 | 0.23 | 1.29 | 0.02 | 1.16 | 0.02 | 1.03 | 0.01 | 1.08 | 0.14 | K7N/T364I/G381L |
| CL00060602 | 1.14 | 0.07 | 1.43 | 0.05 | 1.26 | 0.04 | 1.09 | 0.04 | 1.28 | 0.06 | K7N/P173Y/G381L |
| CL00060607 | 1.19 | 0.22 | 1.37 | 0.04 | 1.27 | 0.02 | 1.08 | 0.02 | 1.14 | 0.12 | S146P |
| CL00060616 | 1.51 | 0.26 | 1.58 | 0.19 | 1.28 | 0.01 | 1.20 | 0.04 | 1.15 | 0.06 | V67A/T364I |
| CL00060772 | 1.47 | 0.10 | 1.85 | 0.03 | 1.36 | 0.02 | 1.30 | 0.03 | 1.20 | 0.26 | P173N/T364W |
| CL00060776 | 1.60 | 0.16 | 1.69 | 0.02 | 1.36 | 0.02 | 1.19 | 0.03 | 1.27 | 0.33 | V67A/T238G/G381A |
| CL00060786 | 1.32 | 0.12 | 1.47 | 0.02 | 1.27 | 0.01 | 1.23 | 0.02 | 1.42 | 0.22 | T238G |
| CL00060803 | 1.68 | 0.12 | 1.65 | 0.01 | 1.30 | 0.02 | 1.31 | 0.04 | 1.58 | 0.01 | P173S |
| CL00060805 | 1.97 | 0.28 | 2.05 | 0.01 | 1.50 | 0.01 | 1.38 | 0.02 | 1.78 | 0.08 | T238N/T364W |
| CL00060831 | 1.10 | 0.02 | 1.32 | 0.05 | 1.15 | 0.03 | 0.91 | 0.03 | 1.01 | 0.21 | T238A/T364W |
| CL00060837 | 1.53 | 0.05 | 1.52 | 0.01 | 1.28 | 0.01 | 1.35 | 0.03 | 1.48 | 0.16 | V67A |
| CL00060860 | 1.07 | 0.12 | 1.52 | 0.02 | 1.25 | 0.02 | 1.16 | 0.04 | 1.23 | 0.02 | T364W/G381A |
| CL00060966 | 1.09 | 0.03 | 1.76 | 0.04 | 1.31 | 0.02 | 1.08 | 0.02 | 1.20 | 0.17 | V67A/T238A/T364W |
| CL00061015 | 0.88 | 0.12 | 1.41 | 0.02 | 1.17 | 0.01 | 0.97 | 0.03 | 0.99 | 0.02 | V67A/T364W |
| CL00061026 | 0.91 | 0.18 | 1.26 | 0.02 | 1.10 | 0.01 | 0.86 | 0.03 | 0.98 | 0.13 | T364W |
| CL00061030 | 1.08 | 0.07 | 1.58 | 0.05 | 1.25 | 0.03 | 1.03 | 0.04 | 1.25 | 0.15 | T238A/T364W/G381A |
| CL00061037 | 0.78 | 0.24 | 1.22 | 0.01 | 1.04 | 0.01 | 1.05 | 0.01 | 1.05 | 0.02 | T364I |
| CL00061038 | 0.95 | 0.09 | 1.76 | 0.03 | 1.27 | 0.02 | 1.10 | 0.01 | 1.23 | 0.10 | V67A/P173N/T238A/T364W |
| CL00061055 | 1.39 | 0.22 | 1.57 | 0.17 | 1.24 | 0.05 | 1.14 | 0.06 | 1.42 | 0.17 | P173N/T238N |
| CL00061110 | 0.94 | 0.15 | 1.37 | 0.02 | 1.10 | 0.01 | 0.97 | 0.02 | 1.11 | 0.08 | P173T |
| CL00061134 | 1.51 | 0.12 | 1.72 | 0.01 | 1.35 | 0.02 | 1.19 | 0.03 | 1.46 | 0.14 | V67A/T238A |
| CL00061158 | 1.25 | 0.07 | 1.56 | 0.01 | 1.23 | 0.01 | 1.19 | 0.01 | 1.56 | 0.09 | P173T/G381A |
| CL00061221 | 1.25 | 0.08 | 1.43 | 0.03 | 1.25 | 0.03 | 1.21 | 0.03 | 1.40 | 0.14 | S119R/L279F |
| CL00061257 | 1.16 | 0.19 | 0.98 | 0.05 | 1.13 | 0.01 | 1.19 | 0.01 | 1.34 | 0.12 | N244I/T280N |
| CL00061264 | 1.31 | 0.24 | 1.67 | 0.06 | 1.37 | 0.01 | 0.98 | 0.02 | 1.67 | 0.13 | T238P/T280N/P371Y/A403W |
| CL00061290 | 1.14 | 0.08 | 1.17 | 0.03 | 1.11 | 0.01 | 1.02 | 0.02 | 1.13 | 0.07 | S119R/A403K |
| CL00061324 | 2.04 | 0.04 | 1.86 | 0.05 | 1.46 | 0.02 | 1.44 | 0.05 | 2.14 | 0.14 | T280N/P371Y/A403W |
| CL00061335 | 0.97 | 0.22 | 1.34 | 0.04 | 1.17 | 0.03 | 0.89 | 0.03 | 1.12 | 0.02 | S119R/P371Y/A403K |
| CL00061370 | 0.95 | 0.17 | 1.29 | 0.04 | 1.13 | 0.02 | 1.02 | 0.01 | 1.19 | 0.05 | T280N/A403K |
| CL00061376 | 1.17 | 0.14 | 1.29 | 0.01 | 1.14 | 0.02 | 1.08 | 0.05 | 1.37 | 0.07 | T280N |
| CL00061404 | 0.76 | 0.18 | 1.06 | 0.03 | 1.05 | 0.03 | 0.82 | 0.03 | 1.16 | 0.05 | T280N/P371Y |
| CL00061427 | 1.15 | 0.28 | 1.47 | 0.02 | 1.25 | 0.03 | 1.09 | 0.06 | 1.44 | 0.12 | T238Y |
| CL00061431 | 1.44 | 0.06 | 1.66 | 0.02 | 1.33 | 0.03 | 1.07 | 0.03 | 1.53 | 0.05 | T238P/P371Y |
| CL00061446 | 1.42 | 0.19 | 1.43 | 0.06 | 1.28 | 0.05 | 0.96 | 0.05 | 1.44 | 0.15 | P371Y/A403W |

FIGURE 2B

| Colony Tracking Number | Total Activity Improvement | | Temp and/or BSA Tolerance Improvement | | | | pH Tolerance Improvement | | | | AA Mutations w.r.t. GSP (SEQ ID NO:2) |
|---|---|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH3.0) | PF STD (pH3.0) | PF AVG (pH2.0) | PF STD (pH2.0) | |
| CL00061459 | 1.13 | 0.13 | 1.19 | 0.01 | 1.14 | 0.02 | 1.09 | 0.04 | 1.12 | 0.08 | S119R/T280N |
| CL00061472 | 1.26 | 0.15 | 1.42 | 0.00 | 1.25 | 0.01 | 1.23 | 0.03 | 1.51 | 0.05 | T238P |
| CL00061483 | 1.05 | 0.02 | 1.31 | 0.02 | 1.23 | 0.02 | 1.06 | 0.04 | 1.13 | 0.11 | S119R/P371Y/A403L |
| CL00061536 | 1.03 | 0.14 | 1.24 | 0.02 | 1.16 | 0.03 | 0.96 | 0.02 | 1.15 | 0.10 | P371Y/A403L |
| CL00061559 | 0.55 | 0.09 | 0.72 | 0.01 | 0.75 | 0.02 | 0.60 | 0.02 | 0.70 | 0.06 | S119R |
| CL00061561 | 1.16 | 0.08 | 1.30 | 0.01 | 1.18 | 0.00 | 1.09 | 0.03 | 1.37 | 0.09 | T238Y/A403W |
| CL00061579 | 0.97 | 0.09 | 1.28 | 0.02 | 1.17 | 0.00 | 0.99 | 0.05 | 0.98 | 0.06 | S119R/T280N/P371Y |
| CL00061603 | 1.10 | 0.10 | 1.22 | 0.03 | 1.18 | 0.02 | 1.09 | 0.01 | 1.18 | 0.06 | A403W |
| CL00061669 | 3.79 | 0.11 | 3.14 | 0.18 | 1.37 | 0.01 | 1.53 | 0.02 | 2.39 | 0.13 | R65G/L410R |
| CL00061673 | 4.32 | 0.25 | 4.06 | 0.09 | 1.39 | 0.03 | 1.78 | 0.05 | 2.72 | 0.03 | Q346T/S409V/L410A |
| CL00061700 | 4.01 | 0.49 | 3.34 | 0.03 | 1.36 | 0.01 | 1.55 | 0.03 | 2.10 | 0.08 | E182T/D362G |
| CL00061776 | 1.91 | 0.11 | 2.15 | 0.10 | 1.26 | 0.02 | 1.32 | 0.01 | 1.72 | 0.04 | E182S/S187T/P281S |
| CL00061786 | 2.58 | 0.61 | 1.99 | 0.23 | 1.27 | 0.00 | 1.37 | 0.06 | 1.87 | 0.15 | D362G/S409V |
| CL00061792 | 1.69 | 0.03 | 2.15 | 0.22 | 1.27 | 0.02 | 1.31 | 0.02 | 1.73 | 0.06 | P281S/S409H |
| CL00061833 | 4.06 | 0.22 | 3.68 | 0.18 | 1.37 | 0.01 | 1.59 | 0.02 | 2.10 | 0.23 | E182T/A202R |
| CL00061836 | 3.35 | 0.57 | 3.64 | 0.04 | 1.36 | 0.02 | 1.47 | 0.01 | 2.31 | 0.09 | R65G/S187T/Q346T |
| CL00061838 | 2.96 | 0.30 | 3.38 | 0.09 | 1.38 | 0.03 | 1.63 | 0.04 | 2.27 | 0.03 | P281S/Q346T |
| CL00061848 | 1.87 | 0.54 | 2.08 | 0.21 | 1.26 | 0.02 | 1.31 | 0.01 | 1.75 | 0.01 | E182S/P281S |
| CL00061857 | 2.12 | 0.06 | 1.77 | 0.04 | 1.30 | 0.02 | 1.36 | 0.02 | 1.71 | 0.06 | P281S |
| CL00061865 | 2.71 | 0.19 | 3.12 | 0.16 | 1.34 | 0.02 | 1.47 | 0.04 | 1.91 | 0.06 | S187T/Q346T/L410A |
| CL00061954 | 2.16 | 0.59 | 1.67 | 0.26 | 1.25 | 0.01 | 1.16 | 0.01 | 1.63 | 0.13 | R65G/P281S/S409V |
| CL00061969 | 2.65 | 0.19 | 2.55 | 0.31 | 1.28 | 0.01 | 1.46 | 0.07 | 1.71 | 0.16 | D31N |
| CL00061970 | 2.53 | 0.17 | 2.63 | 0.08 | 1.30 | 0.01 | 1.53 | 0.02 | 1.97 | 0.05 | D31N/D362G/L410A |
| CL00061975 | 5.72 | 0.63 | 5.12 | 0.11 | 1.47 | 0.02 | 1.98 | 0.04 | 2.88 | 0.15 | Q346T/L410A |
| CL00062013 | 1.95 | 0.43 | 2.04 | 0.10 | 1.24 | 0.02 | 1.27 | 0.04 | 1.69 | 0.05 | P281S/Q346S |
| CL00062023 | 1.98 | 0.47 | 2.96 | 0.21 | 1.32 | 0.02 | 1.60 | 0.03 | 2.11 | 0.02 | D31N/P281S/Q346T |
| CL00062026 | 1.58 | 0.70 | 1.63 | 0.34 | 1.15 | 0.01 | 1.22 | 0.07 | 1.45 | 0.09 | S409H/L410A |
| CL00062036 | 0.94 | 0.18 | 1.83 | 0.26 | 1.16 | 0.02 | 1.21 | 0.03 | 1.39 | 0.10 | D31N/Q346P |
| CL00062051 | 3.23 | 0.34 | 2.56 | 0.26 | 1.31 | 0.01 | 1.44 | 0.04 | 1.81 | 0.07 | E182S/S187T |
| CL00062091 | 1.04 | 0.07 | 0.98 | 0.04 | 1.15 | 0.01 | 0.94 | 0.05 | 1.08 | 0.12 | R65G/P281S |
| CL00062195 | 0.91 | 0.11 | 1.34 | 0.03 | 1.12 | 0.02 | 0.98 | 0.01 | 1.05 | 0.04 | A202R/P281S/D362G/L410R |
| CL00062213 | 3.84 | 0.11 | 4.09 | 0.09 | 1.42 | 0.00 | 1.74 | 0.01 | 2.40 | 0.05 | D31N/R65G/S187T/S409V/L410A |
| CL00062217 | 2.27 | 0.21 | 3.41 | 0.12 | 1.35 | 0.03 | 1.48 | 0.04 | 2.16 | 0.07 | D31N/P281S/Q346S/D362G/K363R/S409H |
| CL00062271 | 2.32 | 0.30 | 2.78 | 0.20 | 1.33 | 0.03 | 1.46 | 0.08 | 1.83 | 0.10 | Q346S |
| CL00062284 | 2.90 | 0.64 | 2.87 | 0.20 | 1.29 | 0.02 | 1.47 | 0.03 | 1.96 | 0.14 | E182S/Q346S |
| CL00062336 | 1.69 | 0.30 | 2.00 | 0.15 | 1.36 | 0.01 | 1.25 | 0.04 | 1.65 | 0.15 | N401P |
| CL00062431 | 1.18 | 0.21 | 1.55 | 0.09 | 1.32 | 0.02 | 1.14 | 0.01 | 1.38 | 0.08 | P4N/N401P |
| CL00062437 | 1.24 | 0.31 | 1.39 | 0.11 | 1.25 | 0.05 | 1.10 | 0.03 | 1.24 | 0.03 | T292G/T378A |
| CL00062439 | 1.23 | 0.04 | 1.38 | 0.20 | 1.26 | 0.02 | 0.78 | 0.03 | 1.10 | 0.16 | D362G/N401P |
| CL00062482 | 1.11 | 0.15 | 1.14 | 0.09 | 1.06 | 0.01 | 0.97 | 0.05 | 0.98 | 0.02 | E182A/T292G |
| CL00062505 | 1.22 | 0.33 | 1.29 | 0.27 | 1.16 | 0.01 | 1.10 | 0.02 | 1.16 | 0.10 | P4N/T292G |
| CL00062531 | 1.59 | 0.20 | 1.65 | 0.03 | 1.26 | 0.01 | 1.21 | 0.05 | 1.43 | 0.09 | P4N/D362G/G395P |
| CL00062541 | 1.17 | 0.32 | 1.41 | 0.07 | 1.25 | 0.02 | 1.21 | 0.02 | 1.43 | 0.07 | G395P |
| CL00062628 | 1.23 | 0.09 | 1.27 | 0.04 | 1.31 | 0.01 | 1.22 | 0.02 | 1.54 | 0.06 | P4N/G395P |
| CL00062712 | 1.90 | 0.30 | 1.81 | 0.17 | 1.27 | 0.02 | 1.47 | 0.01 | 1.73 | 0.11 | P4N |
| CL00062781 | 1.67 | 0.14 | 1.76 | 0.10 | 1.33 | 0.01 | 1.53 | 0.02 | 1.94 | 0.10 | P4N/I110L/G395P |
| CL00062795 | 1.74 | 0.17 | 1.54 | 0.14 | 1.22 | 0.00 | 1.38 | 0.05 | 1.62 | 0.10 | P4N/D31I |
| CL00062883 | 1.31 | 0.18 | 1.13 | 0.03 | 1.15 | 0.03 | 1.23 | 0.02 | 1.35 | 0.09 | P4N/D31I/E182A |
| CL00062886 | 1.23 | 0.07 | 1.11 | 0.12 | 1.12 | 0.02 | 1.20 | 0.01 | 1.55 | 0.13 | D31I |
| CL00062959 | 1.77 | 0.35 | 1.78 | 0.23 | 1.25 | 0.02 | 1.44 | 0.05 | 1.54 | 0.07 | P4N/S240G |
| CL00062982 | 1.67 | 0.08 | 1.40 | 0.06 | 1.23 | 0.02 | 1.34 | 0.03 | 1.41 | 0.03 | P4N/I110L/S240R |
| CL00062985 | 0.95 | 0.15 | 1.23 | 0.13 | 1.18 | 0.01 | 0.90 | 0.06 | 1.12 | 0.30 | D31I/S240A/N401P |
| CL00063010 | 1.84 | 0.28 | 1.60 | 0.15 | 1.25 | 0.00 | 1.37 | 0.04 | 1.41 | 0.03 | T378A |
| CL00063017 | 1.39 | 0.13 | 1.33 | 0.14 | 1.17 | 0.01 | 1.23 | 0.04 | 1.58 | 0.18 | D31I/S240A/D362G |
| CL00063061 | 1.05 | 0.13 | 0.34 | 0.04 | 0.76 | 0.01 | 1.09 | 0.05 | 1.18 | 0.19 | G76C/A394M |
| CL00063099 | 1.52 | 0.16 | 1.62 | 0.07 | 1.30 | 0.02 | 1.03 | 0.03 | 1.41 | 0.16 | R65G/E165P/Q242E |
| CL00063104 | 1.62 | 0.22 | 1.80 | 0.09 | 1.29 | 0.01 | 1.16 | 0.05 | 1.46 | 0.21 | R65S/E165P/D362S |
| CL00063147 | 1.55 | 0.18 | 1.76 | 0.10 | 1.24 | 0.02 | 1.13 | 0.03 | 1.44 | 0.05 | R65S/A193I/Q346P |
| CL00063162 | 1.60 | 0.21 | 1.54 | 0.15 | 1.21 | 0.01 | 1.28 | 0.02 | 1.43 | 0.06 | Q242E/Q346P |
| CL00063173 | 1.49 | 0.16 | 1.45 | 0.10 | 1.24 | 0.01 | 0.68 | 0.01 | 1.22 | 0.20 | R65G/E165P/D362S |
| CL00063185 | 1.78 | 0.09 | 1.78 | 0.02 | 1.28 | 0.02 | 1.16 | 0.02 | 1.32 | 0.16 | R65P/E165P |
| CL00063209 | 1.60 | 0.10 | 1.83 | 0.09 | 1.29 | 0.03 | 1.25 | 0.01 | 1.57 | 0.02 | R65S/E165P |
| CL00063219 | 1.64 | 0.03 | 1.52 | 0.09 | 1.29 | 0.03 | 1.23 | 0.01 | 1.73 | 0.06 | R65S/E165P/Q242E/A394M |
| CL00063234 | 1.78 | 0.20 | 2.00 | 0.10 | 1.31 | 0.02 | 0.99 | 0.03 | 1.74 | 0.12 | R65G/E165P |
| CL00063245 | 1.23 | 0.07 | 0.29 | 0.06 | 0.38 | 0.01 | 1.11 | 0.02 | 1.31 | 0.06 | R65C/A193S/A394P |
| CL00063261 | 0.92 | 0.07 | 1.33 | 0.04 | 1.13 | 0.02 | 0.99 | 0.03 | 1.16 | 0.02 | R65G/Q346P |
| CL00063267 | 1.61 | 0.21 | 1.66 | 0.10 | 1.28 | 0.01 | 1.25 | 0.02 | 1.52 | 0.12 | R65S/E165P/Q242E/D362S |
| CL00063289 | 1.48 | 0.03 | 1.42 | 0.12 | 1.26 | 0.01 | 1.28 | 0.00 | 1.41 | 0.17 | R65G |
| CL00063290 | 1.55 | 0.04 | 1.46 | 0.01 | 1.23 | 0.01 | 1.32 | 0.05 | 1.69 | 0.06 | R65S |

FIGURE 2C

| Colony Tracking Number | Total Activity Improvement | | Temp and/or BSA Tolerance Improvement | | | | pH Tolerance Improvement | | | | AA Mutations w.r.t. GAP (CL00048541) |
|---|---|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH3.0) | PF STD (pH3.0) | PF AVG (pH2.0) | PF STD (pH2.0) | |
| CL00063304 | 1.95 | 0.13 | 1.99 | 0.02 | 1.30 | 0.01 | 1.02 | 0.01 | 1.84 | 0.24 | R65S/E165P/D362S/A394P |
| CL00063378 | 1.61 | 0.20 | 1.78 | 0.11 | 1.22 | 0.02 | 1.33 | 0.03 | 1.71 | 0.02 | Q346P |
| CL00063417 | 1.20 | 0.13 | 1.09 | 0.07 | 1.01 | 0.02 | 0.97 | 0.01 | 1.17 | 0.05 | Q242E |
| CL00063465 | 1.76 | 0.23 | 2.32 | 0.31 | 1.32 | 0.01 | 1.20 | 0.00 | 2.16 | 0.18 | R65S/E165P/S240K |
| CL00063548 | 1.72 | 0.15 | 2.32 | 0.09 | 1.32 | 0.00 | 1.18 | 0.01 | 1.75 | 0.22 | R65S/E165P/G381R |
| CL00063551 | 1.01 | 0.13 | 1.05 | 0.15 | 1.18 | 0.02 | 1.15 | 0.03 | 1.36 | 0.03 | R65S/A394I |
| CL00063556 | 0.97 | 0.19 | 1.49 | 0.05 | 1.16 | 0.03 | 0.80 | 0.04 | 1.22 | 0.10 | E165P/S240K/D362S |
| CL00063560 | 1.48 | 0.13 | 1.76 | 0.06 | 1.22 | 0.02 | 1.16 | 0.04 | 1.58 | 0.17 | R65G/Q242E |
| CL00063573 | 1.46 | 0.28 | 1.50 | 0.20 | 1.24 | 0.01 | 1.36 | 0.04 | 1.82 | 0.09 | Q242E/A394P |
| CL00063582 | 1.09 | 0.08 | 1.41 | 0.08 | 1.22 | 0.01 | 1.11 | 0.02 | 1.44 | 0.04 | R65G/D362S |
| CL00063597 | 0.98 | 0.04 | 1.37 | 0.07 | 1.10 | 0.03 | 0.57 | 0.04 | 1.14 | 0.19 | R65S/E165P/Q346P |
| CL00063647 | 1.60 | 0.19 | 1.72 | 0.16 | 1.18 | 0.01 | 1.07 | 0.02 | 1.33 | 0.07 | R65G/S240K/Q242E |
| CL00063658 | 0.79 | 0.07 | 0.85 | 0.03 | 1.02 | 0.01 | 0.97 | 0.04 | 1.05 | 0.15 | A394L |
| CL00063721 | 1.26 | 0.03 | 1.73 | 0.04 | 1.50 | 0.01 | 1.35 | 0.06 | 1.83 | 0.02 | E5K/A153S/P281S/S409L |
| CL00063728 | 1.25 | 0.02 | 1.80 | 0.06 | 1.53 | 0.02 | 1.42 | 0.05 | 1.97 | 0.18 | E5K/P281S/S409H |
| CL00063731 | 1.21 | 0.03 | 1.44 | 0.02 | 1.38 | 0.03 | 1.00 | 0.01 | 1.52 | 0.11 | S151F/A153S/P281S/L410G |
| CL00063739 | 1.22 | 0.02 | 1.43 | 0.06 | 1.31 | 0.03 | 1.27 | 0.03 | 1.59 | 0.14 | A153N/P281S |
| CL00063752 | 1.28 | 0.01 | 1.75 | 0.02 | 1.41 | 0.04 | 1.45 | 0.01 | 1.82 | 0.09 | E5K/P281S |
| CL00063753 | 1.16 | 0.04 | 1.55 | 0.05 | 1.28 | 0.03 | 1.28 | 0.06 | 1.65 | 0.14 | E5K |
| CL00063795 | 1.02 | 0.04 | 1.23 | 0.10 | 1.16 | 0.04 | 1.10 | 0.05 | 1.20 | 0.02 | P281S/L410R |
| CL00063923 | 1.30 | 0.01 | 1.65 | 0.03 | 1.45 | 0.01 | 1.29 | 0.02 | 1.77 | 0.04 | P281S/Q346K/S409L/L410G |
| CL00063981 | 1.18 | 0.04 | 1.32 | 0.06 | 1.15 | 0.03 | 0.98 | 0.04 | 1.40 | 0.09 | E5K/V111/Q346K |
| CL00064007 | 1.08 | 0.01 | 1.18 | 0.02 | 1.14 | 0.01 | 1.04 | 0.06 | 1.18 | 0.07 | V111/P281S |
| CL00064037 | 1.06 | 0.01 | 1.16 | 0.01 | 1.08 | 0.02 | 1.09 | 0.07 | 1.27 | 0.10 | A153S |
| CL00064068 | 1.37 | 0.07 | 1.95 | 0.08 | 1.52 | 0.04 | 1.54 | 0.03 | 2.00 | 0.18 | E5K/P365W |
| CL00064080 | 1.26 | 0.01 | 1.70 | 0.02 | 1.40 | 0.03 | 1.38 | 0.01 | 1.51 | 0.09 | E5K/P281S/L410G |
| CL00064092 | 1.26 | 0.04 | 1.70 | 0.03 | 1.38 | 0.05 | 1.26 | 0.05 | 1.86 | 0.16 | E5K/T111I/P281S/P365W |
| CL00064109 | 1.19 | 0.01 | 1.62 | 0.03 | 1.32 | 0.01 | 1.35 | 0.02 | 1.73 | 0.10 | E5K/A153N/P281S |
| CL00064110 | 1.23 | 0.03 | 1.65 | 0.04 | 1.33 | 0.04 | 1.15 | 0.02 | 1.58 | 0.11 | E5K/A153N/P281S/Q346K |
| CL00064111 | 1.21 | 0.01 | 1.39 | 0.03 | 1.27 | 0.01 | 1.21 | 0.07 | 1.42 | 0.02 | Q346K |
| CL00064136 | 1.28 | 0.03 | 1.55 | 0.03 | 1.50 | 0.01 | 1.64 | 0.03 | 1.74 | 0.09 | A153N/S409L |
| CL00064137 | 1.25 | 0.02 | 1.83 | 0.01 | 1.47 | 0.02 | 1.57 | 0.04 | 1.80 | 0.11 | E5K/A153N/P281S/L410G |
| CL00064142 | 1.26 | 0.04 | 1.77 | 0.03 | 1.45 | 0.04 | 1.22 | 0.03 | 1.44 | 0.21 | E5K/A153N/P281S/P365W |
| CL00064168 | 1.14 | 0.04 | 0.80 | 0.06 | 1.14 | 0.04 | 1.18 | 0.03 | 1.27 | 0.15 | K7E/S409H |
| CL00064217 | 1.20 | 0.02 | 1.62 | 0.01 | 1.37 | 0.04 | 1.20 | 0.02 | 1.33 | 0.04 | E5K/A153N/P281S/S409R |
| CL00064240 | 1.26 | 0.03 | 1.62 | 0.02 | 1.33 | 0.03 | 1.21 | 0.04 | 1.55 | 0.22 | E5K/P281S/L410I |
| CL00064326 | 1.36 | 0.04 | 1.85 | 0.03 | 1.55 | 0.02 | 1.48 | 0.01 | 1.79 | 0.11 | E5K/A153S/P281S |

FIGURE 3

| Colony Tracking Number | Total Activity Improvement | | Temp and/or BSA Tolerance Improvement | | | | pH Tolerance Improvement | | | | AA Mutations w.r.t. OSP (CL00068516) |
|---|---|---|---|---|---|---|---|---|---|---|---|
| | PF AVG (pH5.5) | PF STD (pH5.5) | PF AVG (75°C, pH5.5) | PF STD (75°C, pH5.5) | PF AVG (90°C, pH5.5) | PF STD (90°C, pH5.5) | PF AVG (pH3.0) | PF STD (pH3.0) | PF AVG (pH2.0) | PF STD (pH2.0) | |
| CL00068891 | 1.62 | 0.07 | 1.52 | 0.07 | 1.38 | 0.09 | 1.83 | 0.05 | 1.89 | 0.06 | P121A |
| CL00068943 | 1.02 | 0.21 | 1.06 | 0.07 | 1.12 | 0.06 | 0.72 | 0.31 | 0.40 | 0.29 | D136G |
| CL00068951 | 1.26 | 0.10 | 1.16 | 0.04 | 1.12 | 0.01 | 1.31 | 0.20 | 1.30 | 0.20 | T130G |
| CL00068968 | 1.30 | 0.07 | 1.17 | 0.06 | 1.27 | 0.07 | 1.33 | 0.05 | 1.44 | 0.10 | Q174E |
| CL00069040 | 1.21 | 0.30 | 1.09 | 0.10 | 1.10 | 0.10 | 1.14 | 0.50 | 1.16 | 0.67 | Q174A |
| CL00069049 | 0.95 | 0.34 | 1.00 | 0.13 | 1.06 | 0.11 | 0.81 | 0.58 | 0.69 | 0.74 | Q27D |
| CL00069076 | 1.02 | 0.12 | 1.06 | 0.05 | 0.98 | 0.07 | 1.04 | 0.30 | 0.91 | 0.30 | Q134A |
| CL00069279 | 1.49 | 0.04 | 1.38 | 0.02 | 1.35 | 0.08 | 1.55 | 0.05 | 1.65 | 0.08 | T161D |
| CL00069284 | 1.27 | 0.08 | 1.25 | 0.05 | 1.28 | 0.03 | 1.35 | 0.13 | 1.32 | 0.19 | T130R |
| CL00069548 | 0.97 | 0.08 | 1.12 | 0.05 | 1.03 | 0.04 | 0.93 | 0.11 | 0.89 | 0.18 | Q27P |
| CL00069554 | 1.34 | 0.20 | 1.37 | 0.13 | 1.33 | 0.10 | 1.30 | 0.27 | 1.10 | 0.28 | E53N |
| CL00069605 | 1.53 | 0.01 | 1.53 | 0.01 | 1.37 | 0.05 | 1.28 | 0.03 | 1.04 | 0.02 | D136F |
| CL00069748 | 1.07 | 0.12 | 1.01 | 0.05 | 0.99 | 0.06 | 0.87 | 0.20 | 0.47 | 0.18 | S151R |
| CL00069783 | 1.04 | 0.16 | 1.06 | 0.05 | 1.15 | 0.05 | 0.86 | 0.27 | 0.79 | 0.37 | Q27V |
| CL00069871 | 1.29 | 0.03 | 1.22 | 0.04 | 1.28 | 0.02 | 1.21 | 0.07 | 1.20 | 0.18 | Q134T |
| CL00069966 | 1.24 | 0.28 | 1.15 | 0.13 | 1.15 | 0.13 | 1.24 | 0.46 | 1.20 | 0.55 | E53D |
| CL00069982 | 1.52 | 0.06 | 1.41 | 0.02 | 1.35 | 0.03 | 1.49 | 0.06 | 1.58 | 0.08 | D136S |
| CL00070425 | 1.13 | 0.07 | 1.15 | 0.06 | 1.13 | 0.06 | 1.21 | 0.06 | 1.06 | 0.02 | T295N |
| CL00070459 | 1.24 | 0.02 | 1.21 | 0.01 | 1.22 | 0.02 | 1.17 | 0.04 | 1.05 | 0.03 | S189L |
| CL00070629 | 1.16 | 0.05 | 1.20 | 0.07 | 1.15 | 0.03 | 1.15 | 0.04 | 1.08 | 0.05 | S189T |
| CL00070809 | 1.03 | 0.06 | 1.04 | 0.06 | 1.03 | 0.11 | 1.17 | 0.07 | 0.85 | 0.06 | T191S |
| CL00070893 | 1.08 | 0.08 | 1.11 | 0.09 | 1.12 | 0.10 | 1.16 | 0.11 | 0.96 | 0.05 | P230S |
| CL00070949 | 1.13 | 0.03 | 1.28 | 0.05 | 1.13 | 0.04 | 1.06 | 0.06 | 1.00 | 0.03 | S189N |
| CL00071011 | 1.43 | 0.03 | 1.37 | 0.05 | 1.23 | 0.01 | 1.26 | 0.01 | 1.08 | 0.01 | E197S |
| CL00071024 | 1.23 | 0.04 | 1.11 | 0.04 | 1.04 | 0.02 | 1.16 | 0.05 | 0.89 | 0.03 | L194I |
| CL00071077 | 1.41 | 0.03 | 1.27 | 0.02 | 1.28 | 0.02 | 1.29 | 0.03 | 1.37 | 0.03 | P4N/R35D/T378A |
| CL00071109 | 1.26 | 0.05 | 1.07 | 0.02 | 1.16 | 0.02 | 1.40 | 0.10 | 1.21 | 0.15 | S409V |
| CL00071134 | 1.48 | 0.14 | 1.33 | 0.14 | 1.35 | 0.09 | 1.18 | 0.11 | 0.75 | 0.14 | T378A |
| CL00071148 | 1.54 | 0.14 | 1.47 | 0.08 | 1.45 | 0.07 | 1.44 | 0.18 | 1.04 | 0.11 | P4N |
| CL00071188 | 1.09 | 0.06 | 0.84 | 0.05 | 1.00 | 0.05 | 1.14 | 0.13 | 1.34 | 0.20 | R35D/T378A |
| CL00071206 | 1.12 | 0.12 | 0.83 | 0.04 | 0.95 | 0.06 | 1.06 | 0.17 | 1.30 | 0.27 | R35D |
| CL00071272 | 1.43 | 0.24 | 1.22 | 0.10 | 1.31 | 0.12 | 1.68 | 0.45 | 1.83 | 0.65 | P4N/R35D |
| CL00071374 | 1.03 | 0.06 | 0.89 | 0.06 | 1.02 | 0.06 | 1.00 | 0.06 | 0.99 | 0.07 | R35D/T111I |
| CL00071381 | 1.34 | 0.08 | 1.28 | 0.08 | 1.20 | 0.04 | 1.53 | 0.18 | 1.33 | 0.22 | P4N/T378A |
| CL00071477 | 1.20 | 0.03 | 1.32 | 0.02 | 1.08 | 0.06 | 1.30 | 0.03 | 1.01 | 0.02 | P173S/E182S |
| CL00071480 | 1.73 | 0.05 | 1.88 | 0.02 | 1.55 | 0.15 | 1.82 | 0.09 | 1.61 | 0.05 | P173S/E182T/Q346T |
| CL00071500 | 1.63 | 0.11 | 1.90 | 0.06 | 1.38 | 0.03 | 1.70 | 0.14 | 1.54 | 0.08 | P173S/E182T |
| CL00071567 | 1.05 | 0.08 | 1.34 | 0.03 | 1.17 | 0.04 | 1.05 | 0.09 | 1.07 | 0.10 | P173S/E182T/S187T/G238N |
| CL00071580 | 1.09 | 0.06 | 1.28 | 0.01 | 1.16 | 0.03 | 1.12 | 0.07 | 1.06 | 0.03 | E182S/G238N |
| CL00071616 | 1.28 | 0.11 | 1.50 | 0.07 | 1.47 | 0.06 | 1.06 | 0.12 | 1.13 | 0.12 | G238N/Q346T |
| CL00071671 | 1.58 | 0.07 | 1.72 | 0.03 | 1.63 | 0.05 | 1.56 | 0.10 | 1.46 | 0.15 | Q346S |
| CL00071716 | 1.63 | 0.08 | 1.70 | 0.08 | 1.53 | 0.04 | 1.65 | 0.10 | 1.72 | 0.06 | E182T/G238N/Q346S |
| CL00071721 | 1.30 | 0.06 | 1.25 | 0.09 | 1.05 | 0.08 | 1.31 | 0.11 | 1.11 | 0.14 | P173S |
| CL00071731 | 1.74 | 0.11 | 1.72 | 0.13 | 1.53 | 0.07 | 1.80 | 0.15 | 1.63 | 0.04 | E182T/G238N |
| CL00071734 | 1.62 | 0.01 | 1.73 | 0.02 | 1.34 | 0.03 | 1.69 | 0.06 | 1.58 | 0.04 | P173S/E182T/G238N |
| CL00071756 | 1.82 | 0.06 | 1.96 | 0.04 | 1.53 | 0.04 | 1.84 | 0.09 | 1.60 | 0.15 | P173S/E182S/G238N |
| CL00071784 | 1.56 | 0.02 | 1.57 | 0.01 | 1.45 | 0.04 | 1.32 | 0.01 | 1.08 | 0.14 | E182S |
| CL00071799 | 1.58 | 0.05 | 1.63 | 0.08 | 1.46 | 0.05 | 1.41 | 0.10 | 1.14 | 0.13 | Q346T |
| CL00071802 | 1.63 | 0.14 | 1.64 | 0.09 | 1.39 | 0.05 | 1.42 | 0.17 | 1.24 | 0.23 | P173S/Q346T |
| CL00073767 | 1.10 | 0.02 | 1.23 | 0.03 | 1.13 | 0.04 | 1.08 | 0.04 | 0.95 | 0.05 | R65S |
| CL00074053 | 1.04 | 0.04 | 1.03 | 0.03 | 1.02 | 0.03 | 1.02 | 0.02 | 1.02 | 0.01 | A153N |
| CL00074344 | 1.15 | 0.04 | 1.10 | 0.02 | 1.18 | 0.04 | 1.07 | 0.01 | 1.02 | 0.00 | K363R |

FIGURE 4A

| Colony Tracking Number | Total Activity Improvement | | Temp and/or BSA Tolerance Improvement | | | | | | pH Tolerance Improvement | | AA Mutations w.r.t. GGP (CL00088812) |
|---|---|---|---|---|---|---|---|---|---|---|---|
| | PF AVG (pH5.5) | PF STD (pH5.5) | PF AVG (65°C, pH5.5) | PF STD (65°C, pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00080833 | 1.08 | 0.01 | 1.20 | 0.03 | 1.23 | 0.02 | 1.24 | 0.05 | 1.15 | 0.02 | N176K/D185N/H282N/A288R/R385T |
| CL00080834 | 0.91 | 0.01 | 0.93 | 0.02 | 0.92 | 0.00 | 1.02 | 0.01 | 0.97 | 0.05 | N139A/D185N/G315S/R385T |
| CL00080982 | 0.92 | 0.02 | 1.00 | 0.03 | 0.94 | 0.01 | 1.00 | 0.01 | 1.02 | 0.03 | N139H/N176K/D185N/A288R |
| CL00080988 | 1.18 | 0.03 | 1.18 | 0.01 | 1.21 | 0.04 | 1.21 | 0.04 | 1.17 | 0.03 | T161D/A288R |
| CL00080996 | 1.18 | 0.01 | 1.20 | 0.02 | 1.20 | 0.02 | 1.22 | 0.02 | 1.20 | 0.07 | N139H/N176K/D185N |
| CL00081013 | 1.17 | 0.02 | 1.30 | 0.05 | 1.18 | 0.03 | 1.33 | 0.05 | 1.30 | 0.04 | N139A/T161D/N176K/D185N |
| CL00081115 | 1.41 | 0.03 | 1.55 | 0.04 | 1.57 | 0.04 | 1.56 | 0.06 | 1.41 | 0.02 | D185N/H282N |
| CL00081144 | 1.44 | 0.05 | 1.46 | 0.06 | 1.28 | 0.05 | 1.47 | 0.09 | 1.55 | 0.04 | N139P/N176K/D185N/K363A |
| CL00081435 | 1.34 | 0.03 | 1.48 | 0.06 | 1.39 | 0.02 | 1.53 | 0.09 | 1.35 | 0.04 | D185N |
| CL00081483 | 1.45 | 0.01 | 1.64 | 0.03 | 1.52 | 0.03 | 1.63 | 0.03 | 1.44 | 0.01 | D185N/R385T |
| CL00081538 | 0.89 | 0.01 | 1.00 | 0.03 | 0.93 | 0.01 | 1.09 | 0.06 | 0.89 | 0.01 | A288R |
| CL00081583 | 1.34 | 0.03 | 1.47 | 0.05 | 1.32 | 0.07 | 1.45 | 0.05 | 1.31 | 0.06 | R385T |
| CL00081590 | 1.41 | 0.02 | 1.58 | 0.05 | 1.53 | 0.04 | 1.58 | 0.05 | 1.53 | 0.03 | D185N/H282N/L341V/R385T |
| CL00081594 | 1.41 | 0.02 | 1.57 | 0.02 | 1.49 | 0.01 | 1.61 | 0.02 | 1.46 | 0.02 | H282N |
| CL00081726 | 1.19 | 0.03 | 1.24 | 0.03 | 1.12 | 0.04 | 1.28 | 0.04 | 1.41 | 0.05 | N139A/D185N/H282N/A288R/K363A/R385T |
| CL00081736 | 1.76 | 0.02 | 2.07 | 0.04 | 1.94 | 0.03 | 2.24 | 0.05 | 1.94 | 0.03 | N176K/D185N |
| CL00081762 | 1.18 | 0.01 | 1.25 | 0.01 | 1.18 | 0.02 | 1.22 | 0.02 | 1.32 | 0.03 | N139A/N176K/D185N |
| CL00081764 | 0.97 | 0.04 | 0.99 | 0.06 | 0.98 | 0.04 | 1.03 | 0.08 | 1.06 | 0.04 | N176K/L341V |
| CL00081771 | 1.18 | 0.03 | 1.36 | 0.07 | 1.32 | 0.02 | 1.47 | 0.07 | 1.24 | 0.04 | D185N/H282N/A288R |
| CL00081772 | 1.26 | 0.01 | 1.43 | 0.00 | 1.20 | 0.03 | 1.37 | 0.01 | 1.34 | 0.04 | N139A/N176K/D185N/L341V |
| CL00081775 | 1.36 | 0.01 | 1.50 | 0.02 | 1.49 | 0.02 | 1.50 | 0.03 | 1.40 | 0.01 | T161D/D185N |
| CL00082087 | 1.08 | 0.05 | 1.13 | 0.04 | 1.16 | 0.05 | 1.15 | 0.05 | 1.01 | 0.08 | P4N/G238N/T378A |
| CL00082111 | 1.19 | 0.03 | 1.27 | 0.06 | 1.23 | 0.01 | 1.34 | 0.07 | 1.04 | 0.07 | P4N/D136F/E197S/T378A |
| CL00082112 | 1.02 | 0.02 | 1.12 | 0.06 | 1.10 | 0.03 | 1.09 | 0.04 | 1.03 | 0.02 | P4N/E197S/G238N/T378A |
| CL00082124 | 1.37 | 0.03 | 1.44 | 0.01 | 1.42 | 0.01 | 1.44 | 0.04 | 1.47 | 0.05 | P4N/Q346S |
| CL00082149 | 1.12 | 0.03 | 1.12 | 0.02 | 1.23 | 0.01 | 1.18 | 0.01 | 0.97 | 0.03 | P4N/P121A/E182T/E197S/G238N/Q346S/T378A |
| CL00082193 | 1.37 | 0.02 | 1.64 | 0.08 | 1.51 | 0.02 | 1.72 | 0.09 | 1.20 | 0.01 | P4N/D136S/E182T/G238N/T378A |
| CL00082203 | 1.08 | 0.05 | 1.25 | 0.08 | 1.22 | 0.02 | 1.21 | 0.09 | 0.68 | 0.09 | P4N/P121A/D136F/E182S/G238N/Q346S |
| CL00082211 | 1.04 | 0.04 | 1.12 | 0.03 | 1.12 | 0.04 | 1.07 | 0.02 | 1.05 | 0.05 | P4N/P121A/E197S/G238N |
| CL00082214 | 1.22 | 0.02 | 1.23 | 0.02 | 1.30 | 0.02 | 1.28 | 0.02 | 1.25 | 0.04 | P4N/E197S/G238N/Q346S |
| CL00082223 | 1.23 | 0.02 | 1.32 | 0.06 | 1.33 | 0.02 | 1.43 | 0.08 | 1.20 | 0.06 | P4N/G238N/Q346S |
| CL00082227 | 1.47 | 0.04 | 1.77 | 0.15 | 1.51 | 0.07 | 1.71 | 0.09 | 1.04 | 0.09 | P4N/D136S/N173S/E182S/G238N/Q346S |
| CL00082332 | 1.22 | 0.03 | 1.31 | 0.07 | 1.34 | 0.02 | 1.36 | 0.00 | 0.68 | 0.05 | P4N/D136S/N173S/E182S/G238N/Q346S/T378A |
| CL00082333 | 1.33 | 0.06 | 1.63 | 0.13 | 1.44 | 0.07 | 1.72 | 0.14 | 1.13 | 0.07 | P4N/D136S/E182T/G238N |
| CL00082346 | 1.09 | 0.03 | 1.09 | 0.02 | 1.14 | 0.02 | 1.15 | 0.01 | 1.05 | 0.04 | P4N/E197S/G238N/Q346S/T378A |
| CL00082370 | 1.44 | 0.03 | 1.68 | 0.05 | 1.58 | 0.01 | 1.72 | 0.06 | 1.27 | 0.00 | E182T/E197S/T378A |
| CL00082394 | 1.19 | 0.01 | 1.35 | 0.04 | 1.30 | 0.00 | 1.38 | 0.03 | 1.25 | 0.01 | G238N/Q346S |
| CL00082395 | 1.23 | 0.04 | 1.40 | 0.04 | 1.44 | 0.04 | 1.43 | 0.01 | 1.04 | 0.05 | P4N/D136F/E182T/E197S/G238N |
| CL00082400 | 1.41 | 0.02 | 1.58 | 0.01 | 1.59 | 0.02 | 1.64 | 0.02 | 1.33 | 0.04 | P4N/P121A/D136S/Q346S/T378A |
| CL00082447 | 1.09 | 0.01 | 1.05 | 0.06 | 1.12 | 0.01 | 1.06 | 0.07 | 0.94 | 0.01 | P4N/D136S/E197S/G238N/Q346S/T378A |

FIGURE 4B

| Colony Tracking Number | Total Activity Improvement | | Temp and/or BSA Tolerance Improvement | | | | | | pH Tolerance Improvement | | AA Mutations w.r.t. G6P (CL0008812) |
|---|---|---|---|---|---|---|---|---|---|---|---|
| | PF AVG (pH5.5) | PF STD (pH5.5) | PF AVG (65°C, pH5.5) | PF STD (65°C, pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00082491 | 1.46 | 0.06 | 1.67 | 0.06 | 1.73 | 0.05 | 1.64 | 0.05 | 1.20 | 0.09 | P4N/P121A/D136S/E182T/G238N/T378A |
| CL00082565 | 1.06 | 0.01 | 1.04 | 0.00 | 1.19 | 0.01 | 1.04 | 0.02 | 0.51 | 0.01 | P121A/D136S/N173S/E182S/E197S/G238N/T378A |
| CL00082666 | 0.67 | | 1.08 | | 0.66 | | 0.65 | | 0.89 | | Q62W/P80S/D142E/A288R/E402D |
| CL00082668 | 0.78 | | 1.01 | | 0.77 | | 0.80 | | 1.06 | | W46E/Q62W/A73P/K75G/A288R/E402D |
| CL00082743 | 1.03 | | 1.05 | | 1.12 | | 1.03 | | 0.96 | | A288R/E402D |
| CL00082759 | 0.80 | | 0.86 | | 0.57 | | 0.54 | | 1.35 | | Q62W/A73P/K75G/D142E/F179L/E402D |
| CL00082766 | 0.78 | | 0.89 | | 0.62 | | 0.64 | | 1.17 | | Q62W/A288R/E402D |
| CL00082777 | 0.85 | | 0.83 | | 0.57 | | 0.56 | | 1.25 | | Q62W/G70E/A73P/D142E/F179L/E402D |
| CL00082783 | 1.10 | | 1.25 | | 1.23 | | 1.21 | | 1.24 | | E402D |
| CL00082825 | 1.28 | | 1.30 | | 0.99 | | 1.22 | | 1.39 | | Q62W/G70E/K75G/E402D |
| CL00082828 | 1.07 | | 1.19 | | 1.09 | | 1.14 | | 0.76 | | K75G/E402D |
| CL00082834 | 0.75 | | 1.24 | | 0.76 | | 0.77 | | 0.76 | | S146E/A288R |
| CL00082836 | 0.92 | | 0.97 | | 0.81 | | 0.71 | | 1.39 | | Q62W/P80S/D142E/S146E/A288R/E402D |
| CL00082837 | 1.01 | | 0.93 | | 0.72 | | 0.69 | | 1.49 | | Q62W/D142E/S146E/E402D |
| CL00082854 | 1.55 | | 1.57 | | 1.59 | | 1.54 | | 1.57 | | D142E |
| CL00082898 | 1.15 | | 1.05 | | 0.80 | | 0.83 | | 1.25 | | Q62W/E402D |
| CL00082901 | 1.17 | | 1.17 | | 1.32 | | 1.14 | | 0.73 | | A73P/P80S/D142E/Q346T |
| CL00082915 | 1.06 | | 1.01 | | 0.94 | | 1.00 | | 1.05 | | Q62W/G70E/K75G/P80S/D142E/E402D |
| CL00082945 | 0.94 | | 0.93 | | 0.75 | | 0.73 | | 1.26 | | Q62W/D142E/E402D |
| CL00083001 | 0.92 | | 1.09 | | 0.82 | | 0.76 | | 1.35 | | Q62W/D142E/A288R/E402D |
| CL00083138 | 1.12 | 0.02 | 1.28 | 0.02 | 1.03 | 0.01 | 1.23 | 0.02 | 1.30 | 0.07 | R35Y |
| CL00083179 | 1.02 | 0.10 | 0.94 | 0.11 | 0.76 | 0.07 | 0.92 | 0.14 | 0.96 | 0.11 | N7Q |
| CL00083201 | 1.16 | 0.01 | 0.59 | 0.03 | 0.38 | 0.01 | 0.43 | 0.03 | 1.20 | 0.01 | W364C |
| CL00083203 | 1.05 | 0.04 | 1.19 | 0.02 | 1.04 | 0.00 | 1.18 | 0.01 | 0.86 | 0.14 | K75I |
| CL00083254 | 1.23 | 0.04 | 1.16 | 0.05 | 1.16 | 0.02 | 1.17 | 0.06 | 1.30 | 0.07 | R35N |
| CL00083259 | 1.01 | 0.08 | 1.03 | 0.09 | 0.96 | 0.09 | 1.02 | 0.09 | 1.05 | 0.09 | W364Q |
| CL00083267 | 0.92 | 0.06 | 1.00 | 0.11 | 0.84 | 0.05 | 0.99 | 0.09 | 1.00 | 0.07 | W364E |
| CL00083268 | 1.04 | 0.04 | 0.96 | 0.01 | 1.06 | 0.04 | 0.99 | 0.01 | 0.64 | 0.03 | H158W |
| CL00083270 | 1.01 | 0.02 | 0.90 | 0.04 | 0.90 | 0.01 | 0.89 | 0.04 | 1.10 | 0.07 | N7K |
| CL00083281 | 1.04 | 0.03 | 0.96 | 0.02 | 1.02 | 0.02 | 0.95 | 0.02 | 0.86 | 0.03 | A381L |
| CL00083286 | 1.16 | 0.05 | 1.10 | 0.02 | 1.11 | 0.04 | 1.09 | 0.03 | 1.10 | 0.06 | A381N |
| CL00083299 | 1.01 | 0.04 | 0.99 | 0.04 | 0.98 | 0.03 | 0.98 | 0.04 | 1.01 | 0.00 | P137I |
| CL00083309 | 1.21 | 0.03 | 1.28 | 0.02 | 1.30 | 0.02 | 1.24 | 0.03 | 1.16 | 0.06 | G403K |
| CL00083355 | 1.12 | 0.02 | 1.12 | 0.02 | 1.05 | 0.03 | 1.11 | 0.00 | 1.27 | 0.02 | W364S |
| CL00083356 | 1.06 | 0.06 | 1.03 | 0.06 | 1.02 | 0.06 | 1.02 | 0.05 | 1.10 | 0.06 | G238R |
| CL00083363 | 1.20 | 0.05 | 1.04 | 0.03 | 1.06 | 0.03 | 1.06 | 0.03 | 1.08 | 0.02 | E165S |
| CL00083384 | 1.06 | 0.12 | 1.10 | 0.13 | 1.11 | 0.11 | 1.07 | 0.12 | 0.89 | 0.19 | K75S |
| CL00083390 | 1.19 | 0.01 | 1.47 | 0.02 | 1.22 | 0.04 | 1.44 | 0.02 | 1.16 | 0.01 | G403L |
| CL00083450 | 1.06 | 0.08 | 0.98 | 0.06 | 0.99 | 0.03 | 0.99 | 0.04 | 0.95 | 0.08 | E165T |
| CL00083520 | 1.20 | 0.04 | 1.35 | 0.05 | 1.15 | 0.03 | 1.32 | 0.03 | 1.40 | 0.08 | R35F |

FIGURE 4C

| Colony Tracking Number | Total Activity Improvement | | Temp and/or BSA Tolerance Improvement | | | | | | pH Tolerance Improvement | | AA Mutations w.r.t. C&P (CL00088812) |
|---|---|---|---|---|---|---|---|---|---|---|---|
| | PF AVG (pH5.5) | PF STD (pH5.5) | PF AVG (65°C, pH5.5) | PF STD (65°C, pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00083532 | 1.11 | 0.03 | 1.14 | 0.03 | 1.14 | 0.03 | 1.12 | 0.02 | 1.10 | 0.04 | A381R |
| CL00083594 | 1.05 | 0.01 | 1.13 | 0.04 | 1.09 | 0.01 | 1.08 | 0.03 | 1.05 | 0.03 | G403N |
| CL00083600 | 1.08 | 0.02 | 1.13 | 0.04 | 1.00 | 0.01 | 1.10 | 0.03 | 1.04 | 0.03 | N7S |
| CL00083624 | 1.04 | 0.04 | 1.16 | 0.03 | 1.07 | 0.02 | 1.11 | 0.01 | 1.03 | 0.07 | G238Q |
| CL00083629 | 1.21 | 0.03 | 1.26 | 0.04 | 1.24 | 0.05 | 1.27 | 0.05 | 1.18 | 0.01 | W364N |
| CL00083651 | 1.11 | 0.02 | 1.16 | 0.00 | 1.07 | 0.02 | 1.13 | 0.02 | 1.10 | 0.01 | K75M |
| CL00083672 | 1.11 | 0.02 | 1.09 | 0.03 | 0.95 | 0.01 | 1.07 | 0.04 | 1.15 | 0.03 | N69Y |
| CL00083699 | 1.07 | 0.05 | 1.09 | 0.04 | 1.05 | 0.01 | 1.06 | 0.05 | 1.06 | 0.05 | K75R |
| CL00083701 | 1.10 | 0.07 | 1.03 | 0.05 | 0.99 | 0.05 | 1.02 | 0.05 | 1.05 | 0.07 | K75Q |
| CL00084075 | 1.04 | 0.02 | 1.10 | 0.04 | 1.00 | 0.03 | 1.06 | 0.04 | 1.30 | 0.04 | W364T |
| CL00084160 | 1.24 | 0.00 | 1.48 | 0.02 | 1.29 | 0.02 | 1.46 | 0.05 | 1.56 | 0.01 | R35D |
| CL00084169 | 1.11 | 0.01 | 1.10 | 0.02 | 1.11 | 0.03 | 1.07 | 0.00 | 1.12 | 0.03 | R120K |
| CL00084214 | 1.19 | 0.05 | 1.43 | 0.11 | 1.46 | 0.04 | 1.41 | 0.06 | 1.09 | 0.11 | V55L |
| CL00084225 | 1.37 | 0.03 | 1.33 | 0.06 | 1.25 | 0.05 | 1.27 | 0.07 | 1.40 | 0.04 | R35E |
| CL00084290 | 1.11 | 0.02 | 1.16 | 0.01 | 1.05 | 0.01 | 1.14 | 0.00 | 0.99 | 0.01 | R120S |
| CL00084295 | 1.17 | 0.01 | 1.18 | 0.01 | 1.18 | 0.01 | 1.14 | 0.02 | 1.23 | 0.00 | G403Q |
| CL00084418 | 1.28 | 0.04 | 1.30 | 0.04 | 1.17 | 0.01 | 1.29 | 0.05 | 1.17 | 0.03 | N69R |
| CL00084446 | 1.07 | 0.02 | 1.01 | 0.02 | 0.95 | 0.01 | 1.01 | 0.04 | 1.18 | 0.03 | W364V |
| CL00084447 | 1.13 | 0.01 | 1.12 | 0.01 | 0.95 | 0.01 | 1.10 | 0.02 | 1.03 | 0.02 | G403I |
| CL00084488 | 1.11 | 0.04 | 1.08 | 0.04 | 1.09 | 0.03 | 1.08 | 0.03 | 1.11 | 0.07 | Q157G |
| CL00084514 | 1.13 | 0.02 | 1.24 | 0.06 | 1.11 | 0.01 | 1.22 | 0.06 | 1.09 | 0.04 | Q157A |
| CL00084528 | 1.12 | 0.06 | 1.14 | 0.06 | 1.19 | 0.06 | 1.09 | 0.07 | 1.18 | 0.06 | D142A |
| CL00084530 | 1.11 | 0.02 | 1.04 | 0.01 | 0.99 | 0.01 | 1.02 | 0.01 | 1.22 | 0.06 | N69L |
| CL00084569 | 1.30 | 0.04 | 1.41 | 0.10 | 0.62 | 0.05 | 1.34 | 0.11 | 1.12 | 0.13 | N7L |
| CL00084607 | 1.01 | 0.03 | 1.07 | 0.08 | 0.98 | 0.03 | 1.06 | 0.09 | 0.98 | 0.05 | W364L |
| CL00084681 | 1.11 | 0.00 | 1.15 | 0.04 | 1.16 | 0.04 | 1.15 | 0.04 | 1.11 | 0.04 | G238N |
| CL00084747 | 1.43 | 0.03 | 1.38 | 0.02 | 1.41 | 0.02 | 1.32 | 0.02 | 1.39 | 0.01 | D142R |
| CL00086469 | 1.23 | 0.01 | 1.24 | 0.00 | 1.22 | 0.02 | 1.30 | 0.08 | 1.28 | 0.02 | L6F |
| CL00086495 | 1.44 | 0.04 | 1.42 | 0.05 | 1.46 | 0.07 | 1.63 | 0.04 | 1.34 | 0.02 | L135Y |
| CL00086792 | 1.10 | 0.01 | 1.18 | 0.01 | 1.20 | 0.02 | 1.17 | 0.01 | 1.07 | 0.00 | S266A |
| CL00086833 | 1.07 | 0.09 | 1.08 | 0.09 | 1.18 | 0.11 | 1.26 | 0.13 | 1.06 | 0.10 | L135F |
| CL00086853 | 1.16 | 0.09 | 1.34 | 0.06 | 1.30 | 0.07 | 1.37 | 0.05 | 0.68 | 0.10 | R63A |
| CL00087082 | 1.43 | 0.02 | 1.41 | 0.01 | 1.41 | 0.02 | 1.47 | 0.01 | 1.44 | 0.05 | L352M |
| CL00087210 | 1.47 | 0.00 | 1.43 | 0.03 | 1.38 | 0.01 | 1.44 | 0.00 | 1.10 | 0.02 | R181T |
| CL00087329 | 1.26 | 0.08 | 1.34 | 0.07 | 1.26 | 0.08 | 1.31 | 0.06 | 1.14 | 0.07 | S10A |
| CL00087397 | 1.13 | 0.08 | 1.20 | 0.05 | 1.26 | 0.03 | 1.21 | 0.04 | 1.17 | 0.10 | L6Y |
| CL00087499 | 1.16 | 0.06 | 1.23 | 0.05 | 1.23 | 0.11 | 1.22 | 0.09 | 1.05 | 0.11 | S10Q |
| CL00087570 | 1.18 | 0.07 | 1.21 | 0.06 | 1.20 | 0.08 | 1.31 | 0.09 | 1.17 | 0.06 | S266Y |
| CL00087796 | 1.31 | 0.00 | 1.26 | 0.02 | 1.27 | 0.04 | 1.29 | 0.01 | 1.12 | 0.01 | G311A |
| CL00087809 | 1.22 | 0.01 | 1.25 | 0.02 | 1.35 | 0.04 | 1.19 | 0.02 | 1.19 | 0.02 | L6M |
| CL00087945 | 1.27 | 0.07 | 1.15 | 0.04 | 1.19 | 0.04 | 1.19 | 0.08 | 1.18 | 0.04 | V89T |
| CL00087997 | 1.14 | 0.02 | 1.16 | 0.01 | 1.16 | 0.02 | 1.18 | 0.00 | 1.22 | 0.04 | G233A |
| CL00089112 | 1.24 | 0.02 | 1.20 | 0.01 | 1.05 | 0.00 | 1.20 | 0.01 | 1.08 | 0.01 | S10N/A25F/K75E/P80S/Q225E |
| CL00089367 | 1.36 | 0.00 | 1.33 | 0.01 | 1.13 | 0.01 | 1.33 | 0.01 | 1.39 | 0.01 | A25F/Q225E |
| CL00089395 | 1.22 | 0.01 | 1.24 | 0.02 | 1.44 | 0.03 | 1.24 | 0.02 | 1.22 | 0.05 | P137V/D185N |
| CL00089711 | 1.33 | 0.07 | 1.40 | 0.09 | 1.43 | 0.06 | 1.40 | 0.09 | 1.45 | 0.05 | Q225E |
| CL00089816 | 1.20 | 0.02 | 1.29 | 0.03 | 1.49 | 0.01 | 1.29 | 0.03 | 1.14 | 0.00 | P80S/D185N |
| CL00090029 | 1.32 | 0.01 | 1.35 | 0.02 | 1.28 | 0.03 | 1.35 | 0.02 | 1.18 | 0.03 | A25F/H158R |

FIGURE 4D

| Colony Tracking Number | Total Activity Improvement | | Temp and/or BSA Tolerance Improvement | | | | | | pH Tolerance Improvement | | AA Mutations w.r.t. G4P (CL00580812) |
|---|---|---|---|---|---|---|---|---|---|---|---|
| | PF AVG (pH5.5) | PF STD (pH5.5) | PF AVG (65°C, pH5.5) | PF STD (65°C, pH5.5) | PF AVG (75°C, pH5.5) | PF STD (75°C, pH5.5) | PF AVG (90°C, pH5.5) | PF STD (90°C, pH5.5) | PF AVG (pH2.0) | PF STD (pH2.0) | |
| CL00090060 | 1.25 | 0.04 | 1.09 | 0.03 | 1.15 | 0.02 | 1.09 | 0.03 | 1.20 | 0.02 | S10N/A25F/Q62W/D90N/T114H/H158R/N176K/D185N |
| CL00090328 | 1.57 | | | | 1.59 | | | | 1.61 | | R35E/D142E/E197S/H282N/W364T |
| CL00090392 | 0.95 | | | | 0.88 | | | | 1.43 | | R35F/D142E/N176K/W364T/E402D |
| CL00090433 | 1.51 | | | | 1.69 | | | | 2.26 | | P4N/R35N/D142E/E197S/H282N |
| CL00090447 | 1.52 | | | | 1.70 | | | | 2.34 | | P4N/R35N/D142E/E197S/W364T/E402D |
| CL00090511 | 1.82 | | | | 1.97 | | | | 2.52 | | P4N/R35D/D142E/N176K/H282N/A288R/E402D |
| CL00090520 | 1.62 | | | | 1.77 | | | | 2.47 | | P4N/R35N |
| CL00090529 | 1.19 | | | | 1.27 | | | | 0.97 | | R35E/D142E/H282N/A288R/E402D |
| CL00090536 | 1.15 | | | | 1.12 | | | | 1.82 | | R35F/D142E/N176K/E197S/W364T |
| CL00090556 | 1.42 | | | | 1.55 | | | | 2.37 | | P4N/R35N/E197S/W364T/E402D |
| CL00090567 | 1.40 | | | | 1.56 | | | | 2.04 | | P4N/R35N/D142E/E197S |
| CL00090580 | 1.55 | | | | 1.59 | | | | 1.96 | | P4N/R35D/E402D |
| CL00090581 | 1.48 | | | | 1.61 | | | | 1.31 | | P4N/R35E/D142E/E197S/H282N |
| CL00090582 | 1.70 | | | | 1.83 | | | | 2.23 | | P4N/R35D |
| CL00090695 | 1.19 | | | | 0.09 | | | | 1.31 | | R35D/D142E/H282N/E402D |
| CL00090750 | 1.64 | | | | 1.76 | | | | 2.15 | | P4N/R35F/D142E |
| CL00090775 | 1.59 | | | | 1.65 | | | | 2.40 | | P4N/R35D/W364T/E402D |
| CL00090818 | 0.82 | | | | 0.95 | | | | 1.03 | | R35N/D142E/N176K/E197S/E402D |
| CL00090911 | 1.58 | | | | 1.42 | | | | 2.62 | | P4N/R35F/W364T/E402D |
| CL00090915 | 1.66 | | | | 1.57 | | | | 2.21 | | P4N/R35F |
| CL00090943 | 1.62 | | | | 1.49 | | | | 2.29 | | P4N/R35E/W364T/E402D |
| CL00090952 | 1.58 | | | | 1.41 | | | | 2.39 | | P4N/R35F/D142E/W364T/E402D |
| CL00090994 | 0.76 | | | | 1.73 | | | | 2.73 | | P4N/R35N/D142E/W364T/E402D |
| CL00091085 | 1.60 | | | | 1.81 | | | | 2.13 | | R35E/N176K/D185N/S240K |
| CL00091187 | 1.52 | | | | 1.73 | | | | 2.33 | | P4N/D142R/D185N/S240K |
| CL00091189 | 1.47 | | | | 1.77 | | | | 2.28 | | P4N/D142A/N176K/D185N/Q192K/S240K/R385T |
| CL00091192 | 1.54 | | | | 1.78 | | | | 2.65 | | P4N/R35N/D142R/D185N/W364T |
| CL00091255 | 1.59 | | | | 1.65 | | | | 2.98 | | R35F/N176K/D185N/R385T |
| CL00091303 | 1.31 | | | | 1.63 | | | | 1.70 | | R35N/N176K/D185N/S240K |
| CL00091330 | 1.37 | | | | 1.34 | | | | 3.01 | | P121A/D142A/N176K/D185N/K363A/W364T |
| CL00091350 | 1.76 | | | | 1.53 | | | | 2.79 | | P4N/R35F/P121A/D142E/N176K/D185N/S240K/R385T/A394P/G403N |
| CL00091358 | 1.78 | | | | 1.79 | | | | 2.91 | | P4N/R35F/P121A/D142E/N176K/D185N |
| CL00091362 | 1.83 | | | | 1.69 | | | | 2.71 | | R35D/N176K/D185N/Q192K/R385T/A394P/G403N |
| CL00091418 | 1.61 | | | | 1.05 | | | | 3.44 | | R35Y/S240K/K363A/W364T |
| CL00091424 | 1.74 | | | | 1.31 | | | | 2.89 | | R35D/L410A |
| CL00091425 | 1.72 | | | | 1.51 | | | | 3.63 | | R35N/D142A/D185N/Q192K/R385T/A394P/G403N/L410G |
| CL00091432 | 1.56 | | | | 1.19 | | | | 3.00 | | R35D/P121A/D142R/S240K/H282N/K363A/W364S/R385T/A394P/L410G |
| CL00091437 | 1.90 | | | | 1.64 | | | | 4.07 | | R35E/D142R/N176K/D185N/W364T/R385T |
| CL00091445 | 1.71 | | | | 1.21 | | | | 3.58 | | R35F/P121A/W364T/R385T/L410G |

FIGURE 4E

| Colony Tracking Number | Total Activity Improvement PF AVG (pH5.5) | Total Activity Improvement PF STD (pH5.5) | Temp and/or BSA Tolerance Improvement PF AVG (65°C, pH5.5) | PF STD (65°C, pH5.5) | PF AVG (75°C, pH5.5) | PF STD (75°C, pH5.5) | PF AVG (90°C, pH5.5) | PF STD (90°C, pH5.5) | pH Tolerance Improvement PF AVG (pH2.0) | PF STD (pH2.0) | AA Mutations w.r.t. GSP (SEQ ID NO:5) |
|---|---|---|---|---|---|---|---|---|---|---|---|
| CL00091457 | 1.91 | | | | 1.85 | | | | 3.31 | | R35N/D142E/N176K/D185N/S240K |
| CL00091461 | 1.56 | | | | 1.06 | | | | 3.88 | | R35F/D142A/K363A/R385T/A394P/G403N/L410G |
| CL00091465 | 1.57 | | | | 1.61 | | | | 2.95 | | P4N/D142A/D185N/W364T/R385T |
| CL00091486 | 1.51 | | | | 1.25 | | | | 3.15 | | R35F/D142R/N176K/D185N/S240K/R385T/A394P |
| CL00091498 | 1.59 | | | | 1.44 | | | | 3.44 | | D142E/N176K/D185N/Q192K/E197S/A288R/K363A |
| CL00091504 | 1.79 | | | | 1.44 | | | | 2.88 | | R35D/D142E/Q192K/E197S/S240K/K363A/W364S |
| CL00091545 | 1.92 | | | | 1.58 | | | | 3.72 | | R35F/D142A/D185N/K363A/W364S/E402D/L410G |
| CL00091554 | 1.78 | | | | 1.79 | | | | 2.83 | | P4N/R35D/P121A/D142R/N176K/D185N/E197S/S240K |
| CL00091566 | 1.93 | | | | 1.93 | | | | 3.40 | | R35N/D142E/N176K/D185N/S240K/W364T |
| CL00091581 | 1.91 | | | | 1.85 | | | | 3.15 | | P4N/R35N/P121A/D142A/D185N/A288R |
| CL00091585 | 2.20 | | | | 2.07 | | | | 4.43 | | P4N/R35N/D185N/Q192K/E197S |
| CL00091586 | 1.98 | | | | 1.56 | | | | 4.47 | | R35Y/D142E/N176K/D185N/W364S/R385T/A394P |
| CL00091592 | 1.11 | | | | 0.71 | | | | 2.16 | | S240K/K363A/W364T/R385T/A394P/L410A |
| CL00091594 | 1.52 | | | | 1.07 | | | | 2.92 | | R35F/D142R/R385T/A394P/E402D/L410G |
| CL00091602 | 1.79 | | | | 1.43 | | | | 3.48 | | R35N/N176K/D185N/S240K/K363A/W364S/A394P/E402D/L410G |
| CL00091607 | 1.97 | | | | 1.50 | | | | 3.20 | | P4N/R35E/D142E |
| CL00091609 | 1.49 | | | | 0.98 | | | | 3.11 | | R35F/K363A/W364T |
| CL00091643 | 1.71 | | | | 1.50 | | | | 3.67 | | D142E/D185N/W364S/R385T/A394P/G403N/L410G |
| CL00091654 | 1.90 | | | | 1.42 | | | | 4.13 | | R35Y/P121A/S240K/W364S |
| CL00091655 | 1.72 | | | | 1.10 | | | | 4.03 | | R35Y/W364T/L410G |
| CL00091660 | 1.86 | | | | 1.64 | | | | 3.64 | | R35E/D142A/N176K/D185N/S240K/K363A/W364S/R385T/A394P/G403N/L410G |
| CL00091759 | 1.64 | | | | 1.98 | | | | 2.72 | | P4N/R35Y/D142E/D185N |
| CL00091822 | 1.43 | | | | 1.72 | | | | 2.07 | | P4N/R35E/D142A/N176K/D185N/S240K/K363A/L410A |
| CL00091870 | 1.58 | | | | 1.74 | | | | 2.95 | | R35D/N176K/D185N/Q192K/W364S/R385T/A394P/E402D/L410A |
| CL00092038 | 1.62 | | | | 1.36 | | | | 3.46 | | R35D/P121A/D142E/E197S/K363A/W364S |
| CL00092062 | 1.57 | | | | 1.76 | | | | 2.31 | | P4N/N176K/D185N |
| CL00092076 | 0.19 | | | | 0.76 | | | | 0.94 | | D142R/Q192K/S240K/K363A/W364S/R385T/A394P/E402D/L410G |
| CL00092077 | 1.85 | | | | 1.95 | | | | 2.00 | | P4N/D185N |
| CL00092092 | 1.62 | | | | 1.89 | | | | 2.51 | | R35N/N176K/D185N/S240K/R385T |
| CL00092180 | 1.34 | | | | 1.46 | | | | 1.63 | | R35N/S240K |
| CL00092182 | 1.84 | | | | 2.32 | | | | 2.92 | | R35D/D142R/N176K/D185N/S240K |
| CL00092194 | 1.74 | | | | 1.98 | | | | 2.91 | | R35F/P121A/D142E/A153V/D185N/S240K/W364T/R385T |
| CL00092197 | 1.48 | | | | 1.65 | | | | 2.14 | | R35D/D185N/R385T |
| CL00092205 | 1.55 | | | | 1.89 | | | | 1.80 | | P4N/N176K/D185N/S240K |
| CL00092266 | 2.07 | | | | 2.17 | | | | 3.11 | | R35F/D142E/N176K/D185N |
| CL00092271 | 1.47 | | | | 1.65 | | | | 2.12 | | D142R/N176K/D185N/Q192K/S240K/K363A |
| CL00092314 | 1.98 | | | | 2.17 | | | | 2.94 | | P4N/R35N/D142A/N176K/D185N/S240K |

FIGURE 5

| Colony Tracking Number | Total Activity pH5.5, 120hr (72hr*) growth in 24-well plate | Temp and/or BSA Tolerance | | pH Tolerance | | AA Mutations w.r.t. G3P (CL00005023) |
|---|---|---|---|---|---|---|
| | | %Residual at 75°C, pH5.5 | %Residual at 90°C, pH5.5 | %Residual at pH2.0 | %Residual at pH2.5 | |
| CL00005023 (G3P) | 691* | 29.59 | 40.07 | 34.87 | | |
| CL00080812 (G6P) | 955.03* | 67.84 | 79.92 | 28.43 | 50.17 | K7N/D35R/V67A/P173N/T238G/M276K/A277T/E315G/T364W/G381A/A403G/ |
| CL00100223 | 1291.95 | 79.00 | 90.76 | 55.37 | 62.79 | P4N/K7N/D35N/V67A/P121A/D136S/P173N/T238G/M276K/A277T/E315G/Q346S/T364W/T378A/G381A/A403G/ |
| CL00100225 | 1063.52 | 80.53 | 96.23 | 39.74 | 48.91 | K7N/D35R/V67A/P121A/D136S/P173N/T238G/M276K/A277T/E315G/Q346S/T364W/T378A/G381A/A403G/ |
| CL00102257 | 1255.00 | 79.97 | 86.53 | 19.76 | 50.53 | P4N/K7N/D35R/V67A/P121A/D136S/P173N/T238G/M276K/A277T/E315G/T364W/T378A/G381A/A403G/ |
| CL00102259 | 1271.00 | 79.29 | 88.72 | 41.56 | 55.50 | P4N/K7N/D35N/V67A/P121A/D136S/P173N/T238G/M276K/A277T/E315G/T364W/T378A/G381A/A403G/ |
| CL00102276 | 1296.35 | 69.12 | 84.39 | 49.58 | 49.93 | K7N/D35R/V67A/P173N/T238G/M276K/A277T/E315G/Q346T/T364W/G381A/A403G/L410A/ |

FIGURE 6

```
              1                                                                              50
CL00005023    QSEPELKLES  VVIVSRHGVR  APTKATQLMQ  DVTPDAWPTW  PVKLGWLTPR
CL00047720    QSEPELKLES  VVIVSRHGVR  APTKATQLMQ  DVTPDAWPTW  PVKLGWLTPR 51                                                                            100
CL00005023    GGELVAYLGQ  YQRQRLVANG  LLADKGCPQP  GQVAIIADVD  ERTRKTGEAF
CL00047720    GGELVAYLGQ  YQRQRLVANG  LLADKGCPQP  GQVAIIADVD  ERTRKTGEAF 101                                                                           150
CL00005023    AAGLAPDCAI  TVHTQADTSR  PDPLFNPLKT  GVCQLDPANV  TDAILSRA--
CL00047720    AAGLAPDCAI  TVHTQADTSR  PDPLFNPLKT  GVCQLDPANV  TLAILSRAVD 151                                                                           200
CL00005023    ----------  --GGSIADFT  QHYQTAFREL  ERVLNFPQSN  LCFNREKQDE
CL00047720    PANVTHAILS  RAGGSIADFT  QHYQTAFREL  ERVLNFPQSN  LCFNREKQDE 201                                                                           250
CL00005023    SCSLTQALPS  ELKVSADNVS  LTGAVSLASM  LTEIFLLQQA  QGMPEPGWGR
CL00047720    SCSLTQALPS  ELKVSADNVS  LTGAVSLASM  LTEIFLLQQA  QGMPEPGWGR 251                                                                           300
CL00005023    ITDSHQWNTL  LSLHNAQFDL  LQRTPEVARS  RATPLLDLIM  AALTPHPPQK
CL00047720    ITDSHQWNTL  LSLHNAQFDL  LQRTPEVARS  RATPLLDLIM  AALTPHPPQK 301                                                                           350
CL00005023    QAYGVTLPTS  VLFIAGHDTN  LANLGGALEL  NWTLPGQPDN  TPPGGELVFE
CL00047720    QAYGVTLPTS  VLFIAGHDTN  LANLGGALEL  NWTLPGQPDN  TPPGGELVFE 351                                                                           400
CL00005023    RWRRLSDNSQ  WIQVSLVYQT  LQQMRDKTPL  SLNTPPGEVK  LTLPGCEERN
CL00047720    RWRRLSDNSQ  WIQVSLVYQT  LQQMRDKTPL  SLNTPPGEVK  LTLPGCEERN 401              424
CL00005023    AQGMCSLAGF  TQIVNEARIP  ACSL
CL00047720    AQGMCSLAGF  TQIVNEARIP  ACSL
```

FIGURE 7

```
             1                                                   50
CL00005023   QSEPELKLES VVIVSRHGVR APTKATQLMQ DVTPDAWPTW PVKLGWLTPR
CL00047720   QSEPELKLES VVIVSRHGVR APTKATQLMQ DVTPDAWPTW PVKLGWLTPR 51                                                  100
CL00005023   GGELVAYLGQ YQRQRLVANG LLADKGCPQP GQVAIIADVD ERTRKTGEAF
CL00047720   GGELVAYLGQ YQRQRLVANG LLADKGCPQP GQVAIIADVD ERTRKTGEAF 101                                                 150
CL00005023   AAGLAPDCAI TVHTQADTSR PDPLFNPLKT GVCQLD---- ----------
CL00047720   AAGLAPDCAI TVHTQADTSR PDPLFNPLKT GVCQLDPANV TLAILSRAVD 151                                                 200
CL00005023   PANVTDAILS RAGGSIADFT QHYQTAFREL ERVLNFPQSN LCFNREKQDE
CL00047720   PANVTHAILS RAGGSIADFT QHYQTAFREL ERVLNFPQSN LCFNREKQDE 201                                                 250
CL00005023   SCSLTQALPS ELKVSADNVS LTGAVSLASM LTEIFLLQQA QGMPEPGWGR
CL00047720   SCSLTQALPS ELKVSADNVS LTGAVSLASM LTEIFLLQQA QGMPEPGWGR 251                                                 300
CL00005023   ITDSHQWNTL LSLHNAQFDL LQRTPEVARS RATPLLDLIM AALTPHPPQK
CL00047720   ITDSHQWNTL LSLHNAQFDL LQRTPEVARS RATPLLDLIM AALTPHPPQK 301                                                 350
CL00005023   QAYGVTLPTS VLFIAGHDTN LANLGGALEL NWTLPGQPDN TPPGGELVFE
CL00047720   QAYGVTLPTS VLFIAGHDTN LANLGGALEL NWTLPGQPDN TPPGGELVFE 351                                                 400
CL00005023   RWRRLSDNSQ WIQVSLVYQT LQQMRDKTPL SLNTPPGEVK LTLPGCEERN
CL00047720   RWRRLSDNSQ WIQVSLVYQT LQQMRDKTPL SLNTPPGEVK LTLPGCEERN 401                 424
CL00005023   AQGMCSLAGF TQIVNEARIP ACSL
CL00047720   AQGMCSLAGF TQIVNEARIP ACSL
```

FIGURE 8

| Position | AA in G3P | Variants | Position | AA in G3P | Variants |
|---|---|---|---|---|---|
| 4 | P | E, K, L, M, N, Q, T, W | 185 | D | N |
| 5 | E | K | 187 | S | T |
| 6 | L | F, M, Y | 189 | S | L, N, T |
| 7 | K | E, L, N, Q, S | 191 | T | S |
| 10 | S | A, N, Q | 192 | Q | K, L |
| 11 | V | I | 193 | A | I, L, S, T, V |
| 25 | A | D, F, N, W | 194 | L | I |
| 27 | Q | D, P, V | 197 | E | S |
| 31 | D | I, N | 202 | A | R |
| 35 | D | E, F, N, R, Y | 225 | Q | E |
| 46 | W | E, G | 230 | P | S |
| 53 | E | D, N | 233 | G | A |
| 55 | V | L | 238 | T | A, F, G, K, N, P, Q, R, S, Y |
| 58 | L | S | 240 | S | A, G, K, R |
| 61 | Y | C | 242 | Q | E, L |
| 62 | Q | W | 244 | N | I |
| 63 | R | A | 261 | P | L |
| 65 | R | C, G, P, S, V | 266 | S | A, Y |
| 67 | V | A | 272 | L | S |
| 69 | N | L, R, Y | 276 | M | K |
| 70 | G | E | 277 | A | T |
| 72 | L | S | 279 | L | F |
| 73 | A | P | 280 | T | C, G, N, P |
| 75 | K | C, E, G, I, L, M, Q, R, S, W | 281 | P | D, S |
| 76 | G | C | 282 | H | N |
| 80 | P | S | 288 | A | R |
| 89 | V | T | 292 | T | G |
| 90 | D | N | 295 | T | N |
| 110 | I | L | 302 | G | S |
| 111 | T | I | 311 | G | A |
| 113 | H | Q | 315 | E | G, S |
| 114 | T | C, D, F, H, N, P, S | 316 | L | F |
| 119 | S | R | 339 | R | M |
| 120 | R | K, S | 341 | L | V |
| 121 | P | A | 346 | Q | K, P, S, T |
| 130 | T | G, R | 352 | L | M |
| 134 | Q | A, T | 362 | D | G, N, S, Y |
| 135 | L | F, Y | 363 | K | A, R |
| 136 | D | F, G, S | 364 | T | C, E, I, L, N, Q, S, T, V, W |
| 137 | P | C, F, G, H, I, L, M, N, S, V, W, Y | 365 | P | W |
| 139 | N | A, H, P | 366 | L | R |
| 142 | D | A, E, F, G, H, I, K, L, M, N, P, R, S, T, V, Y | 370 | T | K |
| 146 | S | E, P | 371 | P | M, V, W, Y |
| 151 | S | F, R | 372 | P | T |
| 153 | A | N, S, V, Y | 378 | T | A |
| 157 | Q | A, G, P | 381 | G | A, C, L, N, R |
| 158 | H | R, W | 384 | E | D |
| 161 | T | D | 385 | R | T |
| 165 | E | D, P, S, T, W | 394 | A | I, L, M, P |
| 173 | P | N, S, T, Y | 395 | G | P |
| 174 | Q | A, E | 398 | Q | V |
| 176 | N | K | 401 | N | A, L, P |
| 179 | F | L | 402 | E | D |
| 180 | N | K | 403 | A | G, I, K, L, N, Q, W, Y |
| 181 | R | T | 409 | S | H, L, R, V, W |
| 182 | E | A, F, S, T | 410 | L | A, C, E, F, G, I, K, R |

FIGURE 9A

Priority #1 DNA

```
>SEQ ID NO:18 (CL00048541 G4P)
CAGAGTGAGCCTGAGTTGAAACTGGAATCCGTTGTCATCGTCTCTAGACATGGTGTTAGAGCACCAACCA
AGGCCACCCAACTTATGCAAGATGTCACCCCAGACGCTTGGCCAACCTGGCCAGTCAAGCTGGGTTGGTT
GACACCTAGAGGTGGTGAGCTCGTTGCTTACTTGGGTCAATACCAAAGACAGCGTCTTGTTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTGAAGACTGGTGTTTGCCAATTGGACCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCCCACAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCACCGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGACTCCACTGTCTTTGAACACGCCTCCAGGAG
AAGTCAAATTGACCTTGCCTGGATGTGAAGAGAGAAATGCTCAGGGTATGTGTTCCTTGGCTGGTTTCAC
TCAAATCGTTAACGAAGCTAGAATCCCAGCTTGTTCCTTG

>SEQ ID NO:19 (CL00060516 G5P)
CAGAGTGAGCCTGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTGAAGACTGGTGTTTGCCAATTGGACCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCCCACAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGATCCCACTGTCTTTGAACACGCCTCCAGGAG
AAGTCAAATTGACCTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG
```

FIGURE 9B

>SEQ ID NO:20 (CL00080812 G6P)
CAGAGTGAGCCTGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTTGAAGACTGGTGTTTGCCAATTGGACCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGTGGCCACTGTCTTTGAACACGCCTCCAGGAG
AAGTCAAATTGACCTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

>SEQ ID NO:21 (CL00082400)
CAGAGTGAGAACGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGAGCTGATCCATTGTTCAACCCTTTTGAAGACTGGTGTTTGCCAATTGTCTCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTTCTTGGATTCAGGTT
TCGTTGGTCTACCAAACTTTGCAGCAGATGAGAGACAAGTGGCCACTGTCTTTGAACACGCCTCCAGGAG
AAGTCAAATTGGCTTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

FIGURE 9C

>SEQ ID NO:22 (CL00089395)
CAGAGTGAGCCTGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTGAAGACTGGTGTTTGCCAATTGGACGTTGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAAACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGTGGCCACTGTCTTTGAACACGCCTCCAGGAG
AAGTCAAATTGACCTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

>SEQ ID NO:23 (CL00090520)
CAGAGTGAGAACGAGTTGAACCTGGAATCCGTTGTCATCGTCTCTAGACATGGTGTTAGAGCACCAACCA
AGGCCACCCAACTTATGCAAGATGTCACCCCAAACGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTGAAGACTGGTGTTTGCCAATTGGACCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGTGGCCACTGTCTTTGAACACGCCTCCAGGAG
AAGTCAAATTGACCTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

FIGURE 9D

```
>SEQ ID NO:24 (CL00100223)
CAGAGTGAGAACGAGTTGAACCTGGAATCCGTTGTCATCGTCTCTAGACATGGTGTTAGAGCACCAACCA
AGGCCACCCAACTTATGCAAGATGTCACCCCAAATGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGAGCTGATCCATTGTTCAACCCTTTGAAGACTGGTGTTTGCCAATTGTCTCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTTCTTGGATTCAGGTT
TCGTTGGTCTACCAAACTTTGCAGCAGATGAGAGACAAGTGGCCACTGTCTTTGAACACGCCTCCAGGAG
AAGTCAAATTGGCTTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

>SEQ ID NO:25 (CL00102257)
CAGAGTGAGAACGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGAGCTGATCCATTGTTCAACCCTTTGAAGACTGGTGTTTGCCAATTGTCTCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGTGGCCACTGTCTTTGAACACGCCTCCAGGAG
AAGTCAAATTGGCTTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG
```

FIGURE 9E

>SEQ ID NO:26 (CL00102259)
CAGAGTGAGAACGAGTTGAACCTGGAATCCGTTGTCATCGTCTCTAGACATGGTGTTAGAGCACCAACCA
AGGCCACCCAACTTATGCAAGATGTCACCCCAAATGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGAGCTGATCCATTGTTCAACCCTTTGAAGACTGGTGTTTGCCAATTGTCTCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTCAATGGATTCAGGTT
TCGTTGGTCTACCAAACTTTGCAGCAGATGAGAGACAAGTGGCCACTGTCTTTGAACACGCCTCCAGGAG
AAGTCAAATTGGCTTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

Amino Acids

>SEQ ID NO:1 (CL00005023 G3P)

QSEPELKLESVVIVSRHGVRAPTKATQLMQDVTPDAWPTWPVKLGWLTPRGGELVAYLGQYQRQRLVANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFPQSNLCFNREKQDESCSLTQALPSELKVSADNVSLTGA
VSLASMLTEIFLLQQAQGMPEPGWGRITDSHQWNTLLSLHNAQFDLLQRTPEVARSRATPLLDLIMAALT
PHPPQKQAYGVTLPTSVLFIAGHDTNLANLGGALELNWTLPGQPDNTPPGGELVFERWRRLSDNSQWIQV
SLVYQTLQQMRDKTPLSLNTPPGEVKLTLPGCEERNAQGMCSLAGFTQIVNEARIPACSL

Priority #1 Amino Acids

>SEQ ID NO:2 (CL00048541 G4P)
QSEPELKLESVVIVSRHGVRAPTKATQLMQDVTPDAWPTWPVKLGWLTPRGGELVAYLGQYQRQRLVANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFPQSNLCFNREKQDESCSLTQALPSELKVSADNVSLTGA
VSLASMLTEIFLLQQAQGMPEPGWGRITDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKTPLSLNTPPGEVKLTLPGCEERNAQGMCSLAGFTQIVNEARIPACSL

>SEQ ID NO:3 (CL00060516 G5P)
QSEPELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFPQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKIPLSLNTPPGEVKLTLPACEERNAQGMCSLAGFTQIVNEGRIPACSL

FIGURE 9F

>SEQ ID NO:4 (CL00080812 G6P)
QSEPELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKWPLSLNTPPGEVKLTLPACEERNAQGMCSLAGFTQIVNEGRIPACSL

>SEQ ID NO:5 (CL00082400)
QSENELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRADPLFNPLKTGVCQLSPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSSWIQV
SLVYQTLQQMRDKWPLSLNTPPGEVKLALPACEERNAQGMCSLAGFTQIVNEGRIPACSL

>SEQ ID NO:6 (CL00089395)
QSEPELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRPDPLFNPLKTGVCQLDVANV
TDAILSRAGGSIADFTQHYQTAFRELERVLNFNQSNLCFNREKQNESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKWPLSLNTPPGEVKLTLPACEERNAQGMCSLAGFTQIVNEGRIPACSL

>SEQ ID NO:7 (CL00090520)
QSENELNLESVVIVSRHGVRAPTKATQLMQDVTPNAWPTWPVKLGWLTPRGGELVAYLGQYQRQRLAANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKWPLSLNTPPGEVKLTLPACEERNAQGMCSLAGFTQIVNEGRIPACSL

>SEQ ID NO:8 (CL00100223)
QSENELNLESVVIVSRHGVRAPTKATQLMQDVTPNAWPTWPVKLGWLTPRGGELVAYLGQYQRQRLAANG
LLADKGCPQPGQVAIIADVDERTRKTGEAFAAGLAPDCAITVHTQADTSRADPLFNPLKTGVCQLSPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSSWIQV
SLVYQTLQQMRDKWPLSLNTPPGEVKLALPACEERNAQGMCSLAGFTQIVNEGRIPACSL

>SEQ ID NO:9 (CL00102257)
QSENELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRADPLFNPLKTGVCQLSPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKWPLSLNTPPGEVKLALPACEERNAQGMCSLAGFTQIVNEGRIPACSL

FIGURE 9G

\>SEQ ID NO:10 (CL00102259)
QSENELNLESVVIVSRHGVRAPTKATQLMQDVTPNAWPTWPVKLGWLTPRGGELVAYLGQYQRQRLAANG
LLADKGCPQPGQVAIIADVDERTRKTGEAFAAGLAPDCAITVHTQADTSRADPLFNPLKTGVCQLSPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSQWIQV
SLVYQTLQQMRDKWPLSLNTPPGEVKLALPACEERNAQGMCSLAGFTQIVNEGRIPACSL

Priority #2 DNA

\>SEQ ID NO:27 (CL00071716)
CAGAGTGAGCCTGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTGAAGACTGGTGTTTGCCAATTGGACCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCCCACAATCCAACTTGTGCTTTAACCGTACTAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCAACGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTTCTTGGATTCAGGTT
TCGTTGGTCTACCAAACTTTGCAGCAGATGAGAGACAAGATCCCACTGTCTTTGAACACGCCTCCAGGAG
AAGTCAAATTGACCTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

\>SEQ ID NO:28 (CL00100225)
CAGAGTGAGCCTGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGAGCTGATCCATTGTTCAACCCTTTGAAGACTGGTGTTTGCCAATTGTCTCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTTCTTGGATTCAGGTT
TCGTTGGTCTACCAAACTTTGCAGCAGATGAGAGACAAGTGGCCACTGTCTTTGAACACGCCTCCAGGAG
AAGTCAAATTGGCTTTGCCTGCTTGTGAAGAGAGAAATGCTCAGGGTATGTGTTCCTTGGCTGGTTTCAC
TCAAATCGTTAACGAAGGTAGAATCCCAGCTTGTTCCTTG

FIGURE 9H

```
>SEQ ID NO:29 (CL00102276)
CAGAGTGAGCCTGAGTTGAACCTGGAATCCGTTGTCATCGTCTCTAGACATGGTGTTAGAGCACCAACCA
AGGCCACCCAACTTATGCAAGATGTCACCCCAAGAGCTTGGCCAACCTGGCCAGTCAAGCTGGGTTGGTT
GACACCTAGAGGTGGTGAGCTCGTTGCTTACTTGGGTCAATACCAAAGACAGCGTCTTGCTGCCAACGGA
TTGTTGGCCGATAAGGGTTGTCCACAACCAGGTCAAGTAGCTATTATTGCTGACGTCGACGAAAGAACCC
GTAAGACAGGTGAAGCCTTCGCCGCCGGTCTTGCTCCTGACTGTGCCATTACCGTTCACACCCAAGCTGA
CACTTCTAGACCAGATCCATTGTTCAACCCTTTGAAGACTGGTGTTTGCCAATTGGACCCAGCTAACGTT
ACTGACGCTATCTTGTCCAGAGCTGGAGGATCCATTGCTGACTTCACCCAACACTACCAGACTGCCTTCA
GAGAGTTGGAAAGAGTTCTTAACTTCAACCAATCCAACTTGTGCTTTAACCGTGAGAAGCAAGACGAATC
CTGTTCCTTGACTCAAGCATTACCATCTGAGTTGAAGGTCTCCGCCGACAACGTCTCTTTGACCGGTGCT
GTCAGCTTGGCTTCCATGTTGACTGAAATCTTTCTTCTGCAACAAGCTCAAGGTATGCCTGAGCCAGGTT
GGGGTAGAATCGGTGACTCTCACCAATGGAACACCTTGTTGTCCTTGCACAACGCTCAATTCGACTTGCT
GCAGAGAACTCCAGAGGTTGCTAGATCCAGAGCCACCCCATTGTTGGACTTGATCAAGACTGCTTTGACT
CCTCACCCACCTCAAAAGCAAGCCTACGGTGTTACCTTGCCCACTTCTGTCTTGTTCATTGCCGGTCACG
ATACTAACTTGGCAAATCTCGGCGGTGCTTTGGGTTTGAACTGGACTCTTCCTGGTCAACCTGATAACAC
TCCACCAGGTGGTGAGCTCGTTTTCGAAAGATGGCGTAGACTATCTGATAACTCTACTTGGATTCAGGTT
TCGTTGGTCTACCAAACTTTGCAGCAGATGAGAGACAAGTGGCCACTGTCTTTGAACACGCCTCCAGGAG
AAGTCAAATTGACCTTGCCTGCTTGTGAAGAGAGAAATGCTCAGGGTATGTGTTCCTTGGCTGGTTTCAC
TCAAATCGTTAACGAAGGTAGAATCCCAGCTTGTTCCGCT
```

Priority #2 Amino Acids

```
>SEQ ID NO:11 (CL00071716)
QSEPELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFPQSNLCFNRTKQDESCSLTQALPSELKVSADNVSLTGA
VSLASMLTEIFLLQQAQGMPEPGWGRINDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSSWIQV
SLVYQTLQQMRDKIPLSLNTPPGEVKLTLPACEERNAQGMCSLAGFTQIVNEGRIPACSL

>SEQ ID NO:12 (CL00100225)
QSEPELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRADPLFNPLKTGVCQLSPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSSWIQV
SLVYQTLQQMRDKWPLSLNTPPGEVKLALPACEERNAQGMCSLAGFTQIVNEGRIPACSL

>SEQ ID NO:13 (CL00102276)
QSEPELNLESVVIVSRHGVRAPTKATQLMQDVTPRAWPTWPVKLGWLTPRGGELVAYLGQYQRQRLAANG
LLADKGCPQPGQVAIIADVDERTRKTGEAFAAGLAPDCAITVHTQADTSRPDPLFNPLKTGVCQLDPANV
TDAILSRAGGSIADFTQHYQTAFRELERVLNFNQSNLCFNREKQDESCSLTQALPSELKVSADNVSLTGA
VSLASMLTEIFLLQQAQGMPEPGWGRIGDSHQWNTLLSLHNAQFDLLQRTPEVARSRATPLLDLIKTALT
PHPPQKQAYGVTLPTSVLFIAGHDTNLANLGGALGLNWTLPGQPDNTPPGGELVFERWRRLSDNSTWIQV
SLVYQTLQQMRDKWPLSLNTPPGEVKLTLPACEERNAQGMCSLAGFTQIVNEGRIPACSA
```

FIGURE 9I

Priority #3 DNA

```
>SEQ ID NO:30 (CL00047720, Insertion variant)
CAGAGTGAGCCTGAGTTGAAACTGGAATCCGTTGTCATCGTCTCTAGACATGGTGTTAGAGCAC
CAACCAAGGCCACCCAACTTATGCAAGATGTCACCCCAGACGCTTGGCCAACCTGGCCAGTCAA
GCTGGGTTGGTTGACACCTAGAGGTGGTGAGCTCGTTGCTTACTTGGGTCAATACCAAAGACAG
CGTCTTGTTGCCAACGGATTGTTGGCCGATAAGGGTTGTCCACAACCAGGTCAAGTAGCTATTA
TTGCTGACGTCGACGAAAGAACCCGTAAGACAGGTGAAGCCTTCGCCGCCGGTCTTGCTCCTGA
CTGTGCCATTACCGTTCACACCCAAGCTGACACTTCTAGACCAGATCCATTGTTCAACCCTTTG
AAGACTGGTGTTTGCCAATTGGACCCAGCTAACGTTACTTTGGCTATCTTGTCCAGAGCTGTGG
ACCCAGCTAACGTTACTCATGCTATCTTGTCCAGAGCTGGAGGATCCATTGCTGACTTCACCCA
ACACTACCAGACTGCCTTCAGAGAGTTGGAAAGAGTTCTTAACTTCCCACAATCCAACTTGTGC
TTTAACCGTGAGAAGCAAGACGAATCCTGTTCCTTGACTCAAGCATTACCATCTGAGTTGAAGG
TCTCCGCCGACAACGTCTCTTTGACCGGTGCTGTCAGCTTGGCTTCCATGTTGACTGAAATCTT
TCTTCTGCAACAAGCTCAAGGTATGCCTGAGCCAGGTTGGGGTAGAATCACCGACTCTCACCAA
TGGAACACCTTGTTGTCCTTGCACAACGCTCAATTCGACTTGCTGCAGAGAACTCCAGAGGTTG
CTAGATCCAGAGCCACCCCATTGTTGGACTTGATCATGGCTGCTTTGACTCCTCACCCACCTCA
AAAGCAAGCCTACGGTGTTACCTTGCCCACTTCTGTCTTGTTCATTGCCGGTCACGATACTAAC
TTGGCAAATCTCGGCGGTGCTTTGGAGTTGAACTGGACTCTTCCTGGTCAACCTGATAACACTC
CACCAGGTGGTGAGCTCGTTTTCGAAAGATGGCGTAGACTATCTGATAACTCTCAATGGATTCA
GGTTTCGTTGGTCTACCAAACTTTGCAGCAGATGAGAGACAAGACTCCACTGTCTTTGAACACG
CCTCCAGGAGAAGTCAAATTGACCTTGCCTGGATGTGAAGAGAGAAATGCTCAGGGTATGTGTT
CCTTGGCTGGTTTCACTCAAATCGTTAACGAAGCTAGAATCCCAGCTTGTTCCTTG
```

Priority #3 Amino Acids

```
>SEQ ID NO:14 (CL00047720 Insertion Variant)
QSEPELKLESVVIVSRHGVRAPTKATQLMQDVTPDAWPTWPVKLGWLTPRGGELVAYLGQYQRQ
RLVANGLLADKGCPQPGQVAIIADVDERTRKTGEAFAAGLAPDCAITVHTQADTSRPDPLFNPL
KTGVCQLDPANVTLAILSRAVDPANVTHAILSRAGGSIADFTQHYQTAFRELERVLNFPQSNLC
FNREKQDESCSLTQALPSELKVSADNVSLTGAVSLASMLTEIFLLQQAQGMPEPGWGRITDSHQ
WNTLLSLHNAQFDLLQRTPEVARSRATPLLDLIMAALTPHPPQKQAYGVTLPTSVLFIAGHDTN
LANLGGALELNWTLPGQPDNTPPGGELVFERWRRLSDNSQWIQVSLVYQTLQQMRDKTPLSLNT
PPGEVKLTLPGCEERNAQGMCSLAGFTQIVNEARIPACSL >SEQ ID NO:15 (Insertion in CL00047720)
VDPANVTHAILSRA >SEQ ID NO:16 (Insertion in CL00047720)
PANVTLAILSRAVD
```

FIGURE 9J

```
>SEQ ID NO:17 (Wild type, G1P protein)
QSEPELKLESVVIVSRHGVRAPTKATQLMQDVTPDAWPTWPVKLGWLTPRGGELIAYLGHYQRQ
RLVADGLLAKKGCPQPGQVAIIADVDERTRKTGEAFAAGLAPDCAITVHTQADTSSPDPLFNPL
KTGVCQLDNANVTDAILSRAGGSIADFTGHRQTAFRELERVLNFPQSNLCFNREKQDESCSLTQ
ALPSELKVSADNVSLTGAVSLASMLTEIFLLQQAQGMPEPGWGRITDSHQWNTLLSLHNAQFYL
LQRTPEVARSRATPLLDLIMAALTPHPPQKQAYGVTLPTSVLFIAGHDTNLANLGGALELNWTL
PGQPDNTPPGGELVFERWRRLSDNSQWIQVSLVFQTLQQMRDKTPLSLNTPPGEVKLTLAGCEE
RNAQGMCSLAGFTQIVNEARIPACSL
```

ADDITIONAL PHYTASE VARIANTS AND METHODS

CROSS REFERENCE TO RELATED APPLICATIONS

This application claims priority to U.S. Provisional Patent Application No. 62/821,649, filed on Mar. 21, 2019, which is expressly incorporated by reference in its entirety.

SEQUENCE LISTING

The instant application contains a Sequence Listing which has been submitted electronically in ASCII format and is hereby incorporated by reference in its entirety. Said ASCII copy, created on Sep. 4, 2019, is named 114095-5010-US_WO_ST25.txt and is 77 kilobytes in size.

BACKGROUND OF THE INVENTION

Phytate is the major but indigestible form of phosphorus found in plant-based feeds. It is considered as an anti-nutritional factor (ANF) that needs to be reduced or removed from cereal-based foods and feeds. Under acidic conditions, phytate interacts with positively charged dietary proteins leading to the formation of phytate-protein aggregates and precipitates, which results in a decreased accessibility for proteases, and consequently in inefficient protein digestion. Phytate also acts as a strong chelating agent that binds different vital metal ions in foods and feeds in the small intestine of monogastric organisms, leading to nutritional deficiencies of many important minerals like calcium, zinc, etc. in animals.

Phytase is a phosphatase that catalyzes the hydrolysis of O—P bonds in phytate and releases inorganic usable phosphorous. Phytase plays versatile roles in agricultural and feeding fields. Ruminant animals such as cattle and sheep can utilize the phytate in grains as a source of phosphorus since they have bacteria in the gut that produces phytases. Non-ruminants like pigs, poultry, fish, dogs, birds, etc. require extrinsic phytase to liberate inorganic phosphorous. Hence, addition of inorganic phosphorous, a non-renewable and expensive mineral, to feeds for monogastric animals is a common practice, which incurs heavy costs to the feed industry. Consequently, phytase produced from various sources have emerged as one of the most effective and lucrative supplement to these species' diets to enhance the nutritional value of animal feeds and decrease animals' phosphorus excretion that leads to environmental pollution.

Phytase in feeds can be inactivated by temperature during feed processing (pelleting), by the low pH or pepsin in the upper part of the gastrointestinal tract of an animal. Selle and Ravindran laid out the characteristics for an ideal feed enzyme, namely; 1) a high specific activity per unit of protein, 2) good thermostability during feed processing, 3) high activity in the typical pH range of the animal gut, 4) resistance to gastric proteases, and 5) good stability under ambient temperatures. (SELLE, P. H. and RAVINDRAN, V. (2007) Microbial phytase in poultry nutrition. Animal Feed Science and Technology 135: 1-41.)

The heat treatment of feeds can involve heat alone or a combination of both heat and pressure. The most common form of thermal treatment in the manufacture of poultry feeds is pelleting. The pelleting process first involves the mash feed passing through a conditioner. In the conditioner the cold feed is exposed to dry steam which is added under pressure. This process helps to improve pellet durability and also increases mill throughputs and reduces energy consumption. Under these conditions, plant cells are crushed, which is favorable for the digestion process in animals. Nissinen found that moderate conditioning less than 85° C. was optimal for broiler performance and high conditioning temperature at 95° C. resulted in poorer body weight gain and feed conversion ratio (NISSINEN, V. (1994) The effects and interactions of enzymes and hydrothermal pre-treatments and their contribution to feeding value. International Milling Flour and Feed, May: 21-22). Pelleting process at 65-85° C. usually result in improving the availability of nutrients due to the rupture of the cell wall matrix (PICKFORD, J. R. (1992) Effects of processing on the stability of heat labile nutrients in animal feeds, in: GARNSWORTHY, P. C., HARESIGN, W. & COLE, D. J. A. (Eds) Recent Advances in Animal Nutrition, pp. 177-192 (Butterworth-Heinemann, Oxford, U.K.) and deactivation of enzyme inhibitors present in cereals (SAUNDERS, R. M. (1975) α-Amylase inhibitors in wheat and other cereals. Cereal Foods World 20: 282-285). The effect of the damage on the phytase activity due to high pressure appears to be small; it is mainly the high temperature which results from the high energy input that inactivates the enzyme. Thus, developing a thermostable Phytase provides an attractive solution for cost-effective processes in the feed industry.

New applications of phytase in human foods are similarly important as those in animal feeds because indigestible phytate chelates essential minerals and contributes to deficiencies of these nutrients in approximately two to three billion people. The applications of phytase in human health and medicine represent other new exciting areas. In addition, phytase has great potentials for industrial applications including food processing and biofuel production. Thermostable phytase, along with xylanase, have been suggested as effective additives in the pulp and paper industry.

BRIEF SUMMARY OF THE INVENTION

Accordingly, the present invention provides variant phytases and methods of producing and using them. The amino acid sequence numbers of the present invention are listed in Table 1.

TABLE 1

Amino acid sequence numbers.

| | |
|---|---|
| CL00005023 (G3P) | SEQ ID NO: 1 |
| CL00048541 (G4P) | SEQ ID NO: 2 |
| CL00060516 (G5P) | SEQ ID NO: 3 |
| CL00080812 (G6P) | SEQ ID NO: 4 |
| CL00082400 | SEQ ID NO: 5 |
| CL00089395 | SEQ ID NO: 6 |
| CL00090520 | SEQ ID NO: 7 |
| CL00100223 | SEQ ID NO: 8 |
| CL00102257 | SEQ ID NO: 9 |
| CL00102259 | SEQ ID NO: 10 |
| CL00071716 | SEQ ID NO: 11 |
| CL00100225 | SEQ ID NO: 12 |
| CL00102276 | SEQ ID NO: 13 |
| CL00047720 | SEQ ID NO: 14 |
| VDPANVTHAILSRA (an insertion in CL00047720 w.r.t. G3P) | SEQ ID NO: 15 |
| PANVTLAILSRAVD (an insertion in CL00047720 w.r.t. G3P) | SEQ ID NO: 16 |
| G1P (wild type) | SEQ ID NO: 17 |

In one aspect, the invention provides compositions comprising a variant phytase enzyme that has at least 90%, at least 95%, at least 96%, at least 97%, at least 98%, or at least 99% sequence identity to SEQ ID NO:1, wherein said variant phytase enzyme has phytase activity and is not SEQ ID NO:17.

In another aspect, the invention provides compositions comprising a variant phytase enzyme comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme is at least 90% identical to SEQ ID NO:1 and is not SEQ ID NO:17; and wherein said variant phytase enzyme has phytase activity.

In a further aspect, the invention provides compositions comprising a variant phytase enzyme comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme has at least 1.01 fold better phytase activity as compared to SEQ ID NO:1 under a condition comprising 37° C., pH 5.5; and wherein said variant phytase enzyme is at least 90% identical to SEQ ID NO:1 and is not SEQ ID NO:17.

In another aspect, the invention provides compositions comprising a variant phytase enzyme comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, and wherein said variant phytase enzyme has at least 1.01 fold better activity as compared to SEQ ID NO:1 under a condition selected from the group consisting of thermochallenge at about 75° C., thermochallenge at about 80° C., thermochallenge at about 85° C., and thermochallenge at about 90° C.; and wherein said variant phytase enzyme is at least 90% identical to SEQ ID NO:1 and is not SEQ ID NO:17. In some embodiment, the variant phytase enzyme has at least 1.01 fold better phytase activity as compared to SEQ ID NO:1 under the condition further comprising the thermostability in the presence of Bovine Serum Albumin (BSA).

In an additional aspect, the invention provides compositions comprising a variant phytase enzyme comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme has at least 1.01 fold better phytase activity as compared to SEQ ID NO:1 under a condition selected from the group consisting of tolerance against pH 2.0, tolerance against pH 2.5, tolerance against pH 3.0, tolerance against pH 3.5, and tolerance against pH 4.0; and wherein said variant phytase enzyme is at least 90% identical to SEQ ID NO:1 and is not SEQ ID NO:17.

In another aspect, the invention provides compositions comprising a variant phytase enzyme comprising at least one amino acid substitution as compared to SEQ ID NO:1 as described herein, wherein said variant phytase enzyme exhibits at least 95%, at least 96%, at least 97%, at least 98%, or at least 99% sequence identity to SEQ ID NO:1.

In a further aspect, the invention provides variant phytase enzymes with amino acid substitutions at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions or twenty of said positions.

In an additional aspect, the invention provides compositions comprising said variant phytase enzymes comprising the amino acid substitution(s) selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, M276K, A277T, L279F, T280C, T280G, T280N, T280P, P281D, P281S, H282N, A288R, T292G, T295N, G302S, G311A, E315G, E315S, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

In a further aspect, the invention provides compositions comprising variant phytase enzymes comprising at least one amino acid substitution as compared to SEQ ID NO:1, wherein said amino acid substitution(s) is selected from the group consisting of A277T, P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, V67A, G70E, L72S, K75C, K75E, K75G, K75I, K75L, K75M, K75Q, K75R, K75S, K75W, G76C, P80S, V89T, D90N, I110L, H113Q, T114C, T114D, T114F, T114H, T114N, T114P, T114S, S119R, R120K, P121A, T130G, T130R, Q134A, Q134T, L135F, L135Y, D136F, D136G, D136S, P137C, P137F, P137G, P137H, P137I, P137L, P137M, P137V, P137W, P137Y, D142A, D142E, D142F, D142G, D142H, D142I, D142K, D142L, D142M, D142N, D142P, D142R, D142S, D142T, D142V, D142Y, S151F, S151R, A153N, A153S, A153V, A153Y, Q157A, Q157P, H158R, H158W, T161D, E165D, E165P, E165S, E165T, E165W, P173N, P173S, P173T, P173Y, Q174A, Q174E, F179L, R181T, E182A, E182F, E182S, E182T, S187T, T191S, Q192K, Q192L, A193I, A193L, A193S, A193T, A193V, L194I, E197S, A202R, Q225E, P230S, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, L279F, T280C, T280G, T280N, T280P, P281D, P281S, T292G, G302S, L316F, T364C, T364E, T364I, T364L, T364N, T364Q, T364S, T364T, T364V, T364W, P365W, L366R, P371M, P371V, P371W, P371Y, P372T, T378A, G381A, G381C, G381L, G381N, G381R, E384D, A394I, A394L, A394M, A394P, G395P, Q398V, N401A, N401L, N401P, A403G, A403I, A403K, A403L, A403N, A403Q, A403W, A403Y, S409H, S409L, S409R, S409V, S409W, L410A, L410C, L410E, L410F, L410G, L410I, L410K, and L410R;

wherein said variant phytase enzyme is at least 90% identical to SEQ ID NO:1 and is not SEQ ID NO:17; and wherein said variant phytase enzyme has phytase activity.

In an additional aspect, the invention provides compositions comprising said variant phytase enzyme further comprising at least one amino acid substitution, and wherein said amino acid substitution(s) is selected from the group consisting of Q1S, Q1V, Q1N, Q30K, A36K, T39D, H60S, K74P, K74L, R65C, R65G, R65P, R65S, R65V, N69L, N69R, N69Y, A73P, Q79L, Q79R, Q79A, Q79G, Q79F, I85V, A101L, A109D, A109D, A109E, A109G, A109F, A109P, T111I, A116Y, A116P, A116R, A116S, T118R, T118S, R120S, P137N, P137S, A138V, A138H, A138D, A138P, N139A, N139H, N139P, T141E, T141G, T141A, T141R, S146E, S146P, Q157G, N176K, N180K, K183R, Q184S, D185N, E186V, E186A, S189L, S189N, S189T, G233A, T245E, M276K, H282N, A288R, V291I, T295N, V297L, G311A, E315G, E315S, R339M, L341V, Q346K, Q346P, Q346S, Q346T, L352M, D362G, D362N, D362S, D362Y, K363A, K363R, N369P, T370K, A380R, A380T, E383S, R385T, and E402D.

In a further aspect, the invention provides compositions comprising said variant phytase enzymes comprising the amino acid substitutions selected from the group consisting of G70E/A73P/K75C/A277T, Q62W/A73P/G302S, Q62W/A73P/A288R/E315G, G70E/A73P/K75C, W46E/Q62W/S146E/E402D, W46E/Q62W/A73P/N180K/M276K/A277T/E402D, Q62W/A277T/E315G, Q62W/A288R, G70E/P80S/E315G, W46E/Q62W/A73P, M276K/A288R, G70E/A73P/E402D, W46E/Q62W/E315G, W46G/A277T/A288R, W46E/Q62W, W46E/G70E/E315G, Q62W/G70E/F179L/A277T/A288R, W46E/Q62W/P80S/H113Q/E315G/E402D, M276K/E315G, M276K/A277T, K75W/M276K/A288R, W46E/Q62W/A73P/K75C/A277T/A288R/E315G, W46E/Q62W/N180K/E315G, M276K/A288R/E315G, W46E/Q62W/F179L/M276K, W46E/Q62W/M276K, A277T/A288R/E402D, W46G/Q62W/A73P/S146E/A277T, N180K/M276K/A277T/E315G/E402D, G70E/A73P/M276K/E315G, M276K/E315G/E402D, W46E/Q62W/K75C/F179L/A277T, P80S/M276K/E315G, G70E/A288R, M276K/A277T/E315G/E402D, Q62W/P80S/M276K, M276K/A277T/E315G, G70E/A73P/M276K, W46E/Q62W/P80S, W46E/G70E/K75C/A288R, Q62W/P80S/A277T, N180K/M276K/E315G/E402D, F179L/A277T/A288R, Q62W/A73P/P80S/A288R, A73P/E402D, Q62W/A73P/E402D, P137H/L316F, P4L/T280C, T238S/P372T, P4T/T280P, P4K/T280N, T364V/P371M, P4M/T280G, D35Y/T238G, L272S/A403Y, A193T/E384D, L58S/S409R, A153Y/Q157P/E165D/P261L, L72S/L410F, K7N/D35R/V67A/P173N/T238G/M276K/A277T/E315G/T364W/G381A/A403G, P4N/K7N/D35N/V67A/P121A/D136S/P173N/T238G/M276K/A277T/E315G/Q346S/T364W/T378A/G381A/A403G, K7N/D35R/V67A/P121A/D136S/P173N/T238G/M276K/A277T/E315G/Q346S/T364W/T378A/G381A/A403G, P4N/K7N/D35R/V67A/P121A/D136S/P173N/T238G/M276K/A277T/E315G/T364W/T378A/G381A/A403G, P4N/K7N/D35N/V67A/P121A/D136S/P173N/T238G/M276K/A277T/E315G/T364W/T378A/G381A/A403G, and K7N/D35R/V67A/P173N/T238G/M276K/A277T/E315G/Q346T/T364W/G381A/A403G/L410A.

In an additional aspect, the invention provides compositions comprising said variant phytase enzymes comprising the amino acid substitutions M276K/A277T/E315G and at least one further amino acid substitution selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238M, T238N, T238P, T238Q, T238R, T238S, T238Y, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

In a further aspect, the invention provides compositions comprising said variant phytase enzymes comprising the amino acid substitutions selected from the group consisting of M276K/A277T/E315G/A73P/A288R, M276K/A277T/E315G/A288R, M276K/A277T/E315G/Q62W/A288R, M276K/A277T/E315G/Y61C/Q62W/A73P, M276K/A277T/E315G/A73P, M276K/A277T/E315G/Q62W, M276K/A277T/E315G/Q62W/A73P/A288R, M276K/A277T/E315G/K7N/D35R, M276K/A277T/E315G/K7N/D35R/P173Y/T364I, M276K/A277T/E315G/K7N/D35R/Q192K, M276K/A277T/E315G/K7N/D35R/P173Y/T364W, M276K/A277T/E315G/K7N/Q192L/T238A/T364W, M276K/A277T/E315G/K7N/Q192K/T364W/T370K, M276K/A277T/E315G/K7N/V67A/T238A/T364I, M276K/A277T/E315G/K7N/Q192L/T364I, M276K/A277T/E315G/K7N/V67A/Q192K/T364W, M276K/A277T/E315G/K7N/T238G/T364W, M276K/A277T/E315G/K7N/T238A, M276K/A277T/E315G/K7N/P173Y/Q192K/A403G, M276K/A277T/E315G/K7N/D35R/V67A/T238G/T364I/G381A/A403G, M276K/A277T/E315G/K7N/V67A/P173Y/T238A/T364I, M276K/A277T/E315G/K7N/V67A/T364I, M276K/A277T/E315G/K7N/P173Y, M276K/A277T/E315G/K7N/P173Y/A403G, M276K/A277T/E315G/K7N/V67A/Q192K, M276K/A277T/E315G/K7N/V67A/G381L, M276K/A277T/E315G/K7N, M276K/A277T/E315G/K7N/P173Y/Q192K/T364I, M276K/A277T/E315G/K7N/V67A/P173Y, M276K/A277T/E315G/K7N/V67A, M276K/A277T/E315G/K7N/T364I/G381L, M276K/A277T/E315G/K7N/P173Y/G381L, M276K/A277T/E315G/S146P, M276K/A277T/E315G/V67A/T364I, M276K/A277T/E315G/P173N/T364W, M276K/A277T/E315G/V67A/T238G/G381A, M276K/A277T/E315G/T238G, M276K/A277T/E315G/P173S, M276K/A277T/E315G/T238N/T364W, M276K/A277T/E315G/T238A/T364W, M276K/A277T/E315G/V67A, M276K/A277T/E315G/T364W/G381A, M276K/A277T/E315G/V67A/T238A/T364W, M276K/A277T/E315G/V67A/T364W, M276K/A277T/E315G/T364W, M276K/A277T/E315G/T238A/T364W/G381A, M276K/A277T/E315G/T364I, M276K/A277T/E315G/V67A/P173N/T238A/T364W, M276K/A277T/E315G/P173N/T238N, M276K/A277T/E315G/P173T, M276K/A277T/E315G/V67A/T238A, M276K/A277T/E315G/P173T/G381A, M276K/A277T/E315G/S119R/L279F, M276K/A277T/E315G/N244I/T280N, M276K/A277T/E315G/T238P/T280N/P371Y/A403W, M276K/A277T/E315G/S119R/A403K, M276K/A277T/E315G/T280N/P371Y/A403W, M276K/A277T/E315G/S119R/P371Y/A403K, M276K/A277T/E315G/T280N/A403K, M276K/A277T/E315G/T280N, M276K/A277T/E315G/T280N/P371Y, M276K/A277T/E315G/T238Y, M276K/A277T/E315G/T238P/P371Y, M276K/A277T/E315G/P371Y/A403W, M276K/A277T/E315G/S119R/T280N, M276K/A277T/E315G/T238P, M276K/A277T/E315G/S119R/P371Y/A403L, M276K/A277T/E315G/P371Y/A403L, M276K/A277T/E315G/S119R, M276K/A277T/E315G/T238Y/A403W, M276K/A277T/E315G/S119R/T280N/P371Y, M276K/A277T/E315G/A403W, M276K/A277T/E315G/R65/L410R, M276K/A277T/E315G/Q346T/S409V/L410A, M276K/A277T/E315G/E182T/D362G, M276K/A277T/E315G/E182S/S187T/P281S, M276K/A277T/E315G/D362G/S409V, M276K/A277T/E315G/P281S/S409H, M276K/A277T/E315G/E182T/A202R, M276K/A277T/E315G/R65G/S187T/Q346T, M276K/A277T/E315G/P281S/Q346T, M276K/A277T/E315G/E182S/P281S, M276K/A277T/E315G/P281S, M276K/A277T/E315G/S187T/Q346T/L410A, M276K/A277T/E315G/R65G/P281S/S409V, M276K/A277T/E315G/D31N, M276K/A277T/E315G/D31N/D362G/L410A, M276K/A277T/E315G/Q346T/L410A, M276K/A277T/E315G/P281S/Q346S, M276K/A277T/E315G/D31N/P281S/Q346T, M276K/A277T/E315G/S409H/L410A, M276K/A277T/E315G/D31N/Q346P, M276K/A277T/E315G/E182S/S187T, M276K/A277T/E315G/R65G/P281S, M276K/A277T/E315G/A202R/P281S/D362G/L410R, M276K/A277T/E315G/D31N/R65G/S187T/S409V/L410A, M276K/A277T/E315G/D31N/P281S/Q346S/D362G/K363R/S409H, M276K/A277T/E315G/Q346S, M276K/A277T/E315G/E182S/Q346S, M276K/A277T/E315G/N401P, M276K/A277T/E315G/P4N/N401P, M276K/A277T/E315G/T292G/T378A, M276K/A277T/E315G/D362G/N401P, M276K/A277T/E315G/E182A/T292G, M276K/A277T/E315G/P4N/T292G, M276K/A277T/E315G/P4N/D362G/G395P, M276K/A277T/E315G/G395P, M276K/A277T/E315G/P4N/G395P, M276K/A277T/E315G/P4N, M276K/A277T/E315G/P4N/I110L/G395P, M276K/A277T/E315G/P4N/D31I, M276K/A277T/E315G/P4N/D31I/E182A, M276K/A277T/E315G/D31I, M276K/A277T/E315G/P4N/S240G, M276K/A277T/E315G/P4N/I110L/S240R, M276K/A277T/E315G/D31I/S240A/N401P, M276K/A277T/E315G/T378A, M276K/A277T/E315G/D31I/S240A/D362G, M276K/A277T/E315G/G76C/A394M, M276K/A277T/E315G/R65G/E165P/Q242E, M276K/A277T/E315G/R65S/E165P/D362S, M276K/A277T/E315G/R65G/A193I/Q346P, M276K/A277T/E315G/Q242E/Q346P, M276K/A277T/E315G/R65G/E165P/D362S, M276K/A277T/E315G/R65P/E165P, M276K/A277T/E315G/R65S/E165P, M276K/A277T/E315G/R65S/E165P/Q242E/A394M, M276K/A277T/E315G/R65G/E165P, M276K/A277T/E315G/R65C/A193S/A394P, M276K/A277T/E315G/R65G/Q346P, M276K/A277T/E315G/R65S/E165P/Q242E/D362S, M276K/A277T/E315G/R65G, M276K/A277T/E315G/R65S, M276K/A277T/E315G/R65S/E165P/D362S/A394P, M276K/A277T/E315G/Q346P, M276K/A277T/E315G/Q242E, M276K/A277T/E315G/R65S/E165P/S240K, M276K/A277T/E315G/R65S/E165P/G381R, M276K/A277T/E315G/R65S/A394I, M276K/A277T/E315G/E165P/S240K/D362S, M276K/A277T/E315G/R65G/Q242E, M276K/A277T/E315G/Q242E/A394P, M276K/A277T/E315G/R65G/D362S, M276K/A277T/E315G/R65S/E165P/Q346P, M276K/A277T/E315G/R65G/S240K/Q242E, M276K/A277T/E315G/A394L, M276K/A277T/E315G/E5K/A153S/P281S/S409L, M276K/A277T/E315G/E5K/P281S/S409H, M276K/A277T/E315G/S151F/

A153S/P281S/L410G, M276K/A277T/E315G/A153N/P281S, M276K/A277T/E315G/E5K/P281S, M276K/A277T/E315G/A5K, M276K/A277T/E315G/P281S/L410R, M276K/A277T/E315G/P281S/Q346K/S409L/L410G, M276K/A277T/E315G/E5K/V11I/Q346K, M276K/A277T/E315G/V11I/P281S, M276K/A277T/E315G/A153S, M276K/A277T/E315G/E5K/P365W, M276K/A277T/E315G/E5K/P281S/L410G, M276K/A277T/E315G/E5K/T111I/P281S/P365W, M276K/A277T/E315G/E5K/A153N/P281S, M276K/A277T/E315G/E5K/A153N/P281S/Q346K, M276K/A277T/E315G/Q346K, M276K/A277T/E315G/A153N/S409L, M276K/A277T/E315G/E5K/A153N/P281S/L410G, M276K/A277T/E315G/K7E/S409H, M276K/A277T/E315G/E5K/A153N/P281S/S409R, M276K/A277T/E315G/E5K/P281S/L410I and M276K/A277T/E315G/E5K/A153S/P281S.

In an additional aspect, the invention provides compositions comprising said variant phytases comprising the amino acid substitutions M276K/A277T/E315G/K7N/D35R/V67A/T238G/T364I/G381A/A403G and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In a further aspect, the invention provides compositions comprising said variant phytases comprising amino acid substitutions selected from the group consisting of M276K/A277T/E315G/K7N/D35R/V67A/T238G/T364I/G381A/A403G/P121A, M276K/A277T/E315G/K7N/D35R/V67A/T238G/T364I/G381A/A403G/D136G, M276K/A277T/E315G/K7N/D35R/V67A/T238G/T364I/G381A/A403G/T130G, M276K/A277T/E315G/K7N/D35R/V67A/T238G/T364I/G381A/A403G/Q174E, M276K/A277T/E315G/K7N/D35R/V67A/T238G/T364I/G381A/A403G/Q174A, M276K/A277T/E315G/K7N/D35R/V67A/T238G/T364I/G381A/A403G/Q27D, M276K/A277T/E315G/K7N/D35R/V67A/T238G/T364I/G381A/A403G/Q134A, M276K/A277T/E315G/K7N/D35R/V67A/T238G/T364I/G381A/A403G/T161D, M276K/A277T/E315G/K7N/D35R/V67A/T238G/T364I/G381A/A403G/T130R, M276K/A277T/E315G/K7N/D35R/V67A/T238G/T364I/G381A/A403G/Q27P, M276K/A277T/E315G/K7N/D35R/V67A/T238G/T364I/G381A/A403G/E53N, M276K/A277T/E315G/K7N/D35R/V67A/T238G/T364I/G381A/A403G/D136F, M276K/A277T/E315G/K7N/D35R/V67A/T238G/T364I/G381A/A403G/S151R, M276K/A277T/E315G/K7N/D35R/V67A/T238G/T364I/G381A/A403G/Q27V, M276K/A277T/E315G/K7N/D35R/V67A/T238G/T364I/G381A/A403G/Q134T, M276K/A277T/E315G/K7N/D35R/V67A/T238G/T364I/G381A/A403G/E53D, M276K/A277T/E315G/K7N/D35R/V67A/T238G/T364I/G381A/A403G/D136S, M276K/A277T/E315G/K7N/D35R/V67A/T238G/T364I/G381A/A403G/T295N, M276K/A277T/E315G/K7N/D35R/V67A/T238G/T364I/G381A/A403G/S189L, M276K/A277T/E315G/K7N/D35R/V67A/T238G/T364I/G381A/A403G/S189T, M276K/A277T/E315G/K7N/D35R/V67A/T238G/T364I/G381A/A403G/T191S, M276K/A277T/E315G/K7N/D35R/V67A/T238G/T364I/G381A/A403G/P230S, M276K/A277T/E315G/K7N/D35R/V67A/T238G/T364I/G381A/A403G/S189N, M276K/A277T/E315G/K7N/D35R/V67A/T238G/T364I/G381A/A403G/E197S, M276K/A277T/E315G/K7N/D35R/V67A/T238G/T364I/G381A/A403G/L194I, M276K/A277T/E315G/K7N/V67A/T238G/T364I/G381A/A403G/P4N/T378A, M276K/A277T/E315G/K7N/D35R/V67A/T238G/T364I/G381A/A403G/S409V, M276K/A277T/E315G/K7N/D35R/V67A/T238G/T364I/G381A/A403G/T378A, M276K/A277T/E315G/K7N/D35R/V67A/T238G/T364I/G381A/A403G/P4N, M276K/A277T/E315G/K7N/V67A/T238G/T364I/G381A/A403G/T378A, M276K/A277T/E315G/K7N/V67A/T238G/T364I/G381A/A403G, M276K/A277T/E315G/K7N/V67A/T238G/T364I/G381A/A403G/P4N, M276K/A277T/E315G/K7N/V67A/T238G/T364I/G381A/A403G/T111I, M276K/A277T/E315G/K7N/D35R/V67A/T238G/T364I/G381A/A403G/P4N/T378A, M276K/A277T/E315G/K7N/D35R/V67A/T238G/T364I/G381A/A403G/P173S/E182S, M276K/A277T/E315G/K7N/D35R/V67A/T238G/T364I/G381A/A403G/P173S/E182T/Q346T, M276K/A277T/E315G/K7N/D35R/V67A/T238G/T364I/G381A/A403G/P173S/E182T, M276K/A277T/E315G/K7N/D35R/V67A/T238N/T364I/G381A/A403G/P173S/E182T/S187T, M276K/A277T/E315G/K7N/D35R/V67A/T238N/T364I/G381A/A403G/E182S, M276K/A277T/E315G/K7N/D35R/V67A/T238N/T364I/G381A/A403G/Q346T, M276K/A277T/E315G/K7N/D35R/V67A/T238G/T364I/G381A/A403G/Q346S, M276K/A277T/E315G/K7N/D35R/V67A/T238N/T364I/G381A/A403G/E182T/Q346S, M276K/A277T/E315G/K7N/D35R/V67A/T238N/T364I/G381A/A403G/P173S, M276K/A277T/E315G/K7N/D35R/V67A/T238N/T364I/G381A/A403G/E182T, M276K/A277T/E315G/K7N/D35R/V67A/T238N/T364I/G381A/A403G/P173S/E182T, M276K/A277T/E315G/K7N/D35R/V67A/T238N/T364I/G381A/A403G/P173S/E182S, M276K/A277T/E315G/K7N/D35R/V67A/T238G/T364I/G381A/A403G/E182S, M276K/A277T/E315G/K7N/D35R/V67A/T238G/T364I/G381A/A403G/Q346T, M276K/A277T/E315G/K7N/D35R/V67A/T238G/T364I/G381A/A403G/P173S/Q346T, M276K/A277T/E315G/K7N/D35R/V67A/T238G/T364I/G381A/A403G/R65S, M276K/A277T/E315G/K7N/D35R/V67A/T238G/T364I/G381A/A403G/A153N, and M276K/A277T/E315G/K7N/D35R/V67A/T238G/T364I/G381A/A403G/K363R.

In an additional aspect, the invention provides compositions comprising said variant phytases comprising amino acid substitutions K7N/D35R/V67A/P173N/T238G/ M276K/A277T/E315G/T364W/G381A/A403G and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In a further aspect, the invention provides compositions comprising said variant phytases comprising amino acid substitutions selected from the group consisting of K7N/D35R/V67A/P173N/T238G/M276K/A277T/E315G/T364W/G381A/A403G/N176K/D185N/H282N/A288R/R385T, K7N/D35R/V67A/P173N/T238G/M276K/A277T/E315S/T364W/G381A/A403G/N139A/D185N/R385T, K7N/D35R/V67A/P173N/T238G/M276K/A277T/E315G/T364W/G381A/A403G/N139H/N176K/D185N/A288R, K7N/D35R/V67A/P173N/T238G/M276K/A277T/E315G/T364W/G381A/A403G/T161D/A288R, K7N/D35R/V67A/P173N/T238G/M276K/A277T/E315G/T364W/G381A/A403G/N139H/N176K/D185N, K7N/D35R/V67A/P173N/T238G/M276K/A277T/E315G/T364W/G381A/A403G/N139A/T161D/N176K/D185N, K7N/D35R/V67A/P173N/T238G/M276K/A277T/E315G/T364W/G381A/A403G/D185N/H282N, K7N/D35R/V67A/P173N/T238G/M276K/A277T/E315G/T364W/G381A/A403G/N139P/N176K/D185N/K363A, K7N/D35R/V67A/P173N/T238G/M276K/A277T/E315G/T364W/G381A/A403G/D185N, K7N/D35R/V67A/P173N/T238G/M276K/A277T/E315G/T364W/G381A/A403G/D185N/R385T, K7N/D35R/V67A/P173N/T238G/M276K/A277T/E315G/T364W/G381A/A403G/A288R, K7N/D35R/V67A/P173N/T238G/M276K/A277T/E315G/T364W/G381A/A403G/R385T, K7N/D35R/V67A/P173N/T238G/M276K/A277T/E315G/T364W/G381A/A403G/D185N/H282N/L341V/R385T, K7N/D35R/V67A/P173N/T238G/M276K/A277T/E315G/T364W/G381A/A403G/H282N, K7N/D35R/V67A/P173N/T238G/M276K/A277T/E315G/T364W/G381A/A403G/N139A/D185N/H282N/A288R/K363A/R385T, K7N/D35R/V67A/P173N/T238G/M276K/A277T/E315G/T364W/G381A/A403G/N176K/D185N K7N/D35R/V67A/P173N/T238G/M276K/A277T/E315G/T364W/G381A/A403G/N139A/N176K/D185N, K7N/D35R/V67A/P173N/T238G/M276K/A277T/E315G/T364W/G381A/A403G/N176K/L341V, K7N/D35R/V67A/P173N/T238G/M276K/A277T/E315G/T364W/G381A/A403G/D185N/H282N/A288R, K7N/D35R/V67A/P173N/T238G/M276K/A277T/E315G/T364W/G381A/A403G/N139A/N176K/D185N/L341V, K7N/D35R/V67A/P173N/T238G/M276K/A277T/E315G/T364W/G381A/A403G/T161D/D185N, K7N/D35R/V67A/P173N/T238N/M276K/A277T/E315G/T364W/G381A/A403G/P4N/T378A, K7N/D35R/V67A/P173N/T238G/M276K/A277T/E315G/T364W/G381A/A403G/P4N/D136F/E197S/T378A, K7N/D35R/V67A/P173N/T238N/M276K/A277T/E315G/T364W/G381A/A403G/P4N/E197S/T378A, K7N/D35R/V67A/P173N/T238G/M276K/A277T/E315G/T364W/G381A/A403G/P4N/Q346S, K7N/D35R/V67A/P173N/T238N/M276K/A277T/E315G/T364W/G381A/A403G/P4N/P121A/E 182T/E197S/Q346S/T378A, K7N/D35R/V67A/P173N/T238N/M276K/A277T/E315G/T364W/G381A/A403G/P4N/D136S/E182T/T378A, K7N/D35R/V67A/P173N/T238N/M276K/A277T/E315G/T364W/G381A/A403G/P4N/P121A/D 136F/E182S/Q346S, K7N/D35R/V67A/P173N/T238N/M276K/A277T/E315G/T364W/G381A/A403G/P4N/P121A/E 197S, K7N/D35R/V67A/P173N/T238N/M276K/A277T/E315G/T364W/G381A/A403G/P4N/E197S/Q346S, K7N/D35R/V67A/P173N/T238N/M276K/A277T/E315G/T364W/G381A/A403G/P4N/Q346S, K7N/D35R/V67A/P173S/T238N/M276K/A277T/E315G/T364W/G381A/A403G/P4N/D136S/E182S/Q346S, K7N/D35R/V67A/P173S/T238N/M276K/A277T/E315G/T364W/G381A/A403G/P4N/D136S/E182S/Q346S/T378A, K7N/D35R/V67A/P173N/T238N/M276K/A277T/E315G/T364W/G381A/A403G/P4N/D136S/E182T, K7N/D35R/V67A/P173N/T238N/M276K/A277T/E315G/T364W/G381A/A403G/P4N/E197S/Q3 46S/T378A, K7N/D35R/V67A/P173N/T238G/M276K/A277T/E315G/T364W/G381A/A403G/E182T/E197S/T378A, K7N/D35R/V67A/P173N/T238N/M276K/A277T/E315G/T364W/G381A/A403G/Q346S, K7N/D35R/V67A/P173N/T238N/M276K/A277T/E315G/T364W/G381A/A403G/P4N/D136F/E 182T/E197S, K7N/D35R/V67A/P173N/T238G/M276K/A277T/E315G/T364W/G381A/A403G/P4N/P121A/D 136S/Q346S/T378A, K7N/D35R/V67A/P173N/T238N/M276K/A277T/E315G/T364W/G381A/A403G/P4N/D136S/E197S/Q346S/T378A, K7N/D35R/V67A/P173N/T238N/M276K/A277T/E315G/T364W/G381A/A403G/P4N/P121A/D 136S/E182T/T378A, K7N/D35R/V67A/P173S/T238N/M276K/A277T/E315G/T364W/G381A/A403G/P121A/D136S/E182S/E197S/T378A, K7N/D35R/V67A/P173N/T238G/M276K/A277T/E315G/T364W/G381A/A403G/Q62W/P80S/D 142E/A288R/E402D, K7N/D35R/V67A/P173N/T238G/M276K/A277T/E315G/T364W/G381A/A403G/W46E/Q62W/A73P/K75G/A288R/E402D, K7N/D35R/V67A/P173N/T238G/M276K/A277T/E315G/T364W/G381A/A403G/A288R/E402D, K7N/D35R/V67A/P173N/T238G/M276K/A277T/E315G/T364W/G381A/A403G/Q62W/A73P/K 75G/D142E/F179L/E402D, K7N/D35R/V67A/P173N/T238G/M276K/A277T/E315G/T364W/G381A/A403G/Q62W/A288R/E402D, K7N/D35R/V67A/P173N/T238G/M276K/A277T/E315G/T364W/G381A/A403G/Q62W/G70E/A73P/D142E/F179L/E402D, K7N/D35R/V67A/P173N/T238G/M276K/A277T/E315G/T364W/G381A/A403G/E402D, K7N/D35R/V67A/P173N/T238G/M276K/A277T/E315G/T364W/G381A/A403G/Q62W/G70E/K 75G/E402D, K7N/

D35R/V67A/P173N/T238G/M276K/A277T/E315G/
T364W/G381A/A403G/K75G/E402D, K7N/D35R/V67A/
P173N/T238G/M276K/A277T/E315G/T364W/G381A/
A403G/S146E/A288R, K7N/D35R/V67A/P173N/T238G/
M276K/A277T/E315G/T364W/G381A/A403G/Q62W/
P80S/D 142E/S146E/A288R/E402D, K7N/D35R/V67A/
P173N/T238G/M276K/A277T/E315G/T364W/G381A/
A403G/Q62W/D142E/S146E/E402D, K7N/D35R/V67A/
P173N/T238G/M276K/A277T/E315G/T364W/G381A/
A403G/D142E, K7N/D35R/V67A/P173N/T238G/M276K/
A277T/E315G/T364W/G381A/A403G/Q62W/E402D,
K7N/D35R/V67A/P173N/T238G/M276K/A277T/E315G/
T364W/G381A/A403G/A73P/P80S/D142E/Q346T, K7N/
D35R/V67A/P173N/T238G/M276K/A277T/E315G/
T364W/G381A/A403G/Q62W/G70E/K 75G/P80S/D142E/
E402D, K7N/D35R/V67A/P173N/T238G/M276K/A277T/
E315G/T364W/G381A/A403G/Q62W/D142E/E402D,
K7N/D35R/V67A/P173N/T238G/M276K/A277T/E315G/
T364W/G381A/A403G/Q62W/D142E/A288R/E402D,
K7N/D35Y/V67A/P173N/T238G/M276K/A277T/E315G/
T364W/G381A/A403G, K7Q/D35R/V67A/P173N/T238G/
M276K/A277T/E315G/T364W/G381A/A403G, K7N/
D35R/V67A/P173N/T238G/M276K/A277T/E315G/
T364C/G381A/A403G, K7N/D35R/V67A/P173N/T238G/
M276K/A277T/E315G/T364W/G381A/A403G/K75I,
K7N/D35N/V67A/P173N/T238G/M276K/A277T/E315G/
T364W/G381A/A403G, K7N/D35R/V67A/P173N/T238G/
M276K/A277T/E315G/T364Q/G381A/A403G, K7N/
D35R/V67A/P173N/T238G/M276K/A277T/E315G/
T364E/G381A/A403G, K7N/D35R/V67A/P173N/T238G/
M276K/A277T/E315G/T364W/G381A/A403G/H158W,
D35R/V67A/P173N/T238G/M276K/A277T/E315G/
T364W/G381A/A403G, K7N/D35R/V67A/P173N/T238G/
M276K/A277T/E315G/T364W/G381 L/A403G, K7N/
D35R/V67A/P173N/T238G/M276K/A277T/E315G/
T364W/G381N/A403G, K7N/D35R/V67A/P173N/T238G/
M276K/A277T/E315G/T364W/G381A/A403G/P1371,
K7N/D35R/V67A/P173N/T238G/M276K/A277T/E315G/
T364W/G381A/A403K, K7N/D35R/V67A/P173N/T238G/
M276K/A277T/E315G/T364S/G381A/A403G, K7N/
D35R/V67A/P173N/T238R/M276K/A277T/E315G/
T364W/G381A/A403G, K7N/D35R/V67A/P173N/T238G/
M276K/A277T/E315G/T364W/G381A/A403G/E165S,
K7N/D35R/V67A/P173N/T238G/M276K/A277T/E315G/
T364W/G381A/A403G/K75S, K7N/D35R/V67A/P173N/
T238G/M276K/A277T/E315G/T364W/G381A/A403L,
K7N/D35R/V67A/P173N/T238G/M276K/A277T/E315G/
T364W/G381A/A403G/E165T, K7N/D35F/V67A/P173N/
T238G/M276K/A277T/E315G/T364W/G381A/A403G,
K7N/D35R/V67A/P173N/T238G/M276K/A277T/E315G/
T364W/G381R/A403G, K7N/D35R/V67A/P173N/T238G/
M276K/A277T/E315G/T364W/G381A/A403N, K7S/
D35R/V67A/P173N/T238G/M276K/A277T/E315G/
T364W/G381A/A403G, K7N/D35R/V67A/P173N/T238Q/
M276K/A277T/E315G/T364W/G381A/A403G, K7N/
D35R/V67A/P173N/T238G/M276K/A277T/E315G/
T364N/G381A/A403G, K7N/D35R/V67A/P173N/T238G/
M276K/A277T/E315G/T364W/G381A/A403G/K75M,
K7N/D35R/V67A/P173N/T238G/M276K/A277T/E315G/
T364W/G381A/A403G/N69Y, K7N/D35R/V67A/P173N/
T238G/M276K/A277T/E315G/T364W/G381A/A403G/
K75R, K7N/D35R/V67A/P173N/T238G/M276K/A277T/
E315G/T364W/G381A/A403G/K75Q, K7N/D35R/V67A/
P173N/T238G/M276K/A277T/E315G/G381A/A403G,
K7N/V67A/P173N/T238G/M276K/A277T/E315G/
T364W/G381A/A403G, K7N/D35R/V67A/P173N/T238G/
M276K/A277T/E315G/T364W/G381A/A403G/R120K,
K7N/D35R/V67A/P173N/T238G/M276K/A277T/E315G/
T364W/G381A/A403G/V55L, K7N/D35E/V67A/P173N/
T238G/M276K/A277T/E315G/T364W/G381A/A403G,
K7N/D35R/V67A/P173N/T238G/M276K/A277T/E315G/
T364W/G381A/A403G/R120S, K7N/D35R/V67A/P173N/
T238G/M276K/A277T/E315G/T364W/G381A/A403Q,
K7N/D35R/V67A/P173N/T238G/M276K/A277T/E315G/
T364W/G381A/A403G/N69R, K7N/D35R/V67A/P173N/
T238G/M276K/A277T/E315G/T364V/G381A/A403G,
K7N/D35R/V67A/P173N/T238G/M276K/A277T/E315G/
T364W/G381A/A4031, K7N/D35R/V67A/P173N/T238G/
M276K/A277T/E315G/T364W/G381A/A403G/Q157G,
K7N/D35R/V67A/P173N/T238G/M276K/A277T/E315G/
T364W/G381A/A403G/Q157A, K7N/D35R/V67A/P173N/
T238G/M276K/A277T/E315G/T364W/G381A/A403G/
D142A, K7N/D35R/V67A/P173N/T238G/M276K/A277T/
E315G/T364W/G381A/A403G/N69L, K7L/D35R/V67A/
P173N/T238G/M276K/A277T/E315G/T364W/G381A/
A403G, K7N/D35R/V67A/P173N/T238G/M276K/A277T/
E315G/T364L/G381A/A403G, K7N/D35R/V67A/P173N/
T238N/M276K/A277T/E315G/T364W/G381A/A403G,
K7N/D35R/V67A/P173N/T238G/M276K/A277T/E315G/
T364W/G381A/A403G/D142R, K7N/D35R/V67A/P173N/
T238G/M276K/A277T/E315G/T364W/G381A/A403G/
L6F, K7N/D35R/V67A/P173N/T238G/M276K/A277T/
E315G/T364W/G381A/A403G/L135Y, K7N/D35R/V67A/
P173N/T238G/M276K/A277T/E315G/T364W/G381A/
A403G/S266A, K7N/D35R/V67A/P173N/T238G/M276K/
A277T/E315G/T364W/G381A/A403G/L135F, K7N/D35R/
V67A/P173N/T238G/M276K/A277T/E315G/T364W/
G381A/A403G/R63A, K7N/D35R/V67A/P173N/T238G/
M276K/A277T/E315G/T364W/G381A/A403G/L352M,
K7N/D35R/V67A/P173N/T238G/M276K/A277T/E315G/
T364W/G381A/A403G/R181T, K7N/D35R/V67A/P173N/
T238G/M276K/A277T/E315G/T364W/G381A/A403G/
S10A, K7N/D35R/V67A/P173N/T238G/M276K/A277T/
E315G/T364W/G381A/A403G/L6Y, K7N/D35R/V67A/
P173N/T238G/M276K/A277T/E315G/T364W/G381A/
A403G/S10Q, K7N/D35R/V67A/P173N/T238G/M276K/
A277T/E315G/T364W/G381A/A403G/S266Y, K7N/D35R/
V67A/P173N/T238G/M276K/A277T/E315G/T364W/
G381A/A403G/G311A, K7N/D35R/V67A/P173N/T238G/
M276K/A277T/E315G/T364W/G381A/A403G/L6M,
K7N/D35R/V67A/P173N/T238G/M276K/A277T/E315G/
T364W/G381A/A403G/V89T, K7N/D35R/V67A/P173N/
T238G/M276K/A277T/E315G/T364W/G381A/A403G/
G233A, K7N/D35R/V67A/P173N/T238G/M276K/A277T/
E315G/T364W/G381A/A403G/S10N/A25F/K75E/P80S/
Q225E, K7N/D35R/V67A/P173N/T238G/M276K/A277T/
E315G/T364W/G381A/A403G/A25F/Q225E, K7N/D35R/
V67A/P173N/T238G/M276K/A277T/E315G/T364W/
G381A/A403G/P137V/D185N, K7N/D35R/V67A/P173N/
T238G/M276K/A277T/E315G/T364W/G381A/A403G/
Q225E, K7N/D35R/V67A/P173N/T238G/M276K/A277T/
E315G/T364W/G381A/A403G/P80S/D185N, K7N/D35R/
V67A/P173N/T238G/M276K/A277T/E315G/T364W/
G381A/A403G/A25F/H158R, K7N/D35R/V67A/P173N/
T238G/M276K/A277T/E315G/T364W/G381A/A403G/
S10N/A25F/Q 62W/D90N/T114H/H158R/N176K/D185N,
K7N/D35E/V67A/P173N/T238G/M276K/A277T/E315G/
T364T/G381A/A403G/D142E/E197S/H282N, K7N/D35F/
V67A/P173N/T238G/M276K/A277T/E315G/T364T/
G381A/A403G/D142E/N176K/E402D, K7N/D35N/V67A/
P173N/T238G/M276K/A277T/E315G/T364W/G381A/
A403G/P4N/D142E/E 197S/H282N, K7N/D35N/V67A/
P173N/T238G/M276K/A277T/E315G/T364T/G381A/
A403G/P4N/D142E/E197S/E402D, K7N/V67A/P173N/

T238G/M276K/A277T/E315G/T364W/G381A/A403G/
P4N/D142E/N176K/H282N/A288R/E402D, K7N/D35N/
V67A/P173N/T238G/M276K/A277T/E315G/T364W/
G381A/A403G/P4N, K7N/D35E/V67A/P173N/T238G/
M276K/A277T/E315G/T364W/G381A/A403G/D142E/
H282N/A288R/E402D, K7N/D35F/V67A/P173N/T238G/
M276K/A277T/E315G/G381A/A403G/D142E/N176K/
E197S, K7N/D35N/V67A/P173N/T238G/M276K/A277T/
E315G/G381A/A403G/P4N/E197S/E402D, K7N/D35N/
V67A/P173N/T238G/M276K/A277T/E315G/T364W/
G381A/A403G/P4N/D142E/E 197S, K7N/V67A/P173N/
T238G/M276K/A277T/E315G/T364W/G381A/A403G/
P4N/E402D, K7N/D35E/V67A/P173N/T238G/M276K/
A277T/E315G/T364W/G381A/A403G/P4N/D142E/
E197S/H282N, K7N/V67A/P173N/T238G/M276K/A277T/
E315G/T364W/G381A/A403G/P4N, K7N/V67A/P173N/
T238G/M276K/A277T/E315G/T364W/G381A/A403G/
D142E/H282N/E402 D, K7N/D35F/V67A/P173N/T238G/
M276K/A277T/E315G/T364W/G381A/A403G/P4N/
D142E, K7N/V67A/P173N/T238G/M276K/A277T/
E315G/G381A/A403G/P4N/E402D, K7N/D35N/V67A/
P173N/T238G/M276K/A277T/E315G/T364W/G381A/
A403G/D142E/N176K/E197S/E402D, K7N/D35F/V67A/
P173N/T238G/M276K/A277T/E315G/G381A/A403G/
P4N/E402D, K7N/D35F/V67A/P173N/T238G/M276K/
A277T/E315G/T364W/G381A/A403G/P4N, K7N/D35E/
V67A/P173N/T238G/M276K/A277T/E315G/G381A/
A403G/P4N/E402D, K7N/D35F/V67A/P173N/T238G/
M276K/A277T/E315G/G381A/A403G/P4N/D142E/
E402D, K7N/D35N/V67A/P173N/T238G/M276K/A277T/
E315G/G381A/A403G/P4N/D142E/E402D, K7N/D35E/
V67A/P173N/T238G/M276K/A277T/E315G/T364W/
G381A/A403G/N176K/D185N/S240K, K7N/D35R/V67A/
P173N/T238G/M276K/A277T/E315G/T364W/G381A/
A403G/P4N/D142R/D 185N/S240K, K7N/D35R/V67A/
P173N/T238G/M276K/A277T/E315G/T364W/G381A/
A403G/P4N/D142A/N176K/D185N/Q192K/S240K/
R385T, K7N/D35N/V67A/P173N/T238G/M276K/A277T/
E315G/G381A/A403G/P4N/D142R/D185N, K7N/D35F/
V67A/P173N/T238G/M276K/A277T/E315G/T364W/
G381A/A403G/N176K/D185N/R385T, K7N/D35N/V67A/
P173N/T238G/M276K/A277T/E315G/T364W/G381A/
A403G/N176K/D185N/S240K, K7N/D35R/V67A/P173N/
T238G/M276K/A277T/E315G/G381A/A403G/P121A/
D142A/N176K/D185N/K363A, K7N/D35F/V67A/P173N/
T238G/M276K/A277T/E315G/T364W/G381A/A403N/
P4N/P121A/D 142E/N176K/D185N/S240K/R385T/A394P,
K7N/D35F/V67A/P173N/T238G/M276K/A277T/E315G/
T364W/G381A/A403G/P4N/P121A/D 142E/N176K/
D185N, K7N/V67A/P173N/T238G/M276K/A277T/
E315G/T364W/G381A/A403N/N176K/D185N/Q192K/
R385T/A394P, K7N/D35Y/V67A/P173N/T238G/M276K/
A277T/E315G/G381A/A403G/S240K/K363A, K7N/
V67A/P173N/T238G/M276K/A277T/E315G/T364W/
G381A/A403G/L410A, K7N/D35N/V67A/P173N/T238G/
M276K/A277T/E315G/T364W/G381A/A403N/D142A/
D185N/Q192K/R385T/A394P/L410G, K7N/V67A/P173N/
T238G/M276K/A277T/E315G/T364S/G381A/A403G/
P121A/D142R/S240K/H282N/K363A/R385T/A394P/
L410G, K7N/D35E/V67A/P173N/T238G/M276K/A277T/
E315G/G381A/A403G/D142R/N176K/D185N/R385T,
K7N/D35F/V67A/P173N/T238G/M276K/A277T/E315G/
G381A/A403G/P121A/R385T/L410G, K7N/D35N/V67A/
P173N/T238G/M276K/A277T/E315G/T364W/G381A/
A403G/D142E/N176K/D185N/S240K, K7N/D35F/V67A/
P173N/T238G/M276K/A277T/E315G/T364W/G381A/
A403N/D142A/K363A/R385T/A394P/L410G, K7N/D35R/
V67A/P173N/T238G/M276K/A277T/E315G/T364W/G381A/
A403G/P4N/D142A/D185N/R 385T, K7N/D35F/V67A/
P173N/T238G/M276K/A277T/E315G/T364W/G381A/
A403G/D142R/N176K/D185N/S240K/R385T/A394P,
K7N/D35R/V67A/P173N/T238G/M276K/A277T/E315G/
T364W/G381A/A403G/D142E/N176K/D185N/Q192K/
E197S/A288R/K363A, K7N/V67A/P173N/T238G/
M276K/A277T/E315G/T364S/G381A/A403G/D142E/
Q192K/E197S/S240K/K363A, K7N/D35F/V67A/P173N/
T238G/M276K/A277T/E315G/T364S/G381A/A403G/
D142A/D185N/K363A/E402D/L410G, K7N/V67A/
P173N/T238G/M276K/A277T/E315G/T364W/G381A/
A403G/P4N/P121A/D142R/N176K/D185N/E197S/S240K,
K7N/D35N/V67A/P173N/T238G/M276K/A277T/E315G/
G381A/A403G/D142E/N176K/D185N/S240K, K7N/
D35N/V67A/P173N/T238G/M276K/A277T/E315G/
T364W/G381A/A403G/P4N/P121A/D 142A/D185N/
A288R, K7N/D35N/V67A/P173N/T238G/M276K/A277T/
E315G/T364W/G381A/A403G/P4N/D185N/Q192K/
E197S, K7N/D35Y/V67A/P173N/T238G/M276K/A277T/
E315G/T364S/G381A/A403G/D142E/N176K/D185N/
R385T/A394P, K7N/D35R/V67A/P173N/T238G/M276K/
A277T/E315G/G381A/A403G/S240K/K363A/R385T/
A394P/L410A, K7N/D35F/V67A/P173N/T238G/M276K/
A277T/E315G/T364W/G381A/A403G/D142R/R385T/
A394P/E402D/L410G, K7N/D35N/V67A/P173N/T238G/
M276K/A277T/E315G/T364S/G381A/A403G/N176K/
D185N/S240K/K363A/A394P/E402D/L410G, K7N/D35E/
V67A/P173N/T238G/M276K/A277T/E315G/T364W/
G381A/A403G/P4N/D142E, K7N/D35F/V67A/P173N/
T238G/M276K/A277T/E315G/G381A/A403G/K363A,
K7N/D35R/V67A/P173N/T238G/M276K/A277T/E315G/
T364S/G381A/A403N/D142E/D185N/R385T/A394P/
L410G, K7N/D35Y/V67A/P173N/T238G/M276K/A277T/
E315G/T364S/G381A/A403G/P121A/S240K, K7N/D35Y/
V67A/P173N/T238G/M276K/A277T/E315G/G381A/
A403G/L410G, K7N/D35E/V67A/P173N/T238G/M276K/
A277T/E315G/T364S/G381A/A403N/D142A/N176K/
D185N/S240K/K363A/R385T/A394P/L410G, K7N/D35Y/
V67A/P173N/T238G/M276K/A277T/E315G/T364W/
G381A/A403G/P4N/D142E/D 185N, K7N/D35E/V67A/
P173N/T238G/M276K/A277T/E315G/T364W/G381A/
A403G/P4N/D142A/N176K/D185N/S240K/K363A/
L410A, K7N/V67A/P173N/T238G/M276K/A277T/
E315G/T364S/G381A/A403G/N176K/D185N/Q192K/
R385T/A394P/E402D/L410A, K7N/V67A/P173N/T238G/
M276K/A277T/E315G/T364S/G381A/A403G/P121A/
D142E/E197S/K363A, K7N/D35R/V67A/P173N/T238G/
M276K/A277T/E315G/T364W/G381A/A403G/P4N/
N176K/D 185N, K7N/D35R/V67A/P173N/T238G/M276K/
A277T/E315G/T364S/G381A/A403G/D142R/Q192K/
S240K/K363A/R385T/A394P/E402D/L410G, K7N/D35R/
V67A/P173N/T238G/M276K/A277T/E315G/T364W/
G381A/A403G/P4N/D185N, K7N/D35N/V67A/P173N/
T238G/M276K/A277T/E315G/T364W/G381A/A403G/
N176K/D185N/S240K/R385T, K7N/D35N/V67A/P173N/
T238G/M276K/A277T/E315G/T364W/G381A/A403G/
S240K, K7N/V67A/P173N/T238G/M276K/A277T/E315G/
T364W/G381A/A403G/D142R/N176K/D185N/S240K,
K7N/D35F/V67A/P173N/T238G/M276K/A277T/E315G/
G381A/A403G/P121A/D142E/A153V/D185N/S240K/
R385T, K7N/V67A/P173N/T238G/M276K/A277T/E315G/
T364W/G381A/A403G/D185N/R385T, K7N/D35R/V67A/
P173N/T238G/M276K/A277T/E315G/T364W/G381A/
A403G/P4N/N176K/D 185N/S240K, K7N/D35F/V67A/P173N/T238G/M276K/A277T/E315G/T364W/G381A/A403G/D142E/N176K/D185N, K7N/D35R/V67A/P173N/

T238G/M276K/A277T/E315G/T364W/G381A/A403G/ D142R/N176K/D185N/Q192K/S240K/K363A, and K7N/ D35N/V67A/P173N/T238G/M276K/A277T/E315G/ T364W/G381A/A403G/P4N/D142A/N176K/D185N/ S240K.

In a further aspect, the invention provides compositions comprising said variant phytase enzymes comprising amino acid substitutions K7N/D35R/V67A/P173N/T238G/ M276K/A277T/E315G/T364W/G381A/A403G/P4N/ P121A/D 136S/Q346S/T378A and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In an additional aspect, the invention provides compositions comprising said variant phytase enzymes comprising amino acid substitutions K7N/D35R/V67A/P173N/T238G/ M276K/A277T/E315G/T364W/G381A/A403G/P137V/ D185N and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In a further aspect, the invention provides compositions comprising said variant phytase enzymes comprising amino acid substitutions K7N/D35N/V67A/P173N/T238G/ M276K/A277T/E315G/T364W/G381A/A403G/P4N and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In an additional aspect, the invention provides compositions comprising said variant phytase enzymes comprising amino acid substitutions P4N/K7N/D35N/V67A/P121A/ D136S/P173N/T238G/M276K/A277T/E315G/Q346S/ T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In a further aspect, the invention provides compositions comprising said variant phytase enzymes comprising amino acid substitutions P4N/K7N/D35R/V67A/P121A/D136S/P173N/T238G/M276K/A277T/E315G/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In an additional aspect, the invention provides compositions comprising said variant phytase enzymes comprising amino acid substitutions P4N/K7N/D35N/V67A/P121A/D136S/P173N/T238G/M276K/A277T/E315G/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In an additional aspect, the invention provides compositions comprising said variant phytase enzymes having at least 95% sequence identity to SEQ ID NO:2.

In a further aspect, the invention provides compositions comprising said variant phytase enzymes having at least 95% sequence identity to SEQ ID NO:3.

In an additional aspect, the invention provides compositions comprising said variant phytase enzymes having at least 95% sequence identity to SEQ ID NO:4.

In a further aspect, the invention provides compositions comprising said variant phytase enzymes having at least 95% sequence identity to SEQ ID NO:5.

In an additional aspect, the invention provides compositions comprising said variant phytase enzymes having at least 95% sequence identity to SEQ ID NO:6.

In a further aspect, the invention provides compositions comprising said variant phytase enzymes having at least 95% sequence identity to SEQ ID NO:7.

In an additional aspect, the invention provides compositions comprising said variant phytase enzymes having at least 95% sequence identity to SEQ ID NO:8.

In a further aspect, the invention provides compositions comprising said variant phytase enzymes having at least 95% sequence identity to SEQ ID NO:9.

In an additional aspect, the invention provides compositions comprising said variant phytase enzymes having at least 95% sequence identity to SEQ ID NO:10.

In a further aspect, the invention provides compositions comprising a variant phytase enzyme having SEQ ID NO:11.

In an additional aspect, the invention provides compositions comprising a variant phytase enzyme having SEQ ID NO:12.

In a further aspect, the invention provides compositions comprising a variant phytase enzyme having SEQ ID NO:13.

In an additional aspect, the invention provides compositions comprising said variant phytase enzyme described herein further comprising a sequence insertion of SEQ ID NO:15 or SEQ ID NO:16, wherein said variant phytase enzyme has phytase activity.

In a further aspect, the invention provides compositions comprising a variant phytase enzyme having SEQ ID NO:14.

In an additional aspect, the invention provides variant phytase enzymes having an amino acid substitution set selected from the group consisting of those depicted in FIGS. 1-8.

In a further aspect, the invention provides compositions comprising said variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, and wherein said variant phytase enzyme is at least 90% and less than 100% identical to SEQ ID NO:17.

In an additional aspect, the invention provides compositions comprising said variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, and wherein said variant phytase enzyme has at least 1.01 fold better activity as compared to SEQ ID NO:17 under a condition comprising 37° C., pH 5.5; and wherein said variant phytase enzyme is at least 90% and less than 100% identical to SEQ ID NO:17.

In a further aspect, the invention provides compositions comprising said variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, wherein said variant phytase enzyme has at least 1.01 fold better activity as compared to SEQ ID NO:17 under a condition selected from the group consisting of thermochallenge at about 75° C., thermochallenge at about 80° C., thermochallenge at about 85° C., and thermochallenge at about 90° C.; and wherein said variant phytase enzyme is at least 90% and less than 100% identical to SEQ ID NO:17. In some embodiment, the variant phytase enzyme has at least 1.01 fold better activity as compared to SEQ ID NO:17 under the condition further comprising the thermostability in the presence of BSA.

In an additional aspect, the invention provides compositions comprising said variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, wherein said variant phytase enzyme has at least 1.01 fold better activity as compared to SEQ ID NO:17 under a condition selected from the group consisting of tolerance against pH 2.0, tolerance against pH 2.5, tolerance against pH 3.0, tolerance against pH 3.5, and tolerance against pH 4.0; and wherein said variant phytase enzyme is at least 90% and less than 100% identical to SEQ ID NO:17.

In a further aspect, the invention provides variant phytase enzymes with amino acid substitutions at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions, twenty of said positions, twenty-one of said positions, twenty-two of said positions, twenty-three of said positions, twenty-four of said positions, twenty-five of said positions, twenty-six of said positions, twenty-seven of said positions, twenty-eight of said positions, twenty-nine of said positions, or thirty of said positions.

In an additional aspect, the invention provides compositions comprising said variant phytase enzymes comprising amino acid substitution(s) selected from the group consisting of Q1S, Q1V, Q1N, P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, Q30K, D31I, D31N, D35E, D35F, D35N, D35R, D35Y, A36K, T39D, W46E, W46G, E53D, E53N, I55L, I55V, L58S, H60S, H60Q, Y61C, Q62W, R63A, R65H, R65C, R65G, R65P, R65S, R65V, V67A, D69N, D69L, D69R, D69Y, G70E, L72S, A73D, A73E, A73P, K74D, K74P, K74L, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, 5120R, S120K, P121A, T130G, T130R, Q134A, Q134T, L135F, L135Y, D136F, D136G, D136S, N137S, N137P, N137C, N137F, N137G, N137H, N137I, N137L, N137M, N137V, N137W, N137Y, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, G157Q, G157N, G157L, G157R, G157A, G157P, H158R, H158W, R159Y, T161D, E165D, E165P, E165S, E165T, E165W, P173N, P173S, P173T, P173Y, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, T245E, Y255D, P261L, S266A, S266Y, L272S, M276V, M276K, A277T, L279F, T280C, T280G, T280N, T280P, P281D, P281S, H282N, H282P, A288E, A288R, A288V, V291I, T292G, T295N, T295I, V297L, G302S, G311S, G311A, E315G, E315S, L316F, R339M, L341Y, L341V, Q346K, Q346P, Q346S, Q346T, L352M, F354Y, D362G, D362N, D362S, D362Y, K363A, K363L, K363R, T364C, T364E, T364I, T364L, T364N, T364Q, T364S, T364T, T364V, T364W, P365W, L366R, N369P, T370P, T370K, P371M, P371V, P371W, P371Y, P372T, T378A, A380R, A380T, A380P, G381A, G381C, G381L, G381N, G381R, E383S, E384D, R385S, R385V, R385T, A394I, A394L, A394M, A394P, G395P, Q398V, N401A, N401L, N401P, E402R, E402T, E402D, E402P, E402N, A403G, A403I, A403K, A403L, A403N, A403Q, A403W, A403Y, S409H, S409L, S409R, S409V, S409W, L410A, L410C, L410E, L410F, L410G, L410I, L410K, and L410R.

In a further aspect, the invention provides compositions comprising said variant phytase enzymes comprising the amino acid substitutions I55V/H60Q/D69N/K74D/S120R/N137P/G157Q/R159Y/Y255D/F354Y/A380P/M276K/A277T/E315G and at least one further amino acid substitution selected from the group consisting of Q1S, Q1V, Q1N, P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, Q30K, D31I, D31N, D35E, D35F, D35N, D35R, D35Y, A36K, T39D, W46E, W46G, E53D, E53N, L58S, Y61C, Q62W, R63A, R65H, R65C, R65G, R65P, R65S, R65V, V67A, G70E, L72S, A73D, A73E, A73P, K75C, K75E, K75G, K75I, K75L, K75M, K75Q, K75R, K75S, K75W, Q76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, P173N, P173S, P173T, P173Y, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, T378A, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In a further aspect, the invention provides compositions comprising said variant phytase enzymes comprising the amino acid substitutions I55V/H60Q/D69N/K74D/S120R/N137P/G157Q/R159Y/Y255D/F354Y/A380P/K7N/D35R/V67A/P173N/T238G/M276K/A277T/E315G/T364W/G381A/A403G and at least one further amino acid substitution selected from the group consisting of Q1S, Q1V, Q1N, P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, 5146E, 5146P, S151F, 5151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, 5187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, T378A, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In an additional aspect, the invention provides compositions comprising said variant phytase enzymes comprising the amino acid substitutions I55V/H60Q/D69N/K74D/S120R/N137P/G157Q/R159Y/Y255D/F354Y/A380P/K7N/D35R/V67A/P173N/T238G/M276K/A277T/E315G/T364W/G381A/A403G/P4N/P121A/D136S/Q346S/T378A and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, 5187T, S189L, S189N, S189T, T191S, Q192K, Q192L, A1931, A193L, A193S, A193T, A193V, L1941, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, L352M, D362G, D362N, D362S, D362Y, K363A, K363L, K363R, P365W, L366R, N369P, T370P, T370K, P371M, P371V, P371W, P371Y, P372T, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In a further aspect, the invention provides compositions comprising said variant phytase enzymes comprising the amino acid substitutions I55V/H60Q/D69N/K74D/S120R/N137V/G157Q/R159Y/Y255D/F354Y/A380P/K7N/D35R/V67A/P173N/T238G/M276K/A277T/E315G/T364W/G381A/A403G/D185N and at least one further amino acid substitution selected from the group consisting of Q1S, Q1V, Q1N, P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, I55L, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, 5146E, 5146P, 5151F, 5151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, E186V, E186A, 5187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, T378A, E383S, E384D, R3855, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In an additional aspect, the invention provides compositions comprising said variant phytase enzymes comprising the amino acid substitutions I55V/H60Q/D69N/K74D/S120R/N137P/G157Q/R159Y/Y255D/F354Y/A380P/K7N/D35N/V67A/P173N/T238G/M276K/A277T/E315G/T364W/G381A/A403G/P4N and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, I55L, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, T378A, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In a further aspect, the invention provides compositions comprising said variant phytase enzymes comprising the amino acid substitutions I55V/H60Q/D69N/K74D/S120R/N137P/G157Q/R159Y/Y255D/F354Y/A380P/P4N/K7N/D35N/V67A/P121A/D136S/P173N/T238G/M276K/A277T/E315G/Q346S/T364W/T378A/G381A/A403 G and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, I55L, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, T130G, T130R, Q134A, Q134T, L135F, L135Y, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In a further aspect, the invention provides compositions comprising said variant phytase enzymes comprising the amino acid substitutions I55V/H60Q/D69N/K74D/S120R/N137P/G157Q/R159Y/Y255D/F354Y/A380P/P4N/K7N/D35N/V67A/P121A/D136S/P173N/T238G/M276K/A277T/E315G/T364W/T378A/G381A/A403G and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, T130G, T130R, Q134A, Q134T, L135F, L135Y, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In a further aspect, the invention provides compositions comprising said variant phytase enzyme described herein further comprising animal feed.

In an additional aspect, the invention provides nucleic acids encoding the variant phytase enzymes of the invention.

In a further aspect, the invention provides expression vectors comprising the nucleic acids encoding the variant phytase enzymes of the invention.

In an additional aspect, the invention provides host cells comprising the expression vectors or the nucleic acids of the invention.

In a further aspect, the invention provides methods of making a variant phytase enzyme comprising culturing the host cells of the invention under conditions wherein the variant phytase enzyme is produced, and recovering the enzyme.

In some aspects, the invention relates to phytase variants having improved thermal properties, such as thermostability, heat-stability, BSA stability, pH stability, steam stability, temperature profile, and/or pelleting stability, with variant enzymes having high tolerance to high temperature in the presence of BSA and high tolerance to low pH of particular use in many embodiments.

In additional aspects, the invention relates to phytase variants having improved pelleting stability and/or improved acid-stability.

The method of the invention thus relates to phytase variants having an improved pH tolerance profile.

The method of the invention thus relates to phytase variants having improved protease stability, in particular pepsin stability, found in non-ruminant stomachs.

The method of the invention thus relates to phytase variants having improved performance in animal feed (such as an improved release and/or degradation of phytate).

The invention further relates to polynucleotide comprising nucleotide sequences which encode the phytase variants produced by the method, nucleic acid constructs comprising the polynucleotides operably linked to one or more control sequences that direct the production of the polypeptide in an expression host, recombinant expression vectors comprising such nucleic acid constructs, and recombinant host cells comprising a nucleic acid construct and/or an expression vector.

In an additional aspect, the invention relates to methods for producing phytase variants as provided comprising (a) cultivating a host cell to produce a supernatant comprising the phytase; and (b) recovering the phytase.

In a further aspect, the invention relates to methods for improving the nutritional value of an animal feed, by adding a phytase variant of the invention to the feed, processes for reducing phytate levels in animal manure by feeding an animal with an effective amount of the feed, methods for the treatment of vegetable proteins, comprising the step of adding a phytase variant to at least one vegetable protein, and the use of a phytase variant of a composition of the invention.

The invention also provides a method for producing a fermentation product such as, e.g., ethanol, beer, wine, comprising fermenting a carbohydrate material in the presence of a phytase variant, a method for producing ethanol comprising fermenting a carbohydrate material in the presence of a phytase variant and producing ethanol.

BRIEF DESCRIPTION OF THE DRAWINGS

FIGS. 1A-1C show improved G3P variants produced by *Saccharomyces cerevisiae*.

FIGS. 2A-2C show improved G4P variants produced by *Saccharomyces cerevisiae*.

FIG. 3 show improved G5P variants produced by *Saccharomyces cerevisiae*.

FIGS. 4A-4E show improved G6P variants produced by *Saccharomyces cerevisiae*.

FIG. 5 shows activity, thermostability and pH tolerance of G3P, G6P and *Pichia pastoris* produced variants.

FIG. 6 provides sequence alignment of the G3 insertion variant CL00047720 as set forth in SEQ ID NO:14 vs. G3P as set forth in SEQ ID NO:1 (alignment result 1).

FIG. 7 provides sequence alignment of the G3 insertion variant CL00047720 as set forth in SEQ ID NO:14 vs. G3P as set forth in SEQ ID NO:1 (alignment result 2).

FIG. 8 provides a summary of variants with reference to G3P.

FIGS. 9A-9J provide sequence listings. FIG. 9A provides DNA sequences encoding the variant proteins CL00048541 (G4P) and CL00060516 (G5P). FIG. 9B provides DNA sequences encoding the variant proteins CL00080812 (G6P) and CL00082400. FIG. 9C provides DNA sequences encoding the variant proteins CL00089395 and CL00090520.

FIG. 9D provides DNA sequences encoding the variant proteins CL00100223 and CL00102257. FIG. 9E provides a DNA sequence encoding the variant protein CL00102259, and amino acid sequences of the variant proteins CL00005023 (G3P, SEQ ID NO:1), CL00048541 (G4P, SEQ ID NO:2) and CL00060516 (G5P SEQ ID NO:3). FIG. 9F provides amino acid sequences of the variant proteins CL00080812 (G6P, SEQ ID NO:4), CL00082400 (SEQ ID NO:5), CL00089395 (SEQ ID NO:6), CL00090520 (SEQ ID NO:7), CL00100223 (SEQ ID NO:8), and CL00102257 (SEQ ID NO:9). FIG. 9G provides the amino acid sequence of the variant protein CL00102259 (SEQ ID NO:10), and DNA sequences encoding the variant proteins CL00071716 and CL00100225. FIG. 9H provides a DNA sequence encoding the variant protein CL00102276, and amino acid sequences of the variant proteins CL00071716 (SEQ ID NO:11), CL00100225 (SEQ ID NO:12), and CL00102276 (SEQ ID NO:13). FIG. 9I provides a DNA sequence encoding the insertion variant protein CL00047720, the amino acid sequence of the insertion variant protein CL00047720 (SEQ ID NO:14), and insertion amino acid sequences (SEQ ID NO:15 and SEQ ID NO:16) in CL00047720 with reference to G3P based on different alignment results. FIG. 9J provides the amino acid sequence (SEQ ID NO:17) of wild type phytase enzyme (G1P protein).

DETAILED DESCRIPTION OF THE INVENTION

I. Introduction

Phytases decompose phytate (inositol hexakisphosphate (IP6) or phytic acid when in the salt form), which is the primary storage of phosphate in plants. Monogastric animals such as swine, poultry and fish (as well as humans) cannot digest phytate, leading to phosphorus excretion in the manure, which poses an environmental concern in agricultural areas. In addition, the phytate can lead to aggregation of proteins, reducing protein availability, as well as chelate minerals and trace elements, further reducing the available nutrients for the animals.

The addition of phytase to animal feed was introduced several decades ago and can reduce phosphorus excretion by up to 50% while also allowing the animal better access to the available nutrients. However, under the conditions which are used in the processing of many foods, including both animal feeds made from plant sources as well as foods for humans (cereals, etc.) such as higher temperatures and different pHs, many wild type phytases are not very stable, leading to inefficient conversion of the phytate and/or the cost prohibitive addition of more enzyme. Similarly, other uses for phytase such as in the production of biofuels also can include higher temperatures and/or different pHs. Accordingly, it is an object of the present invention to provide variant phytases with improved properties, including thermostability and other biochemical properties as outlined herein, that lead to improved outcomes such as less environmental stress due to lowered phosphorus excretion, better feed conversion to animal weight and better access to nutrients.

II. Definitions

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution I55V refers to a variant polypeptide, in this case a phytase, in which the isoleucine at position 55 is replaced with valine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233#, E233( ) or E233del designates a deletion of glutamic acid at position 233. Additionally, EDA233- or EDA233# designates a deletion of the sequence GluAspAla that begins at position 233.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize wild type G1P (SEQ ID NO:17), G3P (SEQ ID NO:1), G4P (SEQ ID NO:2), G5P (SEQ ID NO:3) or G6P (SEQ ID NO:4) as parent polypeptides.

By "variant protein" or "protein variant", or "variant" as used herein is meant a protein that differs from that of a parent protein by virtue of at least one amino acid modification. Protein variant may refer to the protein itself, a composition comprising the protein, or the amino acid sequence that encodes it. Preferably, the protein variant has at least one amino acid modification compared to the parent protein, e.g. from about one to about seventy amino acid modifications, and preferably from about one to about twenty amino acid modifications compared to the parent. As described below, in some embodiments, the parent polypeptide is a wild type sequence, for example the wild type E. coli phytase designated "G1P" (SEQ ID NO:17). As further discussed below, the protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Thus, by "variant phytase" herein is meant a novel phytase that has at least one amino acid modification in the amino acid sequence as compared to a parent phytase enzyme. As discussed herein, in some cases the parent phytase is a second or higher generation of variant; that is, as shown in FIG. 1, the G3P phytase has 11 amino acid substitutions I55V/H60Q/D69N/K74D/S120R/N137P/G157Q/R159Y/Y255D/F354Y/A380P as compared to the wild type G1P parent. However, as shown in FIG. 2, the G4P has 3 amino acid substitutions M276K/A277T/E315G as compared to the G3P parent, but a total of 14 amino acid substitutions as compared to the G1P (SEQ ID NO:17). Unless otherwise noted or as will be obvious from the context, the variant phytases of the invention generally are compared to the G1P or G3P sequence. Additionally, unless otherwise noted, the variant phytases of the invention are enzymatically active, that is, there is detectable phytase activity using the phytase assay described in the Examples.

As used herein, "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Histidine 82 (also referred to as His82 or H82) is a residue at position 82 in the G1P wild type enzyme.

By "non-naturally occurring modification" as used herein is meant an amino acid modification that is not found in the wild type (e.g. G1P) enzyme.

By "amino acid" and "amino acid identity" as used herein is meant one of the 20 naturally occurring amino acids that are coded for by DNA and RNA.

By "position" as used herein is meant a location in the sequence of a protein. In general, the position number (which is more fully discussed below) is relative to the first amino acid of the mature phytase sequence, e.g. excluding the signal peptide.

By "phytase" herein is meant a protein with phytase activity. By "phytase activity" herein is meant that the enzyme catalyzes the hydrolysis of phytate (myo-inositol hexakisphosphate) to (P6689oldab*1) myo-inositol and/or (2) mono-, di-, tri-, tetra- and/or penta-phosphates thereof and (3) inorganic phosphate. Enzymes having detectable activity in the assay outlined below and in the Examples are considered phytases herein.

The relatedness between two amino acid sequences or between two nucleotide sequences is described by the parameter "sequence identity" or "identity". The degree of identity between an amino acid sequence of the present invention ("invention sequence") and the parent amino acid sequence referred to in the claims (e.g. G3P, SEQ ID NO:1) is calculated as the number of exact matches in an alignment of the two sequences, divided by the length of the "invention sequence," or the length of the SEQ ID NO:1, whichever is the shortest. The result is expressed in percent identity as calculated below.

For purposes of the present invention, the mature polypeptide disclosed in SEQ ID NO:1 is used to determine the corresponding amino acid residue in another phytase of the present invention. The amino acid sequence of another phytase is aligned with the mature polypeptide disclosed in SEQ ID NO:1, and based on the alignment, the amino acid position number corresponding to any amino acid residue in the mature polypeptide disclosed in SEQ ID NO:1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−Total Number of Gaps in Alignment)

Identification of the corresponding amino acid residue in another phytase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 51 1-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), EMBOSS EMMA employing ClustalW (1.83 or later; Thompson et al., 1994, Nucleic Acids Research 22: 4673-4680), and EMBL-EBI employing Clustal Omega (Sievers and Higgins, 2014, Methods Mol Biol. 2014; 1079:105-16), using their respective default parameters.

When the other enzyme has diverged from the polypeptide of SEQ ID NO:1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The standardly accepted IUPAC single letter or three letter amino acid abbreviation is employed.

For an amino acid substitution, the following nomenclature is used herein: Original amino acid, position, substituted amino acid. Accordingly, the substitution of glutamine at position 441 with proline is designated as "Gln441Pro" or "Q441P". Multiple mutations are separated by forward slash marks ("/"), e.g., "I91L/A133G/Y169W", representing substitutions at positions 91, 133 and 169, respectively.

| Abbreviation | 1 letter abbreviation | Amino acid name |
| --- | --- | --- |
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |

By "isolated" in the context of a phytase herein is meant that the polypeptide is devoid of other proteins. In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95 to 98% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

By "recombinant enzyme" herein is meant that the enzyme is produced by recombinant techniques and that nucleic acid encoding the variant enzyme of the invention is operably linked to at least one exogeneous (e.g. not native to the parent phytase) sequence, including, for examples, promoters, terminators, signal sequences, etc., as are more fully outlined below.

The term "nucleic acid construct" refers to a nucleic acid molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a control sequence is placed at an appropriate position relative to the coding sequence of a polynucleotide such that the control sequence directs expression of the coding sequence.

III. Phytases of the Invention

Accordingly, the present invention provides variant phytases with improved activity that can be used in a variety of applications, including animal and human nutritional and feed products and the production of biofuels such as bioethanol.

In general, the variant phytases of the invention have modified, improved biochemical properties as compared to the wild type G1P phytase (SEQ ID NO:17), and/or the Generation 3 variant phytases, (i.e. G3P, SEQ ID NO:1) as shown in FIGS. 1-5. The biochemical properties of the variant phytases that can be improved herein include, but are not limited to, pH activity, pH stability, thermostability in or without the presence of bovine serum albumin (BSA), specific activity, formulation stability (including liquid, solid and pellets), performance in animals and/or animal feed and protease stability.

The variant phytases of the invention have one or more improved properties as compared to G1P and/or G3P. By "improved" herein is meant a desirable change of at least one biochemical property. "Improved function" can be measured as a percentage increase or decrease of a particular activity, or as a "fold" change, with increases of desirable properties (e.g. pH stability, thermostability) or decreases of undesirable properties (e.g. protease sensitivity). That is, a variant phytase may have a 10% increase in thermostability or a 10% decrease in protease sensitivity, as compared to a parental phytase. Alternatively, a variant phytase may have a 2-fold increase in pH stability or a 3-fold decrease in protease sensitivity. In general, percentage changes are used to describe changes in biochemical activity of less than 100%, and fold-changes are used to describe changes in biochemical activity of greater than 100% (as compared to the parental enzyme, in many cases, G1P and/or G3P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the FIG. 1, G4P has a 1.59 fold increase in temperature and/or BSA tolerance as compared to G3P: this is calculated by [(activity of variant)/(activity of parent)]. In many embodiments, the improvement is at least 1.01 fold, 1.1 fold, 2 fold, 3 fold, 4 fold, 5 fold, 6 fold, 7 fold, 8 fold, 9 fold, or 10 fold or higher.

In general, improvements in variant phytases are measured as compared to a parental phytase enzyme using a phytase activity assay, under the same challenge conditions.

A. Phytase Assay

The basic phytase assay is run as shown in Examples 3-5 and 8-10, and as follows: after challenge under the appropriate conditions of temperature, pH, etc., the sample is added to a 0.25 M solution of sodium acetate containing 7.5 mM of sodium phytate substrate ($C_6H_6Na_{12}O_{24}P_6$, FW: 923.81). The reaction is incubated at 37° C., 200 rpm for 30 minutes. Plates were then centrifuged at 4000 rpm at 4° C. for 2 minutes. To quench the reaction, 200 µl of coloring reagent was added to each of the 96 deep well microtiter plates. The coloring reagent was freshly prepared by sequentially mixing two volumes of 5M (~22% w/v) nitric acid, one volume of 100 g/L ammonium heptamolybdate solution [$(NH_4)_6Mo_7O_{24} \cdot 4H_2O$, FW:1235.86 g/mol] dissolved in water with 0.25% ammonia, and one volume 2.35 g/L ammonia metavanadate solution ($NH_4VO_3$, FW: 116.98 g/mol) dissolved in water with 0.1M nitric acid. After adding the coloring reagent to the plates, plates were shaken for 2 minutes and incubated in the dark for 10 minutes. After incubation, they were subjected to centrifugation at 4000 rpm for 2 minutes. 200 µl of the reaction from each well of the centrifuged plates was transferred to NUNC plates and read absorbance at 415 nm. The enzyme activity of variant was compared to the parent of the respective generation under the same conditions to determine activity improvement (X). In some cases, it is useful to use "Phytase Units", or PU, defined as the amount of phytase required to liberate 1 μmol of inorganic phosphate per minute. The enzyme may be a purified sample, a fermentation sample, or a raw sample.

The variant phytases of the invention can have an improvement in one or more of a number of biochemical properties, including, but not limited to, pH activity, pH stability, thermostability, specific activity, formulation stability (including liquid, solid and pellets), BSA stability, performance in animals and/or animal feed and/or protease stability.

B. Thermostability

In many embodiments, the variant phytases of the invention have increased thermostability, particularly under the conditions used to produce animal feeds, for example, which frequently use high temperatures during the pelleting process for periods of time that traditionally inactivate wild type phytases. "Thermostability" in this context means that the variant enzymes are more stable than the parental phytase (e.g. G1P or G3P) under the same thermal challenge conditions, that is, the activity of the variant is higher than that of the parental phytase under identical conditions (generally using the phytase assay as outlined herein and as shown in Examples).

In one embodiment, the variant phytases are more stable than the parent phytase when exposed to temperatures of 50° C., 55° C., 60° C., 65° C., 70° C., 75° C., 80° C., 85° C. and/or 90° C. for a period of time, generally ranging from about 1, 2, 3, 4, 5, 6, 7, 8, 9 or 10 minutes or longer, depending on the ultimate conditions for the use of the variant phytase, with some embodiments utilizing thermal challenge times of 5 minutes to 10 minutes, 5 minutes to 15 minutes, 5 minutes to 60 minutes, 10 minutes to 60 minutes all finding use in the present invention. In some embodiments, a challenge of 65° C., 75° C. or 90° C. in the presence of BSA is used.

Accordingly, in some embodiments the variant phytases have increased thermostability with or without the presence of BSA as compared to a parent phytase, e.g. G1P and/or G3P, for at least 5-10 minutes at 55° C., at least 5-10 minutes at 65° C., at least 5-10 minutes at 70° C., at least 5-10 minutes at 75° C., at least 5-10 minutes at 80° C., at least 5-10 minutes at 85° C., or at least 5-10 minutes at 90° C.

In some embodiments, the variant phytases have increased thermostability with or without the presence of BSA as as compared to a parent phytase for at least 5 minutes at 65° C. at pH 5.5, at least 5 minutes at 75° C. at pH 5.5, or at least 5 minutes at 90° C. at pH 5.5.

Accordingly, as shown in FIGS. 1-5, a number of variant phytases of the invention exhibit increased thermostability.

C. pH Stability

In many embodiments, the variant phytases of the invention have increased pH stability at lower pHs, to address the lower pH of the stomach and gastrointestinal tract of non-ruminant animals. That is, many phytases have pH profiles that are suboptimal for the lowered pH environment where the activity is desired in the animal "Increased pH stability" in this context means that the variant enzymes are more stable than the parent phytase (e.g. G1P and/or G3P) under the same pH challenge conditions, that is, the activity of the variant is higher than that of the parental enzyme under identical conditions (generally using the phytase assay as outlined herein and as shown in Examples).

Accordingly, in some embodiments the variant phytases have increased pH stability as compared to a parent phytase, particularly G1P and/or G3P, for at least 30 minutes at around pH 2.0, at least 30 minutes at around pH 2.5, at least 30 minutes at around pH 3.0, at least 30 minutes at around pH 3.5, or at least 30 minutes at around pH 4.0.

D. Specific Activity Assays

In some embodiments, the variant phytases of the invention have increased specific activity as compared to a parent phytase, particularly G1P and/or G3P. By "specific activity" herein is meant the activity per amount of enzyme, generally determined by dividing the enzymatic activity of a sample (sometimes measure in "phytase units" as discussed herein) by the amount of phytase enzyme, generally determined as is known in the art.

E. Protease Susceptibility

In some embodiments, the variant phytases of the invention are less susceptible to protease degradation than the parent enzyme under identical conditions. In some cases, protease degradation during the production of variant phytases in a production host organism by protease enzymes produced by the host organism can be a problem, thus resulting in lower yield of active enzyme. This is generally determined as is known in the art, for example by allowing proteolytic degradation and then doing N-terminal sequencing on the resulting fragments to determine the cleavage site(s). In some cases, depending on the variant and the host production organism, there may not be significant proteolytic degradation.

As needed, as will be appreciated by those in the art, the specific mutations that can be made will depend on the endogenous proteases that the host organism produces, and also generally occurs in surface exposed loop structures or turns that are therefore accessible to proteases. For example, production of phytases in *A. niger* fungal production organisms can lead to proteolytic degradation; see Wyss et al., Appl. And Environ. Microbiol. February 1999:359-366, hereby incorporated by reference in its entirety.

IV. Specific Variant Phytases

The present invention provides a number of specific variant phytases with one or more improved properties, specifically thermal stability and/or pH stability, and in particular thermal stability at particular pHs and temperature in the presence of BSA as outlined herein.

Accordingly, the present invention provides variant phytases with one or more improved properties as compared to the wild type G1P sequence and/or G3P (SEQ ID NO:1), wherein the variant phytase is not G1P (SEQ ID NO:17).

In some embodiments, the variant phytases of the invention have at least 85% identity to G1P, with enzymes having at least 90%, 91%, 92%, 93%, 94%, 95%, 96%, 97%, 98% and 99% identity (but less than 100% identity) also finding use in the present invention. Accordingly, some embodiments provide variant phytases with from 90% to 99% identity to G1P (SEQ ID NO:17), with other embodiments providing 95% to 99% identity, with the proviso that the phytase is not G1P (SEQ ID NO:17).

In some embodiments, the variant phytases of the invention have at least 85% identity to G3P, with enzymes having at least 90%, 91%, 92%, 93%, 94%, 95%, 96%, 97%, 98% and 99% identity also finding use in the present invention, with the proviso that the phytase is not G1P (SEQ ID NO:17). In some embodiments, the variant phytase is not G3P (SEQ ID NO:1).

In some embodiments, the invention provides variant phytase enzymes comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme is at least 90% identical to SEQ ID NO:1 and is not SEQ ID NO:17 and wherein said variant phytase enzyme has phytase activity.

In some embodiments, the invention provides variant phytase enzymes comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme has phytase activity and has at least 1.01 fold better activity as compared to SEQ ID NO:1 under a condition comprising 37° C., pH 5.5; and wherein said variant phytase enzyme is at least 90% identical to SEQ ID NO:1 and is not SEQ ID NO:17.

In some embodiments, the invention provides variant phytase enzymes comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme has phytase activity and has at least 1.01 fold better activity as compared to SEQ ID NO:1 under a condition selected from the group consisting of thermochallenge at about 75° C., thermochallenge at about 80° C., thermochallenge at about 85° C., and thermochallenge at about 90° C.; and wherein said variant phytase enzyme is at least 90% identical to SEQ ID NO:1 and is not SEQ ID NO:17. In some embodiments, the variant phytase enzyme as described herein has at least 1.01 fold better activity as compared to SEQ ID NO:1 under the condition further comprising the thermostability in the presence of Bovine Serum Albumin (BSA).

In some embodiments, the invention provides variant phytase enzymes comprising at least one amino acid substitution as compared to SEQ ID NO:1, wherein said amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 277, 279, 280, 281, 282, 288, 292, 295, 302, 311, 315, 316, 339, 341, 346, 352, 362, 363, 364, 365, 366, 370, 371, 372, 378, 381, 384, 385, 394, 395, 398, 401, 402, 403, 409 and 410, wherein said variant phytase enzyme has phytase activity and has at least 1.01 fold better activity as compared to SEQ ID NO:1 under a condition selected from the group consisting of tolerance against pH 2.0, tolerance against pH 2.5, tolerance against pH 3.0, tolerance against pH 3.5, and tolerance against pH 4.0; and wherein said variant phytase enzyme is at least 90% identical to SEQ ID NO:1 and is not SEQ ID NO:17.

In some embodiments, the invention provides variant phytase enzymes comprising at least one amino acid substitution as compared to SEQ ID NO:1, wherein said variant phytase enzyme exhibits at least 95%, at least 96%, at least 97%, at least 98%, or at least 99% sequence identity to SEQ ID NO:1.

In some embodiments, the invention provides said variant phytase enzymes as described herein with amino acid substitutions at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions or twenty of said positions.

In some embodiments, the variant phytase has an amino acid substitution of the proline at position 4 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is selected from P4E, P4K, P4L, P4M, P4N, P4Q, P4T and P4W.

In some embodiments, the variant phytase has an amino acid substitution of the glutamic acid at position 5 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is E5K.

In some embodiments, the variant phytase has an amino acid substitution of the leucine at position 6 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine, with some embodiments not utilizing cysteine (due to possible disulfide formation) or proline (due to steric effects). In some embodiments, the amino acid substitution is selected from L6F, L6M and L6Y.

In some embodiments, the variant phytase has an amino acid substitution of the lysine at position 7 of SEQ ID NO:1. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is selected from K7E, K7L, K7N, K7Q, and K7S.

In some embodiments, the variant phytase has an amino acid substitution of the serine at position 10 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is selected from 510A, S10N and 510Q.

In some embodiments, the variant phytase has an amino acid substitution of the valine at position 11 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan and tyrosine, with some embodiments not utilizing cysteine (due to possible disulfide formation) or proline (due to steric effects). In some embodiments, the amino acid substitution is V11I.

In some embodiments, the variant phytase has an amino acid substitution of the alanine at position 25 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is selected from A25D, A25F, A25N and A25W.

In some embodiments, the variant phytase has an amino acid substitution of the glutamine at position 27 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation). In some embodiments, the amino acid substitution is selected from Q27D, Q27P and Q27V.

In some embodiments, the variant phytase has an amino acid substitution of the aspartic acid at position 31 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is D31I or D31N.

In some embodiments, the variant phytase has an amino acid substitution of the aspartic acid at position 35 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is selected from D35E, D35F, D35N, D35R and D35Y.

In some embodiments, the variant phytase has an amino acid substitution of the tryptophan at position 46 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, valine and tyrosine, with some embodiments not utilizing cysteine (due to possible disulfide formation) or proline (due to steric effects). In some embodiments, the amino acid substitution is W46E or W46G.

In some embodiments, the variant phytase has an amino acid substitution of the glutamic acid at position 53 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E53D or E53N.

In some embodiments, the variant phytase has an amino acid substitution of the valine at position 55 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is selected from V55L.

In some embodiments, the variant phytase has an amino acid substitution of the leucine at position 58 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L58S.

In some embodiments, the variant phytase has an amino acid substitution of the tyrosine at position 61 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and valine with some embodiments not utilizing proline (due to steric effects). In some embodiments, the amino acid substitution is selected from Y61C.

In some embodiments, the variant phytase has an amino acid substitution of the glutamine at position 62 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q62W.

In some embodiments, the variant phytase has an amino acid substitution of the arginine at position 63 of SEQ ID NO:1. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R63A.

In some embodiments, the variant phytase has an amino acid substitution of the arginine at position 65 of SEQ ID NO:1. In some embodiments, the substitution is with any other of the 19 naturally occurring amino acids namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine. In some embodiments, the amino acid substitution is selected from R65C, R65G, R65P, R65S, and R65V.

In some embodiments, the variant phytase has an amino acid substitution of the valine at position 67 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine, with some embodiments not utilizing cysteine (due to possible disulfide formation) or proline (due to steric effects). In some embodiments, the amino acid substitution is V67A.

In some embodiments, the variant phytase has an amino acid substitution of the asparagine at position 69 of SEQ ID NO:1. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from N69L, N69R, and N69Y.

In some embodiments, the variant phytase has an amino acid substitution of the glycine at position 70 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G70E.

In some embodiments, the variant phytase has an amino acid substitution of the leucine at position 72 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L72S.

In some embodiments, the variant phytase has an amino acid substitution of the alanine at position 73 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is A73P.

In some embodiments, the variant phytase has an amino acid substitution of the lysine at position 75 of SEQ ID NO:1. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing proline (due to steric effects). In some embodiments, the amino acid substitution is selected from K75C, K75E, K75G, K75I, K75L, K75M, K75Q, K75R, K75S, and K75W.

In some embodiments, the variant phytase has an amino acid substitution of the glycine at position 76 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing proline (due to steric effects). In some embodiments, the amino acid substitution is G76C.

In some embodiments, the variant phytase has an amino acid substitution of the proline at position 80 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P80S.

In some embodiments, the variant phytase has an amino acid substitution of the valine at position 89 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is selected from V89T.

In some embodiments, the variant phytase has an amino acid substitution of the aspartic acid at position 90 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is D90N.

In some embodiments, the variant phytase has an amino acid substitution of the isoleucine at position 110 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine with some embodiments not utilizing cysteine (due to possible disulfide formation) or proline (due to steric effects). In some embodiments, the amino acid substitution is I110L.

In some embodiments, the variant phytase has an amino acid substitution of the threonine at position 111 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T111I.

In some embodiments, the variant phytase has an amino acid substitution of the histidine at position 113 of SEQ ID NO:1. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is H113Q.

In some embodiments, the variant phytase has an amino acid substitution of the threonine at position 114 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine. In some embodiments, the amino acid substitution is selected from T114C, T114D, T114F, T114H, T114N, T114P, and T114S.

In some embodiments, the variant phytase has an amino acid substitution of the serine at position 119 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S119R.

In some embodiments, the variant phytase has an amino acid substitution of the arginine at position 120 of SEQ ID NO:1. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R120K or R120S.

In some embodiments, the variant phytase has an amino acid substitution of the proline at position 121 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P121A.

In some embodiments, the variant phytase has an amino acid substitution of the threonine at position 130 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T130G or T130R.

In some embodiments, the variant phytase has an amino acid substitution of the glutamine at position 134 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q134A or Q134T.

In some embodiments, the variant phytase has an amino acid substitution of the leucine at position 135 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L135F or L135Y.

In some embodiments, the variant phytase has an amino acid substitution of the aspartic acid at position 136 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from D136F, D136G, and D136S.

In some embodiments, the variant phytase has an amino acid substitution of the proline at position 137 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine. In some embodiments, the amino acid substitution is selected from P137C, P137F, P137G, P137H, P137I, P137L, P137M, P137N, P137S, P137V, P137W and P137Y.

In some embodiments, the variant phytase has an amino acid substitution of the asparagine at position 139 of SEQ ID NO:1. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from N139A, N139H, and N139P.

In some embodiments, the variant phytase has an amino acid substitution of the aspartic acid position 142 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from D142A, D142E, D142F, D142G, D142H, D142I, D142K, D142L, D142M, D142N, D142P, D142R, D142S, D142T, D142V, and D142Y.

In some embodiments, the variant phytase has an amino acid substitution of the serine at position 146 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is S146E or S146P.

In some embodiments, the variant phytase has an amino acid substitution of the serine at position 151 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S151F or S151R.

In some embodiments, the variant phytase has an amino acid substitution of the alanine at position 153 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A153N, A153S, A153V, and A153Y.

In some embodiments, the variant phytase has an amino acid substitution of the glutamine at position 157 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from Q157A, Q157G, and Q157P.

In some embodiments, the variant phytase has an amino acid substitution of the histidine at position 158 of SEQ ID NO:1. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from H158R or H158W.

In some embodiments, the variant phytase has an amino acid substitution of the threonine at position 161 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T161D.

In some embodiments, the variant phytase has an amino acid substitution of the glutamic acid at position 165 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from E165D, E165P, E165S, E165T, and E165W.

In some embodiments, the variant phytase has an amino acid substitution of the proline at position 173 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is selected from P173N, P173S, P173T, and P173Y.

In some embodiments, the variant phytase has an amino acid substitution of the glutamine at position 174 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q174A or Q174E.

In some embodiments, the variant phytase has an amino acid substitution of the asparagine at position 176 of SEQ ID NO:1. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is N176K.

In some embodiments, the variant phytase has an amino acid substitution of the phenylalanine at position 179 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, tryptophan, valine and tyrosine with some embodiments not utilizing cysteine (due to possible disulfide formation) or proline (due to steric effects). In some embodiments, the amino acid substitution is F179L.

In some embodiments, the variant phytase has an amino acid substitution of the asparagine at position 180 of SEQ ID NO:1. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is N180K.

In some embodiments, the variant phytase has an amino acid substitution of the arginine at position 181 of SEQ ID NO:1. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R181T.

In some embodiments, the variant phytase has an amino acid substitution of the glutamic acid at position 182 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from E182A, E182F, E182S, and E182T.

In some embodiments, the variant phytase has an amino acid substitution of the aspartic acid at position 185 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is D185N.

In some embodiments, the variant phytase has an amino acid substitution of the serine at position 187 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S187T.

In some embodiments, the variant phytase has an amino acid substitution of the serine at position 189 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S189L, S189N, and S189T.

In some embodiments, the variant phytase has an amino acid substitution of the threonine at position 191 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T191S.

In some embodiments, the variant phytase has an amino acid substitution of the glutamine at position 192 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q192K, or Q192L.

In some embodiments, the variant phytase has an amino acid substitution of the alanine at position 193 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A193I, A193L, A193S, A193T, and A193V.

In some embodiments, the variant phytase has an amino acid substitution of the leucine at position 194 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L194I.

In some embodiments, the variant phytase has an amino acid substitution of the glutamic acid at position 197 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E197S.

In some embodiments, the variant phytase has an amino acid substitution of the alanine at position 202 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A202R.

In some embodiments, the variant phytase has an amino acid substitution of the glutamine at position 225 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q225E.

In some embodiments, the variant phytase has an amino acid substitution of the proline at position 230 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P230S.

In some embodiments, the variant phytase has an amino acid substitution of the glycine at position 233 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G233A.

In some embodiments, the variant phytase has an amino acid substitution of the threonine at position 238 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from T238A, T238F, T238G, T238K, T238N, T238P, T238Q, T238R, T238S, and T238Y.

In some embodiments, the variant phytase has an amino acid substitution of the serine at position 240 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S240A, S240G, S240K, and S240R.

In some embodiments, the variant phytase has an amino acid substitution of the glutamine at position 242 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q242E or Q242L.

In some embodiments, the variant phytase has an amino acid substitution of the asparagine at position 244 of SEQ ID NO:1. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is N244I.

In some embodiments, the variant phytase has an amino acid substitution of the proline at position 261 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P261L.

In some embodiments, the variant phytase has an amino acid substitution of the serine at position 266 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S266A or S266Y.

In some embodiments, the variant phytase has an amino acid substitution of the leucine at position 272 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L272S.

In some embodiments, the variant phytase has an amino acid substitution of the methionine at position 276 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, proline, phenylalanine, tryptophan, valine and tyrosine with some embodiments not utilizing cysteine (due to possible disulfide formation) or proline (due to steric effects). In some embodiments, the amino acid substitution is M276K.

In some embodiments, the variant phytase has an amino acid substitution of the alanine at position 277 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A277T.

In some embodiments, the variant phytase has an amino acid substitution of the leucine at position 279 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L279F.

In some embodiments, the variant phytase has an amino acid substitution of the threonine at position 280 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine. In some embodiments, the amino acid substitution is T280C, T280G, T280N, and T280P.

In some embodiments, the variant phytase has an amino acid substitution of the proline at position 281 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P281D or P281S.

In some embodiments, the variant phytase has an amino acid substitution of the histidine at position 282 of SEQ ID NO:1. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is H282N.

In some embodiments, the variant phytase has an amino acid substitution of the alanine at position 288 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A288R.

In some embodiments, the variant phytase has an amino acid substitution of the threonine at position 292 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T292G.

In some embodiments, the variant phytase has an amino acid substitution of the threonine at position 295 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T295N.

In some embodiments, the variant phytase has an amino acid substitution of the glycine at position 302 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G302S.

In some embodiments, the variant phytase has an amino acid substitution of the glycine at position 311 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G311A.

In some embodiments, the variant phytase has an amino acid substitution of the glutamic acid at position 315 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E315G or E315S.

In some embodiments, the variant phytase has an amino acid substitution of the leucine at position 316 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L316F.

In some embodiments, the variant phytase has an amino acid substitution of the arginine at position 339 of SEQ ID NO:1. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R339M.

In some embodiments, the variant phytase has an amino acid substitution of the leucine at position 341 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L341V.

In some embodiments, the variant phytase has an amino acid substitution of the glutamine at position 346 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from Q346K, Q346P, Q346S, and Q346T.

In some embodiments, the variant phytase has an amino acid substitution of the leucine at position 352 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L352M.

In some embodiments, the variant phytase has an amino acid substitution of the aspartic acid at position 362 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from D362G, D362N, D362S, and D362Y.

In some embodiments, the variant phytase has an amino acid substitution of the lysine at position 363 of SEQ ID NO:1. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is K363A, or K363R.

In some embodiments, the variant phytase has an amino acid substitution of the threonine at position 364 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing proline (due to steric effects). In some embodiments, the amino acid substitution is selected from T364C, T364E, T364I, T364L, T364N, T364Q, T364S, T364T, T364V, and T364W.

In some embodiments, the variant phytase has an amino acid substitution of the proline at position 365 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P365W.

In some embodiments, the variant phytase has an amino acid substitution of the leucine at position 366 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L366R.

In some embodiments, the variant phytase has an amino acid substitution of the threonine at position 370 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T370K.

In some embodiments, the variant phytase has an amino acid substitution of the proline at position 371 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is selected from P371M, P371V, P371W, and P371Y.

In some embodiments, the variant phytase has an amino acid substitution of the proline at position 372 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P372T.

In some embodiments, the variant phytase has an amino acid substitution of the threonine at position 378 of SEQ ID NO:1. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T378A.

In some embodiments, the variant phytase has an amino acid substitution of the glycine at position 381 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing proline (due to steric effects). In some embodiments, the amino acid substitution is selected from G381A, G381C, G381L, G381N, and G381R.

In some embodiments, the variant phytase has an amino acid substitution of the glutamic acid at position 384 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E384D.

In some embodiments, the variant phytase has an amino acid substitution of the arginine at position 385 of SEQ ID NO:1. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R385T.

In some embodiments, the variant phytase has an amino acid substitution of the alanine at position 394 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selected from A394I, A394L, A394M, and A394P.

In some embodiments, the variant phytase has an amino acid substitution of the glycine at position 395 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation). In some embodiments, the amino acid substitution is G395P.

In some embodiments, the variant phytase has an amino acid substitution of the glutamine at position 398 of SEQ ID NO:1. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q398V.

In some embodiments, the variant phytase has an amino acid substitution of the asparagine at position 401 of SEQ ID NO:1. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from N401A, N401L, and N401P.

In some embodiments, the variant phytase has an amino acid substitution of the glutamic acid at position 402 of SEQ ID NO:1. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E402D.

In some embodiments, the variant phytase has an amino acid substitution of the alanine at position 403 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A403G, A403I, A403K, A403L, A403N, A403Q, A403W, and A403Y.

In some embodiments, the variant phytase has an amino acid substitution of the serine at position 409 of SEQ ID NO:1. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S409H, S409L, S409R, S409V, and S409W.

In some embodiments, the variant phytase has an amino acid substitution of the leucine at position 410 of SEQ ID NO:1. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing proline (due to steric effects). In some embodiments, the amino acid substitution is selected from L410A, L410C, L410E, L410F, L410G, L410I, L410K, and L410R.

In some embodiments, the invention provides said variant phytase enzymes comprising the amino acid substitution(s) as compared to SEQ ID NO:1, wherein the amino acid substitution(s) is selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, M276K, A277T, L279F, T280C, T280G, T280N, T280P, P281D, P281S, H282N, A288R, T292G, T295N, G302S, G311A, E315G, E315S, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R; wherein said variant phytase enzyme is not SEQ ID NO:17; and wherein said variant phytase enzyme has phytase activity.

In some embodiments, the invention provides compositions comprising variant phytase enzymes comprising at least one amino acid substitution as compared to SEQ ID NO:1, wherein said amino acid substitution(s) is selected from the group consisting of A277T, P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, V67A, G70E, L72S, K75C, K75E, K75G, K75I, K75L, K75M, K75Q, K75R, K75S, K75W, G76C, P80S, V89T, D90N, I110L, H113Q, T114C, T114D, T114F, T114H, T114N, T114P, T114S, S119R, R120K, P121A, T130G, T130R, Q134A, Q134T, L135F, L135Y, D136F, D136G, D136S, P137C, P137F, P137G, P137H, P137I, P137L, P137M, P137V, P137W, P137Y, D142A, D142E, D142F, D142G, D142H, D142I, D142K, D142L, D142M, D142N, D142P, D142R, D142S, D142T, D142V, D142Y, S151F, S151R, A153N, A153S, A153V, A153Y, Q157A, Q157P, H158R, H158W, T161D, E165D, E165P, E165S, E165T, E165W, P173N, P173S, P173T, P173Y, Q174A, Q174E, F179L, R181T, E182A, E182F, E182S, E182T, S187T, T191S, Q192K, Q192L, A193I, A193L, A193S, A193T, A193V, L194I, E197S, A202R, Q225E, P230S, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, L279F, T280C, T280G, T280N, T280P, P281D, P281S, T292G, G302S, L316F, T364C, T364E, T364I, T364L, T364N, T364Q, T364S, T364T, T364V, T364W, P365W, L366R, P371M, P371V, P371W, P371Y, P372T, T378A, G381A, G381C, G381L, G381N, G381R, E384D, A394I, A394L, A394M, A394P, G395P, Q398V, N401A, N401L, N401P, A403G, A403I, A403K, A403L, A403N, A403Q, A403W, A403Y, S409H, S409L, S409R, S409V, S409W, L410A, L410C, L410E, L410F, L410G, L410I, L410K, and L410R; wherein said variant phytase enzyme is at least 90% identical to SEQ ID NO:1 and is not SEQ ID NO:17; and wherein said variant phytase enzyme has phytase activity.

In some embodiments, the invention provides compositions comprising said variant phytase enzyme further comprising at least one amino acid substitution, and wherein said amino acid substitution(s) is selected from the group consisting of Q1S, Q1V, Q1N, Q30K, A36K, T39D, H60S, K74P, K74L, R65C, R65G, R65P, R65S, R65V, N69L, N69R, N69Y, A73P, Q79L, Q79R, Q79A, Q79G, Q79F, I85V, A101L, A109D, A109N, A109E, A109G, A109F, A109P, T111I, A116Y, A116P, A116K, A116S, T118R, T118S, R120S, P137N, P137S, A138V, A138H, A138D, A138P, N139A, N139H, N139P, T141E, T141G, T141A, T141R, S146E, S146P, Q157G, N176K, N180K, K183R, Q184S, D185N, E186V, E186A, S189L, S189N, S189T, G233A, T245E, M276K, H282N, A288R, V291I, T295N, V297L, G311A, E315G, E315S, R339M, L341V, Q346K, Q346P, Q346S, Q346T, L352M, D362G, D362N, D362S, D362Y, K363A, K363R, N369P, T370K, A380R, A380T, E383S, R385T, and E402D.

In some embodiments, the invention provides said variant phytase enzymes comprising the amino acid substitutions as compared to SEQ ID NO:1, wherein the amino acid substitutions are selected from the group consisting of G70E/A73P/K75C/A277T, Q62W/A73P/G302S, Q62W/A73P/A288R/E315G, G70E/A73P/K75C, W46E/Q62W/S146E/E402D, W46E/Q62W/A73P/N180K/M276K/A277T/E402D, Q62W/A277T/E315G, Q62W/A288R, G70E/P80S/E315G, W46E/Q62W/A73P, M276K/A288R, G70E/A73P/E402D, W46E/Q62W/E315G, W46G/A277T/A288R, W46E/Q62W, W46E/G70E/E315G, Q62W/G70E/F179L/A277T/A288R, W46E/Q62W/P80S/H113Q/E315G/E402D, M276K/E315G, M276K/A277T, K75W/M276K/A288R, W46E/Q62W/A73P/K75C/A277T/A288R/E315G, W46E/Q62W/N180K/E315G, M276K/A288R/E315G, W46E/Q62W/F179L/M276K, W46E/Q62W/M276K, A277T/A288R/E402D, W46G/Q62W/A73P/S146E/A277T, N180K/M276K/A277T/E315G/E402D, G70E/A73P/M276K/E315G, M276K/E315G/E402D, W46E/Q62W/K75C/F179L/A277T, P80S/M276K/E315G, G70E/A288R, M276K/A277T/E315G/E402D, Q62W/P80S/M276K, M276K/A277T/E315G, G70E/A73P/M276K, W46E/Q62W/P80S, W46E/G70E/K75C/A288R, Q62W/P80S/A277T, N180K/M276K/E315G/E402D, F179L/A277T/A288R, Q62W/A73P/P80S/A288R, A73P/E402D, Q62W/A73P/E402D, P137H/L316F, P4L/T280C, T238S/P372T, P4T/T280P, P4K/T280N, T364V/P371M, P4M/T280G, D35Y/T238G, L272S/A403Y, A193T/E384D, L58S/S409R, A153Y/Q157P/E165D/P261L, L72S/L410F, K7N/D35R/V67A/P173N/T238G/M276K/A277T/E315G/T364W/G381A/A403G, P4N/K7N/D35N/V67A/P121A/D136S/P173N/T238G/M276K/A277T/E315G/Q346S/T364W/P378A/G381A/A403G, K7N/D35R/V67A/P121A/D136S/P173N/T238G/M276K/A277T/E315G/Q346S/T364W/

T378A/G381A/A403G, P4N/K7N/D35R/V67A/P121A/D136S/P173N/T238G/M276K/A277T/E315G/T364W/T378A/G381A/A403G, P4N/K7N/D35R/V67A/P121A/D136S/P173N/T238G/M276K/A277T/E315G/T364W/T378A/G381A/A403G, and K7N/D35R/V67A/P173N/T238G/M276K/A277T/E315G/Q346T/T364W/G381A/A403G/L410A.

In some embodiments, the invention provides said variant phytase enzymes comprising amino acid substitutions as compared to SEQ ID NO:1, wherein the amino acid substitutions comprise M276K/A277T/E315G and at least one further amino acid substitution selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76P, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401N, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

In some embodiments, the invention provides said variant phytase enzymes comprising the amino acid substitutions as compared to SEQ ID NO:1, wherein the amino acid substitutions are selected from the group consisting of M276K/A277T/E315G/A73P/A288R, M276K/A277T/E315G/A288R, M276K/A277T/E315G/Q62W/A288R, M276K/A277T/E315G/Y61C/Q62W/A73P, M276K/A277T/E315G/A73P, M276K/A277T/E315G/Q62W, M276K/A277T/E315G/Q62W/A73P/A288R, M276K/A277T/E315G/K7N/D35R, M276K/A277T/E315G/K7N/D35R/P173Y/T364I, M276K/A277T/E315G/K7N/D35R/Q192K, M276K/A277T/E315G/K7N/D35R/P173Y/T364W, M276K/A277T/E315G/K7N/Q192L/T238A/T364W, M276K/A277T/E315G/K7N/Q192K/T364W/T370K, M276K/A277T/E315G/K7N/V67A/T238A/T364I, M276K/A277T/E315G/K7N/Q192L/T364I, M276K/A277T/E315G/K7N/V67A/Q192K/T364W, E315G/K7N/V67A/Q192K/T364W, E315G/K7N/T238G/T364W, M276K/A277T/E315G/K7N/T238A, M276K/A277T/E315G/K7N/P173Y/Q192K/A403G, M276K/A277T/E315G/K7N/D35R/V67A/T238G/T364I/G381A/A403G, M276K/A277T/E315G/K7N/V67A/P173Y/T238A/T364I, M276K/A277T/E315G/K7N/V67A/T364I, M276K/A277T/E315G/K7N/P173Y, M276K/A277T/E315G/K7N/P173Y/A403G, M276K/A277T/E315G/K7N/V67A/Q192K, M276K/A277T/E315G/K7N/V67A/G381L, M276K/A277T/E315G/K7N, M276K/A277T/E315G/K7N/P173Y/Q192K/T364I, M276K/A277T/E315G/K7N/V67A/P173Y, M276K/A277T/E315G/K7N/V67A, M276K/A277T/E315G/K7N/T364I/G381L, M276K/A277T/E315G/K7N/P173Y/G381L, M276K/A277T/E315G/S146P, M276K/A277T/E315G/V67A/T364I, M276K/A277T/E315G/P173N/T364W, M276K/A277T/E315G/V67A/T238G/G381A, M276K/A277T/E315G/T238G, M276K/A277T/E315G/P173S, M276K/A277T/E315G/T238N/T364W, M276K/A277T/E315G/T238A/T364W, M276K/A277T/E315G/V67A, M276K/A277T/E315G/T364W/G381A, M276K/A277T/E315G/V67A/T238A/T364W, M276K/A277T/E315G/V67A/T364W, M276K/A277T/E315G/T364W, M276K/A277T/E315G/T364I, M276K/A277T/E315G/T238A/T364W/G381A, M276K/A277T/E315G/T364I, M276K/A277T/E315G/V67A/P173N/T238A/T364W, M276K/A277T/E315G/P173N/T238N, M276K/A277T/E315G/P173T, M276K/A277T/E315G/V67A/T238A, M276K/A277T/E315G/P173T/G381A, M276K/A277T/E315G/S119R/L279F, M276K/A277T/E315G/N244I/T280N, M276K/A277T/E315G/T238P/T280N/P371Y/A403W, M276K/A277T/E315G/S119R/A403K, M276K/A277T/E315G/T280N/P371Y/A403W, M276K/A277T/E315G/S119R/P371Y/A403K, M276K/A277T/E315G/T280N/A403K, M276K/A277T/E315G/T280N, M276K/A277T/E315G/T280N/P371Y, M276K/A277T/E315G/T238Y, M276K/A277T/E315G/T238P/P371Y, M276K/A277T/E315G/P371Y/A403W, M276K/A277T/E315G/S119R/T280N, M276K/A277T/E315G/T238P, M276K/A277T/E315G/S119R/P371Y/A403L, M276K/A277T/E315G/P371Y/A403L, M276K/A277T/E315G/S119R, M276K/A277T/E315G/T238Y/A403W, M276K/A277T/E315G/S119R/T280N/P371Y, M276K/A277T/E315G/A403W, M276K/A277T/E315G/R65G/L410R, M276K/A277T/E315G/Q346T/S409V/L410A, M276K/A277T/E315G/E182T/D362G, M276K/A277T/E315G/E182S/S187T/P281S, M276K/A277T/E315G/D362G/S409V, M276K/A277T/E315G/P281S/S409H, M276K/A277T/E315G/E182T/A202R, M276K/A277T/E315G/R65G/S187T/Q346T, M276K/A277T/E315G/P281S/Q346T, M276K/A277T/E315G/E182S/P281S, M276K/A277T/E315G/P281S, M276K/A277T/E315G/S187T/Q346T/L410A, M276K/A277T/E315G/R65G/P281S/S409V, M276K/A277T/E315G/D31N, M276K/A277T/E315G/D31N/D362G/L410A, M276K/A277T/E315G/Q346T/L410A, M276K/A277T/E315G/P281S/Q346S, M276K/A277T/E315G/D31N/P281S/Q346T, M276K/A277T/E315G/S409H/L410A, M276K/A277T/E315G/D31N/Q346P, M276K/A277T/E315G/E182S/S187T, M276K/A277T/E315G/R65G/P281S, M276K/A277T/E315G/A202R/P281S/D362G/L410R, M276K/A277T/E315G/D31N/R65G/S187T/S409V/L410A, M276K/A277T/E315G/D31N/P281S/Q346S/D362G/K363R/S409H, M276K/A277T/E315G/Q346S, M276K/A277T/E315G/E182S/Q346S, M276K/A277T/E315G/N401P, M276K/A277T/E315G/P4N/N401P, M276K/A277T/E315G/T292G/T378A, M276K/A277T/E315G/D362G/N401P, M276K/A277T/E315G/E182A/T292G, M276K/

A277T/E315G/P4N/T292G, M276K/A277T/E315G/P4N/ D362G/G395P, M276K/A277T/E315G/G395P, M276K/ A277T/E315G/P4N/G395P, M276K/A277T/E315G/P4N, M276K/A277T/E315G/P4N/I110L/G395P, M276K/A277T/ E315G/P4N/D31I, M276K/A277T/E315G/P4N/D31I/ E182A, M276K/A277T/E315G/D31I, M276K/A277T/ E315G/P4N/S240G, M276K/A277T/E315G/P4N/I110L/ S240R, M276K/A277T/E315G/D31I/S240A/N401P, M276K/A277T/E315G/T378A, M276K/A277T/E315G/ D31I/S240A/D362G, M276K/A277T/E315G/G76C/ A394M, M276K/A277T/E315G/R65G/E165P/Q242E, M276K/A277T/E315G/R65S/E165P/D362S, M276K/ A277T/E315G/R65S/A193I/Q346P, M276K/A277T/ E315G/Q242E/Q346P, M276K/A277T/E315G/R65G/ E165P/D362S, M276K/A277T/E315G/R65P/E165P, M276K/A277T/E315G/R65S/E165P, M276K/A277T/ E315G/R65S/E165P/Q242E/A394M, M276K/A277T/ E315G/R65G/E165P, M276K/A277T/E315G/R65C/ A193S/A394P, M276K/A277T/E315G/R65G/Q346P, M276K/A277T/E315G/R65S/E165P/Q242E/D362S, M276K/A277T/E315G/R65G, M276K/A277T/E315G/ R65S, M276K/A277T/E315G/R65S/E165P/D362S/A394P, M276K/A277T/E315G/Q346P, M276K/A277T/E315G/ Q242E, M276K/A277T/E315G/R65S/E165P/S240K, M276K/A277T/E315G/R65S/E165P/G381R, M276K/ A277T/E315G/R65S/A394I, M276K/A277T/E315G/ E165P/S240K/D362S, M276K/A277T/E315G/R65G/ Q242E, M276K/A277T/E315G/Q242E/A394P, M276K/ A277T/E315G/R65G/D362S, M276K/A277T/E315G/ R65S/E165P/Q346P, M276K/A277T/E315G/R65G/S240K/ Q242E, M276K/A277T/E315G/A394L, M276K/A277T/ E315G/E5K/A153S/P281S/S409L, M276K/A277T/E315G/ E5K/P281S/S409H, M276K/A277T/E315G/S151F/A153S/ P281S/L410G, M276K/A277T/E315G/A153N/P281S, M276K/A277T/E315G/E5K/P281S, M276K/A277T/ E315G/E5K, M276K/A277T/E315G/P281S/L410R, M276K/A277T/E315G/P281S/Q346K/S409L/L410G, M276K/A277T/E315G/E5K/V11I/Q346K, M276K/A277T/ E315G/V11I/P281S, M276K/A277T/E315G/A153S, M276K/A277T/E315G/E5K/P365W, M276K/A277T/ E315G/E5K/P281S/L410G, M276K/A277T/E315G/E5K/ T111I/P281S/P365W, M276K/A277T/E315G/E5K/A153N/ P281S, M276K/A277T/E315G/E5K/A153N/P281S/ Q346K, M276K/A277T/E315G/Q346K, M276K/A277T/ E315G/A153N/S409L, M276K/A277T/E315G/E5K/ A153N/P281S/L410G, M276K/A277T/E315G/K7E/ S409H, M276K/A277T/E315G/E5K/A153N/P281S/ S409R, M276K/A277T/E315G/E5K/P281S/L410I and M276K/A277T/E315G/E5K/A153S/P281S.

In some embodiments, the invention provides said variant phytases comprising the amino acid substitutions as compared to SEQ ID NO:1, wherein the amino acid substitutions comprise M276K/A277T/E315G/K7N/D35R/V67A/ T238G/T364I/G381A/A403G and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193N, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363P, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising amino acid substitutions as compared to SEQ ID NO:1, wherein the amino acid substitutions are selected from the group consisting of M276K/A277T/ E315G/K7N/D35R/V67A/T238G/T364I/G381A/A403G/ P121A, M276K/A277T/E315G/K7N/D35R/V67A/T238G/ T364I/G381A/A403G/D136G, M276K/A277T/E315G/ K7N/D35R/V67A/T238G/T364I/G381A/A403G/T130G, M276K/A277T/E315G/K7N/D35R/V67A/T238G/T364I/ G381A/A403G/Q174E, M276K/A277T/E315G/K7N/ D35R/V67A/T238G/T364I/G381A/A403G/Q174A, M276K/A277T/E315G/K7N/D35R/V67A/T238G/T364I/ G381A/A403G/Q27D, M276K/A277T/E315G/K7N/D35R/ V67A/T238G/T364I/G381A/A403G/Q134A, M276K/ A277T/E315G/K7N/D35R/V67A/T238G/T364I/G381A/ A403G/T161D, M276K/A277T/E315G/K7N/D35R/V67A/ T238G/T364I/G381A/A403G/T130R, M276K/A277T/ E315G/K7N/D35R/V67A/T238G/T364I/G381A/A403G/ Q27P, M276K/A277T/E315G/K7N/D35R/V67A/T238G/ T364I/G381A/A403G/E53N, M276K/A277T/E315G/K7N/ D35R/V67A/T238G/T364I/G381A/A403G/D136F, M276K/A277T/E315G/K7N/D35R/V67A/T238G/T364I/ G381A/A403G/S151R, M276K/A277T/E315G/K7N/ D35R/V67A/T238G/T364I/G381A/A403G/Q27V, M276K/ A277T/E315G/K7N/D35R/V67A/T238G/T364I/G381A/ A403G/Q134T, M276K/A277T/E315G/K7N/D35R/V67A/ T238G/T364I/G381A/A403G/E53D, M276K/A277T/ E315G/K7N/D35R/V67A/T238G/T364I/G381A/A403G/ D1365, M276K/A277T/E315G/K7N/D35R/V67A/T238G/ T364I/G381A/A403G/T295N, M276K/A277T/E315G/ K7N/D35R/V67A/T238G/T364I/G381A/A403G/S189L, M276K/A277T/E315G/K7N/D35R/V67A/T238G/T364I/ G381A/A403G/S189T, M276K/A277T/E315G/K7N/D35R/ V67A/T238G/T364I/G381A/A403G/T191S, M276K/ A277T/E315G/K7N/D35R/V67A/T238G/T364I/G381A/ A403G/P230S, M276K/A277T/E315G/K7N/D35R/V67A/ T238G/T364I/G381A/A403G/S189N, M276K/A277T/ E315G/K7N/D35R/V67A/T238G/T364I/G381A/A403G/ E197S, M276K/A277T/E315G/K7N/D35R/V67A/T238G/ T364I/G381A/A403G/L194I, M276K/A277T/E315G/ K7N/V67A/T238G/T364I/G381A/A403G/P4N/T378A, M276K/A277T/E315G/K7N/D35R/V67A/T238G/T364I/ G381A/A403G/S409V, M276K/A277T/E315G/K7N/ D35R/V67A/T238G/T364I/G381A/A403G/T378A, M276K/A277T/E315G/K7N/D35R/V67A/T238G/T364I/ G381A/A403G/P4N, M276K/A277T/E315G/K7N/V67A/

T238G/T364I/G381A/A403G/T378A, M276K/A277T/
E315G/K7N/V67A/T238G/T364I/G381A/A403G, M276K/
A277T/E315G/K7N/V67A/T238G/T364I/G381A/A403G/
P4N, M276K/A277T/E315G/K7N/V67A/T238G/T364I/
G381A/A403G/T111I, M276K/A277T/E315G/K7N/D35R/
V67A/T238G/T364I/G381A/A403G/P4N/T378A, M276K/
A277T/E315G/K7N/D35R/V67A/T238G/T364I/G381A/
A403G/P173S/E182S, M276K/A277T/E315G/K7N/D35R/
V67A/T238G/T364I/G381A/A403G/P173S/E182T/Q346T,
M276K/A277T/E315G/K7N/D35R/V67A/T238G/T364I/
G381A/A403G/P173S/E182T, M276K/A277T/E315G/
K7N/D35R/V67A/T238N/T364I/G381A/A403G/P173S/
E182T/S187T, M276K/A277T/E315G/K7N/D35R/V67A/
T238N/T364I/G381A/A403G/E182S, M276K/A277T/
E315G/K7N/D35R/V67A/T238N/T364I/G381A/A403G/
Q346T, M276K/A277T/E315G/K7N/D35R/V67A/T238G/
T364I/G381A/A403G/Q346S, M276K/A277T/E315G/
K7N/D35R/V67A/T238N/T364I/G381A/A403G/E182T/
Q346S, M276K/A277T/E315G/K7N/D35R/V67A/T238N/
T364I/G381A/A403G/P173S, M276K/A277T/E315G/
K7N/D35R/V67A/T238N/T364I/G381A/A403G/E182T,
M276K/A277T/E315G/K7N/D35R/V67A/T238N/T364I/
G381A/A403G/P173S/E182T, M276K/A277T/E315G/
K7N/D35R/V67A/T238N/T364I/G381A/A403G/P173S/
E182S, M276K/A277T/E315G/K7N/D35R/V67A/T238G/
T364I/G381A/A403G/E182S, M276K/A277T/E315G/
K7N/D35R/V67A/T238G/T364I/G381A/A403G/Q346T,
M276K/A277T/E315G/K7N/D35R/V67A/T238G/T364I/
G381A/A403G/P173S/Q346T, M276K/A277T/E315G/
K7N/D35R/V67A/T238G/T364I/G381A/A403G/R65S,
M276K/A277T/E315G/K7N/D35R/V67A/T238G/T364I/
G381A/A403G/A153N, and M276K/A277T/E315G/K7N/
D35R/V67A/T238G/T364I/G381A/A403G/K363R.

In some embodiments, the invention provides said variant phytases comprising amino acid substitutions as compared to SEQ ID NO:1, wherein the amino acid substitutions comprise K7N/D35R/V67A/P173N/T238G/M276K/A277T/E315G/T364W/G381A/A403G and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising amino acid substitutions as compared to SEQ ID NO:1, wherein the amino acid substitutions are selected from the group consisting of K7N/D35R/V67A/P173N/T238G/M276K/A277T/E315G/T364W/G381A/A403G/N176K/D185N/H282N/A288R/R385T, K7N/D35R/V67A/P173N/T238G/M276K/A277T/E315S/T364W/G381A/A403G/N139A/D185N/R385T, K7N/D35R/V67A/P173N/T238G/M276K/A277T/E315G/T364W/G381A/A403G/N139H/N176K/D185N/A288R, K7N/D35R/V67A/P173N/T238G/M276K/A277T/E315G/T364W/G381A/A403G/T161D/A288R, K7N/D35R/V67A/P173N/T238G/M276K/A277T/E315G/T364W/G381A/A403G/N139H/N176K/D185N, K7N/D35R/V67A/P173N/T238G/M276K/A277T/E315G/T364W/G381A/A403G/N139A/T161D/N176K/D185N, K7N/D35R/V67A/P173N/T238G/M276K/A277T/E315G/T364W/G381A/A403G/D185N/H282N, K7N/D35R/V67A/P173N/T238G/M276K/A277T/E315G/T364W/G381A/A403G/N139P/N176K/D185N/K363A, K7N/D35R/V67A/P173N/T238G/M276K/A277T/E315G/T364W/G381A/A403G/D185N, K7N/D35R/V67A/P173N/T238G/M276K/A277T/E315G/T364W/G381A/A403G/D185N/R385T, K7N/D35R/V67A/P173N/T238G/M276K/A277T/E315G/T364W/G381A/A403G/A288R, K7N/D35R/V67A/P173N/T238G/M276K/A277T/E315G/T364W/G381A/A403G/R385T, K7N/D35R/V67A/P173N/T238G/M276K/A277T/E315G/T364W/G381A/A403G/D185N/H282N/L341V/R385T, K7N/D35R/V67A/P173N/T238G/M276K/A277T/E315G/T364W/G381A/A403G/H282N, K7N/D35R/V67A/P173N/T238G/M276K/A277T/E315G/T364W/G381A/A403G/N139A/D185N/H282N/A288R/K363A/R385T, K7N/D35R/V67A/P173N/T238G/M276K/A277T/E315G/T364W/G381A/A403G/N176K/D185N K7N/D35R/V67A/P173N/T238G/M276K/A277T/E315G/T364W/G381A/A403G/N139A/N176K/D185N, K7N/D35R/V67A/P173N/T238G/M276K/A277T/E315G/T364W/G381A/A403G/N176K/L341V, K7N/D35R/V67A/P173N/T238G/M276K/A277T/E315G/T364W/G381A/A403G/D185N/H282N/A288R, K7N/D35R/V67A/P173N/T238G/M276K/A277T/E315G/T364W/G381A/A403G/N139A/N176K/D185N/L341V, K7N/D35R/V67A/P173N/T238G/M276K/A277T/E315G/T364W/G381A/A403G/T161D/D185N, K7N/D35R/V67A/P173N/T238N/M276K/A277T/E315G/T364W/G381A/A403G/P4N/T378A, K7N/D35R/V67A/P173N/T238G/M276K/A277T/E315G/T364W/G381A/A403G/P4N/D136F/E197S/T378A, K7N/D35R/V67A/P173N/T238N/M276K/A277T/E315G/T364W/G381A/A403G/P4N/E197S/T378A, K7N/D35R/V67A/P173N/T238G/M276K/A277T/E315G/T364W/G381A/A403G/P4N/Q346S, K7N/D35R/V67A/P173N/T238N/M276K/A277T/E315G/T364W/G381A/A403G/P4N/P121A/E182T/E197S/Q346S/T378A, K7N/D35R/V67A/P173N/T238N/M276K/A277T/E315G/T364W/G381A/A403G/P4N/D136S/E182T/T378A, K7N/D35R/V67A/P173N/T238N/M276K/A277T/E315G/T364W/G381A/A403G/P4N/P121A/D136F/E182S/Q346S, K7N/D35R/V67A/P173N/T238N/M276K/A277T/E315G/T364W/G381A/A403G/P4N/P121A/E197S, K7N/D35R/V67A/P173N/T238N/M276K/A277T/E315G/T364W/G381A/A403G/P4N/E197S/Q346S, K7N/D35R/V67A/P173N/T238N/M276K/A277T/E315G/T364W/G381A/A403G/P4N/Q346S, K7N/D35R/V67A/P173S/T238N/M276K/A277T/

E315G/T364W/G381A/A403G/P4N/D136S/E182S/Q346S, K7N/D35R/V67A/P173S/T238N/M276K/A277T/E315G/T364W/G381A/A403G/P4N/D136S/E182S/Q346S/T378A, K7N/D35R/V67A/P173N/T238N/M276K/A277T/E315G/T364W/G381A/A403G/P4N/D136S/E182T, K7N/D35R/V67A/P173N/T238N/M276K/A277T/E315G/T364W/G381A/A403G/P4N/E197S/Q346S/T378A, K7N/D35R/V67A/P173N/T238G/M276K/A277T/E315G/T364W/G381A/A403G/E182T/E197S/T378A, K7N/D35R/V67A/P173N/T238N/M276K/A277T/E315G/T364W/G381A/A403G/Q346S, K7N/D35R/V67A/P173N/T238N/M276K/A277T/E315G/T364W/G381A/A403G/P4N/D136F/E 182T/E197S, K7N/D35R/V67A/P173N/T238G/M276K/A277T/E315G/T364W/G381A/A403G/P4N/P121A/D 136S/Q346S/T378A, K7N/D35R/V67A/P173N/T238N/M276K/A277T/E315G/T364W/G381A/A403G/P4N/D136S/E197S/Q346S/T378A, K7N/D35R/V67A/P173N/T238N/M276K/A277T/E315G/T364W/G381A/A403G/P4N/P121A/D 136S/E182T/T378A, K7N/D35R/V67A/P173S/T238N/M276K/A277T/E315G/T364W/G381A/A403G/P121A/D136S/E182S/E197S/T378A, K7N/D35R/V67A/P173N/T238G/M276K/A277T/E315G/T364W/G381A/A403G/Q62W/P80S/D 142E/A288R/E402D, K7N/D35R/V67A/P173N/T238G/M276K/A277T/E315G/T364W/G381A/A403G/W46E/Q62W/A73P/K75G/A288R/E402D, K7N/D35R/V67A/P173N/T238G/M276K/A277T/E315G/T364W/G381A/A403G/A288R/E402D, K7N/D35R/V67A/P173N/T238G/M276K/A277T/E315G/T364W/G381A/A403G/Q62W/A73P/K 75G/D142E/F179L/E402D, K7N/D35R/V67A/P173N/T238G/M276K/A277T/E315G/T364W/G381A/A403G/Q62W/A288R/E402D, K7N/D35R/V67A/P173N/T238G/M276K/A277T/E315G/T364W/G381A/A403G/Q62W/G70E/A73P/D142E/F179L/E402D, K7N/D35R/V67A/P173N/T238G/M276K/A277T/E315G/T364W/G381A/A403G/E402D, K7N/D35R/V67A/P173N/T238G/M276K/A277T/E315G/T364W/G381A/A403G/Q62W/G70E/K 75G/E402D, K7N/D35R/V67A/P173N/T238G/M276K/A277T/E315G/T364W/G381A/A403G/K75G/E402D, K7N/D35R/V67A/P173N/T238G/M276K/A277T/E315G/T364W/G381A/A403G/S146E/A288R, K7N/D35R/V67A/P173N/T238G/M276K/A277T/E315G/T364W/G381A/A403G/Q62W/P80S/D 142E/S146E/A288R/E402D, K7N/D35R/V67A/P173N/T238G/M276K/A277T/E315G/T364W/G381A/A403G/Q62W/D142E/S146E/E402D, K7N/D35R/V67A/P173N/T238G/M276K/A277T/E315G/T364W/G381A/A403G/D142E, K7N/D35R/V67A/P173N/T238G/M276K/A277T/E315G/T364W/G381A/A403G/Q62W/E402D, K7N/D35R/V67A/P173N/T238G/M276K/A277T/E315G/T364W/G381A/A403G/A73P/P80S/D142E/Q346T, K7N/D35R/V67A/P173N/T238G/M276K/A277T/E315G/T364W/G381A/A403G/Q62W/G70E/K 75G/P80S/D142E/E402D, K7N/D35R/V67A/P173N/T238G/M276K/A277T/E315G/T364W/G381A/A403G/Q62W/D142E/E402D, K7N/D35R/V67A/P173N/T238G/M276K/A277T/E315G/T364W/G381A/A403G/Q62W/D142E/A288R/E402D, K7N/D35Y/V67A/P173N/T238G/M276K/A277T/E315G/T364W/G381A/A403G, K7Q/D35R/V67A/P173N/T238G/M276K/A277T/E315G/T364W/G381A/A403G, K7N/D35R/V67A/P173N/T238G/M276K/A277T/E315G/T364C/G381A/A403G, K7N/D35R/V67A/P173N/T238G/M276K/A277T/E315G/T364W/G381A/A403G/K75I, K7N/D35N/V67A/P173N/T238G/M276K/A277T/E315G/T364W/G381A/A403G, K7N/D35R/V67A/P173N/T238G/M276K/A277T/E315G/T364Q/G381A/A403G, K7N/D35R/V67A/P173N/T238G/M276K/A277T/E315G/T364E/G381A/A403G, K7N/D35R/V67A/P173N/T238G/M276K/A277T/E315G/T364W/G381A/A403G/H158W, D35R/V67A/P173N/T238G/M276K/A277T/E315G/T364W/G381A/A403G, K7N/D35R/V67A/P173N/T238G/M276K/A277T/E315G/T364W/G381 L/A403G, K7N/D35R/V67A/P173N/T238G/M276K/A277T/E315G/T364W/G381N/A403G, K7N/D35R/V67A/P173N/T238G/M276K/A277T/E315G/T364W/G381A/A403G/P1371, K7N/D35R/V67A/P173N/T238G/M276K/A277T/E315G/T364W/G381A/A403K, K7N/D35R/V67A/P173N/T238G/M276K/A277T/E315G/T364S/G381A/A403G, K7N/D35R/V67A/P173N/T238R/M276K/A277T/E315G/T364W/G381A/A403G, K7N/D35R/V67A/P173N/T238G/M276K/A277T/E315G/T364W/G381A/A403G/E165S, K7N/D35R/V67A/P173N/T238G/M276K/A277T/E315G/T364W/G381A/A403G/K75S, K7N/D35R/V67A/P173N/T238G/M276K/A277T/E315G/T364W/G381A/A403L, K7N/D35R/V67A/P173N/T238G/M276K/A277T/E315G/T364W/G381A/A403G/E165T, K7N/D35F/V67A/P173N/T238G/M276K/A277T/E315G/T364W/G381A/A403G, K7N/D35R/V67A/P173N/T238G/M276K/A277T/E315G/T364W/G381R/A403G, K7N/D35R/V67A/P173N/T238G/M276K/A277T/E315G/T364W/G381A/A403N, K7S/D35R/V67A/P173N/T238G/M276K/A277T/E315G/T364W/G381A/A403G, K7N/D35R/V67A/P173N/T238Q/M276K/A277T/E315G/T364W/G381A/A403G, K7N/D35R/V67A/P173N/T238G/M276K/A277T/E315G/T364N/G381A/A403G, K7N/D35R/V67A/P173N/T238G/M276K/A277T/E315G/T364W/G381A/A403G/K75M, K7N/D35R/V67A/P173N/T238G/M276K/A277T/E315G/T364W/G381A/A403G/N69Y, K7N/D35R/V67A/P173N/T238G/M276K/A277T/E315G/T364W/G381A/A403G/K75R, K7N/D35R/V67A/P173N/T238G/M276K/A277T/E315G/T364W/G381A/A403G/K75Q, K7N/D35R/V67A/P173N/T238G/M276K/A277T/E315G/G381A/A403G, K7N/V67A/P173N/T238G/M276K/A277T/E315G/T364W/G381A/A403G, K7N/D35R/V67A/P173N/T238G/M276K/A277T/E315G/T364W/G381A/A403G/R120K, K7N/D35R/V67A/P173N/T238G/M276K/A277T/E315G/T364W/G381A/A403G/V55L, K7N/D35E/V67A/P173N/T238G/M276K/A277T/E315G/T364W/G381A/A403G, K7N/D35R/V67A/P173N/T238G/M276K/A277T/E315G/T364W/G381A/A403G/R120S, K7N/D35R/V67A/P173N/T238G/M276K/A277T/E315G/T364W/G381A/A403Q, K7N/D35R/V67A/P173N/T238G/M276K/A277T/E315G/T364W/G381A/A403G/N69R, K7N/D35R/V67A/P173N/T238G/M276K/A277T/E315G/T364V/G381A/A403G, K7N/D35R/V67A/P173N/T238G/M276K/A277T/E315G/T364W/G381A/A4031, K7N/D35R/V67A/P173N/T238G/M276K/A277T/E315G/T364W/G381A/A403G/Q157G, K7N/D35R/V67A/P173N/T238G/M276K/A277T/E315G/T364W/G381A/A403G/Q157A, K7N/D35R/V67A/P173N/T238G/M276K/A277T/E315G/T364W/G381A/A403G/D142A, K7N/D35R/V67A/P173N/T238G/M276K/A277T/E315G/T364W/G381A/A403G/N69L, K7L/D35R/V67A/P173N/T238G/M276K/A277T/E315G/T364W/G381A/A403G, K7N/D35R/V67A/P173N/T238G/M276K/A277T/E315G/T364L/G381A/A403G, K7N/D35R/V67A/P173N/T238N/M276K/A277T/E315G/T364W/G381A/A403G, K7N/D35R/V67A/P173N/T238G/M276K/A277T/E315G/T364W/G381A/A403G/D142R, K7N/D35R/V67A/P173N/T238G/M276K/A277T/E315G/T364W/G381A/A403G/L6F, K7N/D35R/V67A/P173N/T238G/M276K/A277T/E315G/T364W/G381A/A403G/L135Y, K7N/D35R/V67A/P173N/T238G/M276K/A277T/E315G/T364W/G381A/A403G/S266A, K7N/D35R/V67A/P173N/T238G/M276K/A277T/E315G/T364W/G381A/A403G/L135F, K7N/D35R/V67A/P173N/T238G/M276K/A277T/E315G/T364W/

G381A/A403G/R63A, K7N/D35R/V67A/P173N/T238G/
M276K/A277T/E315G/T364W/G381A/A403G/L352M,
K7N/D35R/V67A/P173N/T238G/M276K/A277T/E315G/
T364W/G381A/A403G/R181T, K7N/D35R/V67A/P173N/
T238G/M276K/A277T/E315G/T364W/G381A/A403G/
S10A, K7N/D35R/V67A/P173N/T238G/M276K/A277T/
E315G/T364W/G381A/A403G/L6Y, K7N/D35R/V67A/
P173N/T238G/M276K/A277T/E315G/T364W/G381A/
A403G/S10Q, K7N/D35R/V67A/P173N/T238G/M276K/
A277T/E315G/T364W/G381A/A403G/S266Y, K7N/D35R/
V67A/P173N/T238G/M276K/A277T/E315G/T364W/
G381A/A403G/G311A, K7N/D35R/V67A/P173N/T238G/M276K/A277T/E315G/T364W/G381A/A403G/L6M, K7N/D35R/V67A/P173N/T238G/M276K/A277T/E315G/T364W/G381A/A403G/V89T, K7N/D35R/V67A/P173N/T238G/M276K/A277T/E315G/T364W/G381A/A403G/G233A, K7N/D35R/V67A/P173N/T238G/M276K/A277T/E315G/T364W/G381A/A403G/S10N/A25F/K75E/P80S/Q225E, K7N/D35R/V67A/P173N/T238G/M276K/A277T/E315G/T364W/G381A/A403G/A25F/Q225E, K7N/D35R/V67A/P173N/T238G/M276K/A277T/E315G/T364W/G381A/A403G/P137V/D185N, K7N/D35R/V67A/P173N/T238G/M276K/A277T/E315G/T364W/G381A/A403G/Q225E, K7N/D35R/V67A/P173N/T238G/M276K/A277T/E315G/T364W/G381A/A403G/P80S/D185N, K7N/D35R/V67A/P173N/T238G/M276K/A277T/E315G/T364W/G381A/A403G/A25F/H158R, K7N/D35R/V67A/P173N/T238G/M276K/A277T/E315G/T364W/G381A/A403G/S10N/A25F/Q 62W/D90N/T114H/H158R/N176K/D185N, K7N/D35E/V67A/P173N/T238G/M276K/A277T/E315G/T364T/G381A/A403G/D142E/E197S/H282N, K7N/D35F/V67A/P173N/T238G/M276K/A277T/E315G/T364T/G381A/A403G/D142E/N176K/E402D, K7N/D35N/V67A/P173N/T238G/M276K/A277T/E315G/T364W/G381A/A403G/P4N/D142E/E 197S/H282N, K7N/D35N/V67A/P173N/T238G/M276K/A277T/E315G/T364T/G381A/A403G/P4N/D142E/E197S/E402D, K7N/V67A/P173N/T238G/M276K/A277T/E315G/T364W/G381A/A403G/P4N/D142E/N176K/H282N/A288R/E402D, K7N/D35N/V67A/P173N/T238G/M276K/A277T/E315G/T364W/G381A/A403G/P4N, K7N/D35E/V67A/P173N/T238G/M276K/A277T/E315G/T364W/G381A/A403G/D142E/H282N/A288R/E402D, K7N/D35F/V67A/P173N/T238G/M276K/A277T/E315G/G381A/A403G/D142E/N176K/E197S, K7N/D35N/V67A/P173N/T238G/M276K/A277T/E315G/G381A/A403G/P4N/E197S/E402D, K7N/D35N/V67A/P173N/T238G/M276K/A277T/E315G/T364W/G381A/A403G/P4N/D142E/E 197S, K7N/V67A/P173N/T238G/M276K/A277T/E315G/T364W/G381A/A403G/P4N/E402D, K7N/D35E/V67A/P173N/T238G/M276K/A277T/E315G/T364W/G381A/A403G/P4N/D142E/E197S/H282N, K7N/V67A/P173N/T238G/M276K/A277T/E315G/T364W/G381A/A403G/P4N, K7N/V67A/P173N/T238G/M276K/A277T/E315G/T364W/G381A/A403G/D142E/H282N/E402 D, K7N/D35F/V67A/P173N/T238G/M276K/A277T/E315G/T364W/G381A/A403G/P4N/D142E, K7N/V67A/P173N/T238G/M276K/A277T/E315G/G381A/A403G/P4N/E402D, K7N/D35N/V67A/P173N/T238G/M276K/A277T/E315G/T364W/G381A/A403G/D142E/N176K/E197S/E402D, K7N/D35F/V67A/P173N/T238G/M276K/A277T/E315G/G381A/A403G/P4N/E402D, K7N/D35F/V67A/P173N/T238G/M276K/A277T/E315G/T364W/G381A/A403G/P4N, K7N/D35E/V67A/P173N/T238G/M276K/A277T/E315G/G381A/A403G/P4N/E402D, K7N/D35F/V67A/P173N/T238G/M276K/A277T/E315G/G381A/A403G/P4N/D142E/E402D, K7N/D35N/V67A/P173N/T238G/M276K/A277T/E315G/G381A/A403G/P4N/D142E/E402D, K7N/D35E/V67A/P173N/T238G/M276K/A277T/E315G/T364W/G381A/A403G/N176K/D185N/S240K, K7N/D35R/V67A/P173N/T238G/M276K/A277T/E315G/T364W/G381A/A403G/P4N/D142R/D 185N/S240K, K7N/D35R/V67A/P173N/T238G/M276K/A277T/E315G/T364W/G381A/A403G/P4N/D142A/N176K/D185N/Q192K/S240K/R385T, K7N/D35N/V67A/P173N/T238G/M276K/A277T/E315G/G381A/A403G/P4N/D142R/D185N, K7N/D35F/V67A/P173N/T238G/M276K/A277T/E315G/T364W/G381A/A403G/N176K/D185N/R385T, K7N/D35N/V67A/P173N/T238G/M276K/A277T/E315G/T364W/G381A/A403G/N176K/D185N/S240K, K7N/D35R/V67A/P173N/T238G/M276K/A277T/E315G/G381A/A403G/P121A/D142A/N176K/D185N/K363A, K7N/D35F/V67A/P173N/T238G/M276K/A277T/E315G/T364W/G381A/A403N/P4N/P121A/D 142E/N176K/D185N/S240K/R385T/A394P, K7N/D35F/V67A/P173N/T238G/M276K/A277T/E315G/T364W/G381A/A403G/P4N/P121A/D 142E/N176K/D185N, K7N/V67A/P173N/T238G/M276K/A277T/E315G/T364W/G381A/A403N/N176K/D185N/Q192K/R385T/A394P, K7N/D35Y/V67A/P173N/T238G/M276K/A277T/E315G/G381A/A403G/S240K/K363A, K7N/V67A/P173N/T238G/M276K/A277T/E315G/T364W/G381A/A403G/L410A, K7N/D35N/V67A/P173N/T238G/M276K/A277T/E315G/T364W/G381A/A403N/D142A/D185N/Q192K/R385T/A394P/L410G, K7N/V67A/P173N/T238G/M276K/A277T/E315G/T364S/G381A/A403G/P121A/D142R/S240K/H282N/K363A/R385T/A394P/L410G, K7N/D35E/V67A/P173N/T238G/M276K/A277T/E315G/G381A/A403G/D142R/N176K/D185N/R385T, K7N/D35F/V67A/P173N/T238G/M276K/A277T/E315G/G381A/A403G/P121A/R385T/L410G, K7N/D35N/V67A/P173N/T238G/M276K/A277T/E315G/T364W/G381A/A403G/D142E/N176K/D185N/S240K, K7N/D35F/V67A/P173N/T238G/M276K/A277T/E315G/T364W/G381A/A403N/D142A/K363A/R385T/A394P/L410G, K7N/D35R/V67A/P173N/T238G/M276K/A277T/E315G/G381A/A403G/P4N/D142A/D185N/R 385T, K7N/D35F/V67A/P173N/T238G/M276K/A277T/E315G/T364W/G381A/A403G/D142R/N176K/D185N/S240K/R385T/A394P, K7N/D35R/V67A/P173N/T238G/M276K/A277T/E315G/T364W/G381A/A403G/D142E/N176K/D185N/Q192K/E197S/A288R/K363A, K7N/V67A/P173N/T238G/M276K/A277T/E315G/T364S/G381A/A403G/D142E/Q192K/E197S/S240K/K363A, K7N/D35F/V67A/P173N/T238G/M276K/A277T/E315G/T364S/G381A/A403G/D142A/D185N/K363A/E402D/L410G, K7N/V67A/P173N/T238G/M276K/A277T/E315G/T364W/G381A/A403G/P4N/P121A/D142R/N176K/D185N/E197S/S240K, K7N/D35N/V67A/P173N/T238G/M276K/A277T/E315G/G381A/A403G/D142E/N176K/D185N/S240K/, K7N/D35N/V67A/P173N/T238G/M276K/A277T/E315G/T364W/G381A/A403G/P4N/P121A/D 142A/D185N/A288R, K7N/D35N/V67A/P173N/T238G/M276K/A277T/E315G/T364W/G381A/A403G/P4N/D185N/Q192K/E197S, K7N/D35Y/V67A/P173N/T238G/M276K/A277T/E315G/T364S/G381A/A403G/D142E/N176K/D185N/R385T/A394P, K7N/D35R/V67A/P173N/T238G/M276K/A277T/E315G/G381A/A403G/S240K/K363A/R385T/A394P/L410A, K7N/D35F/V67A/P173N/T238G/M276K/A277T/E315G/T364W/G381A/A403G/D142R/R385T/A394P/E402D/L410G, K7N/D35N/V67A/P173N/T238G/M276K/A277T/E315G/T364S/G381A/A403G/N176K/D185N/S240K/K363A/A394P/E402D/L410G, K7N/D35E/V67A/P173N/T238G/M276K/A277T/E315G/T364W/G381A/A403G/P4N/D142E, K7N/D35F/V67A/P173N/

T238G/M276K/A277T/E315G/G381A/A403G/K363A, K7N/D35R/V67A/P173N/T238G/M276K/A277T/E315G/ T364S/G381A/A403N/D142E/D185N/R385T/A394P/ L410G, K7N/D35Y/V67A/P173N/T238G/M276K/A277T/ E315G/T364S/G381A/A403G/P121A/S240K, K7N/D35Y/ V67A/P173N/T238G/M276K/A277T/E315G/G381A/ A403G/L410G, K7N/D35E/V67A/P173N/T238G/M276K/ A277T/E315G/T364S/G381A/A403N/D142A/N176K/ D185N/S240K/K363A/R385T/A394P/L410G, K7N/D35Y/ V67A/P173N/T238G/M276K/A277T/E315G/T364W/ G381A/A403G/P4N/D142E/D 185N, K7N/D35E/V67A/ P173N/T238G/M276K/A277T/E315G/T364W/G381A/ A403G/P4N/D142A/N176K/D185N/S240K/K363A/ L410A, K7N/V67A/P173N/T238G/M276K/A277T/ E315G/T364S/G381A/A403G/N176K/D185N/Q192 K/R385T/A394P/E402D/L410A, K7N/V67A/P173N/ T238G/M276K/A277T/E315G/T364S/G381A/A403G/ P121A/D142E/E197S/K363A, K7N/D35R/V67A/P173N/ T238G/M276K/A277T/E315G/T364W/G381A/A403G/ P4N/N176K/D 185N, K7N/D35R/V67A/P173N/T238G/ M276K/A277T/E315G/T364S/G381A/A403G/D142R/ Q192K/S240K/K363A/R385T/A394P/E402D/L410G, K7N/D35R/V67A/P173N/T238G/M276K/A277T/E315G/ T364W/G381A/A403G/P4N/D185N, K7N/D35N/V67A/ P173N/T238G/M276K/A277T/E315G/T364W/G381A/ A403G/N176K/D185N/S240K/R385T, K7N/D35N/V67A/ P173N/T238G/M276K/A277T/E315G/T364W/G381A/ A403G/S240K, K7N/V67A/P173N/T238G/M276K/ A277T/E315G/T364W/G381A/A403G/D142R/N176K/ D185N/S240K, K7N/D35F/V67A/P173N/T238G/M276K/ A277T/E315G/G381A/A403G/P121A/D142E/A153V/ D185N/S240K/R385T, K7N/V67A/P173N/T238G/M276K/ A277T/E315G/T364W/G381A/A403G/D185N/R385T, K7N/D35R/V67A/P173N/T238G/M276K/A277T/E315G/ T364W/G381A/A403G/P4N/N176K/D 185N/S240K, K7N/ D35F/V67A/P173N/T238G/M276K/A277T/E315G/ T364W/G381A/A403G/D142E/N176K/D185N, K7N/ D35R/V67A/P173N/T238G/M276K/A277T/E315G/ T364W/G381A/A403G/D142R/N176K/D185N/Q192K/ S240K/K363A, and K7N/D35N/V67A/P173N/T238G/ M276K/A277T/E315G/T364W/G381A/A403G/P4N/ D142A/N176K/D185N/S240K.

In some embodiments, the invention provides said variant phytases comprising the amino acid substitutions as compared to SEQ ID NO:1, wherein the amino acid substitutions comprise K7N/D35R/V67A/P173N/T238G/M276K/ A277T/E315G/T364W/G381A/A403G/P4N/P121A/ D136S/Q346S/T378A and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising the amino acid substitutions as compared to SEQ ID NO:1, wherein the amino acid substitutions comprise K7N/D35R/V67A/P173N/T238G/M276K/ A277T/E315G/T364W/G381A/A403G/P137V/D185N and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, 5119R, R120K, R1205, P121A, T130G, T130R, Q134A, Q134T, L135F, L135Y, D136F, D136G, D1365, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising the amino acid substitutions as compared to SEQ ID NO:1, wherein the amino acid substitutions comprise K7N/D35N/V67A/P173N/T238G/M276K/ A277T/E315G/T364W/G381A/A403G/P4N and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising the amino acid substitutions as compared to SEQ ID NO:1, wherein the amino acid substitutions comprise P4N/K7N/D35N/V67A/P121A/D136S/P173N/T238G/M276K/A277T/E315G/Q346S/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising the amino acid substitutions as compared to SEQ ID NO:1, wherein the amino acid substitutions comprise P4N/K7N/D35R/V67A/P121A/D136S/P173N/T238G/M276K/A277T/E315G/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytases comprising the amino acid substitutions as compared to SEQ ID NO:1, wherein the amino acid substitutions comprise P4N/K7N/D35N/V67A/P121A/D136S/P173N/T238G/M276K/A277T/E315G/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

In some embodiments, the invention provides said variant phytase enzymes having at least 95% sequence identity to SEQ ID NO:2.

In some embodiments, the invention provides said variant phytase enzymes having at least 95% sequence identity to SEQ ID NO:3.

In some embodiments, the invention provides said variant phytase enzymes having at least 95% sequence identity to SEQ ID NO:4.

In some embodiments, the invention provides said variant phytase enzymes having at least 95% sequence identity to SEQ ID NO:5.

In some embodiments, the invention provides said variant phytase enzymes having at least 95% sequence identity to SEQ ID NO:6.

In some embodiments, the invention provides said variant phytase enzymes having at least 95% sequence identity to SEQ ID NO:7.

In some embodiments, the invention provides said variant phytase enzymes having at least 95% sequence identity to SEQ ID NO:8.

In some embodiments, the invention provides said variant phytase enzymes having at least 95% sequence identity to SEQ ID NO:9.

In some embodiments, the invention provides said variant phytase enzymes having at least 95% sequence identity to SEQ ID NO:10.

In some embodiments, the invention provides a variant phytase enzyme having SEQ ID NO:11.

In some embodiments, the invention provides a variant phytase enzyme having SEQ ID NO:12.

In some embodiments, the invention provides a variant phytase enzyme having SEQ ID NO:13.

In some embodiments, the invention provides said variant phytase enzyme described herein further comprising a sequence insertion of SEQ ID NO:15 or SEQ ID NO:16, wherein said variant phytase enzyme has phytase activity.

In some embodiments, the invention provides a variant phytase enzyme having SEQ ID NO:14.

In some embodiments, the invention provides variant phytase enzymes having an amino acid substitution set selected from the group consisting of those depicted in FIGS. 1-8.

In some embodiments, the invention provides variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, and wherein said variant phytase enzyme is at least 90% and less than 100% identical to SEQ ID NO:17.

In some embodiments, the invention provides variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, and wherein said variant phytase enzyme has at least 1.01 fold better activity as compared to SEQ ID NO:17 under a condition comprising 37° C., pH 5.5; and wherein said variant phytase enzyme is at least 90% and less than 100% identical to SEQ ID NO:17.

In some embodiments, the invention provides variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, wherein said variant phytase enzyme has at least 1.01 fold better activity as compared to SEQ ID NO:17 under a condition selected from the group consisting of thermochallenge at about 75° C., thermochallenge at about 80° C., thermochallenge at about 85° C., and thermochallenge at about 90° C.; and wherein said variant phytase enzyme is at least 90% and less than 100% identical to SEQ ID NO:17. In some embodiments, the variant phytase enzyme as described herein has at least 1.01 fold better activity as compared to SEQ ID NO:17 under the condition further comprising the thermostability in the presence of BSA.

In some embodiments, the invention provides variant phytase enzymes comprising at least one amino acid substitution as compared to SEQ ID NO:17, wherein said amino acid substitution is at a position number selected from the group consisting of 1, 4, 5, 6, 7, 10, 11, 25, 27, 30, 31, 35, 36, 39, 46, 53, 55, 58, 60, 61, 62, 63, 65, 67, 69, 70, 72, 73, 74, 75, 76, 79, 80, 85, 89, 90, 101, 109, 110, 111, 113, 114, 116, 118, 119, 120, 121, 130, 134, 135, 136, 137, 138, 139, 141, 142, 146, 151, 153, 157, 158, 159, 161, 165, 173, 174, 176, 179, 180, 181, 182, 183, 184, 185, 186, 187, 189, 191, 192, 193, 194, 197, 202, 225, 230, 233, 238, 240, 242, 244, 245, 255, 261, 266, 272, 276, 277, 279, 280, 281, 282, 288, 291, 292, 295, 297, 302, 311, 315, 316, 339, 341, 346, 352, 354, 362, 363, 364, 365, 366, 369, 370, 371, 372, 378, 380, 381, 383, 384, 385, 394, 395, 398, 401, 402, 403, 409 and 410, wherein said variant phytase enzyme has at least 1.01 fold better activity as compared to SEQ ID NO:17 under a condition selected from the group consisting of tolerance against pH 2.0, tolerance against pH 2.5, tolerance against pH 3.0, tolerance against pH 3.5, and tolerance against pH 4.0; and wherein said variant phytase enzyme is at least 90% and less than 100% identical to SEQ ID NO:17.

In some embodiments, the invention provides variant phytase enzymes comprising at least one amino acid substitution as compared to SEQ ID NO:17, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions, twenty of said positions, twenty-one of said positions, twenty-two of said positions, twenty-three of said positions, twenty-four of said positions, twenty-five of said positions, twenty-six of said positions, twenty-seven of said positions, twenty-eight of said positions, twenty-nine of said positions, or thirty of said positions.

In some embodiments, the variant phytase has an amino acid substitution of the glutamine at position 1 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is selected from Q1S, Q1V and Q1N.

In some embodiments, the variant phytase has an amino acid substitution of the proline at position 4 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is selected from P4E, P4K, P4L, P4M, P4N, P4Q, P4T and P4W.

In some embodiments, the variant phytase has an amino acid substitution of the glutamic acid at position 5 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E5K.

In some embodiments, the variant phytase has an amino acid substitution of the leucine at position 6 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is selected from L6F, L6M and L6Y.

In some embodiments, the variant phytase has an amino acid substitution of the lysine at position 7 of SEQ ID NO:17. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from K7E, K7L, K7N, K7Q, and K7S.

In some embodiments, the variant phytase has an amino acid substitution of the serine at position 10 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S10A, S10N and S10Q.

In some embodiments, the variant phytase has an amino acid substitution of the valine at position 11 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is V11I.

In some embodiments, the variant phytase has an amino acid substitution of the alanine at position 25 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A25D, A25F, A25N and A25W.

In some embodiments, the variant phytase has an amino acid substitution of the glutamine at position 27 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from Q27D, Q27P and Q27V.

In some embodiments, the variant phytase has an amino acid substitution of the glutamine at position 30 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q30K.

In some embodiments, the variant phytase has an amino acid substitution of the aspartic acid at position 31 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is D31I or D31N.

In some embodiments, the variant phytase has an amino acid substitution of the aspartic acid at position 35 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from D35E, D35F, D35N, D35R and D35Y.

In some embodiments, the variant phytase has an amino acid substitution of the alanine at position 36 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A36K.

In some embodiments, the variant phytase has an amino acid substitution of the threonine at position 39 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T39D.

In some embodiments, the variant phytase has an amino acid substitution of the tryptophan at position 46 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, valine and tyrosine with some embodiments not utilizing cysteine (due to possible disulfide formation) or proline (due to steric effects). In some embodiments, the amino acid substitution is W46E or W46G.

In some embodiments, the variant phytase has an amino acid substitution of the glutamic acid at position 53 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E53D or E53N.

In some embodiments, the variant phytase has an amino acid substitution of the isoleucine at position 55 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine with some embodiments not utilizing cysteine (due to possible disulfide formation) or proline (due to steric effects). In some embodiments, the amino acid substitution is I55L or I55V.

In some embodiments, the variant phytase has an amino acid substitution of the leucine at position 58 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L58S.

In some embodiments, the variant phytase has an amino acid substitution of the histidine at position 60 of SEQ ID NO:17. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is H60S or H60Q.

In some embodiments, the variant phytase has an amino acid substitution of the tyrosine at position 61 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and valine with some embodiments not utilizing proline (due to steric effects). In some embodiments, the amino acid substitution is selected from Y61C.

In some embodiments, the variant phytase has an amino acid substitution of the glutamine at position 62 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q62W.

In some embodiments, the variant phytase has an amino acid substitution of the arginine at position 63 of SEQ ID NO:17. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R63A.

In some embodiments, the variant phytase has an amino acid substitution of the arginine at position 65 of SEQ ID NO:17. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine. In some embodiments, the amino acid substitution is selected from R65H, R65C, R65G, R65P, R65S, and R65V.

In some embodiments, the variant phytase has an amino acid substitution of the valine at position 67 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is V67A.

In some embodiments, the variant phytase has an amino acid substitution of the aspartic acid at position 69 of SEQ ID NO:1. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from D69N, D69L, D69R, and D69Y.

In some embodiments, the variant phytase has an amino acid substitution of the glycine at position 70 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G70E.

In some embodiments, the variant phytase has an amino acid substitution of the leucine at position 72 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L72S.

In some embodiments, the variant phytase has an amino acid substitution of the alanine at position 73 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selected from A73D, A73E and A73P.

In some embodiments, the variant phytase has an amino acid substitution of the lysine at position 74 of SEQ ID NO:17. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from K74D, K74P and K74L.

In some embodiments, the variant phytase has an amino acid substitution of the lysine at position 75 of SEQ ID NO:17. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing proline (due to steric effects). In some embodiments, the amino acid substitution is selected from K75C, K75E, K75G, K75I, K75L, K75M, K75Q, K75R, K75S, and K75W.

In some embodiments, the variant phytase has an amino acid substitution of the glycine at position 76 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing proline (due to steric effects). In some embodiments, the amino acid substitution is G76C.

In some embodiments, the variant phytase has an amino acid substitution of the glutamine at position 79 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from Q79L, Q79A, Q79G, Q79R and Q79F.

In some embodiments, the variant phytase has an amino acid substitution of the proline at position 80 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P80S.

In some embodiments, the variant phytase has an amino acid substitution of the isoleucine at position 85 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine with some embodiments not utilizing cysteine (due to possible disulfide formation) or proline (due to steric effects). In some embodiments, the amino acid substitution is I85V.

In some embodiments, the variant phytase has an amino acid substitution of the valine at position 89 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is selected from V89T.

In some embodiments, the variant phytase has an amino acid substitution of the aspartic acid at position 90 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is D90N.

In some embodiments, the variant phytase has an amino acid substitution of the alanine at position 101 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A101L.

In some embodiments, the variant phytase has an amino acid substitution of the alanine at position 109 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selected from A109D, A109E, A109F, A109P, and A109G.

In some embodiments, the variant phytase has an amino acid substitution of the isoleucine at position 110 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, leucine, methionine, proline, phenylalanine, tryptophan, valine and tyrosine with some embodiments not utilizing cysteine (due to possible disulfide formation) or proline (due to steric effects). In some embodiments, the amino acid substitution is I110L.

In some embodiments, the variant phytase has an amino acid substitution of the threonine at position 111 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from T111S, T111D, T111Q and T111I.

In some embodiments, the variant phytase has an amino acid substitution of the histidine at position 113 of SEQ ID NO:17. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is H113Q.

In some embodiments, the variant phytase has an amino acid substitution of the threonine at position 114 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine. In some embodiments, the amino acid substitution is selected from T114C, T114D, T114F, T114H, T114N, T114P, and T114S.

In some embodiments, the variant phytase has an amino acid substitution of the alanine at position 116 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selected from A116Y, A116P, A116R, and A116S.

In some embodiments, the variant phytase has an amino acid substitution of the threonine at position 118 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T118R or T118S.

In some embodiments, the variant phytase has an amino acid substitution of the serine at position 119 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S119R.

In some embodiments, the variant phytase has an amino acid substitution of the serine at position 120 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S120R or S120K.

In some embodiments, the variant phytase has an amino acid substitution of the proline at position 121 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P121A.

In some embodiments, the variant phytase has an amino acid substitution of the threonine at position 130 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T130G or T130R.

In some embodiments, the variant phytase has an amino acid substitution of the glutamine at position 134 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q134A or Q134T.

In some embodiments, the variant phytase has an amino acid substitution of the leucine at position 135 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L135F or L135Y.

In some embodiments, the variant phytase has an amino acid substitution of the aspartic acid at position 136 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from D136F, D136G, and D136S.

In some embodiments, the variant phytase has an amino acid substitution of the asparagine at position 137 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine. In some embodiments, the amino acid substitution is selected from N137C, N137F, N137G, N137H, N137I, N137L, N137M, N137S, N137P, N137V, N137W and N137Y.

In some embodiments, the variant phytase has an amino acid substitution of the alanine at position 138 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selected from A138V, A138H, A138P and A138D.

In some embodiments, the variant phytase has an amino acid substitution of the asparagine at position 139 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from N139A, N139H, and N139P.

In some embodiments, the variant phytase has an amino acid substitution of the threonine at position 141 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from T141E, T141G, T141A and T141R.

In some embodiments, the variant phytase has an amino acid substitution of the aspartic acid position 142 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from D142A, D142E, D142F, D142G, D142H, D142I, D142K, D142L, D142M, D142N, D142P, D142R, D142S, D142T, D142V, and D142Y.

In some embodiments, the variant phytase has an amino acid substitution of the serine at position 146 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from S146R, S146E and S146P.

In some embodiments, the variant phytase has an amino acid substitution of the serine at position 151 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S151F or S151R.

In some embodiments, the variant phytase has an amino acid substitution of the alanine at position 153 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A153N, A153S, A153V, and A153Y.

In some embodiments, the variant phytase has an amino acid substitution of the glycine at position 157 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation). In some embodiments, the amino acid substitution is from G157Q, G157N, G157L, G157R, G157A and G157P.

In some embodiments, the variant phytase has an amino acid substitution of the histidine at position 158 of SEQ ID NO:17. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from H158R or H158W.

In some embodiments, the variant phytase has an amino acid substitution of the arginine at position 159 of SEQ ID NO:17. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R159Y.

In some embodiments, the variant phytase has an amino acid substitution of the threonine at position 161 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T161D.

In some embodiments, the variant phytase has an amino acid substitution of the glutamic acid at position 165 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from E165D, E165P, E165S, E165T, and E165W.

In some embodiments, the variant phytase has an amino acid substitution of the proline at position 173 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation) or proline (due to steric effects). In some embodiments, the amino acid substitution is selected from P173N, P173S, P173T, and P173Y.

In some embodiments, the variant phytase has an amino acid substitution of the glutamine at position 174 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q174A or Q174E.

In some embodiments, the variant phytase has an amino acid substitution of the asparagine at position 176 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is N176K.

In some embodiments, the variant phytase has an amino acid substitution of the phenylalanine at position 179 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, tryptophan, valine and tyrosine with some embodiments not utilizing cysteine (due to possible disulfide formation) or proline (due to steric effects). In some embodiments, the amino acid substitution is F179L.

In some embodiments, the variant phytase has an amino acid substitution of the asparagine at position 180 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is N180K, N180T and N180E.

In some embodiments, the variant phytase has an amino acid substitution of the arginine at position 181 of SEQ ID NO:17. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R181T.

In some embodiments, the variant phytase has an amino acid substitution of the glutamic acid at position 182 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from E182A, E182F, E182S, and E182T.

In some embodiments, the variant phytase has an amino acid substitution of the lysine at position 183 of SEQ ID NO:17. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from K183R.

In some embodiments, the variant phytase has an amino acid substitution of the glutamine at position 184 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from Q184S.

In some embodiments, the variant phytase has an amino acid substitution of the aspartic acid at position 185 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is D185N or D185L.

In some embodiments, the variant phytase has an amino acid substitution of the glutamic acid at position 186 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E186V or E186A.

In some embodiments, the variant phytase has an amino acid substitution of the serine at position 187 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S187T.

In some embodiments, the variant phytase has an amino acid substitution of the serine at position 189 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S189L, S189N, and S189T.

In some embodiments, the variant phytase has an amino acid substitution of the threonine at position 191 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T191S.

In some embodiments, the variant phytase has an amino acid substitution of the glutamine at position 192 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q192K or Q192L.

In some embodiments, the variant phytase has an amino acid substitution of the alanine at position 193 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A193I, A193L, A193S, A193T and A193V.

In some embodiments, the variant phytase has an amino acid substitution of the leucine at position 194 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L194I.

In some embodiments, the variant phytase has an amino acid substitution of the glutamic acid at position 197 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E197S.

In some embodiments, the variant phytase has an amino acid substitution of the alanine at position 202 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A202R.

In some embodiments, the variant phytase has an amino acid substitution of the glutamine at position 225 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q225E.

In some embodiments, the variant phytase has an amino acid substitution of the proline at position 230 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P230S.

In some embodiments, the variant phytase has an amino acid substitution of the glycine at position 233 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G233A.

In some embodiments, the variant phytase has an amino acid substitution of the threonine at position 238 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from T238A, T238F, T238G, T238K, T238N, T238P, T238Q, T238R, T238S, and T238Y.

In some embodiments, the variant phytase has an amino acid substitution of the serine at position 240 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S240A, S240G, S240K, and S240R.

In some embodiments, the variant phytase has an amino acid substitution of the glutamine at position 242 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q242E or Q242L.

In some embodiments, the variant phytase has an amino acid substitution of the asparagine at position 244 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is N244I.

In some embodiments, the variant phytase has an amino acid substitution of the threonine at position 245 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T245E.

In some embodiments, the variant phytase has an amino acid substitution of the tyrosine at position 255 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and valine with some embodiments not utilizing cysteine (due to possible disulfide formation) or proline (due to steric effects). In some embodiments, the amino acid substitution is Y255D.

In some embodiments, the variant phytase has an amino acid substitution of the proline at position 261 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P261L.

In some embodiments, the variant phytase has an amino acid substitution of the serine at position 266 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is S266A or S266Y.

In some embodiments, the variant phytase has an amino acid substitution of the leucine at position 272 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L272S.

In some embodiments, the variant phytase has an amino acid substitution of the methionine at position 276 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, proline, phenylalanine, tryptophan, valine and tyrosine with some embodiments not utilizing cysteine (due to possible disulfide formation) or proline (due to steric effects). In some embodiments, the amino acid substitution is M276V or M276K.

In some embodiments, the variant phytase has an amino acid substitution of the alanine at position 277 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A277T.

In some embodiments, the variant phytase has an amino acid substitution of the leucine at position 279 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L279F.

In some embodiments, the variant phytase has an amino acid substitution of the threonine at position 280 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine. In some embodiments, the amino acid substitution is T280C, T280G, T280N, and T280P.

In some embodiments, the variant phytase has an amino acid substitution of the proline at position 281 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P281D or P281S.

In some embodiments, the variant phytase has an amino acid substitution of the histidine at position 282 of SEQ ID NO:17. In some embodiments, the substitution is with any other of the 19 naturally occurring amino acids, namely serine, threonine, asparagine, glutamic acid, glutamine, aspartic acid, lysine, arginine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is H282N or H282P.

In some embodiments, the variant phytase has an amino acid substitution of the alanine at position 288 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is A288E, A288R or A288V.

In some embodiments, the variant phytase has an amino acid substitution of the valine at position 291 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is V291I.

In some embodiments, the variant phytase has an amino acid substitution of the threonine at position 292 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T292G.

In some embodiments, the variant phytase has an amino acid substitution of the threonine at position 295 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T295N or T295I.

In some embodiments, the variant phytase has an amino acid substitution of the valine at position 297 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, phenylalanine, tryptophan, and tyrosine with some embodiments not utilizing cysteine (due to possible disulfide formation) or proline (due to steric effects). In some embodiments, the amino acid substitution is V297L.

In some embodiments, the variant phytase has an amino acid substitution of the glycine at position 302 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G302S.

In some embodiments, the variant phytase has an amino acid substitution of the glycine at position 311 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is G311A or G311S.

In some embodiments, the variant phytase has an amino acid substitution of the glutamic acid at position 315 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E315G or E315S.

In some embodiments, the variant phytase has an amino acid substitution of the leucine at position 316 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L316F.

In some embodiments, the variant phytase has an amino acid substitution of the arginine at position 339 of SEQ ID NO:17. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is R339M.

In some embodiments, the variant phytase has an amino acid substitution of the leucine at position 341 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L341V or L341Y.

In some embodiments, the variant phytase has an amino acid substitution of the glutamine at position 346 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from Q346K, Q346P, Q346S, and Q346T.

In some embodiments, the variant phytase has an amino acid substitution of the leucine at position 352 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L352M.

In some embodiments, the variant phytase has an amino acid substitution of the phenylalanine at position 354 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, proline, tryptophan, valine and tyrosine with some embodiments not utilizing cysteine (due to possible disulfide formation) or proline (due to steric effects). In some embodiments, the amino acid substitution is F354Y.

In some embodiments, the variant phytase has an amino acid substitution of the aspartic acid at position 362 of SEQ ID NO:17. In some embodiments, the substitution is with any other of the 19 naturally occurring amino acids, namely serine, threonine, asparagine, glutamic acid, glutamine, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from D362G, D362N, D362S, and D362Y.

In some embodiments, the variant phytase has an amino acid substitution of the lysine at position 363 of SEQ ID NO:17. In some embodiments, the substitution is with any other of the 19 naturally occurring amino acids, namely serine, threonine, asparagine, glutamic acid, glutamine, aspartic acid, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is K363A, K363L or K363R.

In some embodiments, the variant phytase has an amino acid substitution of the threonine at position 364 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing proline (due to steric effects). In some embodiments, the amino acid substitution is selected from T364C, T364E, T364I, T364L, T364N, T364Q, T364S, T364T, T364V, and T364W.

In some embodiments, the variant phytase has an amino acid substitution of the proline at position 365 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P365W.

In some embodiments, the variant phytase has an amino acid substitution of the leucine at position 366 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing cysteine (due to possible disulfide formation) or proline (due to steric effects). In some embodiments, the amino acid substitution is L366R.

In some embodiments, the variant phytase has an amino acid substitution of the asparagine at position 369 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is N369P.

In some embodiments, the variant phytase has an amino acid substitution of the threonine at position 370 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is T370P or T370K.

In some embodiments, the variant phytase has an amino acid substitution of the proline at position 371 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is selected from P371M, P371V, P371W, and P371Y.

In some embodiments, the variant phytase has an amino acid substitution of the proline at position 372 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine with some embodiments not utilizing cysteine (due to possible disulfide formation). In some embodiments, the amino acid substitution is P372T.

In some embodiments, the variant phytase has an amino acid substitution of the threonine at position 378 of SEQ ID NO:17. In some embodiments, the substitution is with any other of the 19 naturally occurring amino acids, namely serine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is T378A.

In some embodiments, the variant phytase has an amino acid substitution of the alanine at position 380 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selectd from A380R, A380T and A380P.

In some embodiments, the variant phytase has an amino acid substitution of the glycine at position 381 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing proline (due to steric effects). In some embodiments, the amino acid substitution is selected from G381A, G381C, G381L, G381N, and G381R.

In some embodiments, the variant phytase has an amino acid substitution of the glutamic acid at position 383 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing not utilizing cysteine (due to possible disulfide formation) or proline (due to steric effects). In some embodiments, the amino acid substitution is E383S.

In some embodiments, the variant phytase has an amino acid substitution of the glutamic acid at position 384 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is E384D.

In some embodiments, the variant phytase has an amino acid substitution of the arginine at position 385 of SEQ ID NO:17. In some embodiments, the substitution is with any other of the 19 naturally occurring amino acids, namely serine, threonine, asparagine, glutamic acid, glutamine, aspartic acid, lysine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from R385S, R385V and R385T.

In some embodiments, the variant phytase has an amino acid substitution of the alanine at position 394 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation). In some embodiments, the amino acid substitution is selected from A394I, A394L, A394M, and A394P.

In some embodiments, the variant phytase has an amino acid substitution of the glycine at position 395 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine with some embodiments not utilizing cysteine (due to possible disulfide formation). In some embodiments, the amino acid substitution is G395P.

In some embodiments, the variant phytase has an amino acid substitution of the glutamine at position 398 of SEQ ID NO:17. In some embodiments, the substitution is with any other of the 19 naturally occurring amino acids, namely serine, threonine, asparagine, glutamic acid, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is Q398V.

In some embodiments, the variant phytase has an amino acid substitution of the asparagine at position 401 of SEQ ID NO:17. In some embodiments, the substitution is with any other of the 19 naturally occurring amino acids, namely serine, threonine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is selected from N401A, N401L, and N401P.

In some embodiments, the variant phytase has an amino acid substitution of the glutamic acid at position 402 of SEQ ID NO:17. In some embodiments, the substitution is with any other of the 19 naturally occurring amino acids, namely serine, threonine, asparagine, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation). In some embodiments, the amino acid substitution is E402D, E402P, E402N, E402R and E402T.

In some embodiments, the variant phytase has an amino acid substitution of the alanine at position 403 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from A403G, A403I, A403K, A403L, A403N, A403Q, A403W, and A403Y.

In some embodiments, the variant phytase has an amino acid substitution of the serine at position 409 of SEQ ID NO:17. In some embodiments, the substitution is with any other of the 19 naturally occurring amino acids, namely threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine with some embodiments not utilizing cysteine (due to possible disulfide formation) or proline (due to steric effects). In some embodiments, the amino acid substitution is selected from S409H, S409L, S409R, S409V, and S409W.

In some embodiments, the variant phytase has an amino acid substitution of the leucine at position 410 of SEQ ID NO:17. In some embodiments, the substitution is with any other of the 19 naturally occurring amino acids, namely serine, threonine, asparagine, glutamic acid, glutamine, aspartic acid, lysine, arginine, histidine, cysteine, glycine, alanine, isoleucine, methionine, proline, phenylalanine, tryptophan, valine and tyrosine with some embodiments not utilizing proline (due to steric effects). In some embodiments, the amino acid substitution is selected from L410A, L410C, L410E, L410F, L410G, L410I, L410K, and L410R.

In some embodiments, the invention provides variant phytase enzymes comprising at least one amino acid substitution as compared to SEQ ID NO:17, wherein said amino acid substitution(s) is selected from the group consisting of Q1S, Q1V, Q1N, P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, Q30K, D31I, D31N, D35E, D35F, D35N, D35R, D35Y, A36K, T39D, W46E, W46G, E53D, E53N, I55L, I55V, L58S, H60S, H60Q, Y61C, Q62W, R63A, R65H, R65C, R65G, R65P, R65S, R65V, V67A, D69N, D69L, D69R, D69Y, G70E, L72S, A73D, A73E, A73P, K74D, K74P, K74L, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, S120R, S120K, P121A, T130G, T130R, Q134A, Q134T, L135F, L135Y, D136F, D136G, D136S, N137S, N137P, N137C, N137F, N137G, N137H, N137I, N137L, N137M, N137V, N137W, N137Y, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, G157Q, G157N, G157L, G157R, G157A, G157P, H158R, H158W, R159Y, T161D, E165D, E165P, E165S, E165T, E165W, P173N, P173S, P173T, P173Y, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, T245E, Y255D, P261L, S266A, S266Y, L272S, M276V, M276K, A277T, L279F, T280C, T280G, T280N, T280P, P281D, P281S, H282N, H282P, A288E, A288R, A288V, V291I, T292G, T295N, T295I, V297L, G302S, G311S, G311A, E315G, E315S, L316F, R339M, L341Y, L341V, Q346K, Q346P, Q346S, Q346T, L352M, F354Y, D362G, D362N, D362S, D362Y, K363A, K363L, K363R, T364C, T364E, T364I, T364L, T364N, T364Q, T364S, T364T, T364V, T364W, P365W, L366R, N369P, T370P, T370K, P371M, P371V, P371W, P371Y, P372T, T378A, A380R, A380T, A380P, G381A, G381C, G381L, G381N, G381R, E383S, E384D, R385S, R385V, R385T, A394I, A394L, A394M, A394P, G395P, Q398V, N401A, N401L, N401P, E402R, E402T, E402D, E402P, E402N, A403G, A403I, A403K, A403L, A403N, A403Q, A403W, A403Y, S409H, S409L, S409R, S409V, S409W, L410A, L410C, L410E, L410F, L410G, L410I, L410K, and L410R.

In some embodiments, the invention provides variant phytase enzymes comprising at least one amino acid substitution as compared to SEQ ID NO:17, wherein said variant phytase enzyme comprises the amino acid substitutions I55V/H60Q/D69N/K74D/S120R/N137P/G157Q/R159Y/Y255D/F354Y/A380P/M276K/A277T/E315G and at least one further amino acid substitution selected from the group consisting of Q1S, Q1V, Q1N, P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, Q30K, D31I, D31N, D35E, D35F, D35N, D35R, D35Y, A36K, T39D, W46E, W46G, E53D, E53N, L58S, Y61C, Q62W, R63A, R65H, R65C, R65G, R65P, R65S, R65V, V67A, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, P173N, P173S, P173T, P173Y, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, T364C, T364E, T364I, T364L, T364N, T364Q, T364S, T364T, T364V, T364W, P365W, L366R, N369P, T370P, T370K, P371M, P371V, P371W, P371Y, P372T, T378A, G381A, G381C, G381L, G381N, G381R, E383S, E384D, R385S, R385V, R385T, A394I, A394L, A394M, A394P, G395P, Q398V, N401A, N401L, N401P, E402R, E402T, E402D, E402P, E402N, A403G, A403I, A403K, A403L, A403N, A403Q, A403W, A403Y, S409H, S409L, S409R, S409V, S409W, L410A, L410C, L410E, L410F, L410G, L410I, L410K, and L410R.

In some embodiments, the invention provides variant phytase enzymes comprising at least one amino acid substitution as compared to SEQ ID NO:17, wherein said variant phytase enzyme comprises the amino acid substitutions I55V/H60Q/D69N/K74D/S120R/N137P/G157Q/R159Y/Y255D/F354Y/A380P/M276K/A277T/E315G/K7N/D35R/V67A/T238G/T364I/G381A/A403G and at least one further amino acid substitution selected from the group consisting of Q1S, Q1V, Q1N, P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, T378A, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In some embodiments, the invention provides variant phytase enzymes comprising at least one amino acid substitution as compared to SEQ ID NO:17, wherein said variant phytase enzyme comprises the amino acid substitutions I55V/H60Q/D69N/K74D/S120R/N137P/G157Q/R159Y/Y255D/F354Y/A380P/K7N/D35R/V67A/P173N/T238G/M276K/A277T/E315G/T364W/G381A/A403G/P4N/P121A/D136S/Q346S/T378A and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, L352M, D362G, D362N, D362S, D362Y, K363A, K363L, K363R, P365W, L366R, N369P, T370P, T370K, P371M, P371V, P371W, P371Y, P372T, T378A, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In some embodiments, the invention provides variant phytase enzymes comprising at least one amino acid substitution as compared to SEQ ID NO:17, wherein said variant phytase enzyme comprises the amino acid substitutions I55V/H60Q/D69N/K74D/S120R/N137V/G157Q/R159Y/Y255D/F354Y/A380P/K7N/D35R/V67A/P173N/T238G/M276K/A277T/E315G/T364W/G381A/A403G/D185N and at least one further amino acid substitution selected from the group consisting of Q1S, Q1V, Q1N, P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, I55L, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, P121A, T130G, T130R, Q134A, Q134T, L135F, L135Y, D136F, D136G, D136S, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, T378A, E383S, E384D, R385S, R385V, R385T, A394I, A394L, A394M, A394P, G395P, Q398V, N401A, N401E, N401L, N401P, E402R, E402T, E402D, E402P, E402N, S409H, S409L, S409R, S409V, S409W, L410A, L410C, L410E, L410F, L410G, L410I, L410K, and L410R.

In some embodiments, the invention provides variant phytase enzymes comprising at least one amino acid substitution as compared to SEQ ID NO:17, wherein said variant phytase enzyme comprises the amino acid substitutions I55V/H60Q/D69N/K74D/S120R/N137P/G157Q/R159Y/Y255D/F354Y/A380P/P4N/K7N/D35N/V67A/P121A/D136S/P173N/T238G/M276K/A277T/E315G/Q346S/T364W/T378A/G381A/A403G and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, I55L, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, T130G, T130R, Q134A, Q134T, L135F, L135Y, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In some embodiments, the invention provides variant phytase enzymes comprising at least one amino acid substitution as compared to SEQ ID NO:17, wherein said variant phytase enzyme comprises the amino acid substitutions I55V/H60Q/D69N/K74D/S120R/N137P/G157Q/R159Y/Y255D/F354Y/A380P/P4N/K7N/D35R/V67A/P121A/D136S/P173N/T238G/M276K/A277T/E315G/T364W/T378A/G381A/A403G and at least one further amino acid substitution selected from the group consisting of Q1S, Q1V, Q1N, E5K, L6F, L6M, L6Y, S10A, S10N, S10Q, V11I, A25D, A25F, A25N, A25W, Q27D, Q27P, Q27V, Q30K, D31I, D31N, A36K, T39D, W46E, W46G, E53D, E53N, L58S, Y61C, Q62W, R63A, R65H, R65C, R65G, R65P, R65S, R65V, G70E, L72S, A73D, A73E, A73P, K75C, K75E, K75G, K75I, K75L, K75M, K75Q, K75R, K75S, K75W, G76C, Q79L, Q79R, Q79A, Q79G, Q79F, P80S, I85V, V89T, D90N, A101L, A109D, A109D, A109E, A109G, A109F, A109P, I110L, T111S, T111D, T111Q, T111I, H113Q, T114C, T114D, T114F, T114H, T114N, T114P, T114S, A116Y, A116P, A116R, A116S, T118R, T118S, S119R, T130G, T130R, Q134A, Q134T, L135F, L135Y, A138V, A138H, A138D, A138P, N139P, N139A, N139H, T141E, T141G, T141A, T141R, D142A, D142E, D142F, D142G, D142H, D142I, D142K, D142L, D142M, D142N, D142P, D142R, D142S, D142T, D142V, D142Y, S146R, S146E, S146P, S151F, S151R, A153N, A153S, A153V, A153Y, H158R, H158W, T161D, E165D, E165P, E165S, E165T, E165W, Q174A, Q174E, N176K, F179L, N180T, N180E, N180K, R181T, E182A, E182F, E182S, E182T, K183R, Q184S, D185N, D185L, E186V, E186A, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, T245E, P261L, S266A, S266Y, L272S, L279F, T280C, T280G, T280N, T280P, P281D, P281S, H282N, H282P, A288E, A288R, A288V, V291I, T292G, T295N, T295I, V297L, G302S, G311S, G311A, L316F, R339M, L341Y, L341V, Q346K, Q346P, Q346S, Q346T, L352M, D362G, D362N, D362S, D362Y, K363A, K363L, K363R, P365W, L366R, N369P, T370P, T370K, P371M, P371V, P371W, P371Y, P372T, E383S, E384D, R385S, R385V, R385T, A394I, A394L, A394M, A394P, G395P, Q398V, N401A, N401L, N401P, E402R, E402T, E402D, E402P, E402N, S409H, S409L, S409R, S409V, S409W, L410A, L410C, L410E, L410F, L410G, L410I, L410K, and L410R.

In some embodiments, the invention relates to phytase variants having improved thermal properties, such as thermostability, heat-stability, BSA stability, pH stability, steam stability, temperature profile, and/or pelleting stability, with variant enzymes having high tolerance to high temperature in the presence of BSA and high tolerance to low pH of particular use in many embodiments.

In some embodiments, the invention relates phytase variants having improved pelleting stability and/or improved acid-stability.

The compositions and methods of the invention thus relates to phytase variants having an improved pH tolerance profile.

The compositions and methods of the invention thus relates to phytase variants having improved protease stability, in particular pepsin stability, found in non-ruminant stomachs.

The compositions and methods of the invention thus relates to phytase variants having improved performance in animal feed (such as an improved release and/or degradation of phytate).

Suitable variant phytases of the invention are those listed in SEQ ID NOs: 1 to 14, and those depicted in the Figures.

V. Nucleic Acids of the Invention

The present invention additional provides nucleic acids encoding the variant phytases of the invention. As will be appreciated by those in the art, due to the degeneracy of the genetic code, an extremely large number of nucleic acids may be made, all of which encode the variant phytases of the present invention. Thus, having identified a particular amino acid sequence, those skilled in the art could make any number of different nucleic acids, by simply modifying the sequence of one or more codons in a way which does not change the amino acid sequence of the protein. Thus, providing the amino acid sequence allows the generation of a very large number of different nucleic acid sequences encoding the proteins.

In some embodiments, specific variant phytases are encoded by specific nucleic acid sequences, as are listed in FIG. 9.

As is known in the art, the nucleic acids encoding the components of the invention can be incorporated into expression vectors as is known in the art, and depending on the host cells used to produce the heterodimeric antibodies of the invention. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with bacteria and fungi finding use in many embodiments.

A. Preparation of Variants

The nucleic acids encoding the variant phytases of the invention can be prepared using any mutagenesis procedure known in the art, such as site-directed mutagenesis and synthetic gene construction as are well known in the art.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips. A preferred technique is GenScript®.

i. Regulatory sequences

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* phytase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Sac-* charomyces cerevisiae galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators for filamentous fungal host cells are obtained from the genes for *Aspergillus nidulans* anthranilate synthase, *Aspergillus niger* phytase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus sub tilis* SP82 gene (Hue et al., 1995, Journal of Bacteriology 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triose phosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* phytase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a variant and directs the variant phytase being expressed into the cell's secretory pathway. The 5'-end of the coding sequence of the polynucleotide may inherently contain a signal peptide coding sequence naturally linked in translation reading frame with the segment of the coding sequence that encodes the variant phytase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant phytase. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* phytase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. A particular signal sequence is shown in FIG. 1, SEQ ID NO:2.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* phytase promoter, *Aspergillus oryzae* TAKA alpha-amylase promoter, and *Aspergillus oryzae* phytase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

1. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention can be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

2. Codon Optimization

Codon optimization can be employed with any of the variant phytase polypeptides of the present invention, in order to optimize expression in the host cell employed. Such methods are well known in the art and described in, for example, WO 2007/142954. In heterologous expression systems, optimization steps can improve the ability of the host to produce the desired variant phytase polypeptides. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases. The following paragraphs discuss potential problems that may result in reduced heterologous protein expression, and techniques that may overcome these problems.

In some embodiments, reduced heterologous protein expression results from a rare codon-induced translational pause. A rare codon-induced translational pause includes the presence of codons in the polynucleotide of interest that are rarely used in the host organism can have a negative effect on protein translation due to their scarcity in the available tRNA pool. One method of improving optimal translation in the host organism includes performing includes performing codon optimization which can result in rare host codons being modified in the synthetic polynucleotide sequence.

In some embodiments, reduced heterologous protein expression results from by alternate translational initiation. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide sequence.

In some embodiments, reduced heterologous protein expression occurs through repeat-induced polymerase slippage. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage includes altering extended repeats of G or C nucleotides.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can effect heterologous protein expression. By modifying restriction sites that could interfere with subsequent sub-cloning of transcription units into host expression vectors a polynucleotide sequence can be optimized.

Optimizing a DNA sequence can negatively or positively affect gene expression or protein production. For example, modifying a less-common codon with a more common codon may affect the half life of the mRNA or alter its structure by introducing a secondary structure that interferes with translation of the message. It may therefore be necessary, in certain instances, to alter the optimized message.

AUG or a portion of a gene can be optimized. In some embodiments, the desired modulation of expression is achieved by optimizing essentially the entire gene. In other embodiments, the desired modulation will be achieved by optimizing part but not all of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria can include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

Promising candidate sequences are constructed and then evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation can be included.

Modifying the codon usage of a candidate sequence can result in the creation or destruction of either a positive or negative element. In general, a positive element refers to any element whose alteration or removal from the candidate sequence could result in a decrease in expression of the therapeutic protein, or whose creation could result in an increase in expression of a therapeutic protein. For example, a positive element can include an enhancer, a promoter, a downstream promoter element, a DNA binding site for a positive regulator (e.g., a transcriptional activator), or a sequence responsible for imparting or modifying an mRNA secondary or tertiary structure. A negative element refers to any element whose alteration or removal from the candidate sequence could result in an increase in expression of the therapeutic protein, or whose creation would result in a decrease in expression of the therapeutic protein. A negative element includes a silencer, a DNA binding site for a negative regulator (e.g., a transcriptional repressor), a transcriptional pause site, or a sequence that is responsible for imparting or modifying an mRNA secondary or tertiary structure. In general, a negative element arises more frequently than a positive element. Thus, any change in codon usage that results in an increase in protein expression is more likely to have arisen from the destruction of a negative element rather than the creation of a positive element. In addition, alteration of the candidate sequence is more likely to destroy a positive element than create a positive element. In some embodiments, a candidate sequence is chosen and modified so as to increase the production of a therapeutic protein. The candidate sequence can be modified, e.g., by sequentially altering the codons or by randomly altering the codons in the candidate sequence. A modified candidate sequence is then evaluated by determining the level of expression of the resulting therapeutic protein or by evaluating another parameter, e.g., a parameter correlated to the level of expression. A candidate sequence which produces an increased level of a therapeutic protein as compared to an unaltered candidate sequence is chosen.

In some embodiments, one or a group of codons can be modified, e.g., without reference to protein or message structure and tested. Alternatively, one or more codons can be chosen on a message-level property, e.g., location in a region of predetermined, e.g., high or low GC content, location in a region having a structure such as an enhancer or silencer, location in a region that can be modified to introduce a structure such as an enhancer or silencer, location in a region having, or predicted to have, secondary or tertiary structure, e.g., intra-chain pairing, inter-chain pairing, location in a region lacking, or predicted to lack, secondary or tertiary structure, e.g., intra-chain or inter-chain pairing. A particular modified region is chosen if it produces the desired result.

Methods which systematically generate candidate sequences are useful. For example, one or a group, e.g., a contiguous block of codons, at various positions of a synthetic nucleic acid sequence can be modified with common codons (or with non common codons, if for example, the starting sequence has been optimized) and the resulting sequence evaluated. Candidates can be generated by optimizing (or de-optimizing) a given "window" of codons in the sequence to generate a first candidate, and then moving the window to a new position in the sequence, and optimizing (or de-optimizing) the codons in the new position under the window to provide a second candidate. Candidates can be evaluated by determining the level of expression they provide, or by evaluating another parameter, e.g., a parameter correlated to the level of expression. Some parameters can be evaluated by inspection or computationally, e.g., the possession or lack thereof of high or low GC content; a sequence element such as an enhancer or silencer; secondary or tertiary structure, e.g., intra-chain or inter-chain paring.

In some embodiments, the optimized nucleic acid sequence can express the variant phytase polypeptide of the invention, at a level which is at least 110%, 150%, 200%, 500%, 1,000%, 5,000% or even 10,000% of that expressed by nucleic acid sequence that has not been optimized.

Staring with the amino acid sequence of a variant phytase, a candidate DNA sequence can be designed. During the design of the synthetic DNA sequence, the frequency of codon usage can be compared to the codon usage of the host expression organism and rare host codons can be modified in the synthetic sequence. Additionally, the synthetic candidate DNA sequence can be modified in order to remove undesirable enzyme restriction sites and add or alter any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In some embodiments, the general codon usage in a host organism, such as any of those described herein, can be utilized to optimize the expression of the heterologous polynucleotide sequence in the host organism. The percentage and distribution of codons that rarely would be considered as preferred for a particular amino acid in the host expression system can be evaluated. Values of 5% and 10% usage can be used as cutoff values for the determination of rare codons.

VI. Host Cells and Production Strains

As will be appreciated by those in the art, there are a wide variety of production host organisms for the recombinant production of the variant phytases of the invention, including, but not limited to bacterial cells and fungal cells including yeast. In addition, while the parent phytase is unglycoslyated, glycosylation by production in yeast and fungi does not adversely affect the phytase activity.

The present invention also relates to recombinant host cells, comprising a polynucleotide encoding a variant phytase of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source. In some embodiments, the host cell exhibits transitory expression of the variant phytase. In some embodiments, the host cell is a stably transfected host or a host cell that stably (i.e., permanently) expresses the variant phytase. In some embodiments, the host cell is a production host cell.

The host cell can be any cell useful in the recombinant production of a variant, e.g., a prokaryote or a eukaryote. Such host cells include but are not limited to bacterial, fungal, and yeast cells. The host cell can also be a eukaryote, such as a mammalian, insect, plant, or fungal cell.

The host cell can be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell can be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonaturn, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora*

*crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al, 1984, Proc. Natl. Acad. Sci. USA 81: 1470-1474, and Christensen et al., 1988, BiolTechnology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

VII. Compositions

The present invention also provides compositions comprising a variant phytases. In some embodiments, the composition comprises a carrier and/or an excipient. In some embodiments, the compositions are enriched in such a variant phytase polypeptide of the present invention. The term "enriched" indicates that the phytase activity of the composition has been increased, e.g., with an enrichment factor of at least 1. In some embodiments, the compositions are formulated to provide desirable characteristics such as low color, low odor and acceptable storage stability.

In some embodiments, the composition comprises a variant phytase polypeptide of the present invention as the major enzymatic component, e.g., a mono-component composition. In some embodiments, the composition may comprise multiple enzymatic activities, such as an aminopeptidase, alpha-amylase, beta-amylase, phytase, isoamylase, carbohydrase, carboxypeptidase, catalase, cellulase, chitinase, cutinase, cyclodextrin glycosyltransferase, deoxyribonuclease, esterase, alpha-galactosidase, beta-galactosidase, phytase, alpha-glucosidase, beta-glucosidase, haloperoxidase, invertase, laccase, lipase, mannosidase, oxidase, pectinolytic enzyme, peptidoglutaminase, peroxidase, polyphenoloxidase, pullulanase, proteolytic enzyme, ribonuclease, transglutaminase, and/or xylanase.

VIII. Methods of Production

The present invention also relates to methods of producing a variant phytase polypeptide, comprising: (a) cultivating a host cell of the present invention under conditions suitable for expression of the variant phytase polypeptide; and (b) optionally recovering the variant phytase polypeptide.

The host cells are cultivated in a nutrient medium suitable for production of the variant phytase polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant phytase polypeptide is secreted into the nutrient medium, the variant phytase polypeptide can be recovered directly from the medium. If the variant is not secreted, it can be recovered from cell lysates.

The variant phytase polypeptide can be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant phytase polypeptide.

The variant phytase polypeptide can be recovered using methods known in the art. For example, the variant phytase polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant. In a particular embodiment, a variant phytase of the invention is not recovered and the host cell is a yeast host cell. In particular, the yeast is a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell. In some embodiments, the yeast is *Saccharomyces cerevisiae.*

IX. Phytase Formulations and Uses

As discussed herein, the use of phytase in animal feeds has a number of benefits, including a feed cost savings, such as reductions in dietary inorganic phosphate, energy and amino acids, including a fast and efficient breakdown of dietary phytate and increased nutrient availability from phytate, as well as production benefits such as body weight gain for the non-ruminant subjects, the increased release of nutrients from phytate, and a significant benefit in the reduced phosphorus excretion to improve the environmental impacts of non-ruminant animals. In some embodiments, the variant phytases of the invention are formulated and added to feed or can be made as a component of the feed. In the former case, the feed stock addition of phytase can be done by formulating the phytase on a carrier feed such as wheat flour.

As will be appreciated by those in the art, the formulation of the variant phytases of the invention depends on its end use and the associated conditions. Suitable formulations for the variant phytases of the invention include liquid formulations, dried formulations (including spray dried formulations), powdered formulations, granular formulations, and pelleted formulations.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

The above compositions are suitable for use in liquefaction, saccharification, and/or fermentation processes, and in some embodiments, in starch conversion. In some embodiments, the compositions are useful for producing a food product, including a syrup, as well as fermentation products, such as ethanol. In some embodiments, the compositions are useful for the pharmaceutical industry, such as digestive aids.

In one embodiment, the phytases are added to animal feed stock and pelleted as is known in the art, such that the feed is formed with phytase in it. In other embodiments, the phytase can be sprayed or dosed in a liquid form into animal feed.

EXAMPLES

X. Example 1: Phytase G3, G4, G5 and G6 Mutant Colletion Design and Construction The starting enzyme of the present invention is the G3P mature protein (SEQ ID NO:1), which is the "G3P" of the U.S. Patent Application Publication US 2018/0002680 A1, U.S. Pat. Nos. 9,528,096 B1 and 9,605,245 B1, hereby incorporated by reference in its entirety (G3P comprises amino acid substitutions I55V/H60Q/D69N/K74D/S120R/N137P/G157Q/R159Y/Y255D/F354Y/A380P relative to the wild type phytase sequence as set forth in SEQ ID NO:17 of the present invention). To improve the oveall activity and stability of G3P against high temperature, BSA and acid, six, eight, six and nine mutant collections were designed during G3, G4, G5 and G6 improvements respectively based on analyzing sequence, structural and experimental data. The design includes one to multiple specific mutations per mutant. The mutant collections were subsequently constructed using standard site-directed mutagenesis methods and subsequently cloned into the pESC-URA vector (Agilent, USA: catalogue #217454).

XI. Example 2: Preparation of Phytase Produced by Saccharomyces cerevisiae in HTP The Saccharomyces cerevisiae INVSc1 strain (ThermoFisher Scientific, USA: Catalogue # V8251-20) containing recombinant phytase-encoding genes from single colonies were inoculated into individual wells of 96 well plates containing 300 µl synthetic minimal defined medium (SC) with 2% glucose and no uracil supplementation. The cultures were grown overnight at 30° C., 200 rpm and 85% humidity. Appropriate volume of overnight culture from each well needed to obtain an OD600 of 0.4 was added to corresponding wells of the new 96 well plates containing 350 µl of induction medium (SC selective medium containing 2% galactose). The plates were then incubated for 48 hrs. at 30° C., 250 rpm and 85% humidity. The cells were then pelleted using centrifugation at 4000 rpm for 10 min at 4° C. The supernatants were transferred to round bottom plates and stored at −20° C. prior to activity assay.

XII. Example 3: Enzymatic Assay to Determine Saccharomyces cerevisiae Produced Phytase Activity at pH5.5, 37° C.

The supernatant from Example 2 was diluted 10-fold using 0.25M sodium acetate with 0.8 g/L BSA and Triton pH 5.5. 90 µl of 0.25M sodium acetate buffer pH5.5, 10 µl of the diluted supernatant, and 200 µl of 7.5 mM sodium phytate substrate ($C_6H_6Na_{12}O_{24}P_6$, FW: 923.81) prepared in 0.25M sodium acetate pH 5.5 were added sequentially. The reaction was incubated at 37° C. and 200 rpm for 30 minutes. Plates were then centrifuged at 4000 rpm at 4° C. for 2 minutes. To quench the reaction, 200 µl of coloring reagent was added to each of the 96 deep well microtiter plates. The coloring reagent was freshly prepared by sequentially mixing two volumes of 5M (~22% w/v) nitric acid, one volume of 100 g/L ammonium heptamolybdate solution [$(NH_4)_6Mo_7O_{24}\cdot 4H_2O$, FW:1235.86 g/mol] dissolved in water with 0.25% ammonia, and one volume 2.35 g/L ammonia metavanadate solution ($NH_4VO_3$, FW: 116.98 g/mol) dissolved in water with 0.1M nitric acid. After adding the coloring reagent to the plates, plates were shaken for 2 minutes and incubated in the dark for 10 minutes. After incubation, they were subjected to centrifugation at 4000 rpm for 2 minutes. 200 µl of the reaction from each well of the centrifuged plates was transferred to NUNC plates and read absorbance at 415 nm. The enzyme activity of variant was compared to the parent of the respective generation under the same conditions to determine activity improvement (X).

G3-G6 variants identified with improved total activity at pH5.5 are shown in FIGS. 1-4 respectively.

XIII. Example 4: Enzymatic Assay to Determine Saccharomyces cerevisiae Produced Phytase Activity in the Presence of BSA at pH5.5, Thermochallenge at 65° C. or 75° C. or 90° C. for 5 Minutes Followed by 37° C. Reaction The supernatant from Example 2 was diluted 10-fold using 0.25M sodium acetate with 0.8 g/L BSA and Triton pH 5.5. 75 µl of the diluted supernatant was transferred to PCR plates and heated at 65° C. or 75° C. or 90° C. for 5 minutes in thermocyclers to identify improved variants. PCR plates were then centrifuged at 4000 rpm for 2 minutes at 4° C. In 96 deep well microtiter plates, 90 µl of 0.25M sodium acetate buffer pH5.5, 10 µl of the diluted supernatant, and 200 µl of 7.5 mM sodium phytate substrate ($C_6H_6Na_{12}O_{24}P_6$, FW: 923.81) prepared in 0.25M sodium acetate pH 5.5 were added sequentially. The reaction was incubated at 37° C. and 200 rpm for 30 minutes. Plates were then centrifuged at 4000 rpm at 4° C. for 2 minutes. To quench the reaction, 200 µl of coloring reagent was added to each of the 96 deep well microtiter plates. The coloring reagent was freshly prepared by sequentially mixing two volumes of 5M (~22% w/v) nitric acid, one volume of 100 g/L ammonium heptamolybdate solution [(NH$_4$)$_6$Mo$_7$O$_{24}$.4H$_2$O, FW:1235.86 g/mol] dissolved in water with 0.25% ammonia, and one volume 2.35 g/L ammonia metavanadate solution (NH$_4$VO$_3$, FW: 116.98 g/mol) dissolved in water with 0.1M nitric acid. After adding the coloring reagent to the plates, plates were shaken for 2 minutes and incubated in the dark for 10 minutes. After incubation, they were subjected to centrifugation at 4000 rpm for 2 minutes. 200 µl of the reaction from each well of the centrifuged plates was transferred to NUNC plates and read absorbance at 415 nm. The enzyme activity of variant was compared to the parent of the respective generation under the same conditions to determine activity improvement (X).

G3-G6 variants identified with improved stability against high temperature and BSA at pH5.5 are shown in FIGS. 1-4 respectively.

XIV. Example 5: Enzymatic Assay to Determine *Saccharomyces cerevisiae* Produced Phytase Activity at 37° C., pH3 or pH2

The supernatant from Example 2 was diluted 5-fold using 0.25M potassium chloride with 0.8 g/L BSA and Triton pH3 or pH2. In 96 deep well microtiter plates, 90 µl of 0.25M potassium chloride buffer pH3 or pH2, 10 µl of the diluted supernatant, and 200 µl of 7.5 mM sodium phytate substrate (C$_6$H$_6$Na$_{12}$O$_{24}$P$_6$, FW: 923.81) prepared in 0.25M potassium chloride pH3 or pH2 were added sequentially. The reaction was incubated at 37° C. and 200 rpm for 30 minutes. Plates were then centrifuged at 4000 rpm at 4° C. for 2 minutes. To quench the reaction, 200 µl of coloring reagent was added to each of the 96 deep well microtiter plates. The coloring reagent was freshly prepared by sequentially mixing two volumes of 5M (~22% w/v) nitric acid, one volume of 100 g/L ammonium heptamolybdate solution [(NH$_4$)$_6$Mo$_7$O$_{24}$.4H$_2$O, FW:1235.86 g/mol] dissolved in water with 0.25% ammonia, and one volume 2.35 g/L ammonia metavanadate solution (NH$_4$VO$_3$, FW: 116.98 g/mol) dissolved in water with 0.1M nitric acid. After adding the coloring reagent to the plates, plates were shaken for 2 minutes and incubated in the dark for 10 minutes. After incubation, they were subjected to centrifugation at 4000 rpm for 2 minutes. 200 µl of the reaction from each well of the centrifuged plates was transferred to NUNC plates and read absorbance at 415 nm. The enzyme activity of variant was compared to the parent of the respective generation under the same conditions to determine activity improvement (X).

G3-G6 variants identified with improved stability against low pH are shown in FIGS. 1-4 respectively.

XV. Example 6: Design and Construction of Phytase Variants

Eight variants, including G6P, were designed based on the beneficial variants identified in *Saccharomyces cerevisiae*, as well as structure and sequence analysis to improve the total activity and stability against high temperature, BSA and low pH. The variants were subsequently constructed using gene specific primers with 5'Xho1 and 3'Not 1 cloning site. Following PCR and restriction digestion, it was cloned into pPiCZαA vector (EasySelect *Pichia* Expression Kit, Invitrogen by life technologies). The recombinant plasmid was linearized using Pme1 restriction enzyme and was transformed into X33 *Pichia* strain from the same expression kit mentioned earlier. The transformants were then selected on YPD+Zeocin agar plates after 3 days of growth at 30° C.

XVI. Example 7: Preparation of Phytase Variants Produced by *Pichia pastoris* in HTP Phytase-encoding genes from single colonies were inoculated into individual wells of 24 well plates containing 2000 µl of BMGY medium according to ThermoFisher Scientific recipe. The cultures were grown for 18 hrs at 30° C., 200 rpm and 85% humidity. After 18 hrs, centrifuge 24 wells plate and decant the liquid media. Into the pellet, add 2000 µl of BMMY medium according to ThermoFisher Scientific recipe. Add 200 µl of 10% methanol to each plate. The plates were incubated at 30° C., 200 rpm and 85% humidity incubator. At every 24 hrs, add 200 µl of 10% methanol to each plate. Harvest plate at 72 hrs by centrifuging plates at 4,000 rpm at 4° C. for 10 minutes. The supernatants were transferred to costar deep wells plates and stored at −20° C. prior to activity assay.

XVII. Example 8: Enzymatic Assay to Determine *Pichia pastoris* Produced Phytase Variants Activity at pH5.5, 37° C.

The supernatant from Example 7 was diluted at least 600-fold using 0.25M sodium acetate with 0.5 g/L BSA and Triton pH 5.5. In 96 deep well microtiter plates, 90 µl of 0.25M sodium acetate buffer pH5.5, 10 µl of the diluted supernatant, and 200 µl of 7.5 mM sodium phytate substrate (C$_6$H$_6$Na$_{12}$O$_{24}$P$_6$, FW: 923.81) prepared in 0.25M sodium acetate pH 5.5 were added sequentially. The reaction was incubated at 37° C. and 200 rpm for 30 minutes. Plates were then centrifuged at 4000 rpm at 4° C. for 2 minutes. To quench the reaction, 200 µl of coloring reagent was added to each of the 96 deep well microtiter plates. The coloring reagent was freshly prepared by sequentially mixing two volumes of 5M (~22% w/v) nitric acid, one volume of 100 g/L ammonium heptamolybdate solution [(NH$_4$)$_6$Mo$_7$O$_{24}$.4H$_2$O, FW:1235.86 g/mol] dissolved in water with 0.25% ammonia, and one volume 2.35 g/L ammonia metavanadate solution (NH$_4$VO$_3$, FW: 116.98 g/mol) dissolved in water with 0.1M nitric acid. After adding the coloring reagent to the plates, plates were shaken for 2 minutes and incubated in the dark for 10 minutes. After incubation, they were subjected to centrifugation at 4000 rpm for 2 minutes. 200 µl of the reaction from each well of the centrifuged plates was transferred to NUNC plates and read absorbance at 415 nm.

The total activity of variant is shown in FIG. 5.

XVIII. Example 9: Enzymatic Assay to Determine *Pichia pastoris* Produced Phytase Variants Thermostability in the Presence of BSA at pH5.5

The supernatant from Example 7 was diluted to 4 U/mL using 0.25M sodium acetate with 0.5 g/L BSA and Triton pH 5.5. Transfer 5 mL of diluted 4 U/mL enzyme into glass tubes. Thermochallenge those glass tubes for 5 minutes at desired temperatures (e.g. 22° C., 75° C. and 90° C. for 5 minutes. Dilute to 0.5 U/mL with 0.25M sodium aceate with 0.5 g/L BSA and Triton pH5.5 after thermochallenge. Into another tube, add 1.8 mL of 0.2 5M sodium acetate buffer, pH5.5, 0.2 mL of 0.5 U/mL diluted enzyme, 4 mL of 7.5 mM sodium phytate substrate (C$_6$H$_6$Na$_{12}$O$_{24}$P$_6$, FW: 923.81) prepared in 0.25M sodium acetate pH 5.5 were added sequentially. Mix the tubes and place in water bath at 37° C. for 30 minutes. To quench reaction, add 4 mL of coloring reagent and mix the tubes. The coloring reagent was freshly prepared by sequentially mixing two volumes of 5M (~22% w/v) nitric acid, one volume of 100 g/L ammonium heptamolybdate solution [$(NH_4)_6Mo_7O_{24}.4H_2O$, FW:1235.86 g/mol] dissolved in water with 0.25% ammonia, and one volume 2.35 g/L ammonia metavanadate solution ($NH_4VO_3$, FW: 116.98 g/mol) dissolved in water with 0.1M nitric acid. After 2 minutes, centrifuge the tubes and read absorbance at 415 nm using cuvettes. The % residual activity of variant was calculated as [activity at higher temperature]÷[activity at 22° C.]×100%.

As shown in FIG. 5, the new variants have % residual activities 68-81% at 75° C. and 80-96% at 90° C.

XIX. Example 10: Enzymatic Assay to Determine *Pichia pastoris* Produced Phytase Variants Low pH Tolerance at 37° C.

The supernatant from Example 7 was diluted to 0.5 U/mL using, 88.55 mM sodium chloride with 6.58 mM potassium chloride and 0.5 g/L BSA and Triton at pH 2-2.5. Into another tube, add 1.8 mL of 88.55 mM sodium chloride with 6.58 mM potassium chloride buffer, pH2-2.5, 0.2 mL of 0.5 U/mL diluted enzyme, 4 mL of 7.5 mM sodium phytate substrate ($C_6H_6Na_{12}O_{24}P_6$, FW: 923.81) prepared in 88.55 mM sodium chloride, 6.58 mM potassium chloride pH2-2.5 were added sequentially. Mix the tubes and place in water bath at 37° C. for 30 minutes. To quench reaction, add 4 mL of coloring reagent and mix the tubes. The coloring reagent was freshly prepared by sequentially mixing two volumes of 5M (~22% w/v) nitric acid, one volume of 100 g/L ammonium heptamolybdate solution [$(NH_4)_6Mo_7O_{24}.4H_2O$, FW:1235.86 g/mol] dissolved in water with 0.25% ammonia, and one volume 2.35 g/L ammonia metavanadate solution ($NH_4VO_3$, FW: 116.98 g/mol) dissolved in water with 0.1M nitric acid. After 2 minutes, centrifuge the tubes and read absorbance at 415 nm using cuvettes. The enzyme activity of variant was compared to the parent of the respective generation under the same condition to determine activity improvement. The % residual activity of variant was calculated as [activity at lower pH]÷[activity at pH5.5]×100%.

As shown in FIG. 5, the new variants have % residual activities 20-55% at pH2.0 and 49-63% at pH2.5.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

We claim:

1. A composition comprising a variant phytase enzyme comprising one amino acid substitution at position number 277 and one amino acid substitution at position number 315 as compared to SEQ ID NO:1 and at least one further amino acid substitution as compared to SEQ ID NO:1, wherein said further amino acid substitution is at a position number selected from the group consisting of 4, 5, 6, 7, 10, 11, 25, 27, 31, 35, 46, 53, 55, 58, 61, 62, 63, 65, 67, 69, 70, 72, 73, 75, 76, 80, 89, 90, 110, 111, 113, 114, 119, 120, 121, 130, 134, 135, 136, 137, 139, 142, 146, 151, 153, 157, 158, 161, 165, 173, 174, 176, 179, 180, 181, 182, 185, 187, 189, 191, 192, 193, 194, 197, 202, 225, 230, 233, 238, 240, 242, 244, 261, 266, 272, 276, 279, 280, 281, 282, 288, 292, 295, 302, 311, 316, 339, 341, 346, 352, 362, 363, 364, 365, 366, 370, 371, 372, 378, 381, 384, 385, 394, 395, 398, 401, 402, 403, 409 and 410; wherein said variant phytase enzyme is at least 90% identical to SEQ ID NO:1 and is not SEQ ID NO:17; and wherein said variant phytase enzyme has phytase activity.

2. The composition of claim 1, wherein said variant phytase enzyme exhibits at least 95% sequence identity to SEQ ID NO:1.

3. The composition of claim 1, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions, or twenty of said positions.

4. The composition of claim 1, wherein said further amino acid substitution(s) is selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27F, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, M276K, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

5. The composition of claim 1, wherein said amino acid substitutions are selected from the group consisting of Q62W/A277T/E315G, W46E/Q62W/A73P/K75C/A277T/A288R/E315G, N180K/M276K/A277T/E315G/E402D, M276K/A277T/E315G/E402D, M276K/A277T/E315G, K7N/D35R/V67A/P173N/T238G/M276K/A277T/E315G/T364W/G381A/A403G, P4N/K7N/D35N/V67A/P121A/D136S/P173N/T238G/M276K/A277T/E315G/Q346S/T364W/T378A/G381A/A403G, K7N/D35R/V67A/P121A/D136S/P173N/T238G/M276K/A277T/E315G/Q346S/

T364W/T378A/G381A/A403G, P4N/K7N/D35R/V67A/P121A/D136S/P173N/T238G/M276K/A277T/E315G/T364W/T378A/G381A/A403G, P4N/K7N/D35R/V67A/P121A/D136S/P173N/T238G/M276K/A277T/E315G/T364W/T378A/G381A/A403G, and K7N/D35R/V67A/P173N/T238G/M276K/A277T/E315G/Q346T/T364W/G381A/A403G/L410A.

6. The composition of claim 1, wherein said variant phytase enzyme comprises the amino acid substitutions M276K/A277T/E315G and at least one further amino acid substitution selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

7. The composition of claim 1, wherein said amino acid substitutions are selected from the group consisting of M276K/A277T/E315G/A73P/A288R, M276K/A277T/E315G/A288R, M276K/A277T/E315G/Q62W/A288R, M276K/A277T/E315G/Y61C/Q62W/A73P, M276K/A277T/E315G/A73P, M276K/A277T/E315G/Q62W, M276K/A277T/E315G/Q62W/A73P/A288R, M276K/A277T/E315G/K7N/D35R, M276K/A277T/E315G/K7N/D35R/P173Y/T364I, M276K/A277T/E315G/K7N/D35R/Q192K, M276K/A277T/E315G/K7N/D35R/P173Y/T364W, M276K/A277T/E315G/K7N/Q192L/T238A/T364W, M276K/A277T/E315G/K7N/Q192K/T364W/T370K, M276K/A277T/E315G/K7N/V67A/T238A/T364I, M276K/A277T/E315G/K7N/Q192L/T364I, M276K/A277T/E315G/K7N/V67A/Q192K/T364W, M276K/A277T/E315G/K7N/T238G/T364W, M276K/A277T/E315G/K7N/T238A, M276K/A277T/E315G/K7N/P173Y/Q192K/A403G, M276K/A277T/E315G/K7N/D35R/V67A/T238G/T364I/G381A/A403G, M276K/A277T/E315G/K7N/V67A/P173Y/T238A/T364I, M276K/A277T/E315G/K7N/V67A/T364I, M276K/A277T/E315G/K7N/P173Y, M276K/A277T/E315G/K7N/P173Y/A403G, M276K/A277T/E315G/K7N/V67A/Q192K, M276K/A277T/E315G/K7N/V67A/G381L, M276K/A277T/E315G/K7N, M276K/A277T/E315G/K7N/P173Y/Q192K/T364I, M276K/A277T/E315G/K7N/V67A/P173Y, M276K/A277T/E315G/K7N/V67A, M276K/A277T/E315G/K7N/T364I/G381L, M276K/A277T/E315G/K7N/P173Y/G381L, M276K/A277T/E315G/S146P, M276K/A277T/E315G/V67A/T364I, M276K/A277T/E315G/P173N/T364W, M276K/A277T/E315G/V67A/T238G/G381A, M276K/A277T/E315G/T238G, M276K/A277T/E315G/P173S, M276K/A277T/E315G/T238N/T364W, M276K/A277T/E315G/T238A/T364W, M276K/A277T/E315G/V67A, M276K/A277T/E315G/T364W/G381A, M276K/A277T/E315G/V67A/T238A/T364W, M276K/A277T/E315G/V67A/T364W, M276K/A277T/E315G/T364W, M276K/A277T/E315G/T238A/T364W/G381A, M276K/A277T/E315G/T364I, M276K/A277T/E315G/V67A/P173N/T238A/T364W, M276K/A277T/E315G/P173N/T238N, M276K/A277T/E315G/P173T, M276K/A277T/E315G/V67A/T238A, M276K/A277T/E315G/P173T/G381A, M276K/A277T/E315G/S119R/L279F, M276K/A277T/E315G/N244I/T280N, M276K/A277T/E315G/T238P/T280N/P371Y/A403W, M276K/A277T/E315G/S119R/A403K, M276K/A277T/E315G/T280N/P371Y/A403W, M276K/A277T/E315G/S119R/P371Y/A403K, M276K/A277T/E315G/T280N/A403K, M276K/A277T/E315G/T280N, M276K/A277T/E315G/T280N/P371Y, M276K/A277T/E315G/T238Y, M276K/A277T/E315G/T238P/P371Y, M276K/A277T/E315G/P371Y/A403W, M276K/A277T/E315G/S119R/T280N, M276K/A277T/E315G/T238P, M276K/A277T/E315G/S119R/P371Y/A403L, M276K/A277T/E315G/P371Y/A403L, M276K/A277T/E315G/S119R, M276K/A277T/E315G/T238Y/A403W, M276K/A277T/E315G/S119R/T280N/P371Y, M276K/A277T/E315G/A403W, M276K/A277T/E315G/R65G/L410R, M276K/A277T/E315G/Q346T/S409V/L410A, M276K/A277T/E315G/E182T/D362G, M276K/A277T/E315G/E182S/S187T/P281S, M276K/A277T/E315G/D362G/S409V, M276K/A277T/E315G/P281S/S409H, M276K/A277T/E315G/E182T/A202R, M276K/A277T/E315G/R65G/S187T/Q346T, M276K/A277T/E315G/P281S/Q346T, M276K/A277T/E315G/E182S/P281S, M276K/A277T/E315G/P281S, M276K/A277T/E315G/S187T/Q346T/L410A, M276K/A277T/E315G/R65G/P281S/S409V, M276K/A277T/E315G/D31N, M276K/A277T/E315G/D31N/D362G/L410A, M276K/A277T/E315G/Q346T/L410A, M276K/A277T/E315G/P281S/Q346S, M276K/A277T/E315G/D31N/P281S/Q346T, M276K/A277T/E315G/S409H/L410A, M276K/A277T/E315G/D31N/Q346P, M276K/A277T/E315G/E182S/S187T, M276K/A277T/E315G/R65G/P281S, M276K/A277T/E315G/A202R/P281S/D362G/L410R, M276K/A277T/E315G/D31N/R65G/S187T/S409V/L410A, M276K/A277T/E315G/D31N/P281S/Q346S/D362G/K363R/S409H, M276K/A277T/E315G/Q346S, M276K/A277T/E315G/E182S/Q346S, M276K/A277T/E315G/N401P, M276K/A277T/E315G/P4N/N401P, M276K/A277T/E315G/T292G/T378A, M276K/A277T/E315G/D362G/N401P, M276K/A277T/E315G/E182A/T292G, M276K/A277T/E315G/P4N/T292G, M276K/A277T/E315G/P4N/D362G/G395P, M276K/A277T/E315G/G395P, M276K/A277T/E315G/P4N/G395P, M276K/

A277T/E315G/P4N, M276K/A277T/E315G/P4N/I110L/ G395P, M276K/A277T/E315G/P4N/D31I, M276K/A277T/ E315G/P4N/D31I/E182A, M276K/A277T/E315G/D31I/ M276K/A277T/E315G/P4N/S240G, M276K/A277T/ E315G/P4N/I110L/S240R, M276K/A277T/E315G/D31I/ S240A/N401P, M276K/A277T/E315G/T378A, M276K/ A277T/E315G/D31I/S240A/D362G, M276K/A277T/ E315G/G76C/A394M, M276K/A277T/E315G/R65G/ E165P/Q242E, M276K/A277T/E315G/R65S/E165P/ D362S, M276K/A277T/E315G/R65S/A193I/Q346P, M276K/A277T/E315G/Q242E/Q346P, M276K/A277T/ E315G/R65/E165P/D362S, M276K/A277T/E315G/ R65P/E165P, M276K/A277T/E315G/R65S/E165P, M276K/A277T/E315G/R65S/E165P/Q242E/A394M, M276K/A277T/E315G/R65G/E165P, M276K/A277T/ E315G/R65C/A193S/A394P, M276K/A277T/E315G/ R65G/Q346P, M276K/A277T/E315G/R65S/E165P/Q242E/ D362S, M276K/A277T/E315G/R65G, M276K/A277T/ E315G/R65S, M276K/A277T/E315G/R65S/E165P/D362S/ A394P, M276K/A277T/E315G/Q346P, M276K/A277T/ E315G/Q242E, M276K/A277T/E315G/R65S/E165P/ S240K, M276K/A277T/E315G/R65S/E165P/G381R, M276K/A277T/E315G/R65S/A394I, M276K/A277T/ E315G/E165P/S240K/D362S, M276K/A277T/E315G/ R65G/Q242E, M276K/A277T/E315G/Q242E/A394P, M276K/A277T/E315G/R65G/D362S, M276K/A277T/ E315G/R65S/E165P/Q346P, M276K/A277T/E315G/R65G/ S240K/Q242E, M276K/A277T/E315G/A394L, M276K/ A277T/E315G/E5K/A153S/P281S/S409L, M276K/A277T/ E315G/E5K/P281S/S409H, M276K/A277T/E315G/S151F/ A153S/P281S/L410G, M276K/A277T/E315G/A153N/ P281S, M276K/A277T/E315G/E5K/P281S, M276K/ A277T/E315G/E5K, M276K/A277T/E315G/P281S/ L410R, M276K/A277T/E315G/P281S/Q346K/S409L/ L410G, M276K/A277T/E315G/E5K/V11I/Q346K, M276K/A277T/E315G/V11I/P281S, M276K/A277T/ E315G/A153S, M276K/A277T/E315G/E5K/P365W, M276K/A277T/E315G/E5K/P281S/L410G, M276K/ A277T/E315G/E5K/T111I/P281S/P365W, M276K/A277T/ E315G/E5K/A153N/P281S, M276K/A277T/E315G/E5K/ A153N/P281S/Q346K, M276K/A277T/E315G/Q346K, M276K/A277T/E315G/A153N/S409L, M276K/A277T/ E315G/E5K/A153N/P281S/L410G, M276K/A277T/ E315G/K7E/S409H, M276K/A277T/E315G/E5K/A153N/ P281S/S409R, M276K/A277T/E315G/E5K/P281S/L410I and M276K/A277T/E315G/E5K/A153S/P281S.

8. The composition of claim 1, wherein said variant phytase enzyme comprises the amino acid substitutions M276K/A277T/E315G/K7N/D35R/V67A/T238G/T364I/ G381A/A403G and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

9. The composition of claim 1, wherein said amino acid substitutions are selected from the group consisting of M276K/A277T/E315G/K7N/D35R/V67A/T238G/T364I/ G381A/A403G/P121A, M276K/A277T/E315G/K7N/ D35R/V67A/T238G/T364I/G381A/A403G/D136G, M276K/A277T/E315G/K7N/D35R/V67A/T238G/T364I/ G381A/A403G/T130G, M276K/A277T/E315G/K7N/ D35R/V67A/T238G/T364I/G381A/A403G/Q174E, M276K/A277T/E315G/K7N/D35R/V67A/T238G/T364I/ G381A/A403G/Q174A, M276K/A277T/E315G/K7N/ D35R/V67A/T238G/T364I/G381A/A403G/Q27D, M276K/ A277T/E315G/K7N/D35R/V67A/T238G/T364I/G381A/ A403G/Q134A, M276K/A277T/E315G/K7N/D35R/V67A/ T238G/T364I/G381A/A403G/T161D, M276K/A277T/ E315G/K7N/D35R/V67A/T238G/T364I/G381A/A403G/ T130R, M276K/A277T/E315G/K7N/D35R/V67A/T238G/ T364I/G381A/A403G/Q27P, M276K/A277T/E315G/K7N/ D35R/V67A/T238G/T364I/G381A/A403G/E53N, M276K/A277T/E315G/K7N/D35R/V67A/T238G/T364I/ G381A/A403G/D136F, M276K/A277T/E315G/K7N/ D35R/V67A/T238G/T364I/G381A/A403G/S151R, M276K/A277T/E315G/K7N/D35R/V67A/T238G/T364I/ G381A/A403G/Q27V, M276K/A277T/E315G/K7N/D35R/ V67A/T238G/T364I/G381A/A403G/Q134T, M276K/ A277T/E315G/K7N/D35R/V67A/T238G/T364I/G381A/ A403G/E53D, M276K/A277T/E315G/K7N/D35R/V67A/ T238G/T364I/G381A/A403G/D136S, M276K/A277T/ E315G/K7N/D35R/V67A/T238G/T364I/G381A/A403G/ T295N, M276K/A277T/E315G/K7N/D35R/V67A/T238G/ T364I/G381A/A403G/S189L, M276K/A277T/E315G/ K7N/D35R/V67A/T238G/T364I/G381A/A403G/S189T, M276K/A277T/E315G/K7N/D35R/V67A/T238G/T364I/ G381A/A403G/T191S, M276K/A277T/E315G/K7N/ D35R/V67A/T238G/T364I/G381A/A403G/P230S, M276K/A277T/E315G/K7N/D35R/V67A/T238G/T364I/ G381A/A403G/S189N, M276K/A277T/E315G/K7N/ D35R/V67A/T238G/T364I/G381A/A403G/E197S, M276K/A277T/E315G/K7N/D35R/V67A/T238G/T364I/ G381A/A403G/L194I, M276K/A277T/E315G/K7N/ V67A/T238G/T364I/G381A/A403G/P4N/T378A, M276K/ A277T/E315G/K7N/D35R/V67A/T238G/T364I/G381A/ A403G/S409V, M276K/A277T/E315G/K7N/D35R/V67A/ T238G/T364I/G381A/A403G/T378A, M276K/A277T/ E315G/K7N/D35R/V67A/T238G/T364I/G381A/A403G/ P4N, M276K/A277T/E315G/K7N/V67A/T238G/T364I/ G381A/A403G/T378A, M276K/A277T/E315G/K7N/ V67A/T238G/T364I/G381A/A403G, M276K/A277T/ E315G/K7N/V67A/T238G/T364I/G381A/A403G/P4N, M276K/A277T/E315G/K7N/V67A/T238G/T364I/G381A/ A403G/T111I, M276K/A277T/E315G/K7N/D35R/V67A/

T238G/T3641/G381A/A403G/P4N/T378A, M276K/
A277T/E315G/K7N/D35R/V67A/T238G/T3641/G381A/
A403G/P173S/E182S, M276K/A277T/E315G/K7N/D35R/
V67A/T238G/T3641/G381A/A403G/P173S/E182T/Q346T,
M276K/A277T/E315G/K7N/D35R/V67A/T238G/T364I/
G381A/A403G/P173S/E182T, M276K/A277T/E315G/
K7N/D35R/V67A/T238N/T364I/G381A/A403G/P173S/
E182T/S187T, M276K/A277T/E315G/K7N/D35R/V67A/
T238N/T364I/G381A/A403G/E182S, M276K/A277T/
E315G/K7N/D35R/V67A/T238N/T364I/G381A/A403G/
Q346T, M276K/A277T/E315G/K7N/D35R/V67A/T238G/
T364I/G381A/A403G/Q346S, M276K/A277T/E315G/
K7N/D35R/V67A/T238N/T364I/G381A/A403G/E182T/
Q346S, M276K/A277T/E315G/K7N/D35R/V67A/T238N/
T364I/G381A/A403G/P173S, M276K/A277T/E315G/
K7N/D35R/V67A/T238N/T364I/G381A/A403G/E182T,
M276K/A277T/E315G/K7N/D35R/V67A/T238N/T364I/
G381A/A403G/P173S/E182T, M276K/A277T/E315G/
K7N/D35R/V67A/T238N/T364I/G381A/A403G/P173S/
E182S, M276K/A277T/E315G/K7N/D35R/V67A/T238G/
T364I/G381A/A403G/E182S, M276K/A277T/E315G/
K7N/D35R/V67A/T238G/T364I/G381A/A403G/Q346T,
M276K/A277T/E315G/K7N/D35R/V67A/T238G/T364I/
G381A/A403G/P173S/Q346T, M276K/A277T/E315G/
K7N/D35R/V67A/T238G/T364I/G381A/A403G/R65S,
M276K/A277T/E315G/K7N/D35R/V67A/T238G/T364I/
G381A/A403G/A153N, and M276K/A277T/E315G/K7N/
D35R/V67A/T238G/T364I/G381A/A403G/K363R.

10. The composition of claim 1, wherein said variant phytase enzyme comprises the amino acid substitutions K7N/D35R/V67A/P173N/T238G/M276K/A277T/E315G/ T364W/G381A/A403G and at least one further amino acid substitution selected from the group consisting of P4E, P4K, P4L, P4M, P4N, P4Q, P4T, P4W, E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

11. The composition of claim 1, wherein said amino acid substitutions are selected from the group consisting of K7N/D35R/V67A/P173N/T238G/M276K/A277T/E315G/
T364W/G381A/A403G/N176K/D185N/H282N/A288R/
R385T, K7N/D35R/V67A/P173N/T238G/M276K/A277T/
E315S/T364W/G381A/A403G/N139A/D185N/R385T,
K7N/D35R/V67A/P173N/T238G/M276K/A277T/E315G/
T364W/G381A/A403G/N139H/N176K/D 185N/A288R,
K7N/D35R/V67A/P173N/T238G/M276K/A277T/E315G/
T364W/G381A/A403G/T161D/A288R, K7N/D35R/V67A/
P173N/T238G/M276K/A277T/E315G/T364W/G381A/
A403G/N139H/N176K/D 185N, K7N/D35R/V67A/P173N/
T238G/M276K/A277T/E315G/T364W/G381A/A403G/
N139A/T161D/N176K/D185N, K7N/D35R/V67A/P173N/
T238G/M276K/A277T/E315G/T364W/G381A/A403G/
D185N/H282N, K7N/D35R/V67A/P173N/T238G/M276K/
A277T/E315G/T364W/G381A/A403G/N139P/N176K/
D185N/K363A, K7N/D35R/V67A/P173N/T238G/M276K/
A277T/E315G/T364W/G381A/A403G/D185N, K7N/
D35R/V67A/P173N/T238G/M276K/A277T/E315G/
T364W/G381A/A403G/D185N/R385T, K7N/D35R/V67A/
P173N/T238G/M276K/A277T/E315G/T364W/G381A/
A403G/A288R, K7N/D35R/V67A/P173N/T238G/M276K/
A277T/E315G/T364W/G381A/A403G/R385T, K7N/
D35R/V67A/P173N/T238G/M276K/A277T/E315G/
T364W/G381A/A403G/D185N/H282N/L341V/R385T,
K7N/D35R/V67A/P173N/T238G/M276K/A277T/E315G/
T364W/G381A/A403G/H282N, K7N/D35R/V67A/P173N/
T238G/M276K/A277T/E315G/T364W/G381A/A403G/
N139A/D185N/H 282N/A288R/K363A/R385T, K7N/
D35R/V67A/P173N/T238G/M276K/A277T/E315G/
T364W/G381A/A403G/N176K/D185N, K7N/D35R/
V67A/P173N/T238G/M276K/A277T/E315G/T364W/
G381A/A403G/N139A/N176K/D185N, K7N/D35R/V67A/
P173N/T238G/M276K/A277T/E315G/T364W/G381A/
A403G/N176K/L341V, K7N/D35R/V67A/P173N/T238G/
M276K/A277T/E315G/T364W/G381A/A403G/D185N/
H282N/A 288R, K7N/D35R/V67A/P173N/T238G/M276K/
A277T/E315G/T364W/G381A/A403G/N139A/N176K/
D185N/L341V, K7N/D35R/V67A/P173N/T238G/M276K/
A277T/E315G/T364W/G381A/A403G/T161D/D185N,
K7N/D35R/V67A/P173N/T238N/M276K/A277T/E315G/
T364W/G381A/A403G/P4N/T378A, K7N/D35R/V67A/
P173N/T238G/M276K/A277T/E315G/T364W/G381A/
A403G/P4N/D136F/E197S/T378A, K7N/D35R/V67A/
P173N/T238N/M276K/A277T/E315G/T364W/G381A/
A403G/P4N/E197S/T378A, K7N/D35R/V67A/P173N/
T238G/M276K/A277T/E315G/T364W/G381A/A403G/
P4N/Q346S, K7N/D35R/V67A/P173N/T238N/M276K/
A277T/E315G/T364W/G381A/A403G/P4N/P121A/E182
T/E197S/Q346S/T378A, K7N/D35R/V67A/P173N/T238N/
M276K/A277T/E315G/T364W/G381A/A403G/P4N/
D136S/E182 T/T378A, K7N/D35R/V67A/P173N/T238N/
M276K/A277T/E315G/T364W/G381A/A403G/P4N/
P121A/D136F/E182S/Q346S, K7N/D35R/V67A/P173N/
T238N/M276K/A277T/E315G/T364W/G381A/A403G/
P4N/P121A/E197 S, K7N/D35R/V67A/P173N/T238N/
M276K/A277T/E315G/T364W/G381A/A403G/P4N/
E197S/Q346 S, K7N/D35R/V67A/P173N/T238N/M276K/
A277T/E315G/T364W/G381A/A403G/P4N/Q346S, K7N/
D35R/V67A/P173S/T238N/M276K/A277T/E315G/
T364W/G381A/A403G/P4N/D136S/E182S/Q346S, K7N/
D35R/V67A/P173S/T238N/M276K/A277T/E315G/
T364W/G381A/A403G/P4N/D136S/E182S/Q346S/T378A,
K7N/D35R/V67A/P173N/T238N/M276K/A277T/E315G/
T364W/G381A/A403G/P4N/D136S/E182 T, K7N/D35R/
V67A/P173N/T238N/M276K/A277T/E315G/T364W/
G381A/A403G/P4N/E197S/Q346 S/T378A, K7N/D35R/
V67A/P173N/T238G/M276K/A277T/E315G/T364W/

G381A/A403G/E182T/E197S/T378A, K7N/D35R/V67A/P173N/T238N/M276K/A277T/E315G/T364W/G381A/A403G/Q346S, K7N/D35R/V67A/P173N/T238N/M276K/A277T/E315G/T364W/G381A/A403G/P4N/D136F/E182T/E197S, K7N/D35R/V67A/P173N/T238G/M276K/A277T/E315G/T364W/G381A/A403G/P4N/P121A/D136S/Q346S/T378A, K7N/D35R/V67A/P173N/T238N/M276K/A277T/E315G/T364W/G381A/A403G/P4N/D136S/E197S/Q346S/T378A, K7N/D35R/V67A/P173N/T238N/M276K/A277T/E315G/T364W/G381A/A403G/P4N/P121A/D136 S/E182T/T378A, K7N/D35R/V67A/P173S/T238N/M276K/A277T/E315G/T364W/G381A/A403G/P121A/D136S/E182S/E197S/T378A, K7N/D35R/V67A/P173N/T238G/M276K/A277T/E315G/T364W/G381A/A403G/Q62W/P80S/D142 E/A288R/E402D, K7N/D35R/V67A/P173N/T238G/M276K/A277T/E315G/T364W/G381A/A403G/W46E/Q62W/A73P/K75G/A288R/E402D, K7N/D35R/V67A/P173N/T238G/M276K/A277T/E315G/T364W/G381A/A403G/A288R/E402D, K7N/D35R/V67A/P173N/T238G/M276K/A277T/E315G/T364W/G381A/A403G/Q62W/A73P/K75 G/D142E/F179L/E402D, K7N/D35R/V67A/P173N/T238G/M276K/A277T/E315G/T364W/G381A/A403G/Q62W/A288R/E402D, K7N/D35R/V67A/P173N/T238G/M276K/A277T/E315G/T364W/G381A/A403G/Q62W/G70E/A73P/D142E/F179L/E402D, K7N/D35R/V67A/P173N/T238G/M276K/A277T/E315G/T364W/G381A/A403G/E402D, K7N/D35R/V67A/P173N/T238G/M276K/A277T/E315G/T364W/G381A/A403G/Q62W/G70E/K75 G/E402D, K7N/D35R/V67A/P173N/T238G/M276K/A277T/E315G/T364W/G381A/A403G/K75G/E402D, K7N/D35R/V67A/P173N/T238G/M276K/A277T/E315G/T364W/G381A/A403G/S146E/A288R, K7N/D35R/V67A/P173N/T238G/M276K/A277T/E315G/T364W/G381A/A403G/Q62W/P80S/D142 E/S146E/A288R/E402D, K7N/D35R/V67A/P173N/T238G/M276K/A277T/E315G/T364W/G381A/A403G/Q62W/D142E/S146E/E402D, K7N/D35R/V67A/P173N/T238G/M276K/A277T/E315G/T364W/G381A/A403G/D142E, K7N/D35R/V67A/P173N/T238G/M276K/A277T/E315G/T364W/G381A/A403G/Q62W/E402D, K7N/D35R/V67A/P173N/T238G/M276K/A277T/E315G/T364W/G381A/A403G/A73P/P80S/D142E/Q346T, K7N/D35R/V67A/P173N/T238G/M276K/A277T/E315G/T364W/G381A/A403G/Q62W/G70E/K75 G/P80S/D142E/E402D, K7N/D35R/V67A/P173N/T238G/M276K/A277T/E315G/T364W/G381A/A403G/Q62W/D142E/E402D, K7N/D35R/V67A/P173N/T238G/M276K/A277T/E315G/T364W/G381A/A403G/Q62W/D142E/A288R/E402D, K7N/D35Y/V67A/P173N/T238G/M276K/A277T/E315G/T364W/G381A/A403G, K7Q/D35R/V67A/P173N/T238G/M276K/A277T/E315G/T364W/G381A/A403G, K7N/D35R/V67A/P173N/T238G/M276K/A277T/E315G/T364C/G381A/A403G, K7N/D35R/V67A/P173N/T238G/M276K/A277T/E315G/T364W/G381A/A403G/K751, K7N/D35N/V67A/P173N/T238G/M276K/A277T/E315G/T364W/G381A/A403G, K7N/D35R/V67A/P173N/T238G/M276K/A277T/E315G/T364Q/G381A/A403G, K7N/D35R/V67A/P173N/T238G/M276K/A277T/E315G/T364E/G381A/A403G, K7N/D35R/V67A/P173N/T238G/M276K/A277T/E315G/T364W/G381A/A403G/H158W, D35R/V67A/P173N/T238G/M276K/A277T/E315G/T364W/G381A/A403G, K7N/D35R/V67A/P173N/T238G/M276K/A277T/E315G/T364W/G381 L/A403G, K7N/D35R/V67A/P173N/T238G/M276K/A277T/E315G/T364W/G381N/A403G, K7N/D35R/V67A/P173N/T238G/M276K/A277T/E315G/T364W/G381A/A403G/P1371, K7N/D35R/V67A/P173N/T238G/M276K/A277T/E315G/T364W/G381A/A403K, K7N/D35R/V67A/P173N/T238G/M276K/A277T/E315G/T364S/G381A/A403G, K7N/D35R/V67A/P173N/T238R/M276K/A277T/E315G/T364W/G381A/A403G, K7N/D35R/V67A/P173N/T238G/M276K/A277T/E315G/T364W/G381A/A403G/E165S, K7N/D35R/V67A/P173N/T238G/M276K/A277T/E315G/T364W/G381A/A403G/K75S, K7N/D35R/V67A/P173N/T238G/M276K/A277T/E315G/T364W/G381A/A403L, K7N/D35R/V67A/P173N/T238G/M276K/A277T/E315G/T364W/G381A/A403G/E165T, K7N/D35F/V67A/P173N/T238G/M276K/A277T/E315G/T364W/G381A/A403G, K7N/D35R/V67A/P173N/T238G/M276K/A277T/E315G/T364W/G381R/A403G, K7N/D35R/V67A/P173N/T238G/M276K/A277T/E315G/T364W/G381A/A403N, K7S/D35R/V67A/P173N/T238G/M276K/A277T/E315G/T364W/G381A/A403G, K7N/D35R/V67A/P173N/T238Q/M276K/A277T/E315G/T364W/G381A/A403G, K7N/D35R/V67A/P173N/T238G/M276K/A277T/E315G/T364N/G381A/A403G, K7N/D35R/V67A/P173N/T238G/M276K/A277T/E315G/T364W/G381A/A403G/K75M, K7N/D35R/V67A/P173N/T238G/M276K/A277T/E315G/T364W/G381A/A403G/N69Y, K7N/D35R/V67A/P173N/T238G/M276K/A277T/E315G/T364W/G381A/A403G/K75R, K7N/D35R/V67A/P173N/T238G/M276K/A277T/E315G/T364W/G381A/A403G/K75Q, K7N/D35R/V67A/P173N/T238G/M276K/A277T/E315G/G381A/A403G, K7N/V67A/P173N/T238G/M276K/A277T/E315G/T364W/G381A/A403G, K7N/D35R/V67A/P173N/T238G/M276K/A277T/E315G/T364W/G381A/A403G/R120K, K7N/D35R/V67A/P173N/T238G/M276K/A277T/E315G/T364W/G381A/A403G/V55L, K7N/D35E/V67A/P173N/T238G/M276K/A277T/E315G/T364W/G381A/A403G, K7N/D35R/V67A/P173N/T238G/M276K/A277T/E315G/T364W/G381A/A403G/R120S, K7N/D35R/V67A/P173N/T238G/M276K/A277T/E315G/T364W/G381A/A403Q, K7N/D35R/V67A/P173N/T238G/M276K/A277T/E315G/T364W/G381A/A403G/N69R, K7N/D35R/V67A/P173N/T238G/M276K/A277T/E315G/T364V/G381A/A403G, K7N/D35R/V67A/P173N/T238G/M276K/A277T/E315G/T364W/G381A/A4031, K7N/D35R/V67A/P173N/T238G/M276K/A277T/E315G/T364W/G381A/A403G/Q157G, K7N/D35R/V67A/P173N/T238G/M276K/A277T/E315G/T364W/G381A/A403G/Q157A, K7N/D35R/V67A/P173N/T238G/M276K/A277T/E315G/T364W/G381A/A403G/D142A, K7N/D35R/V67A/P173N/T238G/M276K/A277T/E315G/T364W/G381A/A403G/N69L, K7L/D35R/V67A/P173N/T238G/M276K/A277T/E315G/T364W/G381A/A403G, K7N/D35R/V67A/P173N/T238G/M276K/A277T/E315G/T364L/G381A/A403G, K7N/D35R/V67A/P173N/T238N/M276K/A277T/E315G/T364W/G381A/A403G, K7N/D35R/V67A/P173N/T238G/M276K/A277T/E315G/T364W/G381A/A403G/D142R, K7N/D35R/V67A/P173N/T238G/M276K/A277T/E315G/T364W/G381A/A403G/L6F, K7N/D35R/V67A/P173N/T238G/M276K/A277T/E315G/T364W/G381A/A403G/L135Y, K7N/D35R/V67A/P173N/T238G/M276K/A277T/E315G/T364W/G381A/A403G/S266A, K7N/D35R/V67A/P173N/T238G/M276K/A277T/E315G/T364W/G381A/A403G/L135F, K7N/D35R/V67A/P173N/T238G/M276K/A277T/E315G/T364W/G381A/A403G/R63A, K7N/D35R/V67A/P173N/T238G/M276K/A277T/E315G/T364W/G381A/A403G/L352M, K7N/D35R/V67A/P173N/T238G/M276K/A277T/E315G/T364W/G381A/A403G/R181T, K7N/D35R/V67A/P173N/T238G/M276K/A277T/E315G/T364W/G381A/A403G/S10A, K7N/D35R/V67A/P173N/T238G/M276K/A277T/E315G/T364W/G381A/A403G/L6Y, K7N/D35R/V67A/P173N/T238G/M276K/A277T/E315G/T364W/G381A/

A403G/S10Q, K7N/D35R/V67A/P173N/T238G/M276K/ A277T/E315G/T364W/G381A/A403G/S266Y, K7N/D35R/ V67A/P173N/T238G/M276K/A277T/E315G/T364W/ G381A/A403G/G311A, K7N/D35R/V67A/P173N/T238G/ M276K/A277T/E315G/T364W/G381A/A403G/L6M, K7N/D35R/V67A/P173N/T238G/M276K/A277T/E315G/ T364W/G381A/A403G/V89T, K7N/D35R/V67A/P173N/ T238G/M276K/A277T/E315G/T364W/G381A/A403G/ G233A, K7N/D35R/V67A/P173N/T238G/M276K/A277T/ E315G/T364W/G381A/A403G/S1ON/A25F/K75E/P80S/ Q225E, K7N/D35R/V67A/P173N/T238G/M276K/A277T/ E315G/T364W/G381A/A403G/A25F/Q225E, K7N/D35R/ V67A/P173N/T238G/M276K/A277T/E315G/T364W/ G381A/A403G/P137V/D185N, K7N/D35R/V67A/P173N/ T238G/M276K/A277T/E315G/T364W/G381A/A403G/ Q225E, K7N/D35R/V67A/P173N/T238G/M276K/A277T/ E315G/T364W/G381A/A403G/P80S/D185N, K7N/D35R/ V67A/P173N/T238G/M276K/A277T/E315G/T364W/ G381A/A403G/A25F/H158R, K7N/D35R/V67A/P173N/ T238G/M276K/A277T/E315G/T364W/G381A/A403G/ S1ON/A25F/Q62 W/D9ON/T114H/H158R/N176K/ D185N, K7N/D35E/V67A/P173N/T238G/M276K/A277T/ E315G/T364T/G381A/A403G/D142E/E197S/H282N, K7N/D35F/V67A/P173N/T238G/M276K/A277T/E315G/ T364T/G381A/A403G/D142E/N176K/E402D, K7N/D35N/ V67A/P173N/T238G/M276K/A277T/E315G/T364W/ G381A/A403G/P4N/D142E/E197 S/H282N, K7N/D35N/ V67A/P173N/T238G/M276K/A277T/E315G/T364T/ G381A/A403G/P4N/D142E/E197S/E402D, K7N/V67A/ P173N/T238G/M276K/A277T/E315G/T364W/G381A/ A403G/P4N/D142E/N176K/H282N/A288R/E402D, K7N/ D35N/V67A/P173N/T238G/M276K/A277T/E315G/ T364W/G381A/A403G/P4N, K7N/D35E/V67A/P173N/ T238G/M276K/A277T/E315G/T364W/G381A/A403G/ D142E/H282N/A288R/E402D, K7N/D35F/V67A/P173N/ T238G/M276K/A277T/E315G/G381A/A403G/D142E/ N176K/E197S, K7N/D35N/V67A/P173N/T238G/M276K/ A277T/E315G/G381A/A403G/P4N/E197S/E402D, K7N/ D35N/V67A/P173N/T238G/M276K/A277T/E315G/ T364W/G381A/A403G/P4N/D142E/E197 S, K7N/V67A/ P173N/T238G/M276K/A277T/E315G/T364W/G381A/ A403G/P4N/E402D, K7N/D35E/V67A/P173N/T238G/ M276K/A277T/E315G/T364W/G381A/A403G/P4N/ D142E/E197S/H282N, K7N/V67A/P173N/T238G/M276K/ A277T/E315G/T364W/G381A/A403G/P4N, K7N/V67A/ P173N/T238G/M276K/A277T/E315G/T364W/G381A/ A403G/D142E/H282N/E402D, K7N/D35F/V67A/P173N/ T238G/M276K/A277T/E315G/T364W/G381A/A403G/ P4N/D142E, K7N/V67A/P173N/T238G/M276K/A277T/ E315G/G381A/A403G/P4N/E402D, K7N/D35N/V67A/ P173N/T238G/M276K/A277T/E315G/T364W/G381A/ A403G/D142E/N176K/E197S/E402D, K7N/D35F/V67A/ P173N/T238G/M276K/A277T/E315G/G381A/A403G/ P4N/E402D, K7N/D35F/V67A/P173N/T238G/M276K/ A277T/E315G/T364W/G381A/A403G/P4N, K7N/D35E/ V67A/P173N/T238G/M276K/A277T/E315G/G381A/ A403G/P4N/E402D, K7N/D35F/V67A/P173N/T238G/ M276K/A277T/E315G/G381A/A403G/P4N/D142E/ E402D, K7N/D35N/V67A/P173N/T238G/M276K/A277T/ E315G/G381A/A403G/P4N/D142E/E402D, K7N/D35E/ V67A/P173N/T238G/M276K/A277T/E315G/T364W/ G381A/A403G/N176K/D185N/S240K, K7N/D35R/V67A/ P173N/T238G/M276K/A277T/E315G/T364W/G381A/ A403G/P4N/D142R/D185N/S240K, K7N/D35R/V67A/ P173N/T238G/M276K/A277T/E315G/T364W/G381A/ A403G/P4N/D142A/N176K/D185N/Q192K/S240K/ R385T, K7N/D35N/V67A/P173N/T238G/M276K/A277T/ E315G/G381A/A403G/P4N/D142R/D185N, K7N/D35F/ V67A/P173N/T238G/M276K/A277T/E315G/T364W/ G381A/A403G/N176K/D185N/R385T, K7N/D35N/V67A/ P173N/T238G/M276K/A277T/E315G/T364W/G381A/ A403G/N176K/D185N/S240K, K7N/D35R/V67A/P173N/ T238G/M276K/A277T/E315G/G381A/A403G/P121A/ D142A/N176K/D185N/K363A, K7N/D35F/V67A/P173N/ T238G/M276K/A277T/E315G/T364W/G381A/A403N/ P4N/P121A/D142 E/N176K/D185N/S240K/R385T/A394P, K7N/D35F/V67A/P173N/T238G/M276K/A277T/E315G/ T364W/G381A/A403G/P4N/P121A/D142 E/N176K/ D185N, K7N/V67A/P173N/T238G/M276K/A277T/ E315G/T364W/G381A/A403N/N176K/D185N/Q192K/ R385T/A394P, K7N/D35Y/V67A/P173N/T238G/M276K/ A277T/E315G/G381A/A403G/S240K/K363A, K7N/ V67A/P173N/T238G/M276K/A277T/E315G/T364W/ G381A/A403G/L410A, K7N/D35N/V67A/P173N/T238G/ M276K/A277T/E315G/T364W/G381A/A403N/D142A/ D185N/Q 192K/R385T/A394P/L410G, K7N/V67A/ P173N/T238G/M276K/A277T/E315G/T364S/G381A/ A403G/P121A/D142R/S240K/H282N/K363A/R385T/ A394P/L410G, K7N/D35E/V67A/P173N/T238G/M276K/ A277T/E315G/G381A/A403G/D142R/N176K/D185N/ R385T, K7N/D35F/V67A/P173N/T238G/M276K/A277T/ E315G/G381A/A403G/P121A/R385T/L410G, K7N/D35N/ V67A/P173N/T238G/M276K/A277T/E315G/T364W/ G381A/A403G/D142E/N176K/D185N/S240K, K7N/ D35F/V67A/P173N/T238G/M276K/A277T/E315G/ T364W/G381A/A403N/D142A/K363A/R385T/A394P/ L410G, K7N/D35R/V67A/P173N/T238G/M276K/A277T/ E315G/G381A/A403G/P4N/D142A/D185N/R385 T, K7N/ D35F/V67A/P173N/T238G/M276K/A277T/E315G/ T364W/G381A/A403G/D142R/N176K/D185N/S240K/ R385T/A394P, K7N/D35R/V67A/P173N/T238G/M276K/ A277T/E315G/T364W/G381A/A403G/D142E/N176K/ D185N/Q192K/E197S/A288R/K363A, K7N/V67A/P173N/ T238G/M276K/A277T/E315G/T364S/G381A/A403G/ D142E/Q192K/E197S/S240K/K363A, K7N/D35F/V67A/ P173N/T238G/M276K/A277T/E315G/T364S/G381A/ A403G/D142A/D185N/K363A/E402D/L410G, K7N/ V67A/P173N/T238G/M276K/A277T/E315G/T364W/ G381A/A403G/P4N/P121A/D142R/N17 6K/D185N/ E197S/S240K, K7N/D35N/V67A/P173N/T238G/M276K/ A277T/E315G/G381A/A403G/D142E/N176K/D185N/ S240K/, K7N/D35N/V67A/P173N/T238G/M276K/A277T/ E315G/T364W/G381A/A403G/P4N/P121A/D142A/ D185N/A288R, K7N/D35N/V67A/P173N/T238G/M276K/ A277T/E315G/T364W/G381A/A403G/P4N/D185N/ Q192K/E197S, K7N/D35Y/V67A/P173N/T238G/M276K/ A277T/E315G/T364S/G381A/A403G/D142E/N176K/ D185N/R385T/A394P, K7N/D35R/V67A/P173N/T238G/ M276K/A277T/E315G/G381A/A403G/S240K/K363A/ R385T/A394P/L410A, K7N/D35F/V67A/P173N/T238G/ M276K/A277T/E315G/T364W/G381A/A403G/D142R/ R385T/A394P/E402D/L410G, K7N/D35N/V67A/P173N/ T238G/M276K/A277T/E315G/T364S/G381A/A403G/ N176K/D185N/S240K/K363A/A394P/E402D/L410G, K7N/D35E/V67A/P173N/T238G/M276K/A277T/E315G/ T364W/G381A/A403G/P4N/D142E, K7N/D35F/V67A/ P173N/T238G/M276K/A277T/E315G/G381A/A403G/ K363A, K7N/D35R/V67A/P173N/T238G/M276K/A277T/ E315G/T364S/G381A/A403N/D142E/D185N/R385T/ A394P/L410G, K7N/D35Y/V67A/P173N/T238G/M276K/ A277T/E315G/T364S/G381A/A403G/P121A/S240K, K7N/D35Y/V67A/P173N/T238G/M276K/A277T/E315G/G381A/A403G/L410G, K7N/D35E/V67A/P173N/T238G/M276K/A277T/E315G/T364S/G381A/A403N/D142A/

N176K/D185N/S240K/K363A/R385T/A394P/L410G, K7N/D35Y/V67A/P173N/T238G/M276K/A277T/E315G/ T364W/G381A/A403G/P4N/D142E/D185N, K7N/D35E/ V67A/P173N/T238G/M276K/A277T/E315G/T364W/ G381A/A403G/P4N/D142A/N176K/D185N/S240K/ K363A/L410A, K7N/V67A/P173N/T238G/M276K/ A277T/E315G/T364S/G381A/A403G/N176K/D185N/ Q192K/R3 85T/A394P/E402D/L410A, K7N/V67A/P173N/ T238G/M276K/A277T/E315G/T364S/G381A/A403G/ P121A/D142E/E197S/K363A, K7N/D35R/V67A/P173N/ T238G/M276K/A277T/E315G/T364W/G381A/A403G/ P4N/N176K/D185N, K7N/D35R/V67A/P173N/T238G/ M276K/A277T/E315G/T364S/G381A/A403G/D142R/ Q192K/S240K/K363A/R385T/A394P/E402D/L410G, K7N/D35R/V67A/P173N/T238G/M276K/A277T/E315G/ T364W/G381A/A403G/P4N/D185N, K7N/D35N/V67A/ P173N/T238G/M276K/A277T/E315G/T364W/G381A/ A403G/N176K/D185N/S240K/R385T, K7N/D35N/V67A/ P173N/T238G/M276K/A277T/E315G/T364W/G381A/ A403G/S240K, K7N/V67A/P173N/T238G/M276K/ A277T/E315G/T364W/G381A/A403G/D142R/N176K/ D185N/S 240K, K7N/D35F/V67A/P173N/T238G/M276K/ A277T/E315G/G381A/A403G/P121A/D142E/A153V/ D185N/S240K/R385T, K7N/V67A/P173N/T238G/M276K/ A277T/E315G/T364W/G381A/A403G/D185N/R385T, K7N/D35R/V67A/P173N/T238G/M276K/A277T/E315G/ T364W/G381A/A403G/P4N/N176K/D185N/S240K, K7N/ D35F/V67A/P173N/T238G/M276K/A277T/E315G/ T364W/G381A/A403G/D142E/N176K/D185N, K7N/ D35R/V67A/P173N/T238G/M276K/A277T/E315G/ T364W/G381A/A403G/D142R/N176K/D185N/Q192K/ S240K/K363A, and K7N/D35N/V67A/P173N/T238G/ M276K/A277T/E315G/T364W/G381A/A403G/P4N/ D142A/N176K/D185N/S240K.

12. The composition of claim 1, wherein said variant phytase enzyme comprises the amino acid substitutions K7N/D35R/V67A/P173N/T238G/M276K/A277T/E315G/ T364W/G381A/A403G/P4N/P121A/D136 S/Q346S/ T378A and at least one further amino acid substitution selected from the group consisting of E5K, L6F, L6M, L6Y, S10A, S1ON, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

13. The composition of claim 1, wherein said variant phytase enzyme comprises the amino acid substitutions K7N/D35R/V67A/P173N/T238G/M276K/A277T/E315G/ T364W/G381A/A403G/P137V/D185N and at least one further amino acid substitution selected from the group consisting of P4E, P4K, P4L, P4M, P4N, P4Q, P4T, P4W, E5K, L6F, L6M, L6Y, S10A, S1ON, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

14. The composition of claim 1, wherein said variant phytase enzyme comprises the amino acid substitutions K7N/D35N/V67A/P173N/T238G/M276K/A277T/E315G/ T364W/G381A/A403G/P4N and at least one further amino acid substitution selected from the group consisting of E5K, L6F, L6M, L6Y, S10A, S1ON, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, T378A, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

15. The composition of claim 1, wherein said variant phytase enzyme comprises the amino acid substitutions P4N/K7N/D35N/V67A/P121A/D136S/P173N/T238G/ M276K/A277T/E315G/Q346S/T364W/T378A/G381A/ A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

16. The composition of claim 1, wherein said variant phytase enzyme comprises the amino acid substitutions P4N/K7N/D35R/V67A/P121A/D136S/P173N/T238G/ M276K/A277T/E315G/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

17. The composition of claim 1, wherein said variant phytase enzyme comprises the amino acid substitutions P4N/K7N/D35N/V67A/P121A/D136S/P173N/T238G/ M276K/A277T/E315G/T364W/T378A/G381A/A403G and at least one further amino acid substitution selected from the group consisting of E5K, L6F, L6M, L6Y, S10A, S10N, S10Q, V11I, A25D, A25F, A25N, A25W, Q27D, Q27P, Q27V, D31I, D31N, W46E, W46G, E53D, E53N, V55L, L58S, Y61C, Q62W, R63A, R65C, R65G, R65P, R65S, R65V, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, T130G, T130R, Q134A, Q134T, L135F, L135Y, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, S240A, S240G, S240K, S240R, Q242E, Q242L, N244I, P261L, S266A, S266Y, L272S, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, P365W, L366R, T370K, P371M, P371V, P371W, P371Y, P372T, E384D, R385T, A394I, A394L, A394M, A394P, G395P, Q398V, N401A, N401L, N401P, E402D, S409H, S409L, S409R, S409V, S409W, L410A, L410C, L410E, L410F, L410G, L410I, L410K, and L410R.

18. The composition of claim 1, wherein said variant phytase enzyme has at least 95% sequence identity to an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

19. The composition of claim 1, wherein said variant phytase enzyme comprises SEQ ID NO:11.

20. The composition of claim 1, wherein said variant phytase enzyme comprises SEQ ID NO:12.

21. The composition of claim 1, wherein said variant phytase enzyme comprises SEQ ID NO:13.

22. The composition of claim 1, wherein said variant phytase enzyme further comprising a sequence insertion of SEQ ID NO:15 or SEQ ID NO:16, wherein said variant phytase enzyme has phytase activity.

23. The composition of claim 1 further comprising animal feed.

24. A nucleic acid encoding the variant phytase enzyme of claim 1.

25. An expression vector comprising the nucleic acid of claim 24.

26. An isolated host cell comprising the nucleic acid of claim 24.

27. A method of making a variant phytase enzyme comprising culturing the host cell of claim 26 under conditions wherein said variant phytase enzyme is produced and recovering said enzyme.

28. An isolated host cell comprising the expression vector of claim 25.

29. A method of making a variant phytase enzyme comprising culturing the host cell of claim 28 under conditions wherein said variant phytase enzyme is produced and recovering said enzyme.

30. The composition according to claim 1, wherein said amino acid substitution at position number 277 is A277T.

31. The composition according to claim 30, wherein said further amino acid substitution(s) is selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, M276K, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

32. The composition according to claim 1, wherein said amino acid substitution at position number 315 is E315G or E315S.

33. The composition according to claim 32, wherein said further amino acid substitution(s) is selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, M276K, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

34. The composition according to claim 33, wherein said amino acid substitution at position number 315 is E315G.

35. The composition according to claim 1, wherein said amino acid substitution at position number 277 is A277T and said amino acid substitution at position number 315 is E315G.

36. The composition according to claim 35, wherein said further amino acid substitution(s) is selected from the group consisting of P4E, P4K, P4L, P4M, P4N, P4Q, P4T, P4W, E5K, L6F, L6M, L6Y, K7E, K7L, K7N, K7Q, K7S, S10A, S10N, S10Q, V11I, A25D, A25F, A25N, A25W, Q27D, Q27P, Q27V, D31I, D31N, D35E, D35F, D35N, D35R, D35Y, W46E, W46G, E53D, E53N, V55L, L58S, Y61C, Q62W, R63A, R65C, R65G, R65P, R65S, R65V, V67A, N69L, N69R, N69Y, G70E, L72S, A73P, K75C, K75E, K75G, K75I, K75L, K75M, K75Q, K75R, K75S, K75W, G76C, P80S, V89T, D90N, I110L, T111I, H113Q, T114C, T114D, T114F, T114H, T114N, T114P, T114S, S119R, R120K, R120S, P121A, T130G, T130R, Q134A, Q134T, L135F, L135Y, D136F, D136G, D136S, P137C, P137F, P137G, P137H, P137I, P137L, P137M, P137N, P137S, P137V, P137W, P137Y, N139A, N139H, N139P, D142A, D142E, D142F, D142G, D142H, D142I, D142K, D142L, D142M, D142N, D142P, D142R, D142S, D142T, D142V, D142Y, S146E, S146P, S151F, S151R, A153N, A153S, A153V, A153Y, Q157A, Q157G, Q157P, H158R, H158W, T161D, E165D, E165P, E165S, E165T, E165W, P173N, P173S, P173T, P173Y, Q174A, Q174E, N176K, F179L, N180K, R181T, E182A, E182F, E182S, E182T, D185N, S187T, S189L, S189N, S189T, T191S, Q192K, Q192L, A193I, A193L, A193S, A193T, A193V, L194I, E197S, A202R, Q225E, P230S, G233A, T238A, T238F, T238G, T238K, T238N, T238P, T238Q, T238R, T238S, T238Y, S240A, S240G, S240K, S240R, Q242E, Q242L, N244I, P261L, S266A, S266Y, L272S, M276K, L279F, T280C, T280G, T280N, T280P, P281D, P281S, H282N, A288R, T292G, T295N, G302S, G311A, L316F, R339M, L341V, Q346K, Q346P, Q346S, Q346T, L352M, D362G, D362N, D362S, D362Y, K363A, K363R, T364C, T364E, T364I, T364L, T364N, T364Q, T364S, T364T, T364V, T364W, P365W, L366R, T370K, P371M, P371V, P371W, P371Y, P372T, T378A, G381A, G381C, G381L, G381N, G381R, E384D, R385T, A394I, A394L, A394M, A394P, G395P, Q398V, N401A, N401L, N401P, E402D, A403G, A403I, A403K, A403L, A403N, A403Q, A403W, A403Y, S409H, S409L, S409R, S409V, S409W, L410A, L410C, L410E, L410F, L410G, L410I, L410K, and L410R.

37. The composition of claim 1, wherein said variant phytase enzyme exhibits at least 96% sequence identity to SEQ ID NO:1.

38. The composition of claim 1, wherein said variant phytase enzyme exhibits at least 97% sequence identity to SEQ ID NO:1.

39. The composition of claim 1, wherein said variant phytase enzyme exhibits at least 98% sequence identity to SEQ ID NO:1.

40. The composition of claim 1, wherein said variant phytase enzyme exhibits at least 99% sequence identity to SEQ ID NO:1.

* * * * *

SEQUENCE LISTING

<160> NUMBER OF SEQ ID NOS: 30

<210> SEQ ID NO 1
<211> LENGTH: 410
<212> TYPE: PRT
<213> ORGANISM: Artificial Sequence
<220> FEATURE:
<223> OTHER INFORMATION: Synthetic Phytase (CL00005023 G3P)

<400> SEQUENCE: 1

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Val Ala Tyr Leu Gly Gln Tyr Gln Arg Gln
        50                  55                  60

Arg Leu Val Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Pro Asp Pro Leu Phe Asn Pro Leu
        115                 120                 125

Lys Thr Gly Val Cys Gln Leu Asp Pro Ala Asn Val Thr Asp Ala Ile
    130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Pro Gln Ser Asn
                165                 170                 175

Leu Cys Phe Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Tyr Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 2
<211> LENGTH: 410
<212> TYPE: PRT
<213> ORGANISM: Artificial Sequence
<220> FEATURE:
<223> OTHER INFORMATION: Synthetic Phytase (CL00048541 G4P)

<400> SEQUENCE: 2

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
 50                  55                  60

Arg Leu Val Ala Asn Gly Leu Leu Ala Asp Lys Gly Cys Pro Gln Pro
 65                  70                  75                  80

Gly Gln Val Ala Ile Ile Ala Asp Val Asp Glu Arg Thr Arg Lys Thr
                     85                  90                  95

Gly Glu Ala Phe Ala Ala Gly Leu Ala Pro Asp Cys Ala Ile Thr Val
                100                 105                 110

His Thr Gln Ala Asp Thr Ser Arg Pro Asp Pro Leu Phe Asn Pro Leu
            115                 120                 125

Lys Thr Gly Val Cys Gln Leu Asp Pro Ala Asn Val Thr Asp Ala Ile
        130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Pro Gln Ser Asn
                165                 170                 175

Leu Cys Phe Asn Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Gly Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Tyr Gln Thr Leu Gln Gln Met Arg Asp Lys Thr Pro Leu Ser Leu
            355                 360                 365

Asn Thr Pro Pro Gly Glu Val Lys Leu Thr Leu Pro Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 3
<211> LENGTH: 410
<212> TYPE: PRT
<213> ORGANISM: Artificial Sequence
<220> FEATURE:
<223> OTHER INFORMATION: Synthetic Phytase (CL00060516 G5P)

<400> SEQUENCE: 3

```
Gln Ser Glu Pro Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Arg Ala Trp Pro Thr Trp Pro Val Lys Leu Gly Trp Leu Thr
            35                  40                  45

Pro Arg Gly Gly Glu Leu Val Ala Tyr Leu Gly Gln Tyr Gln Arg Gln
        50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Arg Pro Asp Pro Leu Phe Asn Pro Leu
            115                 120                 125

Lys Thr Gly Val Cys Gln Leu Asp Pro Ala Asn Val Thr Asp Ala Ile
        130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Pro Gln Ser Asn
                165                 170                 175

Leu Cys Phe Asn Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Gly Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Tyr Gln Thr Leu Gln Gln Met Arg Asp Lys Ile Pro Leu Ser Leu
            355                 360                 365

Asn Thr Pro Pro Gly Glu Val Lys Leu Thr Leu Pro Ala Cys Glu Glu
        370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410
```

-continued

```
<210> SEQ ID NO 4
<211> LENGTH: 410
<212> TYPE: PRT
<213> ORGANISM: Artificial Sequence
<220> FEATURE:
<223> OTHER INFORMATION: Synthetic Phytase (CL00080812 G6P)

<400> SEQUENCE: 4
```

| | | | | | | | | | | | | | | | |
|---|---|---|---|---|---|---|---|---|---|---|---|---|---|---|---|
| Gln | Ser | Glu | Pro | Glu | Leu | Asn | Leu | Glu | Ser | Val | Val | Ile | Val | Ser | Arg |
| 1 | | | | 5 | | | | | 10 | | | | | 15 | |
| His | Gly | Val | Arg | Ala | Pro | Thr | Lys | Ala | Thr | Gln | Leu | Met | Gln | Asp | Val |
| | | | 20 | | | | | 25 | | | | | 30 | | |
| Thr | Pro | Arg | Ala | Trp | Pro | Thr | Trp | Pro | Val | Lys | Leu | Gly | Trp | Leu | Thr |
| | | 35 | | | | | 40 | | | | | 45 | | | |
| Pro | Arg | Gly | Gly | Glu | Leu | Val | Ala | Tyr | Leu | Gly | Gln | Tyr | Gln | Arg | Gln |
| | 50 | | | | | 55 | | | | | 60 | | | | |
| Arg | Leu | Ala | Ala | Asn | Gly | Leu | Leu | Ala | Asp | Lys | Gly | Cys | Pro | Gln | Pro |
| 65 | | | | | 70 | | | | 75 | | | | | 80 | |
| Gly | Gln | Val | Ala | Ile | Ile | Ala | Asp | Val | Asp | Glu | Arg | Thr | Arg | Lys | Thr |
| | | | | 85 | | | | 90 | | | | | 95 | | |
| Gly | Glu | Ala | Phe | Ala | Ala | Gly | Leu | Ala | Pro | Asp | Cys | Ala | Ile | Thr | Val |
| | | | 100 | | | | | 105 | | | | | 110 | | |
| His | Thr | Gln | Ala | Asp | Thr | Ser | Arg | Pro | Asp | Pro | Leu | Phe | Asn | Pro | Leu |
| | | | 115 | | | | | 120 | | | | | 125 | | |
| Lys | Thr | Gly | Val | Cys | Gln | Leu | Asp | Pro | Ala | Asn | Val | Thr | Asp | Ala | Ile |
| 130 | | | | | 135 | | | | | 140 | | | | | |
| Leu | Ser | Arg | Ala | Gly | Gly | Ser | Ile | Ala | Asp | Phe | Thr | Gln | His | Tyr | Gln |
| 145 | | | | | 150 | | | | | 155 | | | | | 160 |
| Thr | Ala | Phe | Arg | Glu | Leu | Glu | Arg | Val | Leu | Asn | Phe | Asn | Gln | Ser | Asn |
| | | | 165 | | | | | 170 | | | | | 175 | | |
| Leu | Cys | Phe | Asn | Arg | Glu | Lys | Gln | Asp | Glu | Ser | Cys | Ser | Leu | Thr | Gln |
| | | | 180 | | | | | 185 | | | | | 190 | | |
| Ala | Leu | Pro | Ser | Glu | Leu | Lys | Val | Ser | Ala | Asp | Asn | Val | Ser | Leu | Thr |
| | | 195 | | | | | 200 | | | | | 205 | | | |
| Gly | Ala | Val | Ser | Leu | Ala | Ser | Met | Leu | Thr | Glu | Ile | Phe | Leu | Leu | Gln |
| | 210 | | | | | 215 | | | | | 220 | | | | |
| Gln | Ala | Gln | Gly | Met | Pro | Glu | Pro | Gly | Trp | Gly | Arg | Ile | Gly | Asp | Ser |
| 225 | | | | | 230 | | | | | 235 | | | | | 240 |
| His | Gln | Trp | Asn | Thr | Leu | Leu | Ser | Leu | His | Asn | Ala | Gln | Phe | Asp | Leu |
| | | | 245 | | | | | 250 | | | | | 255 | | |
| Leu | Gln | Arg | Thr | Pro | Glu | Val | Ala | Arg | Ser | Arg | Ala | Thr | Pro | Leu | Leu |
| | | | 260 | | | | | 265 | | | | | 270 | | |
| Asp | Leu | Ile | Lys | Thr | Ala | Leu | Thr | Pro | His | Pro | Pro | Gln | Lys | Gln | Ala |
| | | 275 | | | | | 280 | | | | | 285 | | | |
| Tyr | Gly | Val | Thr | Leu | Pro | Thr | Ser | Val | Leu | Phe | Ile | Ala | Gly | His | Asp |
| | 290 | | | | | 295 | | | | | 300 | | | | |
| Thr | Asn | Leu | Ala | Asn | Leu | Gly | Gly | Ala | Leu | Gly | Leu | Asn | Trp | Thr | Leu |
| 305 | | | | | 310 | | | | | 315 | | | | | 320 |
| Pro | Gly | Gln | Pro | Asp | Asn | Thr | Pro | Gly | Gly | Glu | Leu | Val | Phe | Glu |
| | | | | 325 | | | | | 330 | | | | | 335 |
| Arg | Trp | Arg | Arg | Leu | Ser | Asp | Asn | Ser | Gln | Trp | Ile | Gln | Val | Ser | Leu |
| | | | 340 | | | | | 345 | | | | | 350 | | |
| Val | Tyr | Gln | Thr | Leu | Gln | Gln | Met | Arg | Asp | Lys | Trp | Pro | Leu | Ser | Leu |
| | | | 355 | | | | | 360 | | | | | 365 | | |

```
Asn Thr Pro Pro Gly Glu Val Lys Leu Thr Leu Pro Ala Cys Glu Glu
            370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 5
<211> LENGTH: 410
<212> TYPE: PRT
<213> ORGANISM: Artificial Sequence
<220> FEATURE:
<223> OTHER INFORMATION: Synthetic Phytase (CL00082400)

<400> SEQUENCE: 5

Gln Ser Glu Asn Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Arg Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
    50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Ala Asp Pro Leu Phe Asn Pro Leu
        115                 120                 125

Lys Thr Gly Val Cys Gln Leu Ser Pro Ala Asn Val Thr Asp Ala Ile
    130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Gly Leu Asn Trp Thr Leu
305                 310                 315                 320
```

```
Pro Gly Gln Pro Asp Asn Thr Pro Pro Gly Glu Leu Val Phe Glu
            325                 330                 335

Arg Trp Arg Arg Leu Ser Asp Asn Ser Ser Trp Ile Gln Val Ser Leu
            340                 345                 350

Val Tyr Gln Thr Leu Gln Gln Met Arg Asp Lys Trp Pro Leu Ser Leu
            355                 360                 365

Asn Thr Pro Pro Gly Glu Val Lys Leu Ala Leu Pro Ala Cys Glu Glu
        370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 6
<211> LENGTH: 410
<212> TYPE: PRT
<213> ORGANISM: Artificial Sequence
<220> FEATURE:
<223> OTHER INFORMATION: Synthetic Phytase (CL00089395)

<400> SEQUENCE: 6

Gln Ser Glu Pro Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Arg Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
    50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Pro Asp Pro Leu Phe Asn Pro Leu
        115                 120                 125

Lys Thr Gly Val Cys Gln Leu Asp Val Ala Asn Val Thr Asp Ala Ile
130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270
```

```
Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Ala Leu Gly Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Tyr Gln Thr Leu Gln Gln Met Arg Asp Lys Trp Pro Leu Ser Leu
        355                 360                 365

Asn Thr Pro Pro Gly Glu Val Lys Leu Thr Leu Pro Ala Cys Glu Glu
370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 7
<211> LENGTH: 410
<212> TYPE: PRT
<213> ORGANISM: Artificial Sequence
<220> FEATURE:
<223> OTHER INFORMATION: Synthetic Phytase (CL00090520)

<400> SEQUENCE: 7

Gln Ser Glu Asn Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asn Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
    50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Pro Asp Pro Leu Phe Asn Pro Leu
        115                 120                 125

Lys Thr Gly Val Cys Gln Leu Asp Pro Ala Asn Val Thr Asp Ala Ile
    130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220
```

```
Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Ala Leu Gly Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Tyr Gln Thr Leu Gln Gln Met Arg Asp Lys Trp Pro Leu Ser Leu
            355                 360                 365

Asn Thr Pro Pro Gly Glu Val Lys Leu Thr Leu Pro Ala Cys Glu Glu
370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 8
<211> LENGTH: 410
<212> TYPE: PRT
<213> ORGANISM: Artificial Sequence
<220> FEATURE:
<223> OTHER INFORMATION: Synthetic Phytase (CL00100223)

<400> SEQUENCE: 8

Gln Ser Glu Asn Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asn Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
    50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Ala Asp Pro Leu Phe Asn Pro Leu
        115                 120                 125

Lys Thr Gly Val Cys Gln Leu Ser Pro Ala Asn Val Thr Asp Ala Ile
    130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175
```

```
Leu Cys Phe Asn Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Gly Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Ser Trp Ile Gln Val Ser Leu
            340                 345                 350

Val Tyr Gln Thr Leu Gln Gln Met Arg Asp Lys Trp Pro Leu Ser Leu
        355                 360                 365

Asn Thr Pro Pro Gly Glu Val Lys Leu Ala Leu Pro Ala Cys Glu Glu
370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 9
<211> LENGTH: 410
<212> TYPE: PRT
<213> ORGANISM: Artificial Sequence
<220> FEATURE:
<223> OTHER INFORMATION: Synthetic Phytase (CL00102257)

<400> SEQUENCE: 9

Gln Ser Glu Asn Glu Leu Asn Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Arg Ala Trp Pro Thr Trp Pro Val Lys Leu Gly Trp Leu Thr
            35                  40                  45

Pro Arg Gly Gly Glu Leu Val Ala Tyr Leu Gly Gln Tyr Gln Arg Gln
        50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Ala Asp Pro Leu Phe Asn Pro Leu
        115                 120                 125
```

Lys Thr Gly Val Cys Gln Leu Ser Pro Ala Asn Val Thr Asp Ala Ile
130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
                290                 295                 300

Thr Asn Leu Ala Asn Leu Gly Gly Ala Leu Gly Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Tyr Gln Thr Leu Gln Gln Met Arg Asp Lys Trp Pro Leu Ser Leu
                355                 360                 365

Asn Thr Pro Pro Gly Glu Val Lys Leu Ala Leu Pro Ala Cys Glu Glu
                370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 10
<211> LENGTH: 410
<212> TYPE: PRT
<213> ORGANISM: Artificial Sequence
<220> FEATURE:
<223> OTHER INFORMATION: Synthetic Phytase (CL00102259)

<400> SEQUENCE: 10

Gln Ser Glu Asn Glu Leu Asn Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asn Ala Trp Pro Thr Trp Pro Val Lys Leu Gly Trp Leu Thr
                35                  40                  45

Pro Arg Gly Gly Glu Leu Val Ala Tyr Leu Gly Gln Tyr Gln Arg Gln
            50                  55                  60

Arg Leu Ala Ala Asn Gly Leu Leu Ala Asp Lys Gly Cys Pro Gln Pro
65                  70                  75                  80

```
Gly Gln Val Ala Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Ala Asp Pro Leu Phe Asn Pro Leu
            115                 120                 125

Lys Thr Gly Val Cys Gln Leu Ser Pro Ala Asn Val Thr Asp Ala Ile
130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Gly Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Tyr Gln Thr Leu Gln Gln Met Arg Asp Lys Trp Pro Leu Ser Leu
            355                 360                 365

Asn Thr Pro Pro Gly Glu Val Lys Leu Ala Leu Pro Ala Cys Glu Glu
            370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 11
<211> LENGTH: 410
<212> TYPE: PRT
<213> ORGANISM: Artificial Sequence
<220> FEATURE:
<223> OTHER INFORMATION: Synthetic Phytase (CL00071716)

<400> SEQUENCE: 11

Gln Ser Glu Pro Glu Leu Asn Leu Glu Ser Val Val Ile Val Ser Arg
1               5                   10                  15

His Gly Val Arg Ala Pro Thr Lys Ala Thr Gln Leu Met Gln Asp Val
                20                  25                  30
```

```
Thr Pro Arg Ala Trp Pro Thr Trp Pro Val Lys Leu Gly Trp Leu Thr
         35                  40                  45

Pro Arg Gly Gly Glu Leu Val Ala Tyr Leu Gly Gln Tyr Gln Arg Gln
 50                  55                  60

Arg Leu Ala Ala Asn Gly Leu Leu Ala Asp Lys Gly Cys Pro Gln Pro
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
                100                 105                 110

His Thr Gln Ala Asp Thr Ser Arg Pro Asp Pro Leu Phe Asn Pro Leu
             115                 120                 125

Lys Thr Gly Val Cys Gln Leu Asp Pro Ala Asn Val Thr Asp Ala Ile
130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Pro Gln Ser Asn
                165                 170                 175

Leu Cys Phe Asn Arg Thr Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Asn Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Ala Leu Gly Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Ser Trp Ile Gln Val Ser Leu
                340                 345                 350

Val Tyr Gln Thr Leu Gln Gln Met Arg Asp Lys Ile Pro Leu Ser Leu
            355                 360                 365

Asn Thr Pro Pro Gly Glu Val Lys Leu Thr Leu Pro Ala Cys Glu Glu
370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
                405                 410

<210> SEQ ID NO 12
<211> LENGTH: 410
<212> TYPE: PRT
<213> ORGANISM: Artificial Sequence
<220> FEATURE:
<223> OTHER INFORMATION: Synthetic Phytase (CL00100225)
```

<400> SEQUENCE: 12

```
Gln Ser Glu Pro Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Arg Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Ala Asp Pro Leu Phe Asn Pro Leu
        115                 120                 125

Lys Thr Gly Val Cys Gln Leu Ser Pro Ala Asn Val Thr Asp Ala Ile
130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Ala Leu Gly Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Ser Trp Ile Val Ser Leu
            340                 345                 350

Val Tyr Gln Thr Leu Gln Gln Met Arg Asp Lys Trp Pro Leu Ser Leu
        355                 360                 365

Asn Thr Pro Pro Gly Glu Val Lys Leu Ala Leu Pro Ala Cys Glu Glu
370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Leu
```

<210> SEQ ID NO 13
<211> LENGTH: 410
<212> TYPE: PRT
<213> ORGANISM: Artificial Sequence
<220> FEATURE:
<223> OTHER INFORMATION: Synthetic Phytase (CL00102276)

<400> SEQUENCE: 13

```
Gln Ser Glu Pro Glu Leu Asn Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Arg Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
    50                  55                  60

Arg Leu Ala Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Pro Asp Pro Leu Phe Asn Pro Leu
        115                 120                 125

Lys Thr Gly Val Cys Gln Leu Asp Pro Ala Asn Val Thr Asp Ala Ile
    130                 135                 140

Leu Ser Arg Ala Gly Gly Ser Ile Ala Asp Phe Thr Gln His Tyr Gln
145                 150                 155                 160

Thr Ala Phe Arg Glu Leu Glu Arg Val Leu Asn Phe Asn Gln Ser Asn
                165                 170                 175

Leu Cys Phe Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Gly Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Gly Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Thr Trp Ile Gln Val Ser Leu
            340                 345                 350

Val Tyr Gln Thr Leu Gln Gln Met Arg Asp Lys Trp Pro Leu Ser Leu
```

```
              355                 360                 365
Asn Thr Pro Pro Gly Glu Val Lys Leu Thr Leu Pro Ala Cys Glu Glu
        370                 375                 380

Arg Asn Ala Gln Gly Met Cys Ser Leu Ala Gly Phe Thr Gln Ile Val
385                 390                 395                 400

Asn Glu Gly Arg Ile Pro Ala Cys Ser Ala
                405                 410

<210> SEQ ID NO 14
<211> LENGTH: 424
<212> TYPE: PRT
<213> ORGANISM: Artificial Sequence
<220> FEATURE:
<223> OTHER INFORMATION: Synthetic Phytase (CL00047720 Insertion
      Variant)

<400> SEQUENCE: 14

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Val Ala Tyr Leu Gly Gln Tyr Gln Arg Gln
    50                  55                  60

Arg Leu Val Ala Asn Gly Leu Leu Ala Asp Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Arg Pro Asp Pro Leu Phe Asn Pro Leu
        115                 120                 125

Lys Thr Gly Val Cys Gln Leu Asp Pro Ala Asn Val Thr Leu Ala Ile
    130                 135                 140

Leu Ser Arg Ala Val Asp Pro Ala Asn Val Thr His Ala Ile Leu Ser
145                 150                 155                 160

Arg Ala Gly Gly Ser Ile Ala Asp Phe Thr Gln His Tyr Gln Thr Ala
                165                 170                 175

Phe Arg Glu Leu Glu Arg Val Leu Asn Phe Pro Gln Ser Asn Leu Cys
            180                 185                 190

Phe Asn Arg Glu Lys Gln Asp Glu Ser Cys Ser Leu Thr Gln Ala Leu
        195                 200                 205

Pro Ser Glu Leu Lys Val Ser Ala Asp Asn Val Ser Leu Thr Gly Ala
    210                 215                 220

Val Ser Leu Ala Ser Met Leu Thr Glu Ile Phe Leu Leu Gln Gln Ala
225                 230                 235                 240

Gln Gly Met Pro Glu Pro Gly Trp Gly Arg Ile Thr Asp Ser His Gln
                245                 250                 255

Trp Asn Thr Leu Leu Ser Leu His Asn Ala Gln Phe Asp Leu Leu Gln
            260                 265                 270

Arg Thr Pro Glu Val Ala Arg Ser Arg Ala Thr Pro Leu Leu Asp Leu
        275                 280                 285

Ile Met Ala Ala Leu Thr Pro His Pro Pro Gln Lys Gln Ala Tyr Gly
    290                 295                 300
```

```
Val Thr Leu Pro Thr Ser Val Leu Phe Ile Ala Gly His Asp Thr Asn
305                 310                 315                 320

Leu Ala Asn Leu Gly Gly Ala Leu Glu Leu Asn Trp Thr Leu Pro Gly
            325                 330                 335

Gln Pro Asp Asn Thr Pro Pro Gly Gly Glu Leu Val Phe Glu Arg Trp
            340                 345                 350

Arg Arg Leu Ser Asp Asn Ser Gln Trp Ile Gln Val Ser Leu Val Tyr
            355                 360                 365

Gln Thr Leu Gln Gln Met Arg Asp Lys Thr Pro Leu Ser Leu Asn Thr
            370                 375                 380

Pro Pro Gly Glu Val Lys Leu Thr Leu Pro Gly Cys Glu Glu Arg Asn
385                 390                 395                 400

Ala Gln Gly Met Cys Ser Leu Ala Gly Phe Thr Gln Ile Val Asn Glu
            405                 410                 415

Ala Arg Ile Pro Ala Cys Ser Leu
            420
```

<210> SEQ ID NO 15
<211> LENGTH: 14
<212> TYPE: PRT
<213> ORGANISM: Artificial Sequence
<220> FEATURE:
<223> OTHER INFORMATION: Synthetic Phytase (Insertion in CL00047720)

<400> SEQUENCE: 15

```
Val Asp Pro Ala Asn Val Thr His Ala Ile Leu Ser Arg Ala
1               5                   10
```

<210> SEQ ID NO 16
<211> LENGTH: 14
<212> TYPE: PRT
<213> ORGANISM: Artificial Sequence
<220> FEATURE:
<223> OTHER INFORMATION: Synthetic Phytase (Insertion in CL00047720)

<400> SEQUENCE: 16

```
Pro Ala Asn Val Thr Leu Ala Ile Leu Ser Arg Ala Val Asp
1               5                   10
```

<210> SEQ ID NO 17
<211> LENGTH: 410
<212> TYPE: PRT
<213> ORGANISM: Artificial Sequence
<220> FEATURE:
<223> OTHER INFORMATION: Phytase (Wild type, G1P protein)

<400> SEQUENCE: 17

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Pro
65                  70                  75                  80

Gly Gln Val Ala Ile Ile Ala Asp Val Asp Glu Arg Thr Arg Lys Thr
            85                  90                  95

Gly Glu Ala Phe Ala Ala Gly Leu Ala Pro Asp Cys Ala Ile Thr Val
```

|   |   |   | 100 |   |   |   | 105 |   |   |   | 110 |   |
|---|---|---|---|---|---|---|---|---|---|---|---|---|

His Thr Gln Ala Asp Thr Ser Ser Pro Asp Pro Leu Phe Asn Pro Leu
        115                     120                   125

Lys Thr Gly Val Cys Gln Leu Asp Asn Ala Asn Val Thr Asp Ala Ile
130                     135                     140

Leu Ser Arg Ala Gly Gly Ser Ile Ala Asp Phe Thr Gly His Arg Gln
145                    150                   155                   160

Thr Ala Phe Arg Glu Leu Glu Arg Val Leu Asn Phe Pro Gln Ser Asn
        165                     170                   175

Leu Cys Phe Asn Arg Glu Lys Gln Asp Glu Ser Cys Ser Leu Thr Gln
            180                  185               190

Ala Leu Pro Ser Glu Leu Lys Val Ser Ala Asp Asn Val Ser Leu Thr
        195                     200                   205

Gly Ala Val Ser Leu Ala Ser Met Leu Thr Glu Ile Phe Leu Leu Gln
    210                     215                     220

Gln Ala Gln Gly Met Pro Glu Pro Gly Trp Gly Arg Ile Thr Asp Ser
225                     230                   235                   240

His Gln Trp Asn Thr Leu Leu Ser Leu His Asn Ala Gln Phe Tyr Leu
            245                  250               255

Leu Gln Arg Thr Pro Glu Val Ala Arg Ser Arg Ala Thr Pro Leu Leu
        260                     265                   270

Asp Leu Ile Met Ala Ala Leu Thr Pro His Pro Pro Gln Lys Gln Ala
    275                     280                     285

Tyr Gly Val Thr Leu Pro Thr Ser Val Leu Phe Ile Ala Gly His Asp
    290                     295                     300

Thr Asn Leu Ala Asn Leu Gly Gly Ala Leu Glu Leu Asn Trp Thr Leu
305                     310                   315                   320

Pro Gly Gln Pro Asp Asn Thr Pro Pro Gly Gly Glu Leu Val Phe Glu
            325                  330               335

Arg Trp Arg Arg Leu Ser Asp Asn Ser Gln Trp Ile Gln Val Ser Leu
            340                  345               350

Val Phe Gln Thr Leu Gln Gln Met Arg Asp Lys Thr Pro Leu Ser Leu
        355                     360               365

Asn Thr Pro Pro Gly Glu Val Lys Leu Thr Leu Ala Gly Cys Glu Glu
    370                     375                 380

Arg Asn Ala Gln Gly Met Cys Ser Leu Ala Gly Phe Thr Gln Ile Val
385                     390                   395                   400

Asn Glu Ala Arg Ile Pro Ala Cys Ser Leu
        405                     410

<210> SEQ ID NO 18
<211> LENGTH: 1230
<212> TYPE: DNA
<213> ORGANISM: Artificial Sequence
<220> FEATURE:
<223> OTHER INFORMATION: Synthetic Phytase (CL00048541 G4P)

<400> SEQUENCE: 18

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcgttgctta cttgggtcaa     180
taccaaagac agcgtcttgt tgccaacgga ttgttggccg ataagggttg tccacaacca     240
ggtcaagtag ctattattgc tgacgtcgac gaaagaaccc gtaagacagg tgaagccttc     300
```

```
gccgccggtc ttgctcctga ctgtgccatt accgttcaca cccaagctga cacttctaga    360
ccagatccat tgttcaaccc tttgaagact ggtgtttgcc aattggaccc agctaacgtt    420
actgacgcta tcttgtccag agctggagga tccattgctg acttcaccca acactaccag    480
actgccttca gagagttgga aagagttctt aacttcccac aatccaactt gtgctttaac    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat cgacttgct gcagagaact     780 ccagaggttg ctagatccag agccaccccca ttgttggact tgatcaagac tgctttgact   840
cctcacccac ctcaaaagca agcctacggt gttaccttgc ccacttctgt cttgttcatt    900
gccggtcacg atactaactt ggcaaatctc ggcggtgctt tgggtttgaa ctggactctt    960
cctggtcaac ctgataacac tccaccaggt ggtgagctcg ttttcgaaag atggcgtaga   1020
ctatctgata actctcaatg gattcaggtt tcgttggtc accaaacttt gcagcagatg    1080
agagacaaga ctccactgtc tttgaacacg cctccaggag aagtcaaatt gaccttgcct   1140
ggatgtgaag agagaaatgc tcagggtatg tgttccttgg ctggtttcac tcaaatcgtt   1200
aacgaagcta gaatcccagc ttgttccttg                                    1230
```

<210> SEQ ID NO 19
<211> LENGTH: 1230
<212> TYPE: DNA
<213> ORGANISM: Artificial Sequence
<220> FEATURE:
<223> OTHER INFORMATION: Synthetic Phytase (CL00060516 G5P)

<400> SEQUENCE: 19

```
cagagtgagc ctgagttgaa cctggaatcc gttgtcatcg tctctagaca tggtgttaga     60
gcaccaacca aggccaccca acttatgcaa gatgtcaccc caagagcttg gccaacctgg    120
ccagtcaagc tgggttggtt gacacctaga ggtggtgagc tcgttgctta cttgggtcaa    180
taccaaagac agcgtcttgc tgccaacgga ttgttggccg ataaggggtt gccacaacca    240
ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
ccagatccat tgttcaaccc tttgaagact ggtgtttgcc aattggaccc agctaacgtt    420
actgacgcta tcttgtccag agctggagga tccattgctg acttcaccca acactaccag    480
actgccttca gagagttgga aagagttctt aacttcccac aatccaactt gtgctttaac    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat cggtgactct    720
caccaatgga acaccttgtt gtccttgcac aacgctcaat cgacttgct gcagagaact     780 ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tgggtttgaa ctggactctt    960
cctggtcaac ctgataacac tccaccaggt ggtgagctcg ttttcgaaag atggcgtaga   1020
ctatctgata actctcaatg gattcaggtt tcgttggtct accaaacttt gcagcagatg   1080
agagacaaga tcccactgtc tttgaacacg cctccaggag aagtcaaatt gaccttgcct   1140
```

```
gcttgtgaag agagaaatgc tcagggtatg tgttccttgg ctggtttcac tcaaatcgtt    1200
aacgaaggta gaatcccagc ttgttccttg                                     1230

<210> SEQ ID NO 20
<211> LENGTH: 1230
<212> TYPE: DNA
<213> ORGANISM: Artificial Sequence
<220> FEATURE:
<223> OTHER INFORMATION: Synthetic Phytase (CL00080812 G6P)

<400> SEQUENCE: 20
cagagtgagc ctgagttgaa cctggaatcc gttgtcatcg tctctagaca tggtgttaga      60
gcaccaacca aggccaccca acttatgcaa gatgtcaccc aagagcttg gccaacctgg     120 ccagtcaagc tgggttggtt gacacctaga ggtggtgagc tcgttgctta cttgggtcaa    180
taccaaagac agcgtcttgc tgccaacgga ttgttggccg ataagggttg tccacaacca    240
ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
ccagatccat tgttcaaccc tttgaagact ggtgtttgcc aattggaccc agctaacgtt    420
actgacgcta tcttgtccag agctggagga tccattgctg acttcaccca acactaccag    480
actgccttca gagagttgga aagagttctt aacttcaacc aatccaactt gtgctttaac    540
cgtgagaagc aagacgaatc ctgttccttg actcaagcat accatctga gttgaaggtc    600 tccgccgaca acgtctcttt gaccggtgct gtcagcttgg cttccatgtt gactgaaatc    660
tttcttctgc aacaagctca aggtatgcct gagccaggtt ggggtagaat cggtgactct    720
caccaatgga caccttgtt gtccttgcac aacgctcaat tcgacttgct gcagagaact    780
ccagaggttg ctagatccag agccacccca ttgttggact tgatcaagac tgctttgact    840
cctcacccac tcaaaagca agcctacggt gttaccttgc ccacttctgt cttgttcatt    900
gccggtcacg atactaactt ggcaaatctc ggcggtgctt tgggtttgaa ctggactctt    960
cctggtcaac tgataacac tccaccaggt ggtgagctcg ttttcgaaag atggcgtaga   1020
ctatctgata actctcaatg gattcaggtt tcgttggtct accaaacttt gcagcagatg   1080
agagacaagt ggccactgtc tttgaacacg cctccaggag aagtcaaatt gaccttgcct   1140
gcttgtgaag agagaaatgc tcagggtatg tgttccttgg ctggtttcac tcaaatcgtt   1200
aacgaaggta gaatcccagc ttgttccttg                                    1230

<210> SEQ ID NO 21
<211> LENGTH: 1230
<212> TYPE: DNA
<213> ORGANISM: Artificial Sequence
<220> FEATURE:
<223> OTHER INFORMATION: Synthetic Phytase (CL00082400)

<400> SEQUENCE: 21
cagagtgaga acgagttgaa cctggaatcc gttgtcatcg tctctagaca tggtgttaga      60
gcaccaacca aggccaccca acttatgcaa gatgtcaccc aagagcttg gccaacctgg     120 ccagtcaagc tgggttggtt gacacctaga ggtggtgagc tcgttgctta cttgggtcaa    180
taccaaagac agcgtcttgc tgccaacgga ttgttggccg ataagggttg tccacaacca    240
ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
```

```
gctgatccat tgttcaaccc tttgaagact ggtgtttgcc aattgtctcc agctaacgtt    420
actgacgcta tcttgtccag agctggagga tccattgctg acttcaccca acactaccag    480
actgccttca gagagttgga aagagttctt aacttcaacc aatccaactt gtgctttaac    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat cggtgactct    720
caccaatgga acaccttgtt gtccttgcac aacgctcaat tcgacttgct gcagagaact    780
ccagaggttg ctagatccag agccacccca ttgttggact tgatcaagac tgctttgact    840
cctcacccac tcaaaagca agcctacggt gttaccttgc ccacttctgt cttgttcatt    900
gccggtcacg atactaactt ggcaaatctc ggcggtgctt tgggtttgaa ctggactctt    960
cctggtcaac tgataacac tccaccaggt ggtgagctcg ttttcgaaag atggcgtaga    1020
ctatctgata actcttcttg gattcaggtt tcgttggtct accaaacttt gcagcagatg    1080
agagacaagt ggccactgtc tttgaacacg cctccaggag aagtcaaatt ggctttgcct    1140
gcttgtgaag agagaaatgc tcagggtatg tgttccttgg ctggtttcac tcaaatcgtt    1200
aacgaaggta gaatcccagc ttgttccttg                                    1230

<210> SEQ ID NO 22
<211> LENGTH: 1230
<212> TYPE: DNA
<213> ORGANISM: Artificial Sequence
<220> FEATURE:
<223> OTHER INFORMATION: Synthetic Phytase (CL00089395)

<400> SEQUENCE: 22
cagagtgagc ctgagttgaa cctggaatcc gttgtcatcg tctctagaca tggtgttaga     60
gcaccaacca aggccaccca acttatgcaa gatgtcaccc aagagcttgg ccaacctgg    120 ccagtcaagc tgggttggtt gacacctaga ggtggtgagc tcgttgctta cttgggtcaa    180
taccaaagac agcgtcttgc tgccaacgga ttgttggccg ataagggttg tccacaacca    240
ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
ccagatccat tgttcaaccc tttgaagact ggtgtttgcc aattggacgt tgctaacgtt    420
actgacgcta tcttgtccag agctggagga tccattgctg acttcaccca acactaccag    480
actgccttca gagagttgga aagagttctt aacttcaacc aatccaactt gtgctttaac    540
cgtgagaagc aaaacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat cggtgactct    720
caccaatgga acaccttgtt gtccttgcac aacgctcaat tcgacttgct gcagagaact    780
ccagaggttg ctagatccag agccacccca ttgttggact tgatcaagac tgctttgact    840
cctcacccac tcaaaagca agcctacggt gttaccttgc ccacttctgt cttgttcatt    900
gccggtcacg atactaactt ggcaaatctc ggcggtgctt tgggtttgaa ctggactctt    960
cctggtcaac tgataacac tccaccaggt ggtgagctcg ttttcgaaag atggcgtaga    1020
ctatctgata actctcaatg gattcaggtt tcgttggtct accaaacttt gcagcagatg    1080
agagacaagt ggccactgtc tttgaacacg cctccaggag aagtcaaatt gaccttgcct    1140
gcttgtgaag agagaaatgc tcagggtatg tgttccttgg ctggtttcac tcaaatcgtt    1200
```

```
aacgaaggta gaatcccagc ttgttccttg                               1230

<210> SEQ ID NO 23
<211> LENGTH: 1230
<212> TYPE: DNA
<213> ORGANISM: Artificial Sequence
<220> FEATURE:
<223> OTHER INFORMATION: Synthetic Phytase (CL00090520)

<400> SEQUENCE: 23
cagagtgaga acgagttgaa cctggaatcc gttgtcatcg tctctagaca tggtgttaga     60
gcaccaacca aggccaccca acttatgcaa gatgtcaccc caaacgcttg gccaacctgg    120
ccagtcaagc tgggttggtt gacacctaga ggtggtgagc tcgttgctta cttgggtcaa    180
taccaaagac agcgtcttgc tgccaacgga ttgttggccg ataaggggttg tccacaacca    240 ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
ccagatccat tgttcaaccc tttgaagact ggtgtttgcc aattggaccc agctaacgtt    420
actgacgcta tcttgtccag agctggagga tccattgctg acttcaccca acactaccag    480
actgccttca gagagttgga aagagttctt aacttcaacc aatccaactt gtgctttaac    540
cgtgagaagc aagacgaatc tgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat cggtgactct    720
caccaatgga acaccttgtt gtccttgcac aacgctcaat tcgacttgct gcagagaact    780
ccagaggttg ctagatccag agccacccca ttgttggact tgatcaagac tgcttttgact    840 cctcacccac ctcaaaagca agcctacggt gttaccttgc ccacttctgt cttgttcatt    900
gccggtcacg atactaactt ggcaaatctc ggcggtgctt tgggtttgaa ctggactctt    960
cctggtcaac ctgataacac tccaccaggt ggtgagctcg ttttcgaaag atggcgtaga   1020
ctatctgata ctctcaatg gattcaggtt tcgttggtct accaaacttt gcagcagatg   1080
agagacaagt ggccactgtc tttgaacacg cctccaggag aagtcaaatt gaccttgcct   1140
gcttgtgaag agaaaatgc tcagggtatg tgttccttgg ctggtttcac tcaaatcgtt   1200
aacgaaggta gaatcccagc ttgttccttg                                    1230

<210> SEQ ID NO 24
<211> LENGTH: 1230
<212> TYPE: DNA
<213> ORGANISM: Artificial Sequence
<220> FEATURE:
<223> OTHER INFORMATION: Synthetic Phytase (CL00100223)

<400> SEQUENCE: 24
cagagtgaga acgagttgaa cctggaatcc gttgtcatcg tctctagaca tggtgttaga     60
gcaccaacca aggccaccca acttatgcaa gatgtcaccc caaatgcttg gccaacctgg    120
ccagtcaagc tgggttggtt gacacctaga ggtggtgagc tcgttgctta cttgggtcaa    180
taccaaagac agcgtcttgc tgccaacgga ttgttggccg ataaggggttg tccacaacca    240 ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
gctgatccat tgttcaaccc tttgaagact ggtgtttgcc aattgtctcc agctaacgtt    420
```

```
actgacgcta tcttgtccag agctggagga tccattgctg acttcaccca acactaccag      480
actgccttca gagagttgga aagagttctt aacttcaacc aatccaactt gtgctttaac      540
cgtgagaagc aagacgaatc ctgttccttg actcaagcat taccatctga gttgaaggtc      600
tccgccgaca acgtctcttt gaccggtgct gtcagcttgg cttccatgtt gactgaaatc      660
tttcttctgc aacaagctca aggtatgcct gagccaggtt ggggtagaat cggtgactct      720
caccaatgga acaccttgtt gtccttgcac aacgctcaat tcgacttgct gcagagaact      780
ccagaggttg ctagatccag agccacccca ttgttggact tgatcaagac tgctttgact      840
cctcacccac ctcaaaagca agcctacggt gttaccttgc ccacttctgt cttgttcatt      900
gccggtcacg atactaactt ggcaaatctc ggcggtgctt tgggtttgaa ctggactctt      960
cctggtcaac ctgataacac tccaccaggt ggtgagctcg ttttcgaaag atggcgtaga     1020
ctatctgata actcttcttg gattcaggtt tcgttggtct accaaacttt gcagcagatg     1080
agagacaagt ggccactgtc tttgaacacg cctccaggag aagtcaaatt ggctttgcct     1140
gcttgtgaag agagaaatgc tcagggtatg tgttccttgg ctggtttcac tcaaatcgtt     1200
aacgaaggta gaatcccagc ttgttccttg                                      1230
```

<210> SEQ ID NO 25
<211> LENGTH: 1230
<212> TYPE: DNA
<213> ORGANISM: Artificial Sequence
<220> FEATURE:
<223> OTHER INFORMATION: Synthetic Phytase (CL00102257)

<400> SEQUENCE: 25

```
cagagtgaga acgagttgaa cctggaatcc gttgtcatcg tctctagaca tggtgttaga      60
gcaccaacca aggccaccca acttatgcaa gatgtcaccc aagagcttg gccaacctgg      120 ccagtcaagc tgggttggtt gacacctaga ggtggtgagc tcgttgctta cttgggtcaa     180
taccaaagac agcgtcttgc tgccaacgga ttgttggccg ataagggttg tccacaacca     240
ggtcaagtag ctattattgc tgacgtcgac gaaagaaccc gtaagacagg tgaagccttc     300
gccgccggtc ttgctcctga ctgtgccatt accgttcaca cccaagctga cacttctaga     360
gctgatccat tgttcaaccc tttgaagact ggtgttttgc caattgtctc agctaacgtt     420
actgacgcta tcttgtccag agctggagga tccattgctg acttcaccca acactaccag     480
actgccttca gagagttgga aagagttctt aacttcaacc aatccaactt gtgctttaac     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat cggtgactct     720
caccaatgga acaccttgtt gtccttgcac aacgctcaat tcgacttgct gcagagaact     780
ccagaggttg ctagatccag agccacccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tgggtttgaa ctggactctt     960
cctggtcaac ctgataacac tccaccaggt ggtgagctcg ttttcgaaag atggcgtaga    1020
ctatctgata actctcaatg gattcaggtt tcgttggtct accaaacttt gcagcagatg    1080
agagacaagt ggccactgtc tttgaacacg cctccaggag aagtcaaatt ggctttgcct    1140
gcttgtgaag agagaaatgc tcagggtatg tgttccttgg ctggtttcac tcaaatcgtt    1200
aacgaaggta gaatcccagc ttgttccttg                                     1230
```

<210> SEQ ID NO 26
<211> LENGTH: 1230
<212> TYPE: DNA
<213> ORGANISM: Artificial Sequence
<220> FEATURE:
<223> OTHER INFORMATION: Synthetic Phytase (CL00102259)

<400> SEQUENCE: 26

| | |
|---|---|
| cagagtgaga acgagttgaa cctggaatcc gttgtcatcg tctctagaca tggtgttaga | 60 |
| gcaccaacca aggccaccca acttatgcaa gatgtcaccc caaatgcttg gccaacctgg | 120 |
| ccagtcaagc tgggttggtt gacacctaga ggtggtgagc tcgttgctta cttgggtcaa | 180 |
| taccaaagac agcgtcttgc tgccaacgga ttgttggccg ataagggttg tccacaacca | 240 |
| ggtcaagtag ctattattgc tgacgtcgac gaaagaaccc gtaagacagg tgaagccttc | 300 |
| gccgccggtc ttgctcctga ctgtgccatt accgttcaca cccaagctga cacttctaga | 360 |
| gctgatccat tgttcaaccc tttgaagact ggtgtttgcc aattgtctcc agctaacgtt | 420 |
| actgacgcta tcttgtccag agctggagga tccattgctg acttcaccca acactaccag | 480 |
| actgccttca gagagttgga aagagttctt aacttcaacc aatccaactt gtgctttaac | 540 |
| cgtgagaagc aagacgaatc ctgttccttg actcaagcat accatctga gttgaaggtc | 600 |
| tccgccgaca acgtctcttt gaccggtgct gtcagcttgg cttccatgtt gactgaaatc | 660 |
| tttcttctgc aacaagctca aggtatgcct gagccaggtt ggggtagaat cggtgactct | 720 |
| caccaatgga cacccttgtt gtccttgcac aacgctcaat cgacttgct gcagagaact | 780 |
| ccagaggttg ctagatccag agccaccca ttgttggact tgatcaagac tgctttgact | 840 |
| cctcacccac ctcaaaagca agcctacggt gttaccttgc ccacttctgt cttgttcatt | 900 |
| gccggtcacg atactaactt ggcaaatctc ggcggtgctt tgggtttgaa ctggactctt | 960 |
| cctggtcaac tgataacac tccaccaggt ggtgagctcg ttttcgaaag atggcgtaga | 1020 |
| ctatctgata actctcaatg gattcaggtt tcgttggtct accaaacttt gcagcagatg | 1080 |
| agagacaagt ggccactgtc tttgaacacg cctccaggag aagtcaaatt ggctttgcct | 1140 |
| gcttgtgaag agagaaatgc tcagggtatg tgttccttgg ctggtttcac tcaaatcgtt | 1200 |
| aacgaaggta gaatcccagc ttgttccttg | 1230 |

<210> SEQ ID NO 27
<211> LENGTH: 1230
<212> TYPE: DNA
<213> ORGANISM: Artificial Sequence
<220> FEATURE:
<223> OTHER INFORMATION: Synthetic Phytase (CL00071716)

<400> SEQUENCE: 27

| | |
|---|---|
| cagagtgagc ctgagttgaa cctggaatcc gttgtcatcg tctctagaca tggtgttaga | 60 |
| gcaccaacca aggccaccca acttatgcaa gatgtcaccc caagagcttg gccaacctgg | 120 |
| ccagtcaagc tgggttggtt gacacctaga ggtggtgagc tcgttgctta cttgggtcaa | 180 |
| taccaaagac agcgtcttgc tgccaacgga ttgttggccg ataagggttg tccacaacca | 240 |
| ggtcaagtag ctattattgc tgacgtcgac gaaagaaccc gtaagacagg tgaagccttc | 300 |
| gccgccggtc ttgctcctga ctgtgccatt accgttcaca cccaagctga cacttctaga | 360 |
| ccagatccat tgttcaaccc tttgaagact ggtgtttgcc aattggaccc agctaacgtt | 420 |
| actgacgcta tcttgtccag agctggagga tccattgctg acttcaccca acactaccag | 480 |

```
actgccttca gagagttgga aagagttctt aacttcccac aatccaactt gtgctttaac    540
cgtactaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caacgactct    720
caccaatgga acaccttgtt gtccttgcac aacgctcaat tcgacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tgggtttgaa ctggactctt    960
cctggtcaac ctgataacac tccaccaggt ggtgagctcg ttttcgaaag atggcgtaga   1020
ctatctgata actcttcttg gattcaggtt tcgttggtct accaaacttt gcagcagatg   1080
agagacaaga tcccactgtc tttgaacacg cctccaggag aagtcaaatt gaccttgcct   1140
gcttgtgaag agagaaatgc tcagggtatg tgttccttgg ctggtttcac tcaaatcgtt   1200
aacgaaggta gaatcccagc ttgttccttg                                    1230
```

<210> SEQ ID NO 28
<211> LENGTH: 1230
<212> TYPE: DNA
<213> ORGANISM: Artificial Sequence
<220> FEATURE:
<223> OTHER INFORMATION: Synthetic Phytase (CL00100225)

<400> SEQUENCE: 28

```
cagagtgagc tgagttgaa cctggaatcc gttgtcatcg tctctagaca tggtgttaga     60
gcaccaacca aggccaccca acttatgcaa gatgtcaccc aagagcttg gccaacctgg    120
ccagtcaagc tgggttggtt gacacctaga ggtggtgagc tcgttgctta cttgggtcaa    180
taccaaagac agcgtcttgc tgccaacgga ttgttggccg ataagggttg tccacaacca    240
ggtcaagtag ctattattgc tgacgtcgac gaaagaaccc gtaagacagg tgaagccttc    300
gccgccggtc ttgctcctga ctgtgccatt accgttcaca cccaagctga cacttctaga    360
gctgatccat tgttcaaccc tttgaagact ggtgttttgcc aattgtctcc agctaacgtt    420
actgacgcta tcttgtccag agctggagga tccattgctg acttcaccca acactaccag    480
actgccttca gagagttgga aagagttctt aacttcaacc aatccaactt gtgctttaac    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat cggtgactct    720
caccaatgga acaccttgtt gtccttgcac aacgctcaat tcgacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tgggtttgaa ctggactctt    960
cctggtcaac ctgataacac tccaccaggt ggtgagctcg ttttcgaaag atggcgtaga   1020
ctatctgata actcttcttg gattcaggtt tcgttggtct accaaacttt gcagcagatg   1080
agagacaagt ggccactgtc tttgaacacg cctccaggag aagtcaaatt ggctttgcct   1140
gcttgtgaag agagaaatgc tcagggtatg tgttccttgg ctggtttcac tcaaatcgtt   1200
aacgaaggta gaatcccagc ttgttccttg                                    1230
```

<210> SEQ ID NO 29
<211> LENGTH: 1230
<212> TYPE: DNA
<213> ORGANISM: Artificial Sequence
<220> FEATURE:
<223> OTHER INFORMATION: Synthetic Phytase (CL00102276)

<400> SEQUENCE: 29

```
cagagtgagc ctgagttgaa cctggaatcc gttgtcatcg tctctagaca tggtgttaga      60
gcaccaacca aggccaccca acttatgcaa gatgtcaccc aagagcttg gccaacctgg      120
ccagtcaagc tgggttggtt gacacctaga ggtggtgagc tcgttgctta cttgggtcaa      180
taccaaagac agcgtcttgc tgccaacgga ttgttggccg ataagggttg tccacaacca      240
ggtcaagtag ctattattgc tgacgtcgac gaaagaaccc gtaagacagg tgaagccttc      300
gccgccggtc ttgctcctga ctgtgccatt accgttcaca cccaagctga cacttctaga      360
ccagatccat tgttcaaccc tttgaagact ggtgtttgcc aattggaccc agctaacgtt      420
actgacgcta tcttgtccag agctggagga tccattgctg acttcaccca acactaccag      480
actgccttca gagagttgga aagagttctt aacttcaacc aatccaactt gtgctttaac      540
cgtgagaagc aagacgaatc ctgttccttg actcaagcat taccatctga gttgaaggtc      600
tccgccgaca acgtctcttt gaccggtgct gtcagcttgg cttccatgtt gactgaaatc      660
tttcttctgc aacaagctca aggtatgcct gagccaggtt ggggtagaat cggtgactct      720
caccaatgga acaccttgtt gtccttgcac aacgctcaat tcgacttgct gcagagaact      780
ccagaggttg ctagatccag agccacccca ttgttggact tgatcaagac tgctttgact      840
cctcacccac ctcaaaagca agcctacggt gttaccttgc ccacttctgt cttgttcatt      900
gccggtcacg atactaactt ggcaaatctc ggcggtgctt tgggtttgaa ctggactctt      960
cctggtcaac ctgataacac tccaccaggt ggtgagctcg ttttcgaaag atggcgtaga     1020
ctatctgata actctacttg gattcaggtt tcgttggtct accaaacttt gcagcagatg     1080
agagacaagt ggccactgtc tttgaacacg cctccaggag aagtcaaatt gaccttgcct     1140
gcttgtgaag agaaaatgc tcagggtatg tgttccttgg ctggtttcac tcaaatcgtt     1200
aacgaaggta gaatcccagc ttgttccgct                                     1230
```

<210> SEQ ID NO 30
<211> LENGTH: 1272
<212> TYPE: DNA
<213> ORGANISM: Artificial Sequence
<220> FEATURE:
<223> OTHER INFORMATION: Synthetic Phytase (Insertion variant)

<400> SEQUENCE: 30

```
cagagtgagc ctgagttgaa actggaatcc gttgtcatcg tctctagaca tggtgttaga      60
gcaccaacca aggccaccca acttatgcaa gatgtcaccc agacgcttg gccaacctgg      120
ccagtcaagc tgggttggtt gacacctaga ggtggtgagc tcgttgctta cttgggtcaa      180
taccaaagac agcgtcttgt tgccaacgga ttgttggccg ataagggttg tccacaacca      240
ggtcaagtag ctattattgc tgacgtcgac gaaagaaccc gtaagacagg tgaagccttc      300
gccgccggtc ttgctcctga ctgtgccatt accgttcaca cccaagctga cacttctaga      360
ccagatccat tgttcaaccc tttgaagact ggtgtttgcc aattggaccc agctaacgtt      420
actttggcta tcttgtccag agctgtggac cagctaacg ttactcatgc tatcttgtcc      480
agagctggag gatccattgc tgacttcacc caacactacc agactgcctt cagagagttg     540
```

```
gaaagagttc ttaacttccc acaatccaac ttgtgcttta accgtgagaa gcaagacgaa    600
tcctgttcct tgactcaagc attaccatct gagttgaagg tctccgccga caacgtctct    660
ttgaccggtg ctgtcagctt ggcttccatg ttgactgaaa tctttcttct gcaacaagct    720
caaggtatgc ctgagccagg ttggggtaga atcaccgact ctcaccaatg gaacaccttg    780
ttgtccttgc acaacgctca attcgacttg ctgcagagaa ctccagaggt tgctagatcc    840
agagccaccc cattgttgga cttgatcatg gctgctttga ctcctcaccc acctcaaaag    900
caagcctacg gtgttacctt gcccacttct gtcttgttca ttgccggtca cgatactaac    960
ttggcaaatc tcggcggtgc tttggagttg aactggactc ttcctggtca acctgataac   1020
actccaccag gtggtgagct cgttttcgaa agatggcgta gactatctga taactctcaa   1080
tggattcagg tttcgttggt ctaccaaact ttgcagcaga tgagagacaa gactccactg   1140
tctttgaaca cgcctccagg agaagtcaaa ttgaccttgc ctggatgtga agagagaaat   1200
gctcagggta tgtgttcctt ggctggtttc actcaaatcg ttaacgaagc tagaatccca   1260
gcttgttcct tg                                                        1272
```